(12) United States Patent
Balasubramanian et al.

(10) Patent No.: US 7,238,725 B2
(45) Date of Patent: Jul. 3, 2007

(54) TRICYCLIC COMPOUNDS USEFUL FOR THE TREATMENT OF INFLAMMATORY AND ALLERGIC DISORDERS: PROCESS FOR THEIR PREPARATION AND PHARMACEUTICAL COMPOSITIONS CONTAINING THEM

(75) Inventors: Gopalan Balasubramanian, Mumbai (IN); Laxmikant A. Gharat, Maharashtra (IN); Aftab D. Lakdawala, Mumbai (IN); Raghu R. Anupindi, Navi Mumbai (IN)

(73) Assignee: Glenmark Pharmaceuticals Ltd., Mumbai (IN)

( * ) Notice: Subject to any disclaimer, the term of this patent is extended or adjusted under 35 U.S.C. 154(b) by 0 days.

(21) Appl. No.: 10/532,273

(22) PCT Filed: Oct. 8, 2003

(86) PCT No.: PCT/IB03/04442

§ 371 (c)(1),
(2), (4) Date: Sep. 26, 2005

(87) PCT Pub. No.: WO2004/037805

PCT Pub. Date: May 6, 2004

(65) Prior Publication Data

US 2006/0178418 A1    Aug. 10, 2006

(30) Foreign Application Priority Data

Oct. 23, 2002 (IN) ................................... 922/2002

(51) Int. Cl.
- *A61K 31/38*   (2006.01)
- *A61K 31/352*  (2006.01)
- *C07D 307/91*  (2006.01)
- *C07D 333/76*  (2006.01)
- *C07D 405/12*  (2006.01)
- *C07D 409/12*  (2006.01)
- *C07D 207/38*  (2006.01)

(52) U.S. Cl. ............... 514/437; 514/455; 514/422; 546/284.7; 546/281.1; 548/518; 548/527; 548/543; 549/48; 549/461

(58) Field of Classification Search .......... 549/461, 549/43; 546/284.7, 281.1; 544/375, 153
See application file for complete search history.

(56) References Cited

U.S. PATENT DOCUMENTS 3,759,948 A    9/1973   Walford et al.
3,846,553 A    11/1974  Shen et al.
4,222,944 A    9/1980   Berger et al.
5,814,651 A    9/1998   Duplantier et al.
6,110,962 A    8/2000   Wrobel et al.

FOREIGN PATENT DOCUMENTS

| DE | 2059358 | 6/1971 |
|---|---|---|
| EP | 62158253 | 7/1987 |
| EP | 0 497 564 A1 | 8/1992 |
| EP | 1 270 577 A1 | 1/2003 |
| GB | 1041861 | 2/1963 |
| GB | 1285398 | 8/1972 |
| JP | 63 014156 | 6/1988 |
| WO | WO 92/10476 A1 | 6/1992 |
| WO | WO 93/19747 A1 | 10/1993 |
| WO | WO 94/02465 A1 | 2/1994 |
| WO | WO-94/08995 | 4/1994 |
| WO | WO 94/20446 A1 | 9/1994 |
| WO | WO 95/01338 A1 | 1/1995 |
| WO | WO 95/04046 A1 | 2/1995 |
| WO | WO 95/09837 A1 | 4/1995 |
| WO | WO 95/20578 A1 | 8/1995 |
| WO | WO 95/24381 A1 | 9/1995 |
| WO | WO 96/03377 | 2/1996 |
| WO | WO-98/09934 | 3/1998 |
| WO | WO 99/47545 A2 | 9/1999 |
| WO | WO 99/58521 | 11/1999 |
| WO | WO 01/27107 A2 | 4/2001 |
| WO | WO 01/70673 A2 | 9/2001 |
| WO | WO 01/70746 A1 | 9/2001 |
| WO | WO 02/060867 A2 | 8/2002 |
| WO | WO-02/072567 | 9/2002 |
| WO | WO 2004/016596 A1 | 2/2004 |
| WO | WO 2004/022536 A1 | 3/2004 |
| WO | WO 2004/037805 A1 | 5/2004 |

OTHER PUBLICATIONS

Nielsen, K.F. et al, Fungal metabolite screening: database of 474 mycotoxins and fungal metabolites for dereplication by standardised liquid chromatography-UV-mass spectrometry methodology. *Journal of Chromatography* 1002, 1-2:111-136.
Koyama et al., Heterocycles 1981; 16(6):969-972.
Hulme et al., Bioorganic and Medicinal Chemistry Letters 1998; 8:175-178.
Silvestre et al., Drugs of the Future 1998; 23(6):607-615.
Fox et al., J. Med. Chem. 2002; 45(2):360-370.

*Primary Examiner*—Joseph K. McKane
*Assistant Examiner*—Yong Chu
(74) *Attorney, Agent, or Firm*—Darby & Darby

(57) ABSTRACT

The present invention relates to novel tricyclic compounds useful for the treatment of inflammatory conditions, diseases of the central nervous and insulin resistant diabetes.

45 Claims, 2 Drawing Sheets

Graph 1
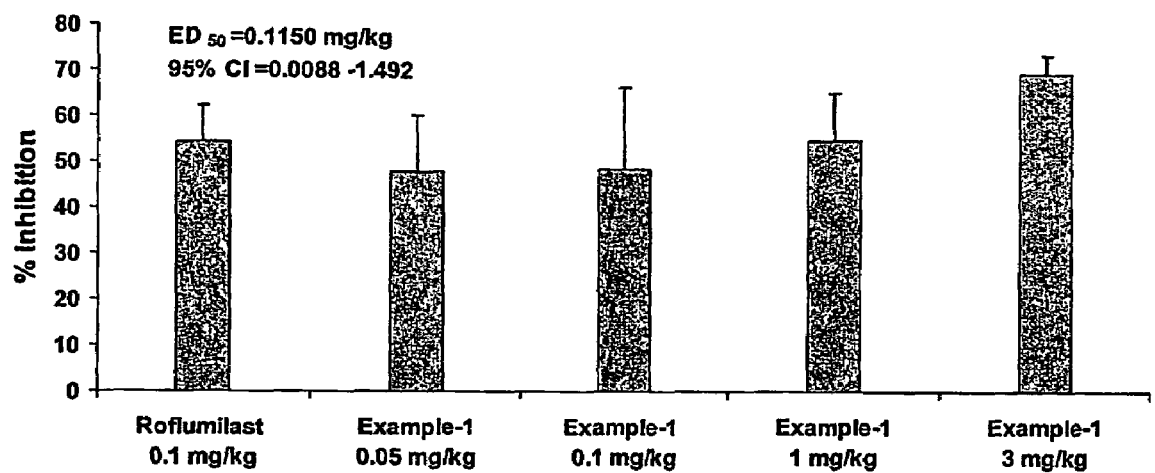

Graph 2
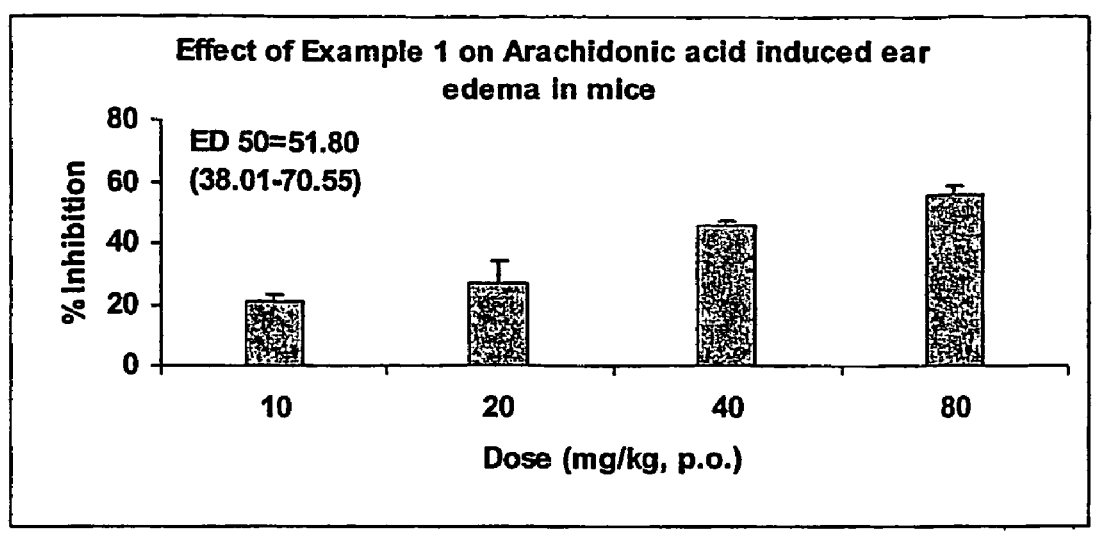

TRICYCLIC COMPOUNDS USEFUL FOR THE TREATMENT OF INFLAMMATORY AND ALLERGIC DISORDERS: PROCESS FOR THEIR PREPARATION AND PHARMACEUTICAL COMPOSITIONS CONTAINING THEM

This application is a national phase of International Application No. PCT/IB2003/004442, filed Oct. 8, 2003, which was published in English as International Publication No. WO 2004/037805 and claims the benefit of Indian Provisional Application No. 922/MUM/2002, filed Oct. 23, 2002.

FIELD OF THE INVENTION

The present invention relates to novel tricyclic compounds, their analogs, their tautomers, their regioisomers, their stereoisomers, their enantiomers, their diastereomers, their polymorphs, their pharmaceutically acceptable salts, their N-oxides, their pharmaceutically acceptable solvates and their pharmaceutical compositions containing them. The present invention more particularly relates to novel Phosphodiesterase type 4 (PDE4) inhibitors of the formula (1A), their analogs, their tautomers, their enantiomers, their diastereomers, their regioisomers, their stereoisomers, their polymorphs, their pharmaceutically acceptable salts, their N-oxides, their pharmaceutically acceptable solvates and the pharmaceutical compositions containing them.

The novel tricyclic compounds are of general formula (IA)

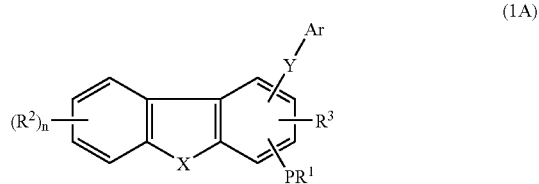

(1A)

wherein:
$R^1$, $R^2$ and $R^3$ may be same or different and are independently selected from the groups consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, —C(O)—$R^1$, —C(O)O—$R^1$, —C(O)N$R^1R^1$, —S(O)$_m$—$R^1$, —S(O)$_m$—N$R^1R^1$, nitro, —OH, cyano, amino, formyl, acetyl, halogen, —O$R^1$, —S$R^1$, protecting groups or when two $R^2$ substitutents are ortho to each other, may be joined to a form a saturated or unsaturated cyclic ring, which may optionally include up to two heteroatoms selected from O, N$R^1$ or S;
wherein P represents oxygen or sulfur,
wherein n represents 0-4;
Ar is substituted or unsubstituted aryl, substituted or unsubstituted arylalkyl, substituted or unsubstituted heterocyclic ring or substituted or unsubstituted heteroaryl ring,
Preferably Ar is optionally substituted phenyl, optionally substituted benzyl, optionally substituted pyramidine, optionally substituted pyridyl selected from 4-pyridyl, 3-pyridyl and 2-pyridyl or optionally substituted pyridyl-N-oxide selected from 4-pyridyl-N-oxide, 3-pyridyl-N-oxide and 2-pyridyl-N-oxide in which optional substituents (one or more) may be same or different and are independently selected from the groups consisting of hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino X is oxygen, S(O)$_m$ or N$R^5$;
$R^5$ represents hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, —C(O)—$R^1$, —C(O)O—$R^1$, —C(O)N$R^1R^1$, —S(O)$_m$—$R^1$, —S(O)$_m$—N$R^1R^1$, nitro, —OH, cyano, amino, formyl, acetyl, halogen, —O$R^1$, —S$R^1$ and protecting groups
Wherein m is 0, 1 or 2;
Y is —C(O)N$R^4$, —N$R^4$SO$_2$, —SO$_2$N$R^4$ or —N$R^4$C(O);
$R^4$ is hydrogen, substituted or unsubstituted alkyl, hydroxyl, —O$R^1$, —COO$R^1$, substituted or unsubstituted aryl) substituted or unsubstituted heterocyclic ring; and their analogs, their tautomers, their regioisomers, their stereoisomers, their enantiomers, their diastereomers, their polymorphs, their pharmaceutically acceptable salts, their N-oxides, their pharmaceutically acceptable solvates and their pharmaceutical compositions containing them or a pharmaceutical acceptable salts thereof.

More particularly, the present invention provides a compound of formula (1)

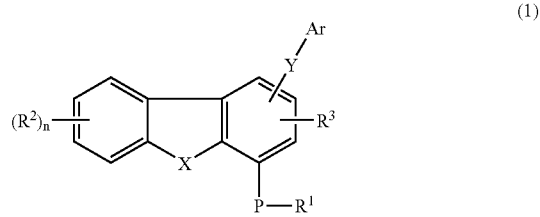

(1)

wherein:
$R^1$, $R^2$ and $R^3$ may be same or different and are independently selected from the groups consisting of hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl substituted or unsubstituted heterocyclic group, substituted or unsubstituted heterocyclylalkyl, substituted or unsubstituted heteroarylalkyl, —C(O)—$R^1$, —C(O)O—$R^1$, —C(O)N$R^1R^1$, —S(O)$_m$—$R^1$, —S(O)$_m$—N$R^1R^1$, nitro, —OH, cyano, amino, formyl, acetyl, halogen, —OR$^1$, —SR$^1$, protecting groups or when two R$^2$ substitutents ortho to each other, may be joined to a form a saturated or unsaturated cyclic ring, which may optionally include up to two heteroatoms selected from O, NR$^1$ or S;

wherein P represents oxygen or sulfur;

wherein n represents 0-4;

Ar is substituted or unsubstituted aryl, substituted or unsubstituted arylalkyl, substituted or unsubstituted heterocyclic ring or substituted or unsubstituted heteroaryl ring;

Preferably Ar is optionally substituted phenyl, optionally substituted benzyl, optionally substituted pyramidine, optionally substituted pyridyl selected from 4-pyridyl, 3-pyridyl and 2-pyridyl or optionally substituted pyridyl-N-oxide selected from 4-pyridyl-N-Oxide, 3-pyridyl-N-Oxide and 2-pyridyl-N-Oxide in which optional substituents (one or more) may be same or different and are independently selected from the groups consisting of hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino X is oxygen, S(O)$_m$ or NR$^5$;

R$^5$ represents hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, —C(O)—R$^1$, —C(O)O—R$^1$, —C(O)NR$^1$R$^1$, —S(O)$_m$—R$^1$, —S(O)$_m$—NR$^1$R$^1$, nitro, —OH, cyano, amino, formyl, acetyl, halogen, —OR$^1$, —SR$^1$ and protecting groups Wherein m is 0, 1 or 2;

Y is —C(O)NR$^4$, —NR$^4$SO$_2$, —SO$_2$NR$^4$ or —NR$^4$C(O);

R$^4$ is hydrogen, substituted or unsubstituted alkyl, hydroxyl, —OR$^1$, —COOR$^1$, substituted or unsubstituted aryl, substituted or unsubstituted heterocyclic ring;

and their analogs, their tautomers, their regioisomers, their stereoisomers, their enantiomers, their diastreomers, their polymorphs, their pharmaceutically acceptable salts, their N-oxides, their pharmaceutically acceptable solvates and their pharmaceutical compositions containing them or a pharmaceutical acceptable salts thereof The present invention also relates to a process for the preparation of the above said novel heterocyclic compounds of formula 1 as defined above. The compounds of general formula (1) more particularly, down regulate or inhibit the production of TNF-α as they are PDE4 inhibitors and therefore are useful in the treatment of variety of allergic and inflammatory diseases including asthma, chronic bronchitis, atopic dermatitis, urticaria, allergic rhinitis, allergic conjunctivitis, vernal conjuctivitis, eosinophilic granuloma, psoriasis, rheumatoid arthritis, septic shock, ulcerative colitis, Crohn's disease, reperfusion injury of the myocardium and reperfusion injury of the brain, chronic glomerulonephritis, endotoxic shock and adult respiratory distress syndrome. The compounds of the present invention are particularly useful for the treatment of asthma.

BACKGROUND OF THE INVENTION

Airway inflammation characterizes a number of severe lung diseases including asthma and chronic obstructive pulmonary disease (COPD). Events leading to airway obstruction include edema of airway walls, infiltration of inflammatory cells into the lung, production of various inflammatory mediators and increased mucous production. The airways of asthmatic patients are infiltrated by inflammatory leukocytes, of which the eosinophil is the most prominent component The magnitude of asthmatic reactions is correlated with the number of eosinophils present in lungs.

The accumulation of eosinophils is found dramatically in the lungs of asthmatic patients although there are very few in the lungs of a normal individual. They are capable of lysing and activating cells and destroying tissues. When activated, they synthesize and release inflammatory cytokines such as IL-1, IL-3, TNF-α and inflammatory mediators such as PAF, LTD4 and related oxygen species that can produce edema and broncho-constriction. Tumor necrosis factor (TNF-α) was also known to be involved in the pathogenesis of a number of autoimmune and inflammatory diseases. Consequently, manipulation of the cytokine signaling or biosynthetic pathways associated with these proteins may provide therapeutic benefit in those disease states. It has been well demonstrated that TNF-α production in pro-inflammatory cells becomes attenuated by an elevation of intracellular cyclic adenosine 3',5'-monophosphate (cAMP). This second messenger is regulated by the phosphodiesterase (PDE) family of enzymes. The phosphodiesterase enzymes play an integral role in cell signaling mechanisms by hydrolyzing cAMP and cGP to their inactive 5' forms. Inhibition of PDE enzymes thus results in an elevation of cAMP and/or cGP levels and alters intracellular responses to extra cellular signals by affecting the processes mediated by cyclic nucleotides. Since eosinophilis are believed to be a critical proinflammatory target for asthma, identification of the expression of the PDE 4 gene family in eosinophils led to PDE 4 as potential therapeutic target for asthma [Rogers, D. F., Giembycz, M. A., *Trends Pharmacol, Sci.*, 19, 160-164 (1998); Barnes, P. J., *Trends Pharmacol. Sci.*, 19, 415-423 (1998) herein incorporated by reference in their entirety].

The mammalian cyclic nucleotide phosphodiesterases (PDEs) are classified into ten families on the basis of their amino acid sequences and/or DNA sequence, substrate specificity and sensitivity to pharmacological agents [Soderling, S. H., Bayuga, S. J., and Beavo, J. A., *Proc. Natl. Acad. Sci., USA*, 96, 7071-7076 (1999); Fujishige, K, Kotera, J., Michibata, H., Yuasa, K., Takebayashi, Si, Okamura, K and Omori, K, *J. Biol. Chem.*, 274, 18438-18445 (1999) herein incorporated by reference in their entirety]. Many cell types express more than one PDE and distribution of isoenzymes between the cells varies markedly. Therefore development of highly isoenzyme selective PDE inhibitors provides a unique opportunity for selective manipulation of various pathophysiological processes.

Phosphodiesterase type 4 (PDE4) is an enzyme which regulates activities in cells which lead to inflammation in the lungs. PDE4, a cAMP-specific and Ca$^{+2}$-independent enzyme, is a key isozyme in the hydrolysis of cAMP in mast cells, basophils, eosinophils, monocytes and lymphocytes. The association between cAMP elevation in inflammatory cells with airway smooth muscle relaxation and inhibition of mediator release has led to widespread interest in the design of PDE4 inhibitors[Trophy, T. J., *Am. J. Respir. Crit. Care Med.*, 157, 351-370 (1998) herein incorporated by reference in their entirety]. Excessive or unregulated TNF-α production has been implicated in mediating or exacerbating a number of undesirable physiological conditions such as diseases including osteoarthritis, and other arthritic conditions; septic shock, endotoxic shock, respiratory distress syndrome and bone resorption diseases since TNF-α also participates in the onset and progress of autoimmune diseases, PDE4 inhibitors may find utility as therapeutic agents for rheumatoid arthritis, multiple sclerosis and Crohn's disease. [*Nature Medicine*, 1, 211-214 (1995) and ibid., 244-248 herein incorporated by reference in their entirety].

Strong interest in drugs capable of selective inhibition of PDE 4 is due to several factors. Tissue distribution of PDE-4 suggests that pathologies related to the central nervous and immune systems could be treated with selective PDE-4 inhibitors. In addition, the increase in intracellular cAMP concentration, the obvious biochemical consequence of PDE-4 inhibition, has been well characterized in immunocompetent cells where it acts as a deactivating signal.

Recently the PDE family has grown to include four subtypes-PDE4A to PDE4D, each encoded by a distinct gene (*British Journal of Pharmacology*; 1999; v.128; p. 1393-1398), herein incorporated by reference in its entirety.

It has been demonstrated that increasing cAMP levels within these cells results in suppression of cell activation, which in turn inhibits the production and release of pro-inflammatory cytokines such as TNF-α. Since eosinophilis are believed to be a critical pro-inflammatory target for asthma, identification of the expression of the PDE-4 gene family in eosinophils led to the PDE-4 as a potential therapeutic target for asthma.

The usefulness of several PDE-4 inhibitors, unfortunately, is limited due to their undesirable side effect profile which include nausea and emesis (due to action on PDE-4 in the central nervous system) and gastric acid secretion due to action on PDE-4 in parietal cells in the gut Barnette, M. S., Grous, M., Cieslinsky, L. B., Burman, M., Christensen, S. B., Trophy, T. J., *J. Pharmacol. Exp. Ther.*, 273,1396-1402 (1995) herein incorporated by reference in their entirety. One of the earliest PDE-4 inhibitors, Rolipram™, was withdrawn from clinical development because of its severe unacceptable side effect profile. Zeller E. et. al., *Pharmacopsychiatr.*, 17, 188-190 (1984) herein incorporated by reference in its entirety. The cause of severe side effects of several PDE-4 inhibitor molecules in human clinical trials has recently become apparent.

There exist two binding sites on mammalian PDE-4at which inhibitor molecules may bind. Also PDE-4 exists in two distinct forms which represent different conformations. They are designated as High affinity Rolipram binding site PDE-4H and Low affinity Rolipram binding site PDE-4L [Jacobitz, S., McLaughlin, M. M., Livi, G. P., Burman, M., Trophy, T. J., *Mol. Pharmaco.*, 50, 891-899 (1996) herein incorporated by reference in their entirety]. It was shown that certain side effects (vomiting and gastric acid secretion) are associated with inhibition of PDE-4H whereas some beneficial actions are associated with PDE-4L inhibition. It was also found that human recombinant PDE-4 exists id 4 isoforms A, B, C and D [Muller, T., Engels, P., Fozard, J. R., *Trends Pharmacol. Sci.*, 17, 294-298 (1996) herein incorporated by reference in its entirety]. Accordingly, compounds displaying more PDE-4D isoenzyme selectivity over the A, B or C are found to have fewer side effects than Rolipram [Hughes. B et.al., *Br. J. Pharmacol.* 1996, 118, 1183-1191 herein incorporated by reference in their entirety]. Therefore, selective inhibitors of PDE-4 isozymes would have therapeutic effects in inflammatory diseases such as asthma and other respiratory diseases.

Although several research groups all over the world are working to find highly selective PDE-4 isozyme inhibitors, so far success has been limited. Various compounds have shown PDE-4 inhibition

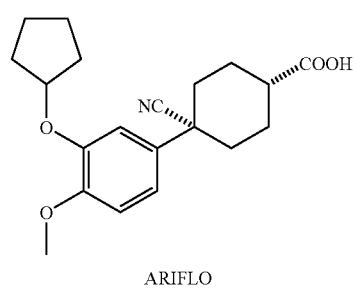

ARIFLO

A

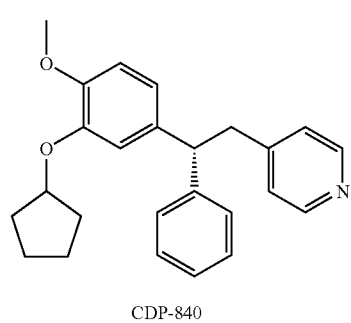

CDP-840

B

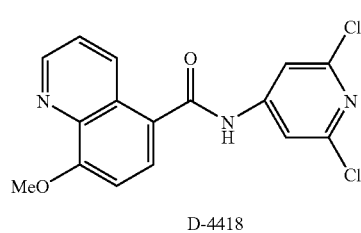

D-4418

C

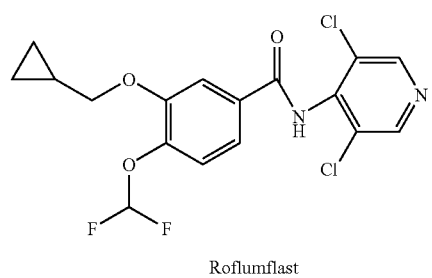

Roflumflast

D

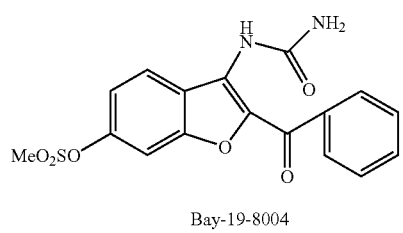

Bay-19-8004

E

-continued

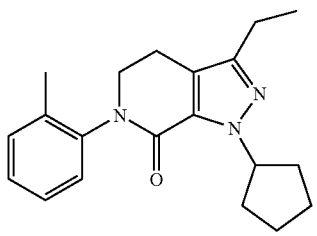
CP - 220, 629

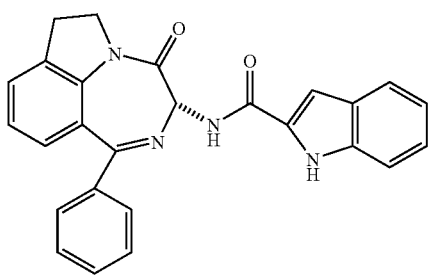
PD-168787

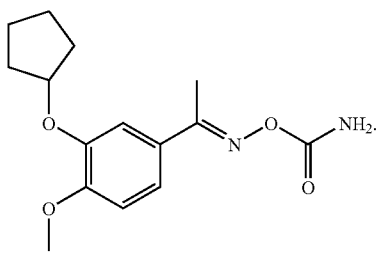
Filaminast

SmithKline Beecham's "Ariflo" which has the formula A, Byk Gulden's Roflumilast which has the formula D and Bayer's Bay-19-8004 which has the formula E have reached advanced stage of human clinical trials. Other compounds which have shown potent PDE-4 inhibitory activity include Celltech's CDP-840 of the formula B, Schering Plough's D-4418 of the formula C, Pfizer's 5CP-220,629 which has the formula F, Parke Davis's PD-168787 which has the formula G and Wyeth's Filaminast which has the formula H. However, recently due to efficacy and side effects problems, Ariflo, CDP-840 and Bay-19-8004 were discontinued from clinical trials as a treatment for asthma. Other compounds of the formulae C and F are presently undergoing phase-1 clinical trials.

U.S. Pat. No. 4,933,351 describes Benzofuran 2-carboxy amides useful as inhibitors of leukoriene biosynthesis, a compound of the formula I and acceptable pharmaceutical carrier:

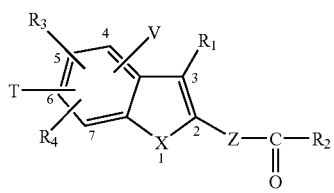
(I)

wherein:

Z is a bond, $CR_{14}$=$CR_5$;

X is O, S, SO or $SO_2$;

$R_2$ is H, OH, $C_1$ to $C_{20}$ alkoxy, including straight chain or branched chain, cycloalkyl, bicycloalkyl, tricycloalkyl or tetracycloalkyl;

$Ar_1$-$C_1$ to $C_3$ alkoxy;

$NR_8Ar_1$, wherein $R_8$ and $Ar_1$ can optionally be joined to form a heterocyclic ring having 5 to 8 atoms;

—$NR_8Het$;

—$N(R_8)CH_2Ar_1$

—$N(R_{13})$—$N(R_{13})_2$ wherein $R_{13}$ is independently hydrogen, $R_8$, $R_9$, $Ar_1$ or Het:

—NH—CH=$C(Ar_1)_2$;

—$O(CH_2)_nNR_8R_9$ wherein N is 2 to 4;

—Z—$Ar_1$;

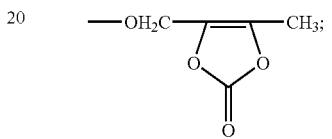

lower acyloxy-lower alkoxy

(e.g. $OCH(CH_3)OCC(CH_3)_3$);

—$CH_2OH$;

—$(CH_2)_nAr_1$ wherein in n is 0 to 3;

—$(CH_2)_nCOOR_6$ wherein n is 0 to 6;

$C_1$ to $C_{20}$ alkyl; $Ar_1$; Het; $(CH_2)_nNR_8R_9$

Wherein n is 1 to 3; or Het;

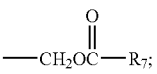

and $R_1$, $R_3$ $R_4$, T and V are independently selected from
1. hydrogen;
2. alkyl having 1 to 6 carbon atoms;
3. alkenyl having 2 to 6 carbon atoms;
4. —$(CH_2)_nM$ wherein n is 0 to 6 except when X is S and M is $OR_5$, in which n is 1 to 6 and M is
   a) —$OR_5$;
   b) halogen;
   c) —$CF_3$;
   d) —$SR_5$;
   e) $Ar_1$;
   f) —$COOR_6$;

g)
   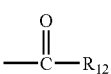

Wherein R$_{12}$ is H, C$_1$ to C$_6$ alkyl, or Ar$_1$;
h) tetrazole;

i)

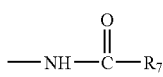

j)

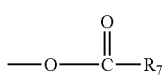

k)

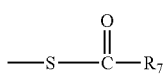

l)

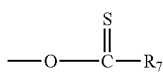

m)

n)
—NHSO$_2$R$_{10}$ Wherein R$_{10}$ is OH, C$_1$ to C$_6$ alkyl, CF$_3$, C$_1$ to C$_6$ alkoxy, or Ar;

o)

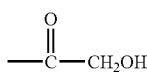

p) —SOR$_5$
q) —CONR$_8$R$_9$;
r) —SO$_2$NR$_8$R$_9$;
s) —SO$_2$R$_5$;
t) —NO$_2$; or
u) —CN or any two of R$_3$,R$_4$,T and V may be joined to form a saturated ring having 5 to 6 ring atoms, said ring atoms comprising 0,1 or 2 atoms selected from oxygen and sulfur, the remaining ring atoms been carbon;

each R$_5$ is independently H, C$_1$ to C$_6$ alkyl, benzene, Ar$_1$, perfluro-C$_1$ to C$_4$ allyl, CH$_2$-R$_{11}$ is C$_1$ to C$_5$ alkyldimethylamino,hydroxyl-C$_2$ to C$_5$ alkyl, CH$_2$COOR$_6$, or CH$_2$CO—R$_7$;

each R$_6$ is independently H, or C$_1$ to C$_6$ alkyl;

each R$_7$ is independently C$_1$ to C$_6$ alkyl, benzyl, Ar$_1$, NR$_8$R$_9$, NHAr$_1$ or O—C$_1$ to C$_4$ alkyl;

each R$_8$ and R$_9$ is independently H or C$_1$ to C$_4$ alkyl, or R$_8$ and R$_9$ may be joined through the N to which they are attached to form a heterocycloalkyl ring having 5 to 8 ring atoms;

each Het is independently an aromatic heterocyclic ring having 5 to 6 ring atoms, one or more of which is selected from N, O and S;

each Ar$_1$ is independently 1- or 2-naphtyl, phenyl or mono- or disubstituted phenyl, wherein the substituents on phenyl are independently selected from C$_1$ to C$_3$ alkyl, I Br, Cl, F, COOR$_6$, (CH$_2$)$_n$—NR$_8$R$_9$ wherein n is 0 to 2, methylenedioxy, C$_1$ to C$_3$ alkoxy, OH, CN,NO$_2$, CF$_3$, C$_1$ to C$_4$ acyl, NR$_8$R$_9$, S—C$_1$ to C$_6$ alkyl, SO—C$_1$ to C$_6$ alkyl, and SO$_2$—C$_1$ to C$_6$ alkyl; and R$_{14}$ and R$_{15}$ are each independently H, C$_1$ to C$_6$ alkyl; or a pharmaceutically acceptable salts thereof WO 94/08995 describes heterocyclic condensed benzoic acid derivatives as 5-HT4 receptor antagonists of formula (I-1) or a pharmaceutically accepted salts thereof:

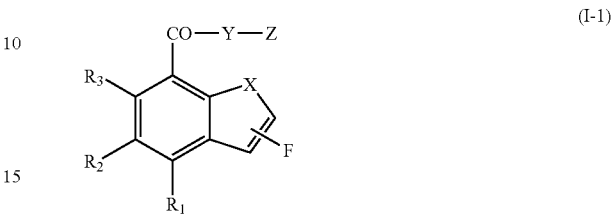

(I-1)

Wherein X is O, or S;
R$_1$ is hydrogen, amino, halo, C$_{1-6}$alkyl, hydroxyl or C$_{1-6}$alkoxy;
R$_2$ is hydrogen, halo, C$_{1-6}$alkyl, C$_{1-6}$alkoxy, nitro, amino, or C$_{1-6}$alkylthio;
R$_3$ is hydrogen, halo, C$_{1-6}$alkyl, C$_{1-6}$alkoxy, or amino; and
R$_4$ is hydrogen or C$_{1-6}$alkyl.

WO 94/08995 also describes

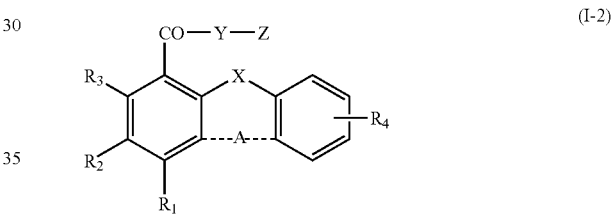

(I-2)

Wherein
X is O or S
A represent a single bond, —CH$_2$— or CO or A is (CH$_2$)$_a$—E—(CH$_2$)$_b$ where one of a and b is 0 and the other is 0 or 1 and E is O,S or NH;
R$_1$ is hydrogen, amino, halo, C$_{1-6}$alkyl, hydroxyl or C$_{1-6}$alkoxy;
R$_2$ is hydrogen, halo, C$_{1-6}$alkyl, C$_{1-6}$alkoxy, nitro, amino, or C$_{1-6}$alkylthio;
R$_3$ is hydrogen, halo, C$_{1-6}$alkyl, C$_{1-6}$alkoxy, or amino; and
R$_4$ is hydrogen or C$_{1-6}$alkyl.

WO 94/08995 also describes

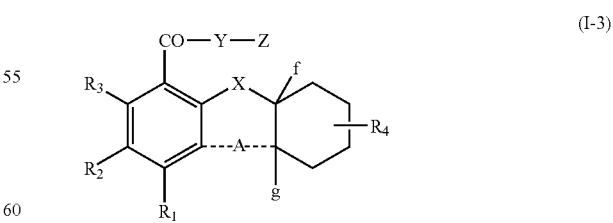

(I-3)

Wherein
X is O or S
A represent a single bond, —CH$_2$— or CO or A is (CH$_2$)$_a$—E—(CH$_2$)$_b$ where one of a and b is 0 and the other is 0 or 1 and E is O,S or NH;
f and g are both hydrogen or together are a bond;

R₁ is hydrogen, amino, halo, $C_{1-6}$alkyl, hydroxyl or $C_{1-4}$alkoxy;
R₂ is hydrogen, halo, $C_{1-6}$alkyl, $C_{1-4}$alkoxy, nitro, amino, or $C_{1-6}$alkylthio;
R₃ is hydrogen, halo, $C_{1-6}$alkyl, $C_{1-6}$alkoxy, or amino; and
R₄ is hydrogen or $C_{1-6}$alkyl.

WO 94/08995 also describes

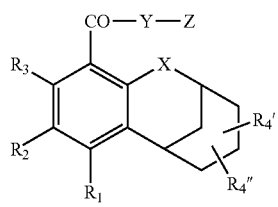
(I-4)

Wherein
X is O or S;
R₁ is hydrogen, amino, halo, $C_{1-6}$alkyl, hydroxyl or $C_{1-6}$alkoxy;
R₂ is hydrogen, halo, $C_{1-6}$alkyl, $C_{1-6}$alkoxy, nitro, amino, or $C_{1-6}$alkylthio;
R₃ is hydrogen, halo, $C_{1-6}$alkyl, $C_{1-6}$alkoxy, or amino; and
$R_4^1$ and $R_4^{11}$ are independently hydrogen or $C_{1-6}$alkyl.

In formulae (I-1) to (I-4) inclusive:
Y is O or NH;
Z is of sub-formula (a), (b) or (c):

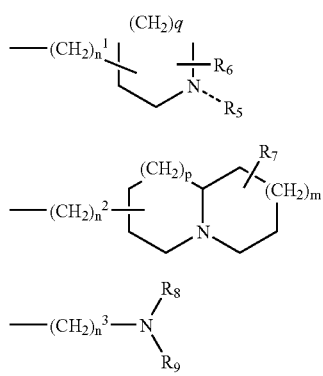

Wherein n¹ is 0,1,2,3 or 4; n² is 0,1,2,3 or 4; n³ is 2,3,4 or 5;
q is 0,1,2 or 3; p is 0,1 or 2; m is 0,1 or 2;
R₅ is hydrogen, $C_{1-12}$ alkyl, aralkyl or R₅ is $(CH_2)_z$—R₁₀ wherein z is 2 or 3 and R₁₀ is selected from cyano, hydroxyl, $C_{1-6}$alkoxy, phenoxy, $C(O)C_{1-6}$alkyl, $COC_6H_5$, —$CONR_{11}R_{12}$, $NR_{11}COR_{12}$, $SO_2NR_{11}R_{12}$ or $NR_{11}SO_2R_{12}$, wherein R₁₁ and R₁₂ are hydrogen or $C_{1-6}$alkyl; and
R₆, R₇ and R₈ are independently hydrogen or $C_{1-6}$alkyl; and
R₉ is hydrogen or $C_{1-10}$alkyl; or a compound of formula (I) wherein the CO—Y linkage is replaced by a heterocyclic bioisostere;

WO 01/58895-A1 describes novel compounds having the formula (i):

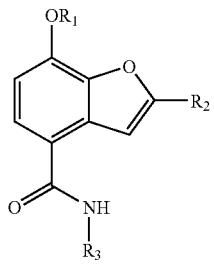

wherein R₁ is $C_{1-3}$alkyl optionally substituted with one or more fluorines;
R₂ is $CH_2OCH_3$ or 2 or 3-tetrahydrofuranyl;
R₃ is a pyrazole, imidazole or isoxazole group of a partial formula (A), (B) or (C)

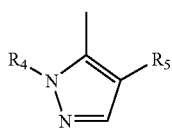
(A)

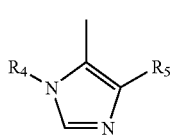
(B)

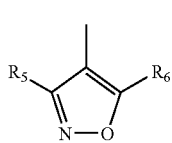
(C)

R₄ is $C_{1-3}$alkyl; and
R₅ and R₆, which may be same or different each represents $C_{1-3}$alkyl, halogen, $CF_3$ or CN;

U.S. Pat. No. 4,769,387 describes compounds of the formula:

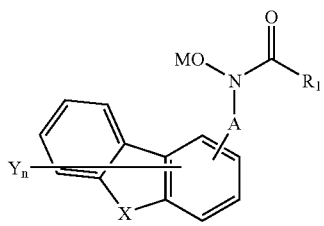

wherein R is (1) hydrogen, (2) $C_1$ to $C_4$ alkyl, (3) $C_2$ to $C_4$ alkenyl, or (4) $NR_2R_3$, wherein R₂ and R₃ are independently selected from hydrogen, $C_1$ to $C_4$ alkyl or hydroxyl, but R₂ and R₃ are not simultaneously hydroxyl;
X (1) oxygen, (2) sulfur, (3) $SO_2$, or (4) $NR_4$ wherein R₄ is (1) hydrogen, (2) $C_1$ to $C_6$ alkyl, (3) $C_1$ to $C_6$ alkoyl, or (4) aroyl;
A is selected from $C_1$ to $C_6$ alkylene and $C_2$ to $C_6$ alkenylene;
Y is selected independently at each occurrence from (1) hydrogen, (2) halogen, (3) hydroxy, (4) cyano (5) halo-substituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) aryl, (11) aryloxy, (12) aroyl, (13) $C_1$ to $C_{12}$ arylalkyl, (14) $C_2$ to $C_{12}$ arylalkenyl, (15) $C_1$ to $C_{12}$ arylalkoxy, (16) $C_1$ to $C_{12}$ arylthioalkoxy, and substituted derivatives of (17) aryl, (18) aryl-oxy, (19) aroyl, (20) $C_1$ to $C_{12}$ arylalkyl, (21) $C_2$ to $C_{12}$ arylalkenyl, (22) $C_1$ to $C_{12}$ arylalkoxy, or (23) $C_1$ to $C_{12}$ arylthioalkoxy, wherein substituents are selected from halo, nitro, cyano $C_1$ to $C_{12}$ alkyl, alkoxy, and halosubstituted alkyl; the number n is 0-4; the group(s) Y may be substituted from any of the positions on the aryl rings;

and M is hydrogen, a pharmaceutically acceptable cation, aroyl, or $C_1$ to $C_{12}$ alkoyl.

U.S. Pat. No. 3,897,453 describes dibenzofuran and dibenzothiophene derivatives of general formula I

(I)

In which Z is

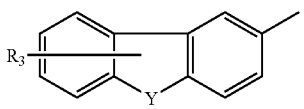

wherein $R_1$ is COOH, CHO, or $CH_2OH$ including functional derivatives thereof; $R_2$ is H or alkyl of 1-4 carbon atoms; $R_3$ is H, alkyl, alkoxy, alkanoyl, monoalkylamino, dialkylamino, or acylamino, each of up to 4 carbon atoms, F, Cl, Br, I, OH, $NH_2$, $NO_2$, CN, or $CF_3$; and Y is O or S; with the proviso that at least one of $R_2$ and $R_3$ is other than H; and the physiologically acceptable salts thereof.

WO 98/09934 describes compounds of formula I

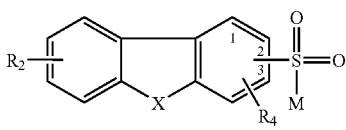
I

Wherein M is a natural (L) alpha amino acid derivative having the structure

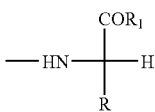

X is O, S, $S(O)_n$, $CH_2$, CO, or $NR_Q$;
$R_Q$ is hydrogen, $C_1$-$C_6$ alkyl or —$C_1$-$C_6$ alkyl-phenyl; R is a side chain of a natural alpha amino acid;
$R_1$ is $C_1$-$C_5$ alkoxy, hydroxy, or —$NHOR_5$;
$R_2$ and $R_4$ are independently hydrogen, —$C_1$-$C_5$ alkyl, phenyl-$NO_2$, halogen, —$OR_5$, —CN, —$CO_2R_5$, —$SO_3R_5$, —CHO, —$COR_5$, —$CONR_5R_6$, —$(CH_2)_nNR_5R_6$, —$CF_3$, or —$NHCOR_5$;
Each $R_5$ and $R_6$ are independently hydrogen, $C_1$-$C_5$ alkyl; and n is 0 to 2, and the pharmaceutically acceptable salts, esters, amides and prodrugs thereof.

SUMMARY OF THE INVENTION

Accordingly, the present invention provides novel heterocyclic compounds of general formula (1)

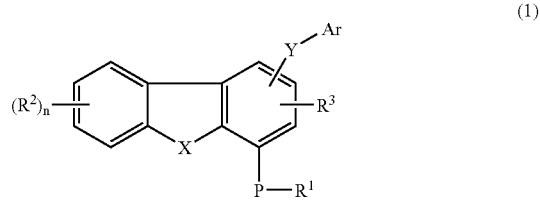
(1)

The invention thus relates to compounds of formula 1, wherein:

$R^1$, $R^2$ and $R^3$ may be same or different and are independently selected from the groups consisting of hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, —$C(O)$—$R^1$, —$C(O)O$—$R^1$, —$C(O)NR^1R^1$, —$S(O)_m$—$R^1$, —$S(O)_m$—$NR^1R^1$, nitro, —OH, cyano, amino, formyl, acetyl, halogen, —$OR^1$, —$SR^1$, protecting groups or when two $R^2$ substitutents ortho to each other, may be joined to a form a saturated or unsaturated cyclic ring, which may optionally include up to two heteroatoms selected from O, $NR^1$ or S;

wherein P represents oxygen or sulfur preferably O;

wherein n represents 0-4;

Ar is substituted or unsubstituted aryl, substituted or unsubstituted arylalkyl, substituted or unsubstituted heterocyclic ring or substituted or unsubstituted heteroaryl ring, Preferably Ar is optionally substituted phenyl, optionally substituted benzyl, optionally substituted pyramidine, optionally substituted pyridyl selected from 4-pyridyl, 3-pyridyl and 2-pyridyl or optionally substituted pyridyl-N-oxide selected from 4-pyridyl-N-oxide, 3-pyridyl-N-oxide and 2-pyridyl-N-oxide in which optional substituents (one or more) may be same or different and are independently selected from the groups consisting of hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino. Further preferred Ar selected from the group consisting of substituted or unsubstituted 4-pyridyl; substituted or unsubstituted 4-pyridyl-N-oxide; substituted or unsubstituted 3 pyridyl, substituted or unsubstituted 3 pyridyl-N-oxide; substituted or unsubstituted 2 pyridyl; and substituted or unsubstituted 2 pyridyl N-oxide. Further preferred is when the Ar is selected from the group consisting of

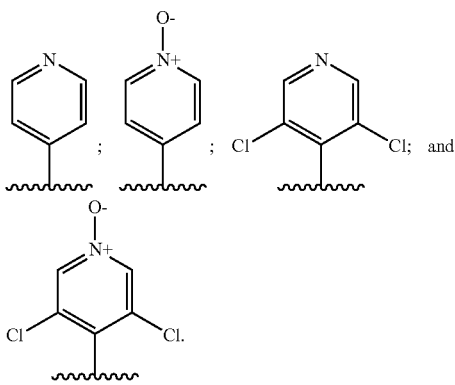

Further preferred Ar is

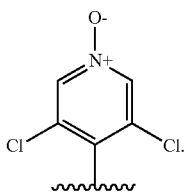

X is oxygen, $S(O)_m$ or $NR^5$;

$R^5$ represents hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, —C(O)—$R^1$, —C(O)O—$R^1$, —C(O)$NR^1R^1$, —$S(O)_m$—$R^1$, —$S(O)_m$—$NR^1R^1$, nitro, —OH, cyano, amino, formyl, acetyl, halogen, —$OR^1$, —$SR^1$ and protecting groups Wherein m is 0, 1 or 2;

Y is —C(O)$NR^4$, —$NR^4SO_2$, —$SO_2NR^4$ or —$NR^4C(O)$ preferably Y is —C(O)NH—;

$R^4$ is hydrogen, substituted or unsubstituted alkyl, hydroxyl, —$OR^1$, —$COOR^1$, substituted or unsubstituted aryl, substituted or unsubstituted heterocyclic ring;

and their analogs, their tautomers, their regioisomers, their stereoisomers, their enantiomers, their diastereomers, their polymorphs, their pharmaceutically acceptable salts, their N-oxides, their pharmaceutically acceptable solvates and their pharmaceutical compositions containing them or a pharmaceutical acceptable salts thereof.

The substituents in the 'substituted alkyl', 'substituted alkoxy' 'substituted alkenyl' 'substituted alkynyl' 'substituted cycloalkyl' 'substituted cycloalkylalkyl' 'substituted cyclocalkenyl' 'substituted arylalkyl' 'substituted aryl' 'substituted heterocyclic ring', 'substituted heteroaryl ring,' 'substituted heteroarylalkyl', 'substituted heterocyclylalkyl ring', 'substituted amino', 'substituted alkoxycarbonyl', 'substituted cyclic ring' 'substituted alkylcarbonyl', 'substituted alkylcarbonyloxy' and may be the same or different which one or more selected from the groups such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocyclylalkyl ring' substituted or unsubstituted heteroarylalkyl, substituted or unsubstituted heterocyclic ring, substituted or unsubstiuted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —$(=N—N(R^x)R^y)$, —$NR^xC(O)OR^y$, —$NR^xR^y$, —$NR^xC(O)R^y$—, —$NR^xC(S)R^y$ —$NR^xC(S)NR^yR^z$, —$SONR^xR^y$—, —$SO_2NR^xR^y$—, —$OR^x$, —$OR^xC(O)NR^yR^z$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, —$ONO_2$, wherein $R^x$, $R^y$ and $R^z$ in each of the above groups can be hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocyclylalkyl ring' substituted or unsubstituted heteroarylalkyl, substituted or unsubstituted heterocyclic ring, Further preferred is $R^1$ is substituted alkyl. Most preferred is $R^1$ is $CHF_2$. Still further preferred $R^1$ is unsubstituted alkyl most preferably methyl. Preferably $R^2$ is alkyl, halogen, cyano, nitro, amino, substituted heterocyclic and $SO_2NR^1R^1$ and n=1, most preferably $R^2$ is chloro. Still further prefered $R^2$ is substituted alkyl most preferably $CF_3$. Still further preferred $R^1$ is —$NH_2$. Still further preferred $R^2$ is $SO_2NR^1R^2$. Most preferably $R^2$ is $SO_2N(CH_3)_2$.

BRIEF DESCRIPTION OF THE DRAWINGS

Graph 1 shows the effect of Example 1 on the inhibition on LPS induced TNFα release in male Balb/C mice.

Graph 2 shows the effect of Example 1 on arachidonic acid induced ear edema in mice.

DETAILED DESCRIPTION OF THE INVENTION

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, e.g., methyl, ethyl, n-propyl 1-methylethyl (isopropyl), n-butyl, n-pentyl, 1,1-dimethylethyl (t-butyl), and the like.

The term "Alkenyl" refers to aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2-butenyl and the like.

The term "Alkynyl" refers to straight or branched chain hydrocarbyl radicals having at least one carbon-carbon triple bond, and having in the range of about 2 up to 12 carbon atoms (with radicals having in the range of about 2 up to 10 carbon atoms presently being preferred) e.g., ethynyl, propynyl, butynyl and the like.

The term "Alkoxy" denotes alkyl group as defined above attached via oxygen linkage to the rest of the molecule. Representative examples of those groups are —OCH$_3$, —OC$_2$H$_5$ and the like.

The term "Alkylcarbonyl" denotes alkyl group as defined above attached via carbonyl linkage to the rest of the molecule. Representative examples of those groups are —C(O)CH$_3$, —C(O)C$_2$H$_5$ and the like.

The term "Alkoxycarbonyl" denotes alkoxy group as defined above attached via carbonyl linkage to the rest of the molecule. Representative examples of those groups are —C(O)—OCH$_3$, —C(O)—OC$_2$H$_5$ and the like.

The term "Alkylcarbonyloxy" denotes alkylcarbonyl group as defined above attached via oxygen linkage to the rest of the molecule. Representative examples of those groups are —O—C(O)CH$_3$, —O—C(O)C$_2$H$_5$ and the like.

The term "Alkylamino" denotes alkyl group as defined above attached via amino linkage to the rest of the molecule. Representative examples of those groups are —NH$_2$CH$_3$, —NH(CH$_3$)$_2$, —N(CH$_3$)$_3$ and the like.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g sprio (4,4) non-2-yl.

The term "cycloalkylalkyl" refers to cyclic ring-containing radicals containing in the range of about 3 up to 8 carbon atoms directly attached to alkyl group which are then attached to the main structure at any carbon from alkyl group that results in the creation of a stable structure such as cyclopropylmethyl, cyclobuyylethyl, cyclopentylethyl, and the like.

The term "cycloalkenyl" refers to cyclic ring-containing radicals containing in the range of about 3 up to 8 carbon atoms with at least one carbon-carbon double bond such as cyclopropenyl, cyclobutenyl, cyclopentenyl and the like.

The term "aryl" refers to aromatic radicals having in the range of 6 up to 14 carbon atoms such as phenyl, naphthyl, tetrahydronapthyl, indanyl, biphenyl and the like.

The term "arylalkyl" refers to an aryl group as defined above directly bonded to an alkyl group as defined above. e.g., —CH$_2$C$_6$H$_5$, —C$_2$H$_5$C$_6$H$_5$ and the like.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl and the like.

The term "heteroaryl" refers to heterocyclic ring radical as defined above. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocylyl ring radical may be attached to the main structure at any heteroatom or carbon atom that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The term "cyclic ring" refers to a cyclic ring containing 3-10 carbon atoms.

The term "protecting group" refers to carbobenzyloxy (CBZ) or Tert.butyloxy, carbonyl (BOC) and the like.

The term "halogen" refers to radicals of fluorine, chlorine, bromine and iodine.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, omithine, lysine, arginine, serine, and the like; quaternary ammonium salts of the compounds of invention with alkyl halides, alkyl sulphats like MeI, (Me)$_2$SO$_4$ and the like, non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates and the like. Pharmaceutically acceptable solvates may be hydrates or comprise other solvents of crystallization such as alcohols.

Another object of the invention is a method of treating inflammatory diseases, disorders and conditions characterized by or associated with an undesirable inflammatory immune response and all disease and conditions induced by or associated with an excessive secretion of TNF-α and PDE-4 which comprises administering to a subject a therapeutically effective amount of a compound according to Formula I.

Another object of the invention is a method of treating inflammatory conditions and immune disorders in a subject in need thereof which comprises administering to said subject a therapeutically effective amount of a compound according to Formula I.

Preferred inflammatory conditions and immune disorders are chosen from the group consisting of asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohns disease, psoraisis, uticaria, adult vernal cojunctivitis, respiratory distress syndrome, rhematoid spondylitis, osteoarthritis, gouty arthritis, uveitis, allergic conjunctivitis, inflammatory bowel conditions, ulcerative coalitis, eczema, atopic dermatitis and chronic inflammation. Further preferred are allergic inflammatory conditions.

Further preferred are inflammatory conditions and immune disorders selected from the group consisting of inflammatory conditions or immune disorders of the lungs, joints, eyes, bowels, skin and heart.

Further preferred are inflammatory conditions chosen from the group consisting of bronchial asthma, nephritis, and allergic rhinitis.

Another object of the invention is a method for abating inflammation in an affected organ or tissue including delivering to the organ or tissue a therapeutically effective amount of a compound represented by a compound according to Formula 1.

Another object of the invention is a method of treating diseases of the central nervous system in a subject in need thereof which comprises administering to said subject a therapeutically effective amount of a compound according to Formula 1.

Preferred diseases of the central nervous system are chosen from the group consisting of depression, amnesia, dementia, Alzheimers disease, cardiac failure, shock and cerebrovascular disease.

Another object of the invention is a method of treating insulin resistant diabetes in a subject in need thereof which comprises administering to said subject a therapeutically effective amount of a compound according to Formula 1.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The benefit to a subject to be treated is either statistically significant or at least perceptible to the patient or to the physician A "therapeutically effective amount" means the amount of a compound that, when administered to a mammal for treating a state, disorder or condition, is sufficient to effect such treatment The "therapeutically effective amount" will vary depending on the compound, the disease and its severity and the age, weight, physical condition and responsiveness of the mammal to be treated.

The four classic symptoms of acute inflammation are redness, elevated temperature, swelling, and pain in the affected area, and loss of function of the affected organ.

Symptoms and signs of inflammation associated with specific conditions include:

rheumatoid arthritis—pain, swelling, warmth and tenderness of the involved joints; generalized and morning stiffness;

insulin-dependent diabetes mellitus- insulitis; this condition can lead to a variety of complications with an inflammatory component, including: retinopathy, neuropathy, nephropathy, coronary artery disease, peripheral vascular disease, and cerebrovascular disease;

autoimmune thyroiditis—weakness, constipation, shortness of breath, puffiness of the face, hands and feet, peripheral edema, bradycardia;

multiple sclerosis—spasticity, blurry vision, vertigo, limb weakness, paresthesias;

uveoretinitis—decreased night vision, loss of peripheral vision;

lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma—Raynaud's disease; swelling of the hands, arms, legs and face; skin thickening; pain, swelling and stiffness of the fingers and knees, gastrointestinal dysfunction, restrictive lung disease; pericarditis,; renal failure;

other arthritic conditions having an inflammatory component such as rheumatoid spondylitis, osteoarthritis, septic arthritis and polyarthritis—fever, pain, swelling, tenderness;

other inflammatory brain disorders, such as meningitis, Alzheimer's disease, AIDS dementia encephalitis—photophobia, cognitive dysfunction, memory loss;

other inflammatory eye inflammations, such as retinitis—decreased visual acuity;

inflammatory skin disorders, such as, eczema, other dermatites (e.g., atopic, contact), psoriasis, burns induced by UV radiation (sun rays and similar UV sources)—erythema, pain, scaling, swelling, tenderness;

inflammatory bowel disease, such as Crohn's disease, ulcerative colitis—pain, diarrhea, constipation, rectal bleeding, fever, arthritis;

asthma—shortness of breath, wheezing, other allergy disorders, such as allergic rhinitis—sneezing, itching, runny nose conditions associated with acute trauma such as cerebral injury following stroke-sensory loss, motor loss, cognitive loss;

heart tissue injury due to myocardial ischemia—pain, shortness of breath;

lung injury such as that which occurs in adult respiratory distress syndrome—shortness of breath, hyperventilation, decreased oxygenation, pulmonary infiltrates;

inflammation accompanying infection, such as sepsis, septic shock, toxic shock syndrome—fever, respiratory failure, tachycardia, hypotension, leukocytosis;

other inflammatory conditions associated with particular organs or tissues, such as nephritis (e.g., glomerulonephritis)—oliguria, abnormal urinalysis;

inflamed appendix—fever, pain, tenderness, leukocytosis;

gout—pain, tenderness, swelling and erythema of the involved joint, elevated serum and/or urinary uric acid;
inflamed gall bladder—abdominal pain and tenderness, fever, nausea, leukocytosis;
chronic obstructive pulmonary disease—shortness of breath, wheezing;
congestive heart failure—shortness of breath, rates, peripheral edema;
Type II diabetes—end organ complications including cardiovascular, ocular, renal, and peripheral vascular disease
lung fibrosis—hyperventilation, shortness of breath, decreased oxygenation;
vascular disease, such as atherosclerosis and restenosis—pain, loss of sensation, diminished pulses, loss of function
and alloimmunity leading to transplant rejection—pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated proinflammatory lymphoid cells recognizing a pathogen or an antigen specific to the organ or tissue. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished e.g., by local or by systemic administration of the active ingredient to the host "A subject" or "a patient" or "a host" refers to mammalian animals, preferably human.

Some of the representative compounds according to the present invention are specified below but should not construed to be limited thereto;

1) N-(3,5-dichloropyrid-4-yl)-4methoxy dibenzo[b,d]furan-1-carboxamide
2) N-(3,5-dichloropyrid-4-yl)-4-methoxy dibenzo[b,d]furan-1-carboxamide-N1-oxide
3) N-(pyrid-4-yl)-4-methoxy dibenzo[b,d]furan-1-carboxamide
4) N-(pyrid-4-yl)-4methoxy dibenzo[b,d]furan-1-carboxamide-N1-oxide
5) N-(2-chloropyrid-3-yl)-4-methoxy dibenzo[b,d]furan-1-carboxamide
6) N-(4-fluorophenyl)-4-methoxy dibenzo[b,d]furan-1-carboxamide
7) N-(pyrid-3-yl)-4-methoxy dibenzo[b,d]furan-1-carboxamide
8) N-(pyrid-3-yl)-4-methoxy dibenzo[b,d]furan-1-carboxamide-N1-oxide
9) N-(3,5-dichloropyrid-4-yl)-4-methoxy-8-trifluoromethyl dibenzo[b,d]furan-1-carboxamide
10) N-(3,5-dichloropyrid-4-yl)-4-methoxy-8-trifluoromethyl dibenzo[b,d]furan-1-carboxamide-N1-oxide
11) N-(pyrid-4yl)-4-methoxy-8-trifluoromethyl dibenzo[b,d]furan-1-carboxamide
12) N-(3,5-dichloropyrid-4-yl)-4-difluoromethoxy-8-trifluoromethyl dibenzo[b,d]furan-1-carboxamide
13) N-(3,5-chloropyrid-4-yl)-4-difluoromethoxy-8-trifluoromethyl dibenzo[b,d]furan-1-carboxamide-N1-oxide
14) N-(pyrid-4-yl)-4fluoromethoxy-8-trifluoromethyl dibenzo[b,d]furan-1-carboxamide
15) N-(pyrid-4-yl)-4-difluoromethoxy-8-trifluoromethyl dibenzo[b,d]furan-1-carboxamide-N1-oxide
16) N-(pyrid-3-yl)-4-difluoromethoxy-8-trifluoromethyl dibenzo[b,d]furan-1-carboxamide
17) N-(pyrid-3-yl)-4-difluoromethoxy-8-trifluoromethyl dibenzo[b,d]furan-1-carboxamide-N1-oxide
18) N-(pyrid-2-yl)-4-difluoromethoxy-8-trifluoromethyl dibenzo[b,d]furan-1-carboxamide
19) N-(3,5-dichloropyrid-4-yl)-4-difluoromethoxy dibenzo[b,d]furan-1-carboxamide
20) N-(pyrid-4yl)-4-difluoromethoxy dibenzo[b,d]furan-1-carboxamide
21) N-(pyrid-4-yl)-4-difluoromethoxy dibenzo[b,d]furan-1-carboxamide-N1-oxide
22) N-(pyrid-3-yl)-4-difluoromethoxy dibenzo[b,d]furan-1-carboxamide
23) N-(pyrid-3-yl)-4-difluoromethoxy dibenzo[b,d]furan-1-carboxamide-N1-oxide
24) N-(5-chloropyrid-2-yl)-4-difluoromethoxy dibenzo[b,d]furan-1-carboxamide
25) N-(3,5-dichloropyrid-4-yl)-4-cyclopropylmethoxy dibenzo[b,d]furan-1-carboxamide
26) N-(3,5-dichloropyrid-4-yl)-4-cyclopropylmethoxy dibenzo[b,d]furan-1-carboxamide-N1-oxide
27) N-(pyrid-4-yl)-4-cyclopropylmethoxy dibenzo[b,d]furan-1-carboxamide
28) N-(pyrid-4-yl)-4-cyclopropylmethoxy dibenzo[b,d]furan-1-carboxamide-N1-oxide
29) N-(pyrid-3-yl)-4-cyclopropylmethoxy dibenzo[b,d]furan-1-carboxamide
30) N-(pyrid-3-yl)-4-cyclopropylmethoxy dibenzo[b,d]furan-1-carboxamide-N1-oxide
31) N-(3,5-dichloropyrid-4-yl)-4-isopropyloxy dibenzo[b,d]furan-1-carboxamide
32) N-(3,5-dichloropyrid-4-yl)-4-isopropyloxy dibenzo[b,d]furan-1-carboxamide -N1-oxide
33) N-(pyrid-4-yl)-4-isopropyloxy dibenzo[b,d]furan-1-carboxamide
34) N-(pyrid-4-yl)-4-isopropyloxy dibenzo[b,d]furan-1-carboxamide-N1-oxide
35) N-(pyrid-3-yl)-4-isopropyloxy dibenzo[b,d]furan-1-carboxamide
36) N-(pyrid-3-yl)-4-isopropyloxy dibenzo[b,d]furan-1-carboxamide-N1-oxide
37) N-(3,5-dichloropyrid-4-yl)-4-benzyloxy dibenzo[b,d]furan-1-carboxamide
38) N-(3,5-dichloropyrid-4-yl)-4-methoxy-8-nitro dibenzo[b,d]furan-1-carboxamide
39) N-(pyrid-4-yl)-4-methoxy-8-nitro dibenzo[b,d]furan-1-carboxamide
40) N-pyrid-3-yl)-4-methoxy-8-nitro dibenzo[b,d]furan-1-carboxamide
41) N-(3,5dichloropyrid-4-yl)-4-methoxy-8-chloro-dibenzo[b,d]furan-1-carboxamide
42) N-(3,5-dichloropyrid-4-yl)-4-methoxy-8-bromo-dibenzo[b,d]furan-1-carboxamide
43) N-(pyrid-4-yl)-4-methoxy-8-bromo-dibenzo[b,d]furan-1-carboxamide
44) N-(pyrid-3-yl)-4-methoxy-8-bromo-dibenzo[b,d]furan-1-carboxamide
45) N-(3,5-dichloropyrid-4yl)-4methoxy-8-iodo-dibenzo[b,d]furan-1-carboxamide
46) N-(pyrid-4-yl)-4-methoxy-8-iodo-dibenzo[b,d]furan-1-carboxamide
47) N-(pyrid-3-yl)-1methoxy-8-iodo-dibenzo[b,d]furan-1-carboxamide 48) N-(4-methylpyrimid-2-yl)-4-methoxy dibenzo [b,d]furan-1-carboxamide
49) N-(2,5- dichlorophenyl)-4-methoxy dibenzo[b,d]furan-1-carboxamide
50) a.N-(3,5-dichloropyrid-4-yl)-4ethoxycarbomethoxy dibenzo[b,d]furan-1-carboxamide
b.N-(3,5-dichloropyrid-4-yl)-4-hydroxycarbomethoxy-dibenzo[b,d]furan-1-carboxamide
51) N-(3,5-dichloropyrid-4-yl)-4-methoxy dibenzo[b,d]furan-2-carboxamide
52) N-(3,5-dichloropyrid-4-yl)-4-methoxy dibenzo[b,d]furan-3-carboxamide
53) N4-(4-methoxy dibenzo[b,d]furan-1-yl) isonicotinamide
54) N-(3,5-dichloropyrid-4-yl)-4-methoxy dibenzo[b,d]furan-1-sulfonamide
55) N-(3,5-dichloropyrid-4-yl)-4-methoxy-8-amino-dibenzo[b,d]furan-1-carboxamide
56) N-(3,5-dichloropyrid-4-yl)-4-difluoromethoxy-dibenzo[b,d]furan-1-carboxamide-N-oxide
57) N-(3,5-dichloropyrid-4-yl)-4-methoxy-8-cyano-dibenzo[b,d]furan-1-carboxamide
58) N-(3,5-dichloropyrid-4-yl)-4-difluoromethoxy-8-nitro-dibenzo[b,d]furan-1-carboxamide
59) N-(3,5-dichloropyrid-4-yl)-4-difluoromethoxy-8-amino-dibenzo[b,d]furan-1-carboxamide
60) 3,5-Dichloro-4-(4-ethoxydibenzo[b,d]furan-1-ylcarboxamido)pyridine
61) N1-Benzyl-4-cyclopentyloxydibenzo[b,d]furan-1-carboxamide
62) 4-(4-Cyclopentyloxydibenzo[b,d]furan-1-ylcarboxamido)pyridine
63) 3,5-Dichloro-4-cyclopentyloxydibenzo[b,d]furan-1-ylcarboxamido)pyridine
64) 4-(4-Methylsulfanyldibenzo[b,d]furan-1-ylcarboxamido)pyridine
65) N3-(4-Methoxydibenzo[b,d]furan-1-yl)nicotinamide
66) N1-Benzyl-4-methoxydibenzo[b,d]furan-1-sulfonamide
67) 4-(4-Methoxydibenzo[b,d]furan-1-ylsulfonamido)pyridine
68) 3,5-Dichloro-4-(4-ethoxydibenzo[b,d]furan-1-ylcarboxamido)pyridine-N -oxide
69) 3,5-Dichloro-4-cyclopentyloxydibenzo[b,d]furan-1-ylcarboxamido)pyridine-N-oxide
70) N-Formyl-1-methoxy-4-[4-methoxyphenylaminosulphonyl]-9H-carbazole
71) 1-methoxy-4-[4-methoxyphenylaminosulphonyl]-9H-carbazole.
72) N-Formyl-1-methoxy-4-[4-methylphenylaminosulphonyl]-9H-carbazole.
73) 1-methoxy-4-[4-methylphenylaminosulphonyl]-9H-carbazole.
74) 1-methoxy-4-[4-methylphenylaminosulphonyl-N'-methyl]-9H-carbazole.
75) 1-methoxy-4-[4-methylphenylaminosulphonyl-N'-methyl]-9methyl carbazole.
76) 1-methoxy-4-[4-pyridinylaminosulphonyl]-9H-carbazole.
77) N4-(2,6-Dichlorophenyl)-1-methoxy-9H-4-carbazolsulphonamide.
78) N4-(2,6-Dichlorophenyl)-9-formyl-1-methoxy-9H-4-carbazolsulphonamide.
79) N4-(4-pyridyl)-1-methoxy-9H-4-carbazole carboxamide.
80) N4-(3,5-dichloro-4-pridyl)-1-methoxy-9H-4-carbazole carboxamide.
81) N4-(3,5dichloro-4-pyridyl)-6-chloro-1-methoxy-9H-4-carbazole carboxamide.
82) N4-(3,5-dichloro-4-pyridyl)-9-benzyl-6-chloro-1-methoxy-9H-4-carbazole carboxamide.
83) N4-(3,5-dichloro-4-pyridyl)-6-chloro-9-cyclohexylmethyl-1-methoxy-9H-4-carbazole carboxamide.
84) N4-(3,5-dichloro-4-pyridyl)-6-chloro-9-(4-fluorobenzyl)-1-methoxy-9H-4-carbazole carboxamide.
85) N4-(3,5-dichloro-4-pyridyl)-6-chloro-9-(4-methoxybenzyl)-1-methoxy-9H-4-carbazolecarboxamide.
86) N4-(3,5chloro-4-pyridyl)-9-(4-fluorobenzyl)-1-methoxy-9H-4-carbazole carboxamide.
87) N4-(4-pyridyl)-9-(4-fluorobenzyl)-1-methoxy -9H-4-carbazole carboxamide.
88) N4-(3,5-dichloro-4-pyridyl)-9-benzyl-1-methoxy-9H-4-carbazolecarboxamide.
89) N4-(3,5-dichloro-4-pyridyl)-9-benzyl-1-ethoxy-9H-4-carbazolecarboxamide.
90) N4-(3,5-dichloro-4-pyridyl)-9-benzyl-6-chloro-1-ethoxy-9H-4-carbazolecarboxamide
91) N4-(4-pyridyl)-9-benzyl-1-ethoxy-9H-4-carbazolecarboxamide
92) N4-(3-pyridyl)-6-chloro-9-(4-fluorobenzyl)-1-methoxy-9H-4-carbazolecarboxamide
93) N4-(4-pyridyl)-6-chloro-9-(4-fluorobenzyl)-1-methoxy-9H-4-carbazolecarboxamide
94) N4-(3,5-dichloro-4-pyridyl)8-chloro-9-cyclohexylmethyl-1-methoxy-9H-4-carbazole carboxamide.
95) N4-(3,5-dichloro-4-pyridyl)-8-chloro-9-(4-Fluorobenzyl)-1-methoxy-9H-4-carbazole carboxamide.
96) N4-(3,5-dichloro-4-pyridyl)-6-chloro-1-methoxy-9-methyl-9H-4-carbazole carboxamide.
97) N4-(3,5-dichloro-4-pyridyl N-oxide)-6-chloro-9-(4-fluorobenzyl)-1-methoxy-9H-4-carbazolecarboxamide.
98) N4-(3,5-dichloro-4-pyridyl N-oxide)-6-chloro-9-(4-methoxybenzyl)-1-methoxy-9H-4-carbazolecarboxamide.
99) N4-(3,5-dichloro-4-pyridyl N-oxide)-6-chloro-9-cyclohexylmethyl-1-methoxy-9H-4-carbazolecarboxamide.
100) N4-(3,5-dichloro-4-pyridyl)-9-methyl-1-methoxy-9H-4-carbazolecarboxamide.
101) 3,5-Dichloro-4-(4-methoxydibenzo[b,d]-thiophen-1-ylcarboxamido)pyridine
102) 3,5-dichloro-4-(4-cyclopentyloxydibenzo[b,d]-thiophen-1-ylcarboxamido)pyridine
103) N1-(4-methoxyphenyl)-4-methoxydibenzo[b,d]thiophene-1-carboxamide
104) N1-(4-methoxyphenyl)-4-methoxydibenzo[b,d]thiophene-1-carboxamide-5,5-dioxide
105) N1-(4-chlorophenyl)-4-methoxydibenzo[b,d]thiophene-1-carboxamide
106) 4-(4-methoxydibenzo[b,d]thiophene-1-ylcarboxamido)pyrdine
107) 4-(4-cylopentyloxydibezo[b,d]thiophene-1-ylcarboxamido)pyridine
108) 3,5-dichloro-4-(4-cyclopentyloxydibenzo[b,d]-thiophen-5,5-dioxide-1-ylcarboxamido)pyridine-N-oxide
109) 3,5-dichloro-4-(4-methoxydibenzo[b,d]-thiophen-5,5-dioxide-1-ylcarboxamido) pyridine-N-oxide
110) 3,5Dichloro-4-(4-methoxydibenzo[b,d]-thiophen-5,5-dioxide-1-ylcarboxamido) pyridine.
111) 3,5Dichloro-4-(4-difluoromethoxydibenzo[b,d]-thiophen-1-ylcarboxamido) pyridine.
112) N1-(4-methoxyphenyl)-4-methoxydibenzo[b,d]thiophene-1-sulfonamide.
113) 2-(4-Methoxydibenzo[b,d]thiophen-1-ylcarboxamido)-pyridine.

114) 4-(4-Ethoxydibenzo[b,d]thiophen-1-ylcarboxamido)-pyridine.
115) N1 4-methoxyphenyl)-N8, 8-dimethyl-4-methoxy-dibenzo[b,d]thiophen-8,1-disulfonamide.
116) 3-(4-Methoxydibenzo[b,d]thiophen-1-ylcarboxamido)-pyridine.
117) 3,5-Dichloro-4-(6-ethyl-4-methoxydibenzo[b,d]-thiophen-1-ylcarboxamido)pyridine
118) 3,5,dichloro-4-(4-ethoxy-dibenzo[b,d ]thiophen-1-yl-carboxamido)pyridine.
119) 3-(4-Methoxydibenzo[b,d]thiophene-5,5dioxide-1-yl-carboxamido)-pyridine.
120) 3,5-Dichloro-4-(4-benzyloxydibenzo[b,d]-thiophen-1-ylcarboxamido)pyridine
121) N-(3,5-dichloropyrid-4-yl)-4-difluoromethoxy-8-(pyr-rolidine-2-one-1-yl) -dibenzo[b,d]furan-1-carboxamide The compounds according to the invention may be prepared by the following processes. The symbols P, Ar, X, Y, $R^1$, $R^2$, $R^3$, $R^4$ and $R^5$ when used in the below formulae below are to be understood to present those groups described above in relation to formula (1) unless otherwise indicated The present invention discloses a process for the preparation of compounds of general formula (1).

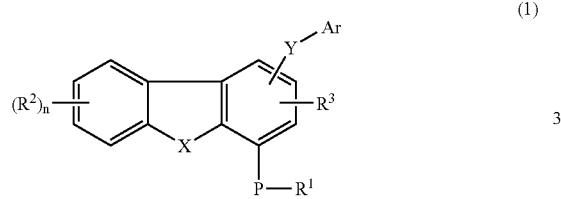

In one embodiment the compounds of formula 1 where Y is —$CONR^4$, can be prepared by reacting the acid halide or the mixed anhydride of the common intermediate of formula (10) (wherein FG is COOH) or of formula (11) (which is obtained from formula (10) wherein FG is alkyl, formyl, cyano, halogen, nitro, amino and the like by conventional methods) with an appropriate amine of the formula $ArNHR^4$ using standard conditions known in the literature.

The common intermediate of the formula (10) and/or of the formula (11) can be synthesized by using any of the general process described in synthetic schemes I to VI.

The desired compounds of formula 1 obtained are then converted into their salts and/or the N-oxides and, if desired, salts of the compounds of formula 1 obtained are then converted into the free compounds.

In the above scheme I wherein P, X $R^1$, $R^2$ and $R^3$ have the meanings described above intermediate (14) can be synthesized by reacting the appropriate substituted nitrobenzene of

GENERAL SYNTHETIC SCHEME I.

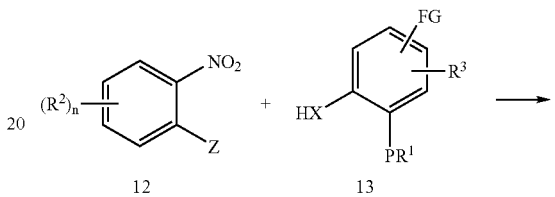

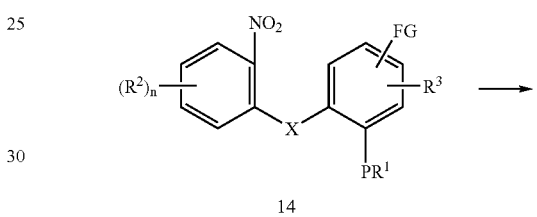

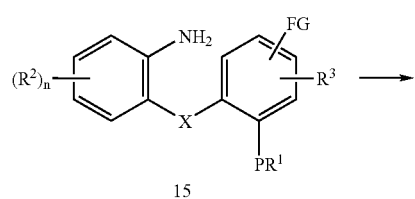

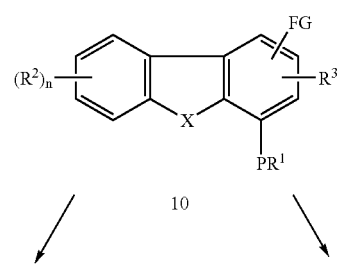

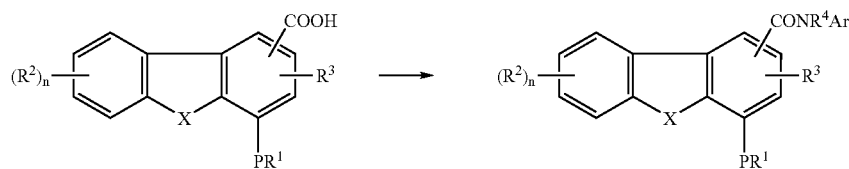

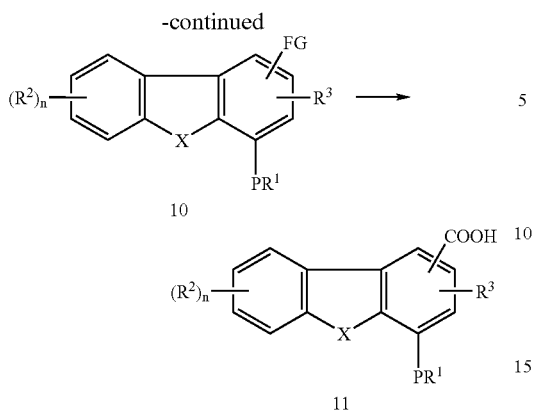

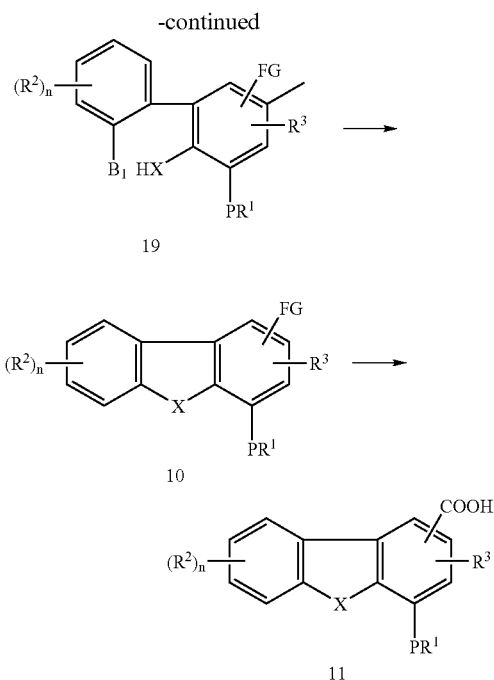

the formula (12) (wherein Z is a halogen,) with an appropriately substituted or unsubstituted aromatic group of the formula (13) (wherein FG is alkyl, formyl, cyano, halogen, nitro, amino, carboxylic acid group and the like) under appropriate basic conditions. Intermediate (14) can be reduced under standard reducing conditions (raney nickel/hydrazine, iron/ammonium chloride, hydrogenation using Pd/C, and the like) to the amino compound of the formula (15). The intermediate (15) can be cyclized to the tricyclic intermediate of the formula (10) by diazotization followed by standard coupling methods (cuprous oxide in 0.1N sulfuric acid, copper in DMSO). If the functional group FG in (13) is other than the carboxylic acid, then it can be converted to the carboxylic acid at any stage of the synthetic process as permitted by the chemistry of the synthetic process. If in the intermediate of formula (10) FG is alkyl formyl, cyano, halogen, nitro, amino, then the intermediate (10) can be transformed to the intermediate of formula (11) by conventional methods described in the literature (for example if FG is methyl then the methyl group can be oxidized using manganese or chromium reagents of to the carboxylic acid group; if FG is cyano group then the cyano group could be hydrolysed to the carboxylic acid; if FG is bromine then it could be transformed to carboxylic acid via lithiation followed by treatment with carbon dioxide).

Alternatively, the common intermediate of formula (10) and/or of formula (11) can be synthesized by the process described in scheme II

SCHEME II.

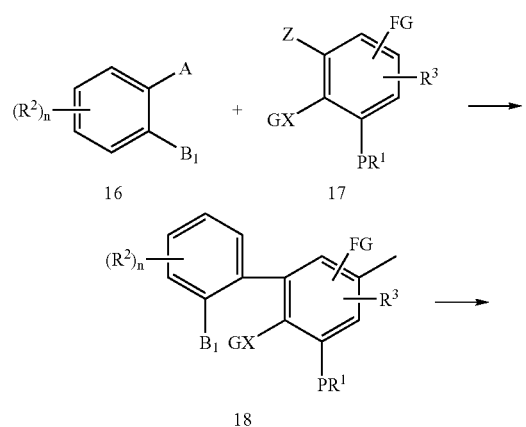

In the above scheme II wherein P, X, $R^1$, $R^2$ and $R^3$ have the meanings described above and wherein A is a halogen, or —OMs or —OTs (Ms=methanesulfonyl group; Ts=p-toluenesulfonyl group) or —B(OH)$_2$, $B_1$ is a halogen, G is an appropriate protecting group (benzyloxy carbonyl, t-butyloxycarbonyl, isopropyl, cyclopentyl, ally, acetyl, benzyl and the likes), FG is alkyl, formyl, cyano, halogen, nitro, amino, carboxylic acid group and the like and Z is a halogen, preferably bromine or iodine, intermediate (18) can synthesized by coupling the substituted aryl group of the formula I with an appropriately substituted aryl group of formula (17) using standard methods known in the literature. (palladium acetate in DMF or glacial acetic acid, nickel catalyst in pyridine or DMF, tetrakistriphenylphosphinepalladium in DMF and the like). Intermediate (18) can be deprotected to obtain intermediate (19) which then further cyclized under basic conditions (potassium salts in DMP or DMSO, NaH in DMF or DMSO and the like) to the tricyclic intermediate of formula (10). If the functional group FG in (17) is other than the carboxylic acid, then it can be converted to the carboxylic acid at any stage of the synthetic process as permitted by the chemistry of the synthetic process. If in the intermediate of formula (10) FG is alkyl, formyl, cyano, halogen, nitro, amino, then intermediate (10) can be transformed to the intermediate of formula (11) by conventional methods described in the literature (for example if FG is methyl then the methyl group can be oxidized using manganese or chromium reagents of to the carboxylic acid group; if FG is cyano group then the cyano group could be hydrolysed to the carboxylic acid; if FG is bromine then it could be transformed to carboxylic acid via lithiation followed by treatment with carbon dioxide).

Alternatively, the common intermediate of formula (10) and/or of formula (11) can be synthesized by the process described in scheme III.

SCHEME III

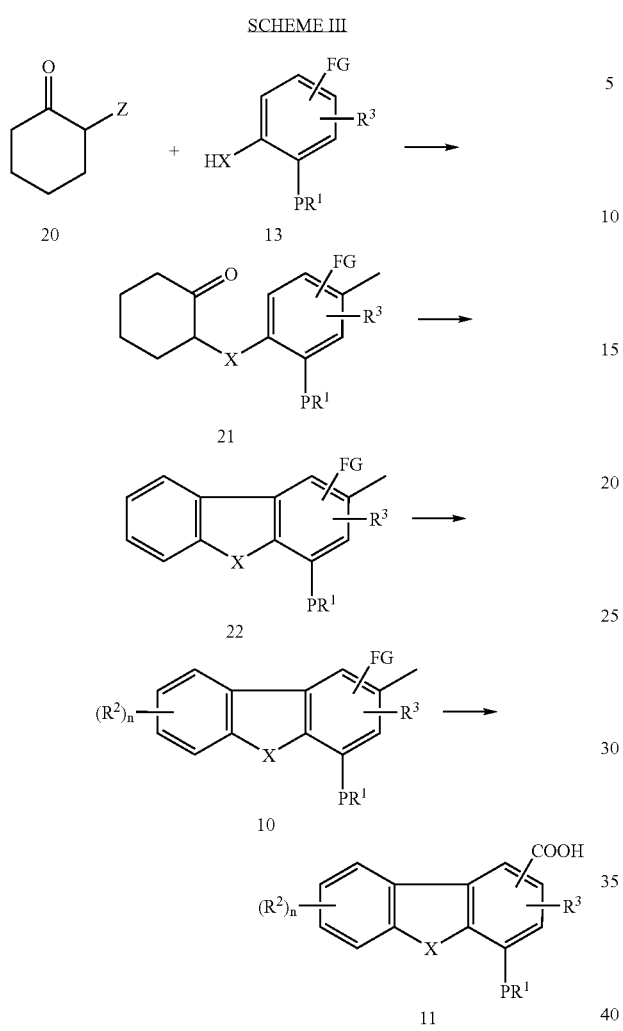

In the above scheme III wherein P, X, $R^1$, $R^2$ and $R^3$ have the meanings described above and wherein Z is a halogen, FG is alkyl, formyl, cyano, halogen, nitro, amino, carboxylic acid group and the like, intermediate (21) can synthesized by reacting the halocyclohexanone of the formula (20) with appropriately substituted aryl group of the formula (13) under basic conditions (potassium salts in DMF or DMSO, NaH in DMF or DMSO and the like). Intermediate (21) can be cyclized under acidic conditions (polyphosphoric acid or methanesulfonic acid) and oxidized (Pd/C in diphenyl ether or dichlorobenzene, DDQ and the like) to the dibenzofuran intermediate of formula (3). The substituents $R^2$ can be introduced by standard electrophilic substitution reactions described in the literature on intermediate (22) to provide the intermediate of the formula (10). If the functional group FG in (13) is other than the carboxylic acid, then it can be converted to the carboxylic acid at any stage of the synthetic process as permitted by the chemistry of the synthetic process. If in the intermediate of formula (10) FG is alkyl, formyl, cyano, halogen, nitro, amino, then the intermediate (10) can be transformed to the intermediate of formula (11) by conventional methods described in the literature. (for example if FG is methyl then the methyl group can be oxidized using manganese or chromium reagents of to the carboxylic acid group; if FG is cyano group then the cyano group could be hydrolysed to the carboxylic acid; if FG is bromine then it could be transformed to carboxylic acid via lithiation followed by treatment with carbon dioxide).

Alternatively, the common intermediate of formula (10) and/or of formula (11) can be synthesized by the process described in scheme IV.

SCHEME IV.

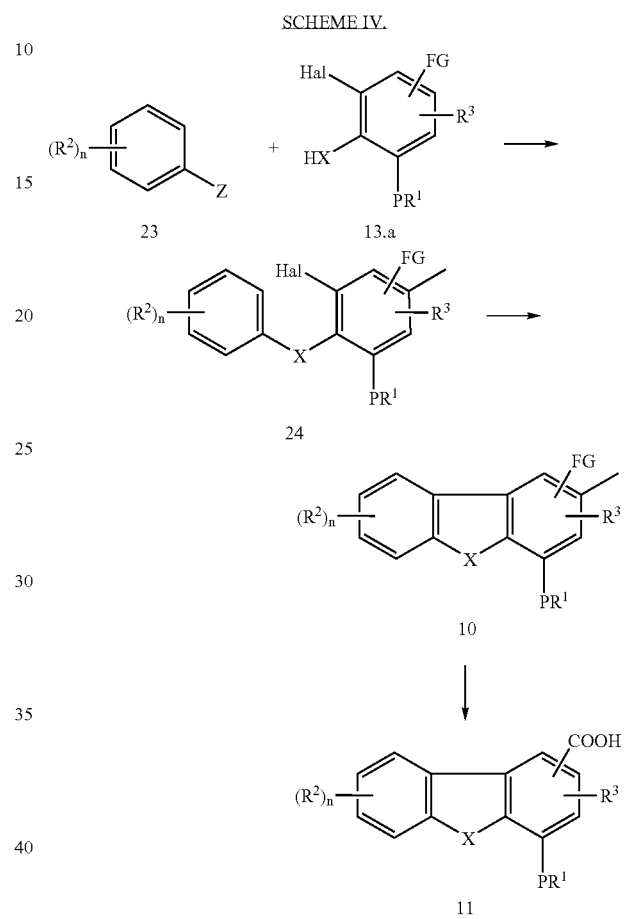

In the above scheme IV wherein P, X, $R^1$, $R^2$ and $R^3$ have the meanings described above and wherein Z is a halogen, FG is alkyl, formyl, cyano, halogen, nitro, amino, carboxylic acid group and the like, Hal is Br or I, intermediate (24) can synthesized by reacting the substituted aryl group of the formula A with appropriately substituted aryl group of the formula (13.a) under standard basic conditions (potassium salts in DMF or DMSO, NaH in DMF or DMSO and the like). Intermediate (24) can be cyclized under standard palladium catalyzed coupling conditions (palladium acetate in DMF or glacial acetic acid, nickel catalyst in pyridine or DMF, tetrakistriphenylphosphinepalladium in DMF and the like) to the dibenzofuran intermediate of the formula (10). If the functional group FG in (13.a) is other than the carboxylic acid, then it can be converted to the carboxylic acid at any stage of the synthetic process as permitted by the chemistry of the synthetic process. If in the intermediate of formula (10) FG is alkyl, formyl, cyano, halogen, nitro, amino, then intermediate (10) can be transformed to the intermediate of formula (11) by conventional methods described in the literature. (for example if FG is methyl then the methyl group can be oxidized using manganese or chromium reagents of to the carboxylic acid group; if FG is cyano group then the cyano group could be hydrolysed to the carboxylic acid; if FG is bromine then it could be transformed to carboxylic acid via lithiation followed by treatment with carbon dioxide).

Alternatively, the common intermediate of formula (10) and/or of formula(11) can be synthesized by the process described in scheme V.

and the like, the substituents $R^2$ and/or $R^3$ can also be introduced by standard electrophilic substitution reactions on the tricyclic intermediate of formula (25) which may be synthesized using any of the above described methods in scheme I, II, III or IV to obtain the desired common intermediates of formula (10) and/or of formula (11).

Alternatively, the common intermediate of formula (11) can be synthesized by the process described in scheme VI.

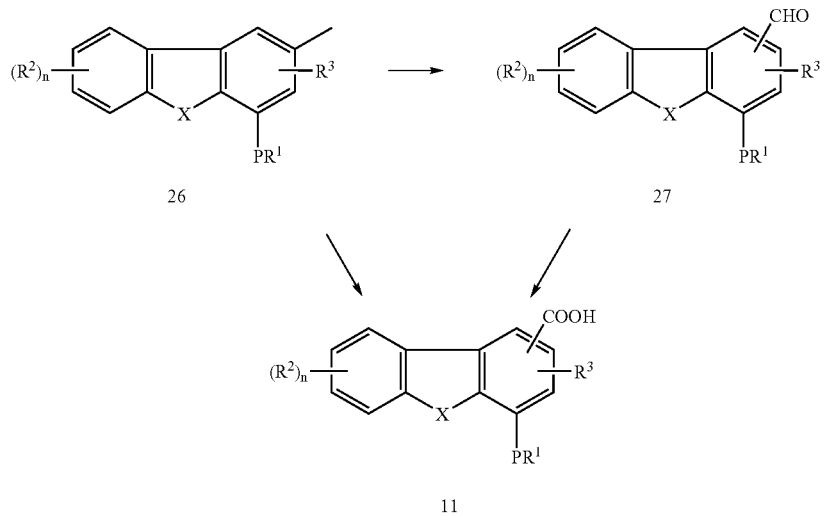

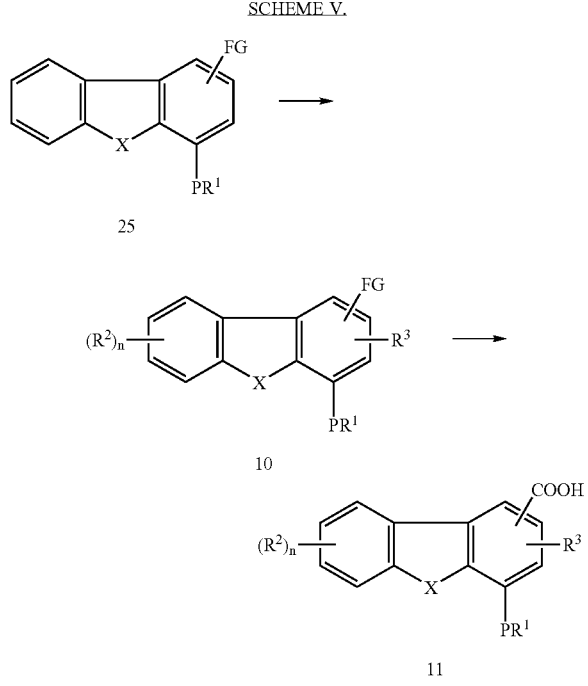

In the above scheme VI wherein P, X, $R^1$, $R^2$ and $R^3$ have the meanings described above the common intermediate (11) can be synthesized by formylation of intermediate (26) using standard formylation methods (dichloromethyl methylether in presence of tin chloride or titanium chloride, $POCl_3$ in DMF, hexamethylenetetramine in TFA and the like) followed by oxidation (manganese or chromium reagents, sodium chlorite, potassium permanganate and the like) of the aldehyde group of formula (27) to the carboxylic acid group by conventional methods known in the literature. The common intermediate (11) can also be synthesized directly from the compound of formula (26) by standard carboxylation methods (for example through sequential bromination, lithiation followed by treatment with carbon dioxide).

In another embodiment the compounds of formula (1) where Y is —$SO_2NR^4$, can be synthesized using the process described in scheme VII.

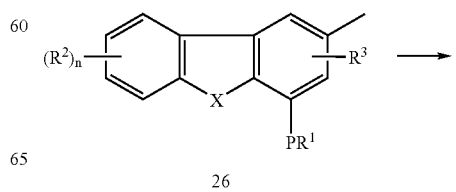

In the above scheme V, wherein P, X, $R^1$, $R^2$ and $R^3$ have the meanings described above and wherein FG is alkyl, formyl, cyano, halogen, nitro, amino, carboxylic acid group -continued

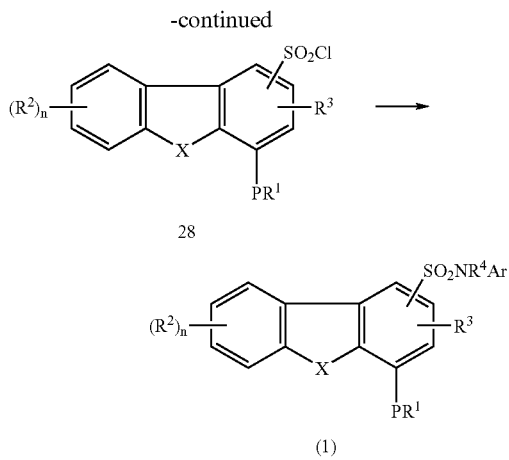

28

(1)

In the above scheme VII wherein P, X, $R^1$, $R^2$ and $R^3$ have the meanings described above the desired compounds of formula 1 can prepared by chlorosulfonylation using chlorosulfonic acid of the compound of formula (26) to obtain an intermediate of the formula (28) followed by sulfonamide formation by reacting intermediate (28) with the amine of the formula ArNHR$^4$ using conventional methods such as using pyridine or diisopropylethylamine or triethylamine in THF or dichloromethane and the like. The desired compounds of formula (1) obtained are then converted into their salts and/or the N-oxides and, if desired, salts of the compounds of formula (1) obtained are then converted into the free compounds.

In yet another embodiment the compounds of formula (1) where Y is NR$^4$SO$_2$ can be synthesized using the process described in scheme VIII.

SCHEME VIII.

-continued

31

(1)

In the above scheme VIII wherein P, X, $R^1$, $R^2$, $R^3$ and $R^4$ have the meanings described above the desired compounds of formula 1 can prepared by nitration of the compound of formula (26) to obtain an intermediate of the formula (29) followed by reduction (raney nickel/hydrazine, iron/ammonium chloride, hydrogenation using Pd/C, and the like) of the nitro to amino group to obtain intermediate (30) using conventional methods. The intermediate (30) can be reacted with appropriate sulfonyl chloride ArSO$_2$Cl to obtain the sulfonamide (31) which can alkylated to the desired compounds of formula 1 using conventional methods like (sodium hydride or potassium carbonate in THF or DMF and the like ). The sulfonamide (31) is also one of the desired compounds wherein $R^4$ is hydrogen.

The desired compounds of formula 1 obtained are then converted into their salts and/or the N-oxides and, if desired, salts of the compounds of formula 1 obtained are then converted into the free compounds.

In yet another embodiment the compounds of formula 1 where Y is —NR$^4$CO, can be synthesized using the process described in scheme IX.

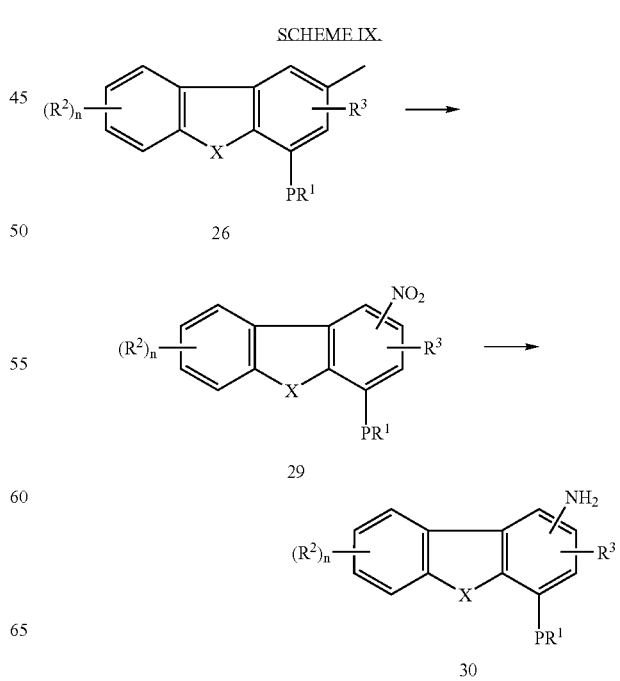

SCHEME IX.

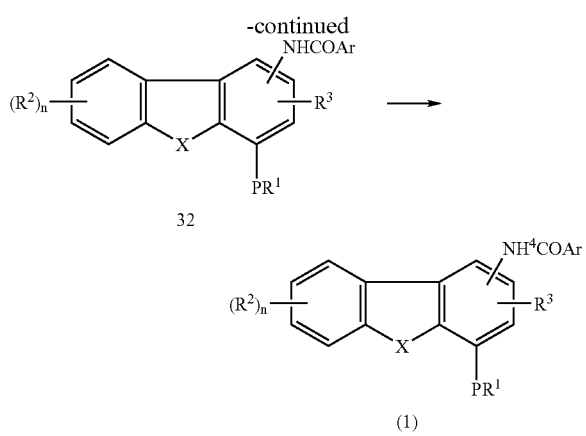

In the above scheme IX wherein P, X, R¹, R², R³ and R⁴ have the meanings described above the desired compounds of formula 1 can prepared by nitration using nitric acid in sulfuric acid, potassium nitrate in sulfuric acid and the like, of the compound of formula (26) to obtain an intermediate of formula (29)followed by reduction (raney nickel/hydrazine, iron/ammonium chloride, hydrogenation using Pd/C, and the like) of the nitro to amino group to obtain intermediate (30) using conventional methods. The intermediate (30) can be reacted with an appropriate acid chloride of the formula ArCOCl or appropriate mixed anhydride of the formula ArCOOCOR⁵ (R⁵ is alkyl, cycloalkyl, aryl, heteroaryl, heterocyclyl) to obtain the amide (32) which can alkylated to the desired compounds of formula (1) using conventional methods. The amide (32) is also one of the desired compounds wherein R⁴ is hydrogen.

The desired compounds of formula (1) obtained are then converted into their salts and/or the N-oxides and, if desired, salts of the compounds of formula (1) obtained are then converted into the free compounds.

The N-oxidation is carried out in a manner likewise familiar to the person of ordinary skill in the art, e.g with the aid of m-chloroperoxybenzoic acid in dichloromethane at room temperature. The person of ordinary skill in the art is familiar with the reaction conditions which are necessary for carrying out the process on the basis of his knowledge.

The substances according to the invention are isolated and purified in a manner known per se, e.g. by distilling off the solvent in vacuum and recrystallizing the residue obtained from a suitable solvent or subjecting it to one of the customary purification methods, such as column chromatography on a suitable support material.

Salts are obtained by dissolving the free compound in a suitable solvent, e.g in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn can be converted into salts.

In general, the ethereal solvents used in the above described processes for the preparation of compounds of the formula (1) are selected from diethyl ether, 1,2-dimethoxyethane, tetrahydrofuran, diisopropyl ether, 1,4 dioxane and the like. The chlorinated solvent which may be employed may be selected from dichloromethane, 1,2-dichloroethane, chloroform, carbontetrachloride and the like. The aromatic solvents which may be employed may be selected from benzene and toluene. The alchoholic solvents which may be employed may be selected from methanol, ethanol, n-propanol, iso propanol, tert-butanol and the like. The aprotic solvents which may be employed may be selected from N,N-dimethylformamide, dimethyl sulfoxide and the like.

In general, the compounds prepared in the above described processes are obtained in pure form by using well known techniques such as crystallization using solvents such as pentane, diethyl ether, isopropyl ether, chloroform, dichloromethane, ethyl acetate, acetone, methanol, ethanol, isopropanol, water or their combinations, or column chromatography using alumina or silica gel and eluting the column with solvents such as hexane, petroleum ether (pet.ether), chloroform, ethyl acetate, acetone, methanol or their combinations.

Various polymorphs of a compound of general formula (1) forming part of this invention may be prepared by crystallization of compound of formula (1) under different conditions, example, using different solvents commonly used or their mixtures for recrystallization; crystallizations at different temperatures, various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides novel heterocyclic compounds, their analogs, their tautomers, their regioisomers, their stereoisomers, their enantiomers, their diastreomers, their polymorphs, their pharmaceutically acceptable salts, their appropriate N-oxides and their pharmaceutically acceptable solvates.

The present invention also provides pharmaceutical compositions, containing compounds of general formula (1) as defined above, their derivatives, their analogs, their tautomeric forms, their stereoisomers, their polymorphs, their enantiomers, their diasteromers, their pharmaceutically acceptable salts or their pharmaceutically acceptable solvates in combination with the usual pharmaceutically employed carriers, diluents and the like. The pharmaceutical compositions according to this invention can be used for the treatment of allergic disorders.

It will be appreciated that some of the compounds of general formula (I) defined above according to the invention can contain one or more asymmetrically substituted carbon atoms. The presence of one or more of these asymmetric centers in the compounds of general formula (1) can give rise to stereoisomers and in each case the invention is to be understood to extend to all such stereoisomers, including enantiomers and diastereomers and their mixtures, including racemic mixtures. The invention may also contain E & Z geometrical isomers wherever possible in the compounds of general formula (1) which includes the single isomer or mixture of both the isomers The pharmaceutical compositions may be in the forms normally employed, such as tablets, capsules, powders, syrups, solutions, suspensions and the like and may contain flavorants, sweeteners etc. in suitable solid or liquid carriers or diluents, or in suitable sterile media to form injectable solutions or suspensions. The active compounds of formula (1) will be present in such pharmaceutical compositions in the amounts sufficient to provide the desired dosage in the range as described above. Thus, for oral administration, the compounds of formula (1) can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds of the formula (1) can be combined with sterile aqueous or organic media to form injectable solutions or suspensions. For example, solutions in sesame or peanut oil, aqueous propylene glycol and the like can be used as well as aqueous solutions of water-soluble pharmaceutically-acceptable acid addition salts or salts with base of the compounds of formula (1) The injectable solutions prepared in this manner can then be administered intravenously, intraperitoneally, subcutaneously, or intramuscularly, with intramuscular administration being preferred in humans.

The compounds can also be administered by inhalation when application within the respiratory tract is intended. Formulation of the present compounds is especially significant for respiratory inhalation, wherein the compound of Formula (1) is to be delivered in the form of an aerosol under pressure. It is preferred to micronize the compound of Formula (1) after it has been homogenised, e.g., in lactose, glucose, higher fatty acids, sodium salt of dioctylsulfosuccinic acid or, most preferably, in carboxymethyl cellulose, in order to achieve a microparticle size of 5 μm or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., Thorax, 1985, 40__61-676; Berenberg, M., J. Asthma USA, 1985, 22:87-92; incorporated herein by reference in their entirety. A Bird nebulizer can also be used. See also U.S. Pat. Nos. 6,402,733; 6,273,086; and 6,228,346, incorporated herein by reference in their entirety. The compound of the structure (1) for inhalation is preferably formulated in the form of a dry powder with micronized particles. The compounds of the invention may also be used in a metered dose inhaler using methods disclosed in U.S. Pat. No. 6,131,566, incorporated herein by reference in its entirety.

In addition to the compounds of formula (1) the pharmaceutical compositions of the present invention may also contain or be co-administered with one or more known drugs selected from other clinically useful therapeutic agents.

The invention is explained in detail in the examples given below which are provided by way of illustration only and therefore should not be construed to limit the scope of the invention.

The following intermediates are used to synthesize the rerpresentative examples of the compounds of the invention.

Intermediate 1: 3-(2-nitrophenoxy)-4-methoxy benzaldehyde

To a stirred suspension of potassium fluoride (5.71 gm, 0.0985 mol) in dry DMSO (20 ml) was added a solution of isovanillin (10.0 gm, 0.0657 mol) in DMSO (20 ml). The reaction contents were heated at 140° C. for 10 min. A solution of 2-fluoronitrobenzene (9.27 gm, 0.0657 mol) in DMSO (10 ml) was added to the above suspension and the reaction mixture was stirred at 140° C. for 3.5 h. The reaction mixture was cooled to room temperature and the contents were poured into water (200 ml) and extracted with ethyl acetate (100 ml×3). The organic extracts were combined and washed with 1N sodium hydroxide (50 ml×2), water and brine and dried over anhydrous sodium sulfate. The dried organic layer was concentrated in vacuo to obtain the product as a pale yellow solid (13.6 gm). IR (KBr) 2940, 2842, 2748, 1690, 1602, 1578, 1523, 1509, 1432, 1345, 1285, 1117, 1017, 815, 737 cm$^{-1}$.

$^1$H NMR (300 MHz, CDCl$_3$) δ 3.91 (s, 3H), 6.9 (d, 1H, J=9.0 Hz), 7.11 (d, 1H, J=9.0 Hz), 7.2 (t, 1H, J=7.8 Hz), 7.48 (t, 1H, J=7.8 Hz), 7.51 (s, 1H), 7.71 (dd, 1H, J=7.8 Hz, 1.8 Hz), 7.95 (d, 1H, J=7.8 Hz,), 9.82 (s, 1H).

Intermediate 2: 3-(2-nitrophenoxy)-4-methoxy-phenyl carboxylic acid

To a solution of intermediate 1 (10 gm, 0.036 mol) in acetone-water mixture in 4:1 ratio (75 ml) was added sulfamic acid (5.32 gm, 0.054 mol) while stirring at 0° C. A solution of 80% sodium chlorite (3.4 gm, 0.045 mol) in water (15.0 ml) was added dropwise to the above reaction mixture over a period of 10 min. and was allowed to stir at 0° C. for additional 30 min. The precipitate obtained was filtered, washed with water and air dried to give 12 gm of the product as white solid.

$^1$H NMR (300 MHz, CDCl$_3$) δ 3.8 (s, 3H), 6.9 (d, 1H, J=9.0 Hz), 7.28 (t, 1H, J=9.0 Hz), 7.30 (d, 1H, J=9.0 Hz), 7.56 (s, 1H), 7.6 (t, 1H, J=7.2 Hz), 7.85 (d, 1H, J=8.4 Hz,), 8.02 (d, 1H, J=8.4 Hz).

Intermediate 3: 3-(2-amiophenoxy)-4-methoxyphenyl carboxylic acid

To a suspension of intermediate 2 (10 gm) in dichloromethane (500 ml) was added 5% Pd/C (10% w/w) and the mixture hydrogenated at 40 psi for 3 h (hours) under hydrogen atmosphere. The catalyst was filtered over celite. The celite bed was washed with methanol. The combined filtrate was concentrated in vacuo to yield the desired product as pale yellow solid (8.5 gm).

IR KBr) 3450, 3368, 2925, 1683, 1601, 1578, 1501, 1438, 1307, 1276, 1217, 1017, 788, 761 cm$^{-1}$.

$^1$H NMR (300 MHz, CDCl$_3$) δ 3.93 (s, 3H), 6.63-6.68 (brm, 1H), 6.75 (m, 3H), 6.91-7.0 (brm, 3H), 7.53 (s, 1H), 7.80 (d, 1H, J=8.4 Hz).

Intermediate 4: 4methoxy dibenzo[b,d]furan-1-carboxylic acid

A suspension of intermediate 3 (2 gm, 0.0077 mol) in a mixture of concentrated hydrochloric acid:water (1:1) (20 ml) is warmed to 45° C. for 10 min. and cooled to −5° C. A solution of sodium nitrite (630 mg, 0.0092 mol) in water (5 ml) is added dropwise to the above suspension at −5° C. The reaction mixture was stirred for 30 min and a chilled solution of sodium fluoroborate (1.26 gm, 0.0115 mol) was added to the above reaction mixture and stirred at −5° C. for 30 min. The diazonium fluoroborate salt obtained (2.3 gm) as a result was filtered and washed with 5% cold sodium fluoroborate solution and air dried. The dried diazonium fluoroborate salt was added to a stirred suspension of cuprous oxide (1.76 gm, 0.0077 mol) in 0.1N sulfuric acid (600 ml) at 35° C. and stirred for 10 min. The resulting precipitate (2.0 gm) was filtered, washed with water, air dried and chromatographed on silica gel column using 20% ethyl acetate in chloroform to give the desired product as a white solid (200 mg); mp: 280° C.

IR (KBr) 2925, 2853, 1688, 1607, 1512, 1490, 1437, 1277, 1221, 1023, cm$^{-1}$.

¹H NMR (300 MHz, DMSO) δ 4.05 (s, 3H), 7.26 (d, 1H, J=8.7 Hz), 7.40 (t, 1H, J=7.2 Hz), 7.50 (t, 1H, J=7.2 Hz), 7.74 (d, 1H, J=8.1 Hz), 8.01 (d, 1H, J=8.4 Hz), (8.85 (d, 1H, J=7.8 Hz).

Intermediate 5: 3-(2-nitro-4-trifluoromethyl phenoxy)-4-methoxy benzaldehyde To a stirred suspension of potassium fluoride (457 mg, 7.8 mmol) in dry DMSO (20 ml) was added a solution of isovanillin (1.0 gm, 6.57 mmol) in dry DMSO (20 ml). The reaction contents were heated at 140° C. for 10 min. A solution of 4-fluoro-3-nitrobenzotrifluoride (1.37 gm, 6.57 mmol) in dry DMSO (10 ml) was added to the above suspension and the reaction mixture was stirred at 140° C. for 4.0 h. The reaction mixture was cooled to room temperature and the contents were poured into water (200 ml) and extracted with ethyl acetate (100 ml×3). The organic extracts were combined and washed with 1N sodium hydroxide (50 ml×2), water and brine and dried over anhydrous sodium sulfate. The organic layer was concentrated in vacuo to obtain 3-(2-nitro-4-trifluoromethyl phenoxy)-4-methoxy benzaldehyde as a pale yellow solid (2.0 gm).

IR (KBr) 3098, 3031, 2953, 2745, 2649, 1694, 1629, 1606, 1540, 1509, 1439, 1333, 1275, 1158, 1118, 1095, 1015, 912, 820 cm$^{-1}$.

¹H NMR (300 MHz, CDCl$_3$) δ 3.86 (s, 3H), 7.05 (d, 1H, J=8.7 Hz), 7.44 (d, 1H, J=8.7 Hz), 7.77 (s, 1H), 7.92 (d, 2H, J=8.4 Hz), 8.45 (s, 1H), 9.87 (s, 1H).

Intermediate 6: 3-(2-nitro-4-trifluoromethyl phenoxy)-4-methoxy-phenyl carboxylic acid To a solution of intermediate 5 (10 gm, 0.036 mol) in acetone-water mixture in 4:1 ratio (75 ml) was added sulfamic acid (5.32 gm, 0.054 mol) while stirring at 0° C. A solution of 80% sodium chlorite (3.4 gm, 0.045 mol) in water (15.0 ml) was added dropwise to the above reaction mixture over a period of 10 min. and was allowed to stir at 0° C. for additional 30 min. The precipitate obtained was filtered, washed with water and air dried to give 12 gm of the product as white solid. IR (KBr) 3445, 2944, 2568, 1694, 1629, 1609, 1542, 1517, 1442, 1334, 1289, 1133, 1016, 766 cm$^{-1}$.

¹H NMR (300 MHz, CDCl$_3$) δ 3.87 (s, 3H), 6.88 (d, 1H, J=8.7 Hz), 7.10 (d, 1H, J =8.7 Hz), 7.65 (dd, 1H, J=8.7 Hz, 1.8 Hz), 7.88 (d, 1H, J=1.8 Hz ), 8.04 (dd, 1H, J=8.4, 1.8 Hz), 8.25 (d, 1H, J=1.8 Hz).

Intermediate 7: 3-(2-amino-4-trifluoromethyl phenoxy)-4-methoxy-phenyl carboxylic acid To a suspension of intermediate 6 (10 gm ) in dichloromethane (500 ml) was added 5% Pd/C (10% w/w) and hydrogenated at 40 psi for 3 h under hydrogen atmosphere. The catalyst was filtered over celite. The celite bed was washed with methanol. The combined filtrate was concentrated in vacuo to yield the desired product.

IR (KBr) 3452, 3367, 3063, 3006, 2937, 2842, 2545, 1692, 1625, 1611, 1514, 1444, 1334, 1278, 1211, 1116, 1023, cm$^{-1}$.

¹H NMR (300 MHz, DMSO) δ 3.85 (s, 3H), 5.5 (s, 2H), 6.6 (d, 1H), 6.8 (d, 1H), 7.1 (s, 1H), 7.3 (d, 1H), 7.4 (d, 1H), 7.8 (s, 1H).

Intermediate 8: 4-methoxy-8-trifluoromethyl dibenzo[b,d]furan-1-carboxylic acid A suspension of intermediate 7 (2 gm, 0.0077 mol) in a mixture of concentrated hydrochloric acid:water (1: 1) (20 ml) is warmed to 45° C. for 10 min. and cooled to −5° C. A solution of sodium nitrite (630 mg, 0.0092 mol) in water (5 ml) is added dropwise to the above suspension at −5° C. The reaction mixture was stirred for 30 min and a chilled solution of sodium fluoroborate (1.26 gm, 0.0115 mol) was added to the above reaction mixture and stirred at −5° C. for 30 min. The diazonium fluoroborate salt obtained (2.3 gm) as a result was filtered and washed with 5% cold sodium fluoroborate solution and air dried. The dried diazonium fluoroborate salt was added to a stirred suspension of cuprous oxide (1.76 gm, 0.0077 mol) in 0.1N sulfuric acid (600 ml) at 35° C. and stirred for 10 min The resulting precipitate (2.0 gm) was filtered, washed with water, air dried and chromatographed on silica gel column using 20% ethyl acetate in chloroform to give the desired product as a white solid was synthesized using the procedure described in step 4 of example 1 from 3-(2-amino-4-trifluoromethyl phenoxy)-4-methoxy-phenyl carboxylic acid.

IR (KBr) 3132, 3024, 2975, 2941, 2916, 2844, 2648, 2546, 1693, 1592, 1575, 1421, 1328,1278,1154,1105,912, 824 cm$^{-1}$.

¹H NMR (300 MHz, DMSO) δ 4.1 (s, 3H), 7.4 (d, 1H, J=8.4 Hz), 7.9 (d, 1H, J=8.7 Hz), 8.0 (d, 1H, J=8.7 Hz), 8.08 (d, 1H, J=8.7 Hz), 9.29 (s, 1H).

Intermediate 9: 3-(2-nitro-4-trifluoromethylphenoxy)-4-difluoromethoxy benzaldehyde A solution of 4-difluoromethoxy-3-hydroxybenzaldehyde (2.0 gm, 10.63 mmol) in DMSO (5 ml) was added to a stirred suspension of potassium fluoride (0.740 gm, 12.76 mmol) in dry DMSO (10 ml). A solution of 4-fluoro-3-nitrobenzotrifluoride (3.22 gm, 10.63 mmol) in DMSO (5 ml) was added to the above suspension and the reaction mixture was stirred at 160° C. for 18 h. The reaction mixture was cooled to room temperature and the contents were poured into water (100 ml) and extracted with ethyl acetate (25 ml×3). The organic extracts were combined and washed with 1N sodium hydroxide (25 ml×2), water and brine and dried over anhydrous sodium sulfate. The dried organic layer was concentrated in vacuo to obtain the product as a pale yellow solid (2.2 gm).

IR (KBr) 3092, 2878, 1697, 1629, 1537, 1352, 1331, 1280, 1158, 1134, 1075, 827 cm$^{-1}$.

¹H NMR (300 MHz, DMSO) δ 7.23 (d, 1H, J=8.7 Hz), 7.35 (t, 1H, J=72.6 Hz), 7.63 (d, 1H, J=8.1 Hz), 7.86 (d, 1H, J=2.1 Hz), 7.93 (dd, 1H, J=8.4 Hz, 1.8 Hz), 7.99 (dd, 1H, J=8.7 Hz, 2.4 Hz ), 8.48 (d, 1H, J=2.4 Hz), 9.94 (s, 1H).

Intermediate 10: 3-(2-nitro-4-trifluoromethyl phenoxy)-4-difluoromethoxy-phenyl carboxylic acid To a solution of intermediate 9 (10 gm, 0.036 mol) in acetone-water mixture in 4: 1 ratio (75 ml) was added sulfamic acid (5.32 gm, 0.054 mol) while stirring at 0° C. A solution of 80% sodium chlorite (3.4 gm, 0.045 mol) in water (15.0 ml) was added dropwise to the above reaction mixture over a period of 10 min. and was allowed to stir at 0° C. for additional 30 min. The precipitate obtained was filtered, washed with water and air dried to give 12 gm of the product as white solid.

IR (KBr) 3436, 3095, 2997, 2889, 2665, 2566, 1695, 1633, 1545, 1447, 1379, 1355, 1284, 1270, 1155, 1120, 1099, 1063, 917, 765 cm$^{-1}$.

$^1$H NMR (300 MHz, DMSO) δ 6.60 (t, 1H, J=72.6 Hz), 6.96 (d, 1H, J=8.7 Hz), 7.44 (d, 1H, J=8.7 Hz), 7.55 (dd, 1H, J=9.0 Hz, 1.8 Hz), 7.86 (d, 1H, J=2.1 Hz), 8.04 (dd, 1H, J=8.4 Hz, 2.4 Hz), 8.27 (d, 1H, J=1.8 Hz),.

Intermediate 11: 3-(2-amino-4-trifluoromethylphenoxy)-4-difluoromethoxy-phenyl carboxylic acid To a suspension of intermediate 10 (10 gm ) in dichloromethane (500 ml) was added 5% Pd/C (10% w/w) and hydrogenated at 40 psi for 3 h under hydrogen atmosphere. The catalyst was filtered over celite. The celite bed was washed with methanol. The combined filtrate was concentrated in vacuo to yield the desired product as pale yellow solid (8.5 gm).

IR (KBr) 3377, 2926, 1702, 1627, 1582, 1515, 1447, 1419, 1335, 1276, 1198, 1116, 1064, 813, 786 cm$^{-1}$.

Intermediate 12: 4-difluoromethoxy-8-trifluoromethyl dibenzo[b,d]furan-1-carboxylic acid A suspension of intermediate 11 (2 gm, 0.0077 mol) in a mixture of concentrated hydrochloric acid:water (1: 1) (20 ml) is warmed to 45° C. for 10 min. and cooled to −5° C. A solution of sodium nitrite (630 mg, 0.0092 mol) in water (5 ml) is added dropwise to the above suspension at −5° C. The reaction mixture was stirred for 30 min and a chilled solution of sodium fluoroborate (1.26 gm, 0.0115 mol) was added to the above reaction mixture and stirred at −5° C. for 30 min. The diazonium fluoroborate salt obtained (2.3 gm) as a result was filtered and washed with 5% cold sodium fluoroborate solution and air dried. The dried diazonium fluoroborate salt was added to a stirred suspension of cuprous oxide (1.76 gm, 0.0077 mol) in 0.1N sulfuric acid (600 ml) at 35° C. and stirred for 10 min. The resulting precipitate (2.0 gm) was filtered, washed with water, air dried and chromatographed on silica gel column using 20% ethyl acetate in chloroform to give the desired product as a white solid (200 mg); mp: 280° C.

IR (KBr) 3020, 2928, 2855, 1698, 1513, 1422, 1326, 1273, 1215, 1066, 757, 669 cm$^{-1}$.

$^1$H NMR (300 MHz, DMSO) δ 6.57 (t, 1H, J=72.6 Hz) 7.03 (d, 1H, J=8.4 Hz), 7.58 (d, 1H, J=8.7 Hz), 7.93 (dd, 1H, J=8.4 Hz, 2.1 Hz), 8.18 (d, 1H, J=8.4 Hz), 9.25 (s, 1H).

Intermediate 13: 3-(2-nitrophenoxy)-4-difluoromethoxy benzaldehyde

To a stirred suspension of potassium fluoride (372 mg, 6.4 mmol) in dry DMSO (10 ml) was added a solution of 3-hydroxy-4-difluoromethoxy benzaldehyde (1.0 gm, 5.3 mmol) in DMSO (10 ml). The reaction contents were heated at 140° C. for 10 min. A solution of 2-fluoronitrobenzene (747 mg, 5.3 mmol) in DMSO (5 ml) was added to the above suspension and the reaction mixture was stirred at 140° C. for 3.5 h. The reaction mixture was cooled to room temperature and the contents were poured into water (200 ml) and extracted with ethyl acetate (100 ml×3). The organic extracts were combined and washed with 1N sodium hydroxide (50 ml×2), water and brine and dried over anhydrous sodium sulfite. The dried organic layer was concentrated in vaccuo to obtain 3-2-nitrophenoxy)-4-difluoromethoxy benzaldehyde as a pale yellow solid (1.4 gm).

IR (KBr) 2916, 1692, 1616, 1530, 1446, 1350, 1283, 1112, 1063, 845, 737 cm$^{-1}$.

Intermediate 14: 3-(2-nitrophenoxy)-4-difluoromethoxy-phenyl carboxylic acid

To a solution of intermediate 13 (10 gm, 0.036 mol) in acetone-water mixture in 4: 1 ratio (75 ml) was added sulfamic acid (5.32 gm, 0.054 mol) while stirring at 0° C. A solution of 80% sodium chlorite (3.4 gm, 0.045 mol) in water (15.0 ml) was added dropwise to the above reaction mixture over a period of 10 min and was allowed to stir at 0° C. for additional 30 min. The precipitate obtained was filtered, washed with water and air dried to give 12 gm of the product as white solid.

$^1$H NMR (300 MHz, CDCl$_3$) δ 6.64 (t, 1H, J=72 Hz), 6.98 (d, 1H, J=8.4 Hz), 7.28 (t, 1H, J=7.2 Hz), 7.39 (d, 1H, J=9.0 Hz), 7.55 (t, 1H, J=7.2 Hz), 7.65 (d, 1H, J=1.8 Hz), 7.90 (d, 1H, J=9.0 Hz, ), 8.01 (d, 1H, J=8.1 Hz, ).

Intermediate 15: 3-(2-aminophenoxy)-4-difluoromethoxy-phenyl carboxylic acid

To a suspension of intermediate 14 (10 gm ) in dichloromethane (500 ml) was added 5% Pd/C (10% w/w) and hydrogenated at 40 psi for 3 h under hydrogen atmosphere. The catalyst was filtered over celite. The celite bed was washed with methanol. The combined filtrate was concentrated in vacuo to yield the desired product IR (KBr) 3367, 2925, 1624, 1579, 1501, 1481, 1384, 1272, 1196, 1170, 1052, 785 cm$^{-1}$.

Intermediate 16: 4-difluoromethoxy dibenzo[b,d]furan-1-carboxylic acid

A suspension of intermediate 15 (2 gm, 0.0077 mol) in a mixture of concentrated hydrochloric acid:water (1: 1) (20 ml) is warmed to 45° C. for 10 min. and cooled to −5° C. A solution of sodium nitrite (630 mg, 0.0092 mol) in water (5 ml) is added dropwise to the above suspension at −5° C. The reaction mixture was stirred for 30 min and a chilled solution of sodium fluoroborate (1.26 gm, 0.0115 mol) was added to the above reaction mixture and stirred at −5° C. for 30 min. The diazonium fluoroborate salt obtained (2.3 gm) as a result was filtered and washed with 5% cold sodium fluoroborate solution and air dried. The dried diazonium fluoroborate salt was added to a stirred suspension of cuprous oxide (1.76 gm, 0.0077 mol) in 0.1N sulfuric acid (600 ml) at 35° C. and stirred for 10 min. The resulting precipitate (2.0 gm) was filtered, washed with water, air dried and chromatographed on silica gel column using 20% ethyl acetate in chloroform to give the desired product.

$^1$H NMR (300 MHz, DMSO) δ 7.56 (t, 1H, J=72 Hz), 7.48 (m, 2H), 7.64 (t, 1H, J=8.1 Hz), 8.30 (d, 1H, J=8.7 Hz), 8.02 (d, 1H, J=8.1 Hz), 8.80 (d, 1H, J=7.8 Hz).

Intermediate 17: 4-Cyclopentyloxydibenzo[b,d]furan

Reaction of dibenzo[b,d]furan-4-ol (1 g, 5.43 mmol) with cyclopentyl bromide (1.60 g, 10.86 mmol) in the presence of 60% sodium hydride (326 mg, 8.12 mmol), gave 1.25 g (92%) of the product as viscous liquid, IR (neat) 2957, 2870, 1449, 1269, 1193 cm$^{-1}$. $^1$H NMR (300 MHz, CDCl$_3$) δ 1.57-1.72 (m, 2H), 1.84-1.89 (m, 2H), 1.93-2.04 (m, 4H), 5.01 (quint., 1H), 6.97 (d, J=8.1 Hz, 1H), 7.22 (t, J=7.9 Hz, 1H), 7.30 (t, J=8.1 Hz, 1H), 7.45 (t, J=8.1 Hz, 1H), 7.51 (d, J=7.8 Hz, 1H), 7.60 (d, J=8.2 Hz, 1H), 7.89 (d, J=8.1 Hz, 1H).

Intermediate 18: 4-Cyclopentyloxydibenzo[b,d]furan-1-carbaldehyde

Reaction of 4-cyclopentyloxydibenzo[b,d]furan (1.0 g, 3.96 mmol) with dichloromethylmethylether (456 mg, 3.96 mmol) in presence of tin(IV)chloride (1.55 g, 5.95 mmol), gave 350 mg (31.5%) of the product as white solid, IR (KBr)) 2960, 2730, 1686, 1565, 1276, 1099 cm$^{-1}$. $^1$H NMR (300 MHz, CDCl$_3$) δ 1.64-1.75 (m, 2H), 1.85-1.98 (m, 2H), 2.03-2.09 (m, 4H), 5.11 (quint, 1H), 7.07 (d, J=8.2 Hz, 1H), 7.38 (t, J=7.9H, 1H), 7.52 (t, J=7.8 Hz, 1H), 7.63 (d, J=8.4 Hz, 1H), 7.77 (d, J=8.2 Hz, 1H), 8.95 (d, J=8.4 Hz, 1H), 10.17 (s, 1H).

Intermediate 19: 4-hydroxy dibenzo[b,d]furan-1-carbaldehyde

Intermediate 18 was heated in HBr (30-33%) in glacial acetic acid (25 ml) at 50° C. for 7-8 h The reaction contents were poured in ice-water and extracted with ethyl acetate. The organic layer was washed with saturated sodium bicarbonate, and extracted with 10% sodium hydroxide (3×25 ml) solution. The aqueous layer was acidified with conc. HCl to give a white precipitate which was filtered and air dried to obtain the crude product as a white solid (3.2 gm).

Intermediate 20: 4-cyclopropylmethoxy dibenzo[b,d]furan-carbaldehyde

Intermediate 19 (500 mg, 2.358 mmol) was dissolved in dry DMF (5 ml). Anhydrous potassium carbonate (650 mg, 4.716 mmol) was added to the above solution and was stirred for 10 min. at 80° C. To this was added cyclopropylmethyl bromide (500 mg, 3.537 mmol) and the reaction mixture was stirred for 1 h. The reaction mixture was cooled to room temperature and diluted with water (100 ml) and extracted with ethyl acetate (3×50 ml). The organic extract was washed with water (50 ml) and brine solution (25 ml) and dried over anhydrous sodium sulfate. Removal of solvent gave the product as a white solid (550 mg).

IR (KBr) 3110, 2890, 2865, 1642, 1567, 1478, 1444, 1358, 1278, 1267, 1206, 1038, 842, 657 cm$^{-1}$.

$^1$H NMR (300 MHz, DMSO) δ 0.452 (m, 2H), 0.66 (m, 2H), 1.38 (m, 1H), δ 4.18 (d, 2H, J=7.2 Hz), δ 7.35 (d, 1H, J=8.4 Hz), δ 7.44 (t, 1H, J=7.2 Hz), δ 7.62 (t, 1H, J=8.1 Hz), δ 7.83 (d, 1H, J=8.4 Hz), δ 8.1 (d, 1H, J=8.4 Hz), δ 8.8. (d, 1H, J=7.2 Hz), δ 10.15 (s, 1H).

Intermediate 21: 4-cyclopropylmethoxy dibenzo[b,d]furan-1-carboxylic acid

To a solution of intermediate 20 (500 mg, 1.879 mmol) in acetone-water mixture in 2: 1 ratio (20 ml) was added sulfamic acid (280 mg, 2.818 mmol) while stirring at 0° C. A solution of 80% sodium chlorite (200 mg, 2.215 mmol) in water (5 ml) was added dropwise to the above reaction mixture over a period of 10 min. and was allowed to stir at room temperature for additional 5 h. The reaction was diluted with water (200 ml) and extracted with ethyl acetate (3×100 ml). The organic extract was washed with water (100 ml) and brine solution (50 ml) and dried over anhydrous sodium sulfate. The organic solvent was evaporated to give 500 mg of the product as white solid.

IR (KBr) 3108, 2885, 2867, 1652, 1558, 1469, 1441, 1349, 1282, 1271, 1204, 1032, 845, 655 cm$^{-1}$ $^1$H NMR (300 MHz, DMSO) δ 0.452 (m, 2H), 0.66 (m, 2H), 1.38 (m, 1H), 4.13 (d, 2H, J=7.5 Hz), 7.20 (d, 1H, J=9.0 Hz), 7.44 (t, 1H, J=6.9 Hz), 7.6 (t, 1H, J=8.1 Hz), 7.8 (d, 1H, J=8.4 Hz), 7.9 (d, 1H, J=7.8 Hz), 8.86 (d, 1H, J=7.5 Hz).

Intermediate 22: 4-isopropyloxy dibenzo[b,d]furan-1-carbaldehyde

Intermediate 19 (500 mg, 2.358 mmol) was dissolved in dry DMF (5 ml). Anhydrous potassium carbonate (650 mg, 4.716 mmol) was added to the above solution and was stirred for 10 min. at 80° C. To this was added isopropyl bromide (431 mg, 3.537mmol) and the reaction mixture was stirred for 4 hrs. The reaction mixture was cooled to room temperature and diluted with water (100 ml) and extracted with ethyl acetate (3×50 ml). The organic extract was washed with water (50 ml) and brine solution (25 ml) and dried over anhydrous sodium sulfate. Removal of solvent gave the product as a white solid (600 mg).

Intermediate 23: 4-isopropyloxy dibenzo[b,d]furan-1-carboxylic acid

To a solution of intermediate 22 (600 mg, 2.35 mmol) in acetone-water mixture in 2: 1 ratio (20 ml) was added sulfamic acid (348 mg, 3.52 mmol) while stirring at 0° C. A solution of 80% sodium chlorite (232 mg, 2.58 mmol) in water (5 ml) was added dropwise to the above reaction mixture over a period of 10 min. and was allowed to stir at room temperature for additional 2 h. The reaction was diluted with water (200 ml) and extracted with ethyl acetate (3×100 ml). The organic extract was washed with water (100 ml) and brine solution (50 ml) and dried over anhydrous sodium sulfate. The organic solvent was evaporated to give the product as white solid (600 mg).

Intermediate 24: 4-benzyloxy dibenzo[b,d]furan-1-carbaldehyde

Intermediate 19 (1 gm, 5.10 mmol) was dissolved in dry DMF (10 ml). Anhydrous potassium carbonate (1.05 gm, 7.65 mmol) was added to the above solution and was stirred for 10 min. at 80° C. To this was added benzyl bromide (0.87 gm, 5.10 mmol) and the reaction mixture was stirred for 2 h. The reaction mixture was cooled to room temperature and diluted with water (100 ml) and extracted with ethyl acetate (3×50 ml). The organic extract was washed with water (50 ml) and brine solution (25 ml) and dried over anhydrous sodium sulfate. Removal of solvent gave the product as a brown solid (1.4 gm).

Intermediate 25: 4-benzyloxy dibenzo[b,d]furan-1-carboxylic acid

To a solution of intermediate 24 (1.4 gm, 4.89 mmol) in acetone-water mixture in 2: 1 ratio (22 ml) was added sulfamic acid (711 mg, 7.33 mmol) while stirring at 6° C. A solution of 80% sodium chlorite (550 mg, 6.11 mmol) in water (5 ml) was added dropwise to the above reaction mixture over a period of 10 min. and was allowed to stir at room temperature for additional 2 h. The reaction was diluted with water (200 ml) and extracted with ethyl acetate (3×100 ml). The organic extract was washed with water (100 ml) and brine solution (50 ml) and dried over anhydrous sodium sulfate. The organic solvent was evaporated to give the product as yellow solid (1.0 gm).

Intermediate 26: 2-Bromoisovanillin

Isovanillin (5 gm, 0.033 mol) was dissolved in glacial acetic acid (30 ml). Anhydrous sodium acetate (5.4 gm) was added to the above solution followed by powdered iron (0.15 gm). The system was flushed thoroughly with nitrogen. A solution of bromine (5.79 gm, 0.0362 mol) in glacial acetic acid (10 ml) was added to the above stirred suspension at 105° C. over a period of 15 min. The reaction mixture was cooled and stirred at room temperature for 45 min. The reaction mixture was poured into aqueous 2% sodium bisulfite (200 ml) and stirred for 10 min. The precipitate was filtered washed with water (100 ml), and dried to obtain 3.5 gm of 2-bromoisovanillin as white powder mp: (200-202° C.).

IR (KBr) 3233, 2990, 2891, 2844, 1669, 1593, 1564, 1494, 1463, 1286, 1238, 1205, 1019, 987, 805, 786 cm$^{-1}$.

$^1$H NMR (300 MHz, CDCl$_3$) δ 3.99 (s, 3H), 6.13 (s, 1H), 6.89 (d, 1H, J=8.4 Hz), 7.55 (d, 1H, J=8.4 Hz), 10.23 (s, 1H).

Intermediate 27: 2-Bromo-3-(p-nitrophenoxy)-4-methoxy benzaldehyde

To a stirred suspension of potassium fluoride (1.89 gm, 0.0326 mol) in dry DMSO (10 ml) was added a solution of intermediate 26 (5.0 gm, 0.0217 mol) in DMSO (10 ml). A solution of 4-fluoronitrobenzene (5.0 gm, 0.0260 mol) in DMSO (5 ml) was added to the above suspension and the reaction mixture was stirred at 140° C. for 4 h. The reaction mixture was cooled to room temperature and the contents were poured into water (150 ml) and extracted with ethyl acetate (50 ml×3). The organic extracts were combined and washed with 1N sodium hydroxide (25 ml×2), water and brine and dried over anhydrous sodium sulfate. The dried organic layer was concentrated in vacuo and the residue was purified by silica-gel column chromatography using 20% ethyl acetate-petroleum ether as the eluent to give 2-bromo-3-(p-nitrophenoxy)-4-methoxy benzaldehyde as a pale yellow solid(5.0 gm)mp: 132-140° C.

IR (KBr) 3084, 2874, 1689, 1584, 1506, 1486, 1348, 1285, 1253, 1234, 1114, 1025, 848, 815,747 cm$^{-1}$.

$^1$H NMR (300 MHz, CDCl$_3$) δ 3.86 (s, 3H), 6.89 (d, 2H, J=7.2 Hz), 7.07 (d, 1H, J=9.0 Hz), 7.92 (d, 1H, J=8.4 Hz), 8.17 (d, 2H, J=9.0 Hz), 10.24 (s, 1H).

Intermediate 28: 4-methoxy-8-nitro-1-formyl dibenzo[b,d]furan

Intermediate 26 (3.5 gm, 0.0087 mol), anhydrous sodium carbonate (1.125 gm, 0.0106 mol) and palladium (II) acetate (0.19 gm, 0.0008 mol), in dimethylacetamide (15 ml) are heated and stirred under nitrogen at 170° C. for 2 h. Water (90 ml) is added to the cooled reaction mixture. The precipitated solid is collected by filteration and washed with 5% hydrochloric acid followed by water. The product was obtained as a yellow solid (3.4 gm).

IR (KBr) 3115, 2925, 2856, 1682, 1609, 1576, 1522, 1343, 1295, 1076, 846, 829 cm$^{-1}$.

$^1$H NMR (300 MHz, DMSO) δ 4.13 (s, 3H), 7.53 (d, 1H, J=9.0 Hz), 8.01 (d, 1H, J=9.0 Hz), 8.16 (d, 1H, J=9.0 Hz), 8.48 (dd, 1H, J=9.0 Hz, 3.0 Hz), 9.79 (d, 1H, J=3.0 Hz), 10.1 (s, 1H).

Intermediate 29: 4-methoxy-8-nitro dibenzo[b,d]furan-1-carboxylic acid

Intermediate 28 (1.1 gm, 0.0034 mol) in acetone (5 ml) was heated to 60-70° C. for 10 min. To the above suspension was added dropwise a hot solution of potassium permanganate (1.07 gm, 0.0068 mol) in water:acetone (1: 3) (15 ml) for 10 min. The reaction was heated to 60-70° C. for 10 min., cooled to room temperature and filtered. The residue washed with acetone and the filterate was extracted with 10% sodium hydroxide solution. Acidification, followed by filteration and washing of the precipitate yielded 4-methoxy-8-nitro-dibenzo[b,d]furan-1-carboxylic acid (0.6 gm) as white solid, mp: 178° C. (dec.)

IR (KBr) 3467, 2942, 1711, 1694, 1633, 1610, 1574, 1522, 1453, 1417, 1344, 1278, 1069, 846, 826, 743 cm$^{-1}$.

$^1$H NMR (300 MHz, DMSO) δ 4.08 (s, 3H), 7.36 (d, 1H, J=8.4 Hz), 7.98 (d, 1H, J=9.0 Hz), 8.07 (d, 1H, J=8.4 Hz), 8.44 (dd, 1H, J=9.0 Hz, 2.7 Hz), 9.79 (d, 1H, J=2.4 Hz).

Intermediate 30: 4-methoxy-8amino-dibenzo[b,d]furan-1-carboxylic acid

To a suspension of intermediate 29 (1.05 gm, 3.105 mmol) in methanol (20 ml) was added activated raney nickel (300 mg, 30% w/w) and refluxed for 1 h. Hydrazine hydrate (0.77 gm, 15.5 mmol) was added slowly to the above suspension over a period of 30 min. The reaction mixture was allowed to reflux under stirring for 30 min. Methanol was evaporated and aqueous ammonia solution (25-28%) was added to the residue to get a clear solution. The suspended raney nickel was filtered and the filterate was acidified to get the product as a white solid (700 mg) mp: 264-273° C.

IR (KBr): 3391, 2938, 1709, 1608, 1581, 1495, 1451, 1396, 1278, 1183, 933, 786, 634 cm$^{-1}$ $^1$H NMR (300 MHz, DMSO) δ 4.01 (s, 3H), 6.81 (d, 1H, J=8.1 Hz), 7.14 (d, 1H), 7.35 (d, 1H, J=8.1), 7.84 (d, 1H), 8.1 (s, 1H),

Intermediate 31: 4-methoxy-8-chloro-dibenzo[b,d]furan-1-carboxylic acid

Intermediate 29 (350 mg, 1.13 mmol) was suspended in mixture of concentrated hydrochloric acid:water (1: 1) (5 ml) and stirred at 50° C. for 30 min. The suspension was cooled to 0° C. and a solution of sodium nitrite (83 mg, 1.2 mmol) in water (2 ml) was added dropwise in 15 min. The reaction was stirred for 90 min. at 0-5° C. and then this suspension was added to a pre-cooled solution of CuCl (123 mg, 1.24 mmol) in concentrated HCl (5 ml). The reaction was allowed to come to room temperature and further heated to 80-90° C. for 2 h. The reaction mixture was then poured into water (100 ml) and the solid was filtered and then purified by column chromatography using 20% ethyl acetate-chloroform as the eluent to obtain 250 mg of the product as white solid; mp: 264-276° C.

IR (KBr): 3432, 2924, 2853, 1739, 1687, 1601, 1571, 1416, 1292, 1259, 1107, 1017, 907, 810, 630 cm$^{-1}$ $^1$H NMR (300 MHz, DMSO) δ 4.05 (s, 3H), 7.29 (d, 1H, J=8.7 Hz), 7.64 (d, 1H, J=8.7 Hz), 7.80 (d, 1H, J=8.7 Hz), 8.01 (d, 1H, J=9.0 Hz), 8.88 (s, 1H), 13.16 (s, 1H).

Intermediate 32:
4-methoxy-8-bromo-dibenzo[b,d]furan-1-carboxylic acid

Intermediate 30 (500 mg, 1.62 mmol) was suspended in mixture of concentrated hydrochloric acid: water (1: 1) (5 ml) and stirred at 50° C. for 30 min. The suspension was cooled to 0° C. and a solution of sodium nitrite (118 mg, 1.72 mmol) in water (2 ml) was added dropwise in 15 min. The reaction was stirred for 90 min. at 0-5° C. and then a chilled solution of sodium fluoroborate (25 mg, 1.62 mmol) in water (4 ml) was added to the above suspension and stirred for 30 min. The solid was filtered rapidly and washed with 5% solution of sodium fluoroborate. The vacuum dried solid (400 mg) was suspended in 47% HBr (5 ml) and cuprous bromide CuBr (512 mg, 1.78 mmol) was added. The reaction was heated to about 80-90° C. for 2 h and then poured into water (100 ml). The resulting solid was filtered, washed with water and vacuum dried and then purified by column chromatography using 20% ethyl acetate-chloroform as the eluent to obtain 120 mg of the product as white solid; mp: 275° C. (dec).

IR (KBr): 3069, 2957, 2924, 2853, 1685, 1598, 1414, 1384, 1292, 1259, 1104, 1056, 978, 808, 728, 628 cm$^{-1}$ $^1$H NMR (300 MHz, DMSO) δ 4.06 (s, 3H), 7.29 (d, 1H, J=8.7 Hz), 7.74 (m, 2H), 8.02 (d, 1H, J=8.7 Hz), 9.04 (s, 1H).

Intermediate 33:
4-methoxy-8-iodo-dibenzo[b,d]furan-1-carboxylic acid

Intermediate 30 (500 mg, 1.62 mmol) was suspended in mixture of concentrated hydrochloric acid: water (1: 1) (5 ml) and stirred at 50° C. for 30 min. The suspension was cooled to 0° C. and a solution of sodium nitrite (118 mg, 1.72 mmol) in water (2 ml) was added dropwise in 15 min. The reaction was stirred for 90 min. at 0-5° C. and then a chilled solution of sodium fluoroborate (25 mg, 1.62 mmol) in water (4 ml) was added to the above suspension and stirred for 30 min. The solid was filtered rapidly and washed with 5% solution of sodium fluoroborate. The vacuum dried solid (400 mg) was suspended in a solution of potassium iodide (400 mg, 2.23. eq.) in water (25 ml). The reaction was heated to about 80-90° C. for 2 h, then diluted with water (100 ml) and extracted with ethyl acetate. The ethyl acetate was evaporated and the resulting crude solid was then purified by column chromatography using 20% ethyl acetate-chloroform as the eluent to obtain 320 mg of the product as white solid; mp: 249° C.

IR (KBr): 3079, 2973, 2934, 2856, 1686, 1628, 1595, 1571, 1412, 1291, 1209, 1104, 892, 722, 628 cm$^{-1}$ $^1$H NMR (300 MHz, DMSO) δ 3.97 (s, 3H), 7.09 (d, 1H, J=8.4 Hz), 7.47 (d, 1H, J=9.0 Hz), 7.72 (d, 1H, J=8.7 Hz), 7.80 (d, 1H, J=8.4 Hz), 9.66 (s, 1H).

Intermediate 34: 4-(2-nitrophenoxy)-3-methoxy benzaldehyde

To a stirred suspension of potassium fluoride (2.3 gm, 0.0395 mol) in dry DMSO (15 ml) was added a solution of vanillin (5.0 gm, 0.0329 mol) in DMSO (15 ml). A solution of 2-fluoronitrobenzene (4.63 gm, 0.0329 mol) in DMSO (15 ml) was added to the above suspension and the reaction mixture was stirred at 140° C. for 3.5 h. The reaction mixture was cooled to room temperature and the contents were poured into water (300 ml) and extracted with ethyl acetate (100 ml×3). The organic extracts were combined and washed with 1N sodium hydroxide (50 ml×2), water and brine and dried over anhydrous sodium sulfate. The dried organic layer was concentrated in vacuo to obtain the product as a pale yellow solid (7.15 gm); mp: 70-77° C.

IR (KBr) 3064, 2982, 2821, 1692, 1588, 1531, 1355, 1238, 1161, 1024, 863, 778 cm$^{-1}$.

$^1$H NMR (300 MHz, CDCl$_3$) δ 3.91 (s, 3H), 6.97 (d, 1H, J=8.4 Hz), 7.03 (d, 1H, J=7.8 Hz), 7.25 (t, 1H, J=8.1 Hz), 7.43 (d, 1H, J=7.8 Hz), 7.52 (t, 1H, J=7.8 Hz), 8.0 (d, 1H, J=7.8 Hz), 9.90 (s, 1H).

Intermediate 35:
4-(2-nitrophenoxy)-3-methoxy-phenyl carboxylic acid

To a solution of intermediate 34 (7.15 gm, 0.0262 mol) in acetone (60 ml) was added sulfamic acid (3.81 gm, 0.0393 mol) while stirring at 0° C. A solution of 80% sodium chlorite (3.31 gm, 0.0366 mol) in water (15.0 ml) was added dropwise to the above reaction mixture over a period of 10 min. and was allowed to stir at 0° C. for additional 30 min. The reaction was diluted with 120 ml of water and stirred for 30 min. The precipitate obtained was filtered, washed with water and air dried to give 7.0 gm of the product as white solid; mp: 153-155° C.

IR (KBr): 3084, 2901, 2655, 1699, 1593, 1531, 1425, 1301, 1228, 1027, 876, 760 cm$^{-1}$.

$^1$H NMR (300 MHz, CDCl$_3$) δ 3.89 (s, 3H), 6.95 (d, 1H, J=8.4 Hz), 6.99 (d, 1H, J=8.7 Hz). 7.25 (t, 1H, J=8.4 Hz), 7.50 (t, 1H, J=7.8 Hz), 7.70-7.73 (m, 2H), 7.99 (d, 1H, J=7.8 Hz).

Intermediate 36:
4-(2-aminophenoxy)-3-methoxy-phenyl carboxylic acid

To a suspension of intermediate 35 (7.0 gm) in dichloromethane (500 ml) was added 5% Pd/C (10% w/w) and hydrogenated at 40 psi for 5 h under hydrogen atmosphere. The catalyst was filtered over celite. The celite bed was washed with methanol. The combined filtrate was concentrated in vacuo to yield the desired product as white solid (5.68 gm); mp: 192-194° C.

IR (KBr) 3391, 3285, 2914, 2587, 1705, 1590, 1501, 1458, 1276, 1205, 1113, 1029, 836, 750 cm$^{-1}$.

$^1$H NMR (300 MHz, CDCl$_3$) δ 3.98 (s, 3H), 6.71-6.77 (brm, 2H), 6.82 (d, 1H, J=7.8 Hz), 6.89 (d, 1H, J=7.8 Hz), 7.02 (t, 1H, J=7.8 Hz), 7.62 (d, 1H, J=7.8 Hz), 7.67 (s, 1H).

Intermediate 37: 4-methoxy dibenzo[b,d]furan-2-carboxylic acid

A suspension of intermediate 36 (5.1 gm, 0.0197 mol) in a mixture of concentrated hydrochloric acid: water (1: 1) (50 ml) is warmed to 45° C. for 30 min. and cooled to −5° C. A solution of sodium nitrite (1.628 gm, 0.0236 mol) in water (5 ml) is added dropwise to the above suspension at −5° C. The reaction mixture was stirred for 30 min and a chilled solution of sodium fluoroborate (3.43 gm, 0.0315 mol) was added to the above reaction mixture and stirred at −5° C. for 30 min. The diazonium fluoroborate salt obtained as a result was filtered and washed with 5% cold sodium fluoroborate solution and air dried. The dried diazonium fluoroborate salt was added to a stirred suspension of cuprous oxide (5.63 gm, 0.0394 mol) in 0.1N sulfuric acid (1800 ml) at 35° C. and stirred for 15 min. The resulting precipitate was filtered, washed with water, air dried and chromatographed on silica gel column using 5% methanol in chloroform to give the desired product as a white solid (700 mg); mp: 229-240° C.

IR (KBr): 3066, 2919, 2850, 2590, 1686, 1588, 1413, 1348, 1276, 1195, 1037, 835, 760, 744 cm$^{-1}$.

$^1$H NMR (300 MHz, DMSO) δ 4.06 (s, 3H), 7.45 (t, 1H, J=7.2 Hz), 7.59 (t, 1H, J=7.2 Hz), 7.68 (s, 1H), 7.78 (d, 1H, J=8.1 Hz), 8.27 (d, 1H, J=7.2 Hz), 13.07 (brs, 1H).

Intermediate 38: 4-Methoxydibenzo[b,d]furan

A solution of dibenzo[b,d]furan-4-ol (5 g, 27.1 mmol) in DMF (5 ml) was added to a stirred and cooled (0° C.) suspension of 60% sodium hydride (1.62 g, 40.62 mmol) in DMF (20). The mixture was stirred at 0° C. for 5 min and methyl iodide (7.71 g, 54.34 mmol) in DMF (5 ml) was added dropwise over a period of 10 min. The cooling bath was removed and the mixture was stirred for 1 h at room temperature. The reaction mixture was diluted with ice-cold water (100 ml) and extracted with EtOAc (3×50 ml). The combined organic extracts were washed with water (2×100 ml), brine (100 ml) and dried (Na$_2$SO$_4$). The product obtained after evaporation of the solvent was purified by silica gel column chromatography using 5% ethyl acetate in petroleum ether to give 5.1 g (95%) of the product as a low melting solid, mp 45-47° C.

IR (KBr) 3053, 2968, 2838, 1451, 1272, 1196, 1095 cm$^{-1}$;

$^1$H NMR (300 MHz, CDCl$_3$) δ 4.06 (s, 3H), 6.98 (d, J=8.5 Hz, 1H), 7.26 (t, J=8.2 Hz, 1H), 7.33 (t, J=8.2 Hz, 1H), 7.45 (t, J=8.2 Hz, 1H), 7.54 (d, J=8.4 Hz, 1H), 7.60 (d, J=8.5 Hz, 1H), 7.93 (d, J=8.4 Hz, 1H).

Intermediate 39: 1-nitro-4-methoxy-dibenzo[b,d]furan

Intermediate 38 (1.0 gm, 5 mmol) was dissolved in glacial acetic acid (15 ml) and to this was added concentrated nitric acid (10 ml) at 20-25° C. in 10 min. The reaction was stirred for 2 h then poured into cold water (200 ml). The resulting yellow solid was filtered and washed with 5% sodium bicarbonate solution and purified through silica gel column using 5% ethyl acetate-petroleum ether to give 600 mg of pure product; mp: 130-132° C.

IR (KBr): 3086, 2926, 1631, 1588, 1571, 1513, 1448, 1321, 1300, 1280, 1209, 1129, 1096, 1008, 987, 814, 742 cm$^{-1}$.

$^1$H NMR (300 MHz, DMSO) δ 4.12 (s, 3H), 7.38 (d, 1H, J=8.7 Hz), 7.53 (t, 1H, J=7.8 Hz), 7.69 (t, 1H, J=7.8 Hz), 7.84 (d, 1H, J=8.1 Hz), 8.32 (d, 1H, J=9.0 Hz), 8.56 (d, 1H, J=9.0 Hz).

Intermediate 40: 1-amino-4-methoxy-dibenzo[b,d]furan

Intermediate 38 (550 mg, 2.26 mmol) was taken in methanol (10 ml) and raney nickel catalyst (100 mg, 18% w/w) was added. The reaction mixture was refluxed and to this was added hydrazine hydrate (99%) solution (2 ml) slowly over a period of 10 min. The refluxing continued for 2 h. The catalyst was filtered and the filtrate was concentrated and diluted with water (100 ml) and further extracted with ethyl acetate (3×25 ml). The organic layer was washed with water and concentrated to give the product as brown solid (500 mg); mp: 167-169° C.

$^1$H NMR (300 MHz, DMSO) δ 3.84 (s, 3H), 5.37 (s, 2H), 6.50 (d, 1H, J=9.0 Hz), 6.90 (d, 1H, J=9.0 Hz), 7.32 (t, 1H, J=6.0 Hz), 7.40 (t, 1H, J=6.0 Hz), 7.61 (d, 1H, J=7.5 Hz), 8.20 (d, 1H, J=7.8 Hz).

Intermediate 41: 4-ethoxycarbomethoxy dibenzo[b,d]furan-1-carbaldehyde

Intermediate 19 (500 mg, 2.358 mmol) was dissolved in dry DMF (5 ml). Anhydrous potassium carbonate (650 mg, 4.716 mmol) was added to the above solution and was stirred for 10 min. at 80° C. To this was added ethylbromoacetate (2.0 eq.) and the reaction mixture was stirred for 1 h. The reaction mixture was cooled to room temperature and diluted with water (100 ml) and extracted with ethyl acetate (3×50 ml). The organic extract was washed with water (50 ml) and brine solution (25 ml) and dried over anhydrous sodium sulfate. Removal of solvent gave the product as a white solid (550 mg).

Intermediate 42: 4-ethoxycarbomethoxy dibenzo[b,d]furan-1-carboxylic acid

To a solution of intermediate 41 (500 mg) in acetone-water mixture in 2:1 ratio (20 ml) was added sulfamic acid (280 mg, 2.818 mmol) while stirring at 0° C. A solution of 80% sodium chlorite (200 mg, 2.215 mmol) in water (5 ml) was added dropwise to the above reaction mixture over a period of 10 min. and was allowed to stir at room temperature for additional 5 h. The reaction was diluted with water (200 ml) and extracted with ethyl acetate (3×100 ml). The organic extract was washed with water (100 ml) and brine solution (50 ml) and dried over anhydrous sodium sulfate. The organic solvent was evaporated to give the product as white solid.

Intermediate 43: 4-methoxy dibenzo[b,d]furan-3-carbaldehyde

Intermediate 38 (3.7 gm, 0.0186 mol) was dissolved in dichloromethane (30 ml) and the solution was cooled to 0° C. Tin (IV) chloride (8.3 gm, 0.0317 mol) was added all at once to the above solution followed by the dropwise addition of 1,1-dichloromethyl methyl ether (2.2 gm, 0.0186 mol). The reaction was stirred and allowed to come to room temperature in 1 h. The reaction mixture was cooled in ice-bath and quenched with ice water (25 ml) with vigorous stirring followed by extraction with chloroform (2×100 ml). The chloroform layer was washed with water (3×50 ml) and dried over anhydrous sodium sulphate. Removal of solvent under vacuo gave the crude product a off-white solid (3.4 gm) which was mixture of 4-methoxy dibenzo[b,d]furan-1-carbaldehyde and 4-methoxy dibenzo[b,d]furan-3-carbaldehyde (80:20). Both the isomers were separated by silica gel coloumn chromatography using 20% ethyl acetate in petroleum ether as eluent to give 4-methoxy dibenzo[b,d]furan-3-carbaldehyde as a white solid (500 mg); mp: 178-180° C.

IR (KBr): 2925, 2847, 1660, 1626, 1597, 1453, 1395, 1255, 1199, 1092, 1005, 820, 754 cm$^{-1}$.

$^1$H NMR (300 MHz, DMSO) δ 4.36 (s, 3H), 7.46 (t, 1H, J=7.2 Hz), 7.63 (t, 1H, J=7.2 Hz), 7.71 (d, 1H, J=9.0 Hz), 7.81 (d, 1H, J=9.0 Hz), 7.92 (d, 1H, J=7.8 Hz), 8.23 (d, 1H, J=7.8 Hz), 10.41 (s, 1H).

Intermediate 44: 4-methoxy dibenzo[b,d]furan-3-carboxylic acid

To a solution of intermediate 43 (250 mg, 1.106 mmol) in acetone-water mixture in 2:1 ratio (15 ml) was added sulfamic acid (130 mg, 1.327 mmol) while stirring at 0° C. A solution of 80% sodium chlorite (150 mg, 1.659 mmol) in water (5 ml) was added dropwise to the above reaction mixture over a period of 10 min. and was allowed to stir at room temperature for additional 1 h. The reaction was diluted with water (100 ml) and extracted with ethyl acetate (3×25 ml). The organic extract was washed with water (50 ml) and brine solution (50 ml) and dried over anhydrous sodium sulfate. The organic solvent was evaporated to give 200 mg of the product as white solid; mp: 208-209° C.

IR (KBr): 2940, 2830, 2692, 1677, 1632, 1598, 1574, 1442, 1414, 1301, 1198, 1091, 1001, 937, 780, 746 cm$^{-1}$.

$^1$H NMR (300 MHz, DMSO) δ 4.11 (s, 3H), 7.44 (t, 1H, J=7.2 Hz), 7.59 (t, 1H, J=7.2 Hz), 7.67 (d, 1H, J=8.4 Hz), 7.77 (d, 1H, J=7.8 Hz), 7.88 (d, 1H, J=8.4 Hz), 8.18 (d, 1H, J=8.4 Hz).

Intermediate 45: 4-cyclopentoxy-3-hydroxy-benzaldehyde

A suspension of 3,4-dihydroxybenzaldehyde (5.0 gm, 0.0362 mol), anhydrous potassium carbonate (6.0 gm, 0.0434 mol) and cyclopentyl bromide (6.5 gm, 0.0434 mol) in dry DMF (50 ml) was heated and stirred at 80° C. for 24 hrs. Reaction mixture was then cooled and diluted with water (500 ml), acidified with 1N HCl and extracted with ethyl acetate (3×100 ml). The ethyl acetate extract was washed 5% sodium bicarbonate and brine and dried over anhydrous sodium sulfate. The dried extract on concentration afforded a residue which was purified by silica gel chromatography using 10% ethyl acetate in petroleum ether as the eluent to provide 5.0 gm of the title product as white solid. mp: 87-89° C.

IR (KBr) 2964, 1670, 1605, 1580, 1500, 1463, 1358, 1271, 1122, 976, 806, 748 cm$^{-1}$ $^1$H NMR (300 MHz, CDCl$_3$) δ 1.65-2.04 (m, 8H), 4.93 (m, 1H), 5.83 (s, 1H), 6.94 (d, 1H), 7.38-7.43 (m, 2H), 9.82 (s, 1H).

Intermediate 46: 2-bromo-4-cyclopentoxy-3-hydroxy-benzaldehyde

Intermediate 45 (1.0 gm, 4.84 mmol) was dissolved in glacial acetic acid (20 ml). Anhydrous sodium acetate (0.8 gm, 9.7 mmol) was added to the above solution followed by powdered iron (0.022 gm). The system was flushed thoroughly with nitrogen. A solution of bromine (0.854 gm, 5.32 mmol) in glacial acetic acid (10 ml) was added to the above stirred suspension at 15° C. over a period of 15 min. The reaction mixture was stirred at 15° C. for 45 min. The reaction mixture was poured into aqueous 2% sodium bisulfite (100 ml) and stirred for 10 min. The precipitate was filtered washed with water (100 ml), and dried to obtain 800 mg of 2-bromo-4-cyclopentoxy-3-hydroxy-benzaldehyde as white powder mp: 107-109° C.

$^1$H NMR (300 MHz, CDCl$_3$) δ 1.66-2.03 (m, 8H), 4.92 (m, 1H), 6.15 (s, 1H), 6.90 (d, 1H), 7.54 (d, 1H), 10.25 (s, 1H).

Intermediate 47: 2-bromo-4-cyclopentoxy-3-(p-nitrophenoxy)-benzaldehyde

To a stirred suspension of potassium fluoride (125 mg, 2.104 mmol) in dry DMSO (2.5 ml) was added a solution of intermediate 46 (500 mg, 1.754 mmol) in DMSO (2.5 ml). A solution of 4-fluoronitrobenzene (500 mg, 2.631 mmol) in DMSO (2.5 ml) was added to the above suspension and the reaction mixture was stirred at 140° C. for 6 h. The reaction mixture was cooled to room temperature and the contents were poured into water (100 ml) and extracted with ethyl acetate (50 ml×3). The organic extracts were combined and washed with 1N sodium hydroxide (25 ml×2), water and brine and dried over anhydrous sodium sulfate. The dried organic layer was concentrated in vacuo to give 2-bromo-3-(p-nitrophenoxy)-4-methoxy benzaldehyde as a pale yellow solid (500 mg) mp: 1.15-117° C.

$^1$H NMR (300 MHz, CDCl$_3$) δ 1.18-1.23 (m, 2H), 1.39-1.53 (m, 4H), 1.73-1.81 (m, 2H), 5.01 (m, 1H), 7.09 (dd, 2H), 7.43 (d, 1H), 7.87 (d, 1H), 8.24 (dd, 2H), 10.13 (s, 1H).

Intermediate 48: 4-cyclopentyloxy-8-nitro-1-formyl dibenzo[b,d]furan

Intermediate 47 (500 mg, 1.09 mmol), anhydrous sodium carbonate (150 mg, 1.325 mmol) and palladium (II) acetate (25 mg, 0.096 mmol), in dimethylformamide (10 ml) are heated and stirred under nitrogen at 130° C. for 7 h. Water (90 ml) is added to the cooled reaction mixture and extracted with ethyl acetate (2×25 ml). The combined organic layer was washed with 5% hydrochloric acid followed by water and dried over anhydrous sodium sulfate to afford the product as a yellow solid (200 mg). mp: 230-240° C.

$^1$H NMR (300 MHz, DMSO) δ 1.70 (m, 2H), 1.77-1.92 (m, 4H), 2.09 (m, 2H), 5.25 (m, 1H), 7.53 (d, 1H), 8.05 (d, 1H), 8.14 (d, 1H, 8.51 (d, 1H), 9.80 (s, 1H), 10.14 (s, 1H).

Intermediate 49: 4-hydroxy-8-nitro-1-formyl dibenzo[b,d]furan

Intermediate 48 (200 mg, 0.530 mol) was heated in HBr (47% in acetic acid) (5 ml) in glacial acetic acid (10 ml) at 50° C. for 7-8 h. The reaction contents were poured in ice-water (200 ml) and extracted with ethyl acetate (3×50 ml). The combined organic layer was washed with saturated sodium bicarbonate, and water and dried over anhydrous sodium sulfate. Removal of the organic solvent in vacuo afforded the crude product as a white solid (150 mg). The crude white solid was used as such without further purification. mp: >270° C.

$^1$H NMR (300 MHz, DMSO) δ 7.28 (d, 1H), 8.01 (d, 1H), 8.04 (d, 1H), 8.50 (d, 1H), 9.83 (s, 1H), 10.09 (s, 1H), 11.92 (s, 1H).

Intermediate 50: 4-difluoromethoxy-8-nitro-1-formyl dibenzo[b,d]furan

A suspension of intermediate 49 (150 mg, 0.485 mmol) and anhydrous potassium carbonate (200 mg, 1.455 mmol) in dry DMF (5.0 ml) was stirred at 80° C. for 10 min. Chlorodifluoromethane gas was purged into the reaction mixture for 45 min. The reaction mixture was cooled, diluted with water (50 ml), and extracted with ethyl acetate (3×25 ml). The combined organic layer was washed with water and dried over anhydrous sodium sulfate. Removal of the organic solvent in vacuo afforded the product as a white solid (150 mg). mp: 245-248° C.

Intermediate 51: 4-difluoromethoxy-8-nitro dibenzo[b,d]furan-1-carboxylic acid Intermediate 50 (150 mg, 0.48 mmol) in acetone (20 ml) and water (5 ml) was heated to 60-70° C. for 10 min. To the above solution was added dropwise a solution of potassium permanganate (150 mg, 0.973 mmol) in water (5 ml) for 10 min. The reaction was heated to 60-70° C. for 30 min., and filtered hot through celite bed. Acidification of the filterate resulted in a precipitate which on filteration and washing with water yielded 4-difluoromethoxy-8-nitro-dibenzo[b,d]furan-1-carboxylic acid (100 mg) as white solid; mp: >270° C.

$^1$H NMR (300 MHz, DMSO) δ 7.61 (t, 1H, J=72 Hz), 7.60 (d, 1H), 8.07 (d, 1H), 8.13 (d, 1H), 8.52 (d, 1H), 9.77 (s, 1H), 13.80 (s, 1H).

Intermediate 52: 4-Ethoxydibenzo[b,d]furan

A solution of Dibenzo[b,d]furan-4-ol (1 g, 5.43 mmol) in DMF (5 ml) was added to a stirred and cooled (0° C.) suspension of 60% sodium hydride (326 mg, 8.12 mmol) in DMF (20 ml). The mixture was stirred at 0° C. for 5 min and ethyl iodide (1.18 g, 10.86 mmol) in DMF (5 ml) was added dropwise over a period of 10 min. The cooling bath was removed and the mixture was stirred for 1 h at room temperature. The reaction mixture was diluted with ice-cold water (100 ml) and extracted with EtOAc (3×50 ml). The combined organic extracts were washed with water (2×100 ml), brine (100 ml) and dried (Na$_2$SO$_4$), to give 0.95 g (82%) of the product as viscous liquid, IR (neat) 3058, 2980, 1449, 1272, 1193 cm$^{-1}$;

$^1$H NMR (300 MHz, CDCl$_3$) δ 1.55 (t, J=7.2 Hz, 3H), 4.29 (q, J=7.2 Hz, 2H), 6.96 (d, J=8.4 Hz, 1H), 7.23 (t, J=8.0 Hz, 1H), 7.30-7.52 (m, 3H), 7.61 (d, J=8.3 Hz, 1H), 7.90 (d, J=8.4 Hz, 1H).

Intermediate 53: 4-Cyclopropylmethoxydibenzo[b,d]furan

A solution of Dibenzo[b,d]furan-4-ol (1 g, 5.43 mmol) in DMF (5 ml) was added to a stirred and cooled (0° C.) suspension of 60% sodium hydride (326 mg, 8.12 mmol) in DMF (20 ml). The mixture was stirred at 0° C. for 5 min and cyclopropylmethyl bromide (1.31 g, 10.85 mmol) in DMF (5 ml) was added dropwise over a period of 10 min. The cooling bath was removed and the mixture was stirred for 1 h at room temperature. The reaction mixture was diluted with ice-cold water (100 ml) and extracted with EtOAc (3×50 ml). The combined organic extracts were washed with water (2×100 ml), brine (100 ml) and dried (Na$_2$SO$_4$), to give 1.16 g (90%) of the product as viscous liquid IR (neat) 3080, 2923, 1449, 1273, 1192 cm$^{-1}$;

$^1$H NMR (300 MHz, CDCl$_3$) δ 0.44-0.49 (m, 2H), 0.70-0.77 (m, 2H), 1.44-1.52 (m, 1H), 4.10 (d, J=6.9 Hz, 2H), 6.99 (d, J=8.1 Hz, 1H), 7.25 (t, J=7.5 Hz, 1H), 7.35 (t, J=8.4 Hz, 1H), 7.47 (t, J=8.4 Hz, 1H), 7.55 (d, J=7.2 Hz, 1H), 7.65 (d, J=8.1 Hz, 1H, 7.94 (d, J=8.1 Hz, 1H).

Intermediate 54: Dibenzo[b,d]furan-4-yl methyl sulfide

To a stirred and cooled (−40° C.) solution of dibenzofuran (5 g, 29.76 mmol) in dry THF (50 ml) was added 15% n-butyllithium in hexane (20 ml, 46.87 mmol) in 5 min. The mixture was allowed to warm to room temperature in 20 min and further stirred at room temperature for 2 h. The brown solution was again cooled to −40° C. and sulfur powder (1.04 g, 32.50 g atom) was added in one portion and maintained at the same temperature for 1 h under stirring. Methyl iodide (5.5 g, 38.73 mmol) was then added dropwise over a period of 10 min. The cooling bath was removed after 30 min and the mixture was stirred at room temperature for 18 h. The reaction mixture was diluted with ice-cold water (100 ml) and extracted with EtOAc (2×100 ml). The combined organic extracts were washed with water (3×100 ml), brine (100 ml) and dried Na$_2$SO$_4$). The product obtained after evaporation of the solvent was purified by silica gel column chromatography using 5% ethyl acetate in petroleum ether to give 4.5 g (70%) of the product as viscous yellow liquid;

IR (KBr) 3054, 2919, 1448, 1407, 1196, 1182 cm$^{-1}$;

$^1$H NMR (300 MHz, CDCl$_3$) δ 2.64 (s, 3H), 7.27-7.38 (m, 3H), 7.46 (t, J=7.6 Hz, 1H), 7.62 (d, J=7.8 Hz, 1H), 7.77 (d, J=7.8 Hz, 1H), 7.94 (d, J=7.8 Hz, 1H).

Intermediate 55: 4-Ethoxydibenzo[b,d]furan-1-carbaldehyde

To a stirred solution of intermediate 52 (850 mg, 4.01 mmol) in dry dichloromethane (10 ml) was added tin) chloride(1.56 g, 6.0 mmol) in one portion followed by drop-wise addition of dichloromethylmethyl ether (460 mg, 4.01 mmol) in dichloromethane (5 ml). The mixture was maintained at 0° C. for a period of 20 min and the dark mixture was quenched by the addition of ice-cold water (50 ml). The aqueous layer was extracted with dichloromethane (20 ml) and the combined organic layer was washed with water (2×25 ml) and brine (25 ml). The crude product obtained after evaporation of the solvent was purified by silica gel column chromatography using 25% ethyl acetate in petroleum ether to give 260 mg (21%) of the product as white solid, mp 92-94° C.;

IR (KBr) 2986, 2936, 1686, 1567, 1281, 1099 cm$^{-1}$;

$^1$H NMR (300 MHz, CDCl$_3$) δ 1.62 (t, J=7.2 Hz, 3H), 4.40 (q, J=7.2 Hz, 2H), 7.09 (d, J=8.4 Hz, 1H), 7.40 (t, J=7.2 Hz, 1H), 7.53 (t, J=7.2 Hz, 1H), 7.65 (d, J=8.2 Hz, 1H), 7.80 (d, J=8.4 Hz, 1H), 8.97 (d, J=7.2 Hz, 1H), 10.18 (s, 1H).

Intermediate 56: 4-Cyclopropylmethoxydibenzo[b,d]furan-1-carbaldehyde

To a stirred solution of intermediate 53 (1.0 g, 4.2 mmol) in dry dichloromethane (10 ml) was added tin(IV)chloride (1.6 g, 6.30 mmol) in one portion followed by drop-wise addition of dichloromethylmethylether (485 mg, 4.2 mmol) in dichloromethane (5 ml). The mixture was maintained at 0° C. for a period of 20 min and the dark mixture was quenched by the addition of ice-cold water (50 ml). The aqueous layer was extracted with dichloromethane (20 ml) and the combined organic layer was washed with water (2×25 ml) and brine (25 ml). The crude product after evaporation of the solvent gave 120 mg (10.8%) of the product as white solid, mp 93-95° C.;

IR (KBr) 2929, 2850, 2729, 1682, 1568, 1280, 1098 cm$^{-1}$.

$^1$H NMR (300 MHz, CDCl$_3$) δ 0.45-0.50 (m, 2H), 0.72-0.79 (m, 2H), 1.41-1.51 (m, 1H), 4.14 (d, J=7.2 Hz, 1H), 7.04 (d, J=8.4 Hz, 1H), 7.37 (t, J=7.2 Hz, 1H), 7.54 (t, J=7.2 Hz, 1H), 7.65 (d, J=8.2 Hz, 1H), 7.76 (d, J=8.4 Hz, 1H), 8.96 (d, J=8.0 Hz, 1H), 10.17 (s, 1H).

Intermediate 57: 4-Methylsulfanyldibenzo[b,d]furan-1-carbaldehyde

To a vigorously stirred and cooled (0° C.) solution of intermediate 54 (4 g, 18.89 mmol) and dichloromethylmethyl ether (3.26 g, 28.36 mmol) in dry dichloromethane (80 ml) was added titanium(IV)chloride (10.64 g, 56.08 mmol) in one portion. After 1 h, the ice bath was removed and the dark brown mixture was quenched by the addition of ice-cold water (200 ml). The layers were separated and the aqueous layer was extracted with dichloromethane (200 ml). The combined organic extracts were washed with water (2×100 ml), brine (100 ml) and dried (Na$_2$SO$_4$). The product obtained after evaporation of the solvent was purified by silica gel column chromatography using 20% ethyl acetate in petroleum ether to give 2.0 g (40%) of the product as white solid, mp 130-133° C.;

IR (KBr) 2923, 2849, 1685, 1586, 1557, 1371, 1058 cm$^{-1}$;

$^1$H NMR (300 MHz, DMSO-d$_6$) δ 2.75 (s, 3H), 7.46 (t, J=7.1 Hz, 1H), 7.58-7.66 (m, 2H), 7.82 (d, J=7.2 Hz, 1H), 8.02 (d, J=7.2 Hz, 1H), 8.88 (d, J=7.2 Hz, 1H), 10.24 (s, 1H).

Intermediate 58:
4Ethoxydibenzo[b,d]furan-1-carboxylic acid

To a stirred and cooled (° C.) solution of intermediate 55 (240 mg, 1.0 mmol) and sulphamic acid (135 mg, 1.5 mmol) in acetone (5 ml) was added aqueous sodium chlorite (126 mg, 1.30 mmol) over a period of 5 minutes. The mixture was warmed to room temperature and allowed to stir at room temperature for 3 h. The mixture was diluted with water (15 ml) and extracted with EtOAc (3×20 ml). The combined organic extracts were washed with water (30 ml), brine (30 ml) and dried (Na$_2$SO$_4$). The crude product obtained after evaporation of the solvent was purified by crystallization from chloroform-hexane to give 180 mg (70%) of the product as white solid, mp 254-256° C.;

IR (KBr) 3434, 2982-2540 (br), 1681, 1283, 1094 cm$^{-1}$;

$^1$H NMR (300 MHz, DMSO-d$_6$ δ 1.47 (t, J=6.9 Hz, 3H), 4.34 (q, J=6.9 Hz, 2H), 7.23 (d, J=8.4 Hz, 1H), 7.40 (t, J=7.2 Hz, 1H), 7.57 (t, J=7.2 Hz, 1H), 7.76 (d, J=8.1 Hz, 1H), 7.97 (d, J=8.4 Hz, 1H), 8.85 (d, J=8.1 Hz, 1H).

Intermediate 59:
4-Cyclopropylmethoxydibenzo[b,d]furan-1-carboxylic acid

To a stirred and cooled (° C.) solution of intermediate 56 (100 mg, 0.37 mmol) and sulphamic acid (51 mg, 0.56 mmol)in acetone (5 ml) was added aqueous sodium chlorite (50 mg, 048 mmol) over a period of 5 minutes. The mixture was warmed to room temperature and allowed to stir at room temperature for 3 h. The mixture was diluted with water (15 ml) and extracted with EtOAc (3×20 ml). The combined organic extracts were washed with water (30 ml), brine (30 ml) and dried (Na$_2$SO$_4$). The crude product obtained after evaporation of the solvent gave 75 mg (71%) of the product as off-white solid;

IR (KBr) 2998-2538 (br), 1682, 1570, 1278, 1093 cm$^{-1}$;

$^1$H NMR (300 MHz, DMSO-d$_4$) δ 0.40-0.45 (m, 2H), 0.62-0.68 (m, 2H), 1.33-1.39 (m, 1H), 4.13 (d, J=6.9 Hz, 1H), 7.22 (d, J=8.4 Hz, 1H), 7.40 (t, J=8.1 Hz, 1H), 7.58 (t, J=7.2 Hz, 1H), 7.79 (d, J=8.1 Hz, 1H), 7.96 (d, J=8.4 Hz, 1H), 8.85 (d, J=8.4 Hz, 1H), 13.02 (brs, 1H).

Intermediate 60:
4-Cyclopentyloxydibenzo[b,d]furan-1-carboxylic acid

To a stirred and cooled (° C.) solution of intermediate 18 (300 mg, 1.06 mmol) and sulphamic acid (160 mg, 1.6 mmol) in acetone (5 ml) was added aqueous sodium chlorite (140 mg, 1.36 mmol) over a period of 5 minutes. The mixture was warmed to room temperature and allowed to stir at room temperature for 3 h. The mixture was diluted with water (15 ml) and extracted with EtOAc (3×20 ml). The combined organic extracts were washed with water (30 ml), brine (30 ml) and dried (Na$_2$SO$_4$). The crude product obtained after evaporation of the solvent gave 220 mg (69.4%) of the product as white solid, mp 233-235° C.;

IR (KBr) 3435, 2969-2543 (br), 1674, 1278, 1093 cm$^{-1}$;

$^1$H NMR (300 MHz, DMSO-d$_6$) δ 1.57-1.65 (m, 2H), 1.75-1.88 (m, 2H), 1.93-1.97 (m, 4H), 2.50 (brs, 1H), 4.99 (quint., J=3.9 Hz, 1H), 6.89 (d, J=8.7 Hz, 1H), 7.23 (t, J=8.3 Hz, 1H), 7.38 (t, J=8.3 Hz, 1H), 7.52 (d, J=8.6 Hz, 1H), 7.95 (d, J=8.7 Hz, 1H), 8.85 (d, J=8.6 Hz, 1H).

Intermediate 61:
4-Methylsulfanyldibenzo[b,d]furan-1-carboxylic acid

To a stirred and cooled (° C.) solution of intermediate 57 (1 g, 4.13 mmol) and sulphamic acid (800 mg, 8.26 mmol) in acetone (5 ml) was added aqueous sodium chlorite (600 mg 6.63 mmol) over a period of 5 minutes. The mixture was warmed to room temperature and allowed to stir at room temperature for 3 h. The mixture was diluted with water (15 ml) and extracted with EtOAc (3×20 ml). The combined organic extracts were washed with water (30 ml), brine (30 ml) and dried (Na$_2$SO$_4$). The crude product obtained after evaporation of the solvent gave 1 g (93%) of the product as white solid, mp 250-253° C.;

IR (KBr) 3421 (br), 2970-2540, 1709, 1379, 1264, 1008 cm$^{-1}$;

$^1$H NMR (300 MHz, DMSO-d$_6$) δ 3.01 (s, 3H), 7.49 (t, J=7.5 Hz, 1H), 7.63 (t, J=7.5 Hz, 1H), 7.82 (d, J=8.1 Hz, 1H), 7.93 (d, J=8.1 Hz, 1H), 8.19 (d, J=8.1 Hz, 1H), 8.80 (d, J=8.0 Hz, 1H).

Intermediate 62:
N-Formyl-1-methoxy-9H-carbazole

In a 50 mL round bottomed flask was dissolved POCl$_3$ (0.6 mL, 15.23 mM) in 20 mL of dry DMF. The reaction mixture was stirred at 0° C. in an ice bath. To this was added slowly, 1-methoxy-9H-carbazole (1 g, 5.07 mM) dissolved in 30 mL of dry DMF. The reaction mixture was stirred for 2 hrs. Water was added to the reaction mixture and the precipitated product was filtered off. The residue was dissolved in EtOAc and was washed with brine and dried over anh. Na$_2$SO$_4$. Ethyl acetate was then evaporated to obtain the desired product as a white fluffy solid with a yield of 96% (1.1 g); mp 161-163° C.

$^1$H NMR (d$_6$-DMSO, 300 MHz) δ 4.02 (3H, s), 7.22 (1H, d, J=7.8 Hz), 7.36 (1H, t, J=8.1 Hz), 7.43 (1H, d of t, J=7.5 Hz, J=0.9 Hz), 7.52 (1H, d of t, J=7.5 Hz, J=0.9 Hz), 7.77 (1H, d, J=7.2 Hz), 8.14 (1H, d, J=7.8 Hz), 8.51 (1H, d, J=8.1 Hz), 10.14 (1H, s).

IR (Neat): 1683, 1429, 1339, 1266, 1139, 743 cm$^{-1}$.

Intermediate 63:
N-Formyl-1-methoxy-4-chlorosulphonyl-9H-carbazole

In a 50 mL round bottomed flask was taken 0.5 g of thionyl chloride and 2 g of chlorosulphonic acid. To it was added intermediate 62 (1 g, 4.44 mM) keeping the temperature below 25° C. The reaction mixture turned black. 1 ml of thionyl chloride was added and the reaction mixture was stirred at room temperature for 3 hrs. It was then quenched with ice and water. The white solid formed was extracted with ethylacetate and the organic layer was washed with water, brine and dried over anh. Na$_2$SO$_4$. It was then evaporated to obtain the desired compound as a beige color solid with a yield of 63% (0.91 g); mp 201-203° C.

¹H NMR (d₆-DMSO, 300 MHz) δ 4.04 (3H, s), 7.17 (1H, d, J=8.7 Hz), 7.36 (1H, d of t, J=8.1 Hz, J=1.2 Hz), 7.49 (1H, d of t, J=8.1 Hz, J=1.2 Hz), 7.77 (1H, d, J=8.4 Hz), 8.54 (1H, d, J=8.1 Hz), 9.11 (1H, d, J=7.5 Hz), 10.26 (1H, s).

IR (KBr): 1693, 1567, 1453, 1393, 1358, 1306, 1278, 1167, 1141 cm⁻¹.

Intermediate 64:
9-tetrahydro-2H-2-pyranyl-9H-carbazole

To a stirred solution of carbazole (20.0 gm, 0.119 moles) in dry chloroform (300 ml) at 0° C., D-10 camphor sulphonic acid (5% W/W, 1.0 gm) was added followed by a solution of 3,4-dihydro 2H-pyran (0.149 moles, 13.6 ml) in dry chloroform (50 ml) dropwise over a period of 30 min. The reaction mixture was gradually warmed to room temperature and stirred at the same temperature for 2 hours. The reaction mixture was diluted with chloroform (400 ml) and washed with a solution of saturated NaHCO₃ (150 ml), followed by water (150 ml), dried over Na₂SO₄ and concentrated to give 31 gm of crude material which was recrystallised from 500 ml of iso-propanol to give 24 gm of the title product as white crystalline powder, m. p: 131-133° C.

IR (KBr, cm⁻¹): 3435, 2949, 1594, 1482, 1451, 1334, 1044 and 751.

¹H NMR (300 MHz, CDCl₃, δ): 1.7-1.8 (m, 1H), 1.8-2.0 (m, 3H), 2.1-2.2 (m, 1H), 2.4-2.6 (m, 1H), 3.8-3.9 (t, J=11.0 Hz, 1H), 4.3-4.4 (d, J=12.0 Hz, 1H), 5.75-5.85 (d, J=12.0 Hz, 1H), 7.2-7.3 (t, J=6.5 Hz, 2H), 7.4-7.5 (t, J=6.4 Hz, 2H), 7.6-7.7 (d, J=8.1 Hz, 2H), 8.1-8.2 (d, J=8.2 Hz, 2H).

Intermediate 65: 1-hydroxy
9-tetrahydro-2H-2-pyranyl-9H-carbazole

To a stirred solution of intermediate 64 (20 gm, 0.0796 moles) in sodium dried hexane (2400 ml) at room temperature, 1.6M n-BuLi (0.175 moles, 110 ml) was added dropwise and the reaction mixture was stirred at the same temperature for 15 hours. The mixture was then refluxed for 4 hours, dry THF (250 ml) was added to it, cooled to 0° C. and dry oxygen gas was passed through the mixture for 5 hours. To the reaction mixture, 1N HCl (200 ml) was added, stirred for 10 minutes and the layers were separated. The aqueous layer was then extracted with ethyl acetate (300 ml). The organic layers were mixed, washed with brine (300 ml), dried over Na₂SO₄ and concentrated to give 24 gm of crude material which was then purified by column chromatography to give 7.0 gm of the title product as pale yellow solid, m. p: 137-140° C.

IR (KBr, cm⁻¹): 3191, 2927, 1580, 1453, 1329, 1238, 1029 and 755.

¹H NMR (300 MHz, CDCl₃, δ): 1.7-2.0 (m, 4H), 2.0-2.15 (m, 2H), 4.0 (t, J=12.0 Hz, 1H), 4.5 (d, J=12.0 Hz, 1H), 5.8-5.9 (d, J=12.0 Hz, 1H), 7.0-7.1 (t, J=8.4 Hz, 1H), 7.2 (t, J=6.4 Hz, 2H), 7.4 (t, J=6.1 Hz, 2H), 7.6-7.7 (d, J=8.1 Hz, 1H), 8.08-8.1 (d, J=8.4 Hz, 1H), 9.05 (s, 1H).

Intermediate 66: 1-methoxy
9-tetrahydro-2H-2-pyranyl-9H carbazole

To a stirred solution of intermediate 65 (3.0 gm, 11 mmoles) in dry DMF (45 ml), at 0° C., sodium hydride (60% suspension, 0.64 gm, 14 mnoles) was added in portions and the reaction mixture was stirred at room temperature for 1 hour. The reaction mixture was cooled to 0° C., methyl iodide (1.05 ml, 16 mmoles) was added to it dropwise and the mixture was stirred at room temperature for 1 hour. The reaction mixture was poured on to ice-water (100 ml), 1N HCl (50 ml) was added and extracted with ethyl acetate (2×75 ml). The organic layer was washed with water (3×50 ml) followed by brine (50 ml), dried over Na₂SO₄ and concentrated to give 3.4 gm of the title product as a thick liquid.

IR (Neat, cm⁻¹): 3400, 2927, 1579, 1455, 1440, 1336, 1262, 1040 and 743.

¹H NMR (300 MHz, CDCl₃, δ): 1.7-1.8 (m, 1H), 1.8-2.0 (m, 3H), 2.0-2.1 (m, 1H), 2.4-2.5 (m, 1H), 3.8 (t, J=11.0 Hz, 1H), 4.0 (s, 3H), 4.3 (d, J=12.0 Hz, 1H), 6.6-6.7 (d, J=12.0 Hz, 1H), 6.9-7.0 (d, J=7.5 Hz, 1H), 7.1-7.15 (t, J=7.5 Hz, 1H), 7.15-7.2 (t, J=7.5 Hz, 1H), 7.3-7.4 (t, J=8.4 Hz, 1H), 7.6-7.7 (d, J=7.5 Hz, 2H), 7.9-8.0 (d, J=8.4 Hz, 1H), 8.0-8.1 (d, J=8.4 Hz, 2H).

Intermediate 67: 1-Methoxy 9H-carbazole

To a stirred solution of intermediate 66 (3.4 gm, 12.08 mmoles) in THF (40 ml), 6N HCl (40 ml) was added and the reaction mixture was refluxed for 2 hours. Solvent was evaporated from the reaction mixture under reduced pressureor and extracted with ethyl acetate (2×40 ml). The organic layer was washed with brine (40 ml), dried over Na₂SO₄ and concentrated to give 2.9 gm of the title product as a thick liquid.

IR (Neat, cm⁻¹): 3422, 2925, 1579, 1456, 1258, 1024 and 743.

¹H NMR (300 MHz, DMSO-d₆, δ): 4.0 (s, 3H), 6.9-7.0 (d, J=7.5 Hz, 1H), 7.0-7.1 (d, J=7.5 Hz, 1H), 7.1-7.2 (t, J=6.9 Hz, 1H), 7.3-7.4 (t, J=6.0 Hz, 1H), 7,4-7.5 (t, J=8.1 Hz, 1H), 7.6-7.7 (d, J=7.8 Hz, 1H), 8.0 (d, J=7.5Hz, 1H), 11.2 (s, 1H)

Intermediate 68: 1-Methoxy 9H-9-carbazole
carbaldehyde

To a stirred solution of intermediate 67 (2.9 gm, 15.21 mmoles) in dry DMF (30 ml) at 0° C., phosphorous oxychloride (4.25 ml, 45.64 mmoles) was added dropwise and the reaction mixture was allowed to stir at room temperature for 30 min. The reaction mixture was poured in to water (50 ml) and extracted with ethyl acetate (3×50 ml). The organic layer was washed with water (3×50 ml) followed by brine (50 ml), dried over Na₂SO₄ and concentrated to give 2.5 gm of the title product as brown crystaline solid, m.p: 143-148° C. (dec).

IR (Neat, cm⁻¹): 3469, 3019, 1691, 1589, 1430, 1266, 1215 and 757.

¹H NMR (300 MHz, CDCl₃, δ): 4.0 (s, 3H), 7.0-7.1 (d, J=7.8 Hz, 1H), 7.3-7.4 (t, J=8.4 Hz, 1H), 7.4-7.5 (t, J=8.1 Hz, 1H), 7.5-7.6 (t, J=8.1 Hz, 1H), 7.6-7.7 (d, J=7.5 Hz, 1H), 7.9-8.0 (d, J=7.5 Hz, 1H), 8.6-8.7 (d, J=7.8 Hz, 1H), 10.3 (s, 1H)

Intermediate 69: 4-bromo-1-methoxy
9H-9-carbazole carbaldehyde

To a stirred solution of intermediate 68 (2.5 gm, 11.1 mmoles) in glacial acetic acid (25 ml) at 0° C., a solution of bromine (0.6 ml, 11.6 mmoles) in glacial acetic acid (10 ml) was added dropwise and the reaction mixture was stirred at the same temperature for 30 min. The reaction mixture was poured in to water (50 ml), stirred for 10 min. and the separated solid was filtered. The solid was washed with water (3×100 ml) and dried to give 3.1 gm of the title product as brown crystalline solid, m. p: 142-144° C. (dec).

IR (KBr, cm$^{-1}$): 3374, 2926, 1695, 1575, 1448, 1392, 1262, 1013 and 759.

$^1$H NMR (300 MHz, DMSO-d$_6$, δ): 4.0 (s, 3H), 7.2 (d, J=8.7 Hz, 1H), 7.5-7.6 (t, J=6.6 Hz, 1H), 7.6 (d, J=8.7 Hz, 1H), 7.6-7.7 (t, J=7.2 Hz, 1H), 8.6-8.7 (d, J=8.4 Hz, 1H), 8.7 (d, J=7.5 Hz, 1H), 10.2 (s, 1H).

Intermediate 70: 4-bromo-1-methoxy 9H-carbazole

To a stirred solution of intermediate 69 (0.6 gm, 1.97 mmoles) in ethanol (10 ml), aqueous 6M NaOH soln.(3.5 ml) was added and the reaction mixture was refluxed for 1 hour. Ethanol was evaporated from the reaction mixture under reduced pressure and extracted with ethyl acetate (2×30 ml). The organic layer was washed with water (2×20 ml), dried over Na$_2$SO$_4$ and concentrated to give 0.5 gm of the title product as a thick liquid.

IR (Neat, cm$^{-1}$): 3463, 2933, 2848, 1573, 1497, 1454, 1402, 1287, 1254, 1099, 1014 and 757.

$^1$H NMR (300 MHz, DMSO-d$_6$, δ): 4.0 (s, 3H), 6.9-7.0 (d, J=7.8 Hz, 1H), 7.2-7.3 (t, J=7.4 Hz, 1H), 7.3 (d, J=7.8 Hz, 1H), 7.4-7.5 (t, J=7.4 Hz, 1H), 7.5-7.6 (d, J=8.1 Hz, 1H), 8.5 (d, J=8.1 Hz, 1H), 11.7 (s, 1H).

Intermediate 71: 1-methoxy 9H-4-carbazole carbaldehyde

To a stirred solution of intermediate 70 (0.5 gm, 1.81 mmoles) in sodium dried ether (20 ml) at room temperature, 2.5M n-BuLi (5.43 mmoles) was added dropwise and the reaction mixture was stirred at the same temperature for 2 hours. The reaction mixture was cooled to 0° C. and dry DMF (0.42 ml, 5.43 mmoles) was added and the reaction mixture was stirred at room temperature for 2 hours. Ice pieces were added to the reaction mixture followed by 1N HCl (10 ml) and extracted with ethyl acetate (2×15 ml). The organic layer was washed with brine (15 ml), dried over Na$_2$SO$_4$ and concentrated to give 0.5 gm of crude material which was purified by column chromatography, to give 0.35 gm of the title compound as an off white solid, m. p: 173-177° C. (dec).

IR (KBr, cm$^{-1}$): 3246, 1657, 1553, 1290,-1167 and 739.

$^1$H NMR (300 MHz, DMSO-d$_6$, δ): 4.2 (s, 3H), 7.1-7.2 (d, J=6.0 Hz, 1H), 7.3 (d, J=8.1 Hz, 1H), 7.5 (t, =6.0 Hz, 1H), 7.6 (d, J=8.1 Hz, 1H), 7.9 (d, J=8.4 Hz, 1H), 9.0 (d, J=8.1 Hz, 1H), 10.2 (s, 1H), 11.8 (s, 1H).

Intermediate 72: 1-methoxy 9H-4-carbazole carboxylic acid

To a solution of intermediate 71 (0.3 gm, 1.333 mmoles) in a 2:1 mixture of acetone and water (15 ml) at 0° C., sulphamic acid (0.259 gm, 2.666 mmoles) was added followed by a solution of sodium chlorite (0.181 gm, 2.0 mmoles) in water (5 ml) and the reaction mixture was stirred at room temperature for 2 hours. Acetone was evaporated from the reaction mixture under reduced pressure and extracted with ethyl acetate (2×25 ml). The organic layer was washed with brine (25 ml), dried over Na$_2$SO$_4$ and concentrated to give 0.3 gm of crude material which was purified by column chromatography, to give 0.25 gm of the title compound as pale brown solid, m. p: 216-218° C. (dec).

IR (KBr, cm$^{-1}$): 3461, 2927, 1682, 1566, 1421, 1294, 1263, 1096, 1011 and 741.

$^1$H NMR (300 MHz, DMSO-d$_6$, δ): 4.21 (s, 3H), 7.0-7.1 (d, J=8.4 Hz, 1H), 7.1-7.2 (t, J=7.2 Hz, 1H), 7.4 (t, J=7.5 Hz, 1H), 7.5 (d, J=8.1 Hz, 1H), 7.8 (d, J=8.4 Hz, 1H), 8.9 (d, J=8.1 Hz, 1H), 11.6 (s, 1H), 12.6 (s, 1H).

Intermediate 73: 1-methoxy 9H-4-carbazole carboxylicacid methyl ester derivatives To a solution of intermediate 71 (0.3 gm, 1.333 mmoles) in a 2:1 mixture of acetone and water (15 ml) at 0° C., sulphamicacid (0.259 gm, 2.666 mmoles) was added followed by a solution of sodium chlorite (0.181 gm, 2.0 mmoles) in water (5 ml) and the reaction mixture was stirred at room temperature for 2 hours. Acetone was evaporated from the reaction mixture under reduced pressureor and extracted with ethyl acetate (2×25 ml). The organic layer was washed with brine (25 ml), dried over Na$_2$SO$_4$ and concentrated to give 0.3 gm of crude material which was suspended in dry chloroform (15 ml), under nitrogen atmosphere, thionyl chloride (0.3 ml, 4.0 mmoles) was added followed by two drops of dry DMF and the reaction mixture was stirred at room temperature for 2 hours. Dry methanol (15 ml) was added to the reaction mixture and continued the stirring for 10 min. The reaction mixture was adsorbed on silica gel and purified by column chromatography to get the desired products as given below.

Intermediate 73a: 1-methoxy 9H-4-carbazole carboxylicacid methyl ester

IR (KBr, cm$^{-1}$): 3326, 2927, 1694, 1623, 1569, 1434, 1299, 1262, 1012, 753 and 646.

$^1$H NMR (300 MHz, DMSO-d$_6$, δ): 3.94 (s, 3H), 4.065 (s, 3H), 7.063-7.091 (d, J=8.4 Hz, 1H), 7.112-7.165 (t, J=7.5 Hz, 1H), 7.377-7.427 (t, J=7.5 Hz, 1H), 7.510-7.537 (d, J=8.1 Hz, 1H), 7.8-7.83 (d, J=8.4 Hz, 1H), 8.77-8.8 (d, J=8.1 Hz, 1H), 11.69 (s, 1H).

Intermediate 73b: 6 chloro-1-methoxy 9H-4-carbazole carboxylicacid methyl ester $^1$H NMR (300 MHz, DMSO-d$_6$, δ): 3.94 (s, 3H), 4.07 (s, 3H), 7.11-7.138 (d, J=8.1 Hz, 1H), 7.419-7.455 (d, J=10.8 Hz, 1H), 7.52-7.547 (d, J=7.5 Hz, 1H), 7.86-7.887 (d, J=8.4 Hz, 1H), 8.894-8.901 (d, J=2.1 Hz, 1H), 11.91 (s, 1H).

Intermediate 73c: 8 chloro-1-methoxy 9H-4-carbazole carboxylicacid methyl ester $^1$H NMR (300 MHz, DMSO-d$_6$, δ): 3.94 (s, 3H), 4.08 (s, 3H), 7.13-7.19 (m, 2H), 7.49-7.52 (d, J=9.0 Hz, 1H), 7.86-7.887 (d, J=8.4 Hz, 1H), 8.763-8.79 (d, J=8.1 Hz, 1H), 11.79 (s, 1H).

Intermediate 74: 1-ethoxy 9-tetrahydro-2H-2-pyranyl-9H-carbazole

To a stirred solution of intermediate 65 (3.0 gm, 11 mmoles) in dry DMF (45 ml), at 0° C., sodium hydride (60% suspension, 0.64 gm, 14 mmoles) was added in portions and the reaction mixture was stirred at room temperature for 1 hour. The reaction mixture was cooled to 0° C., ethyl iodide (1.05 ml, 16 mmoles) was added to it dropwise and the mixture was stirred at room temperature for 1 hour. The reaction mixture was poured on to ice-water (100 ml), 1N HCl (50 ml) was added and extracted with ethyl acetate (2×75 ml). The organic layer was washed with water (3×50 ml) followed by brine (50 ml), dried over Na$_2$SO$_4$ and concentrated to give 3.4 gm of the title product as a thick liquid.

IR (Neat, cm$^{-1}$): 3400, 2927, 1579, 1455, 1440, 1336, 1262, 1040 and 743. $^1$H NMR (300 MHz, CDCl$_3$, δ): 1.7-1.8 (m, 1H), 1.8-2.0 (m, 3H), 2.0-2.1 (m, 1H), 2.4-2.5 (m, 1H), 3.8 (t, J=11.0 Hz, 1H), 4.0 (s, 3H), 4.3 (d, J=12.0 Hz, 1H), 6.6-6.7 (d, J=12.0 Hz, 1H), 6.9-7.0 (d, J=7.5 Hz, 1H), 7.1-7.15 (t, J=7.5 Hz, 1H), 7.15-7.2 (t, J=7.5 Hz, 1H), 7.3-7.4 (t, J=8.4 Hz, 1H), 7.6-7.7 (d, J=7.5 Hz, 2H), 7.9-8.0 (d, J=8.4 Hz, 1H), 8.0-8.1 (d, J=8.4 Hz, 2H).

Intermediate 75: 1-ethoxy 9H-carbazole

To a stirred solution of intermediate 74 (6.2 gm, 20.99 mmoles) in THF (30 ml), 6N HCl (30 ml) was added and the reaction mixture was refluxed for 3 hours. Solvent was evaporated from the reaction mixture under reduced pressure and extracted with ethyl acetate (3×40 ml). The organic layer was washed with brine (40 ml), dried over Na$_2$SO$_4$ and concentrated to give 4.4 gm of the title product as a thick liquid.

IR (Neat, cm$^{-1}$): 669, 755, 929, 1039, 1215, 1257, 1389, 1456, 1507, 1581, 2400, 2942, 3019, and 3473.

$^1$H NMR (300 MHz, DMSO-d$_6$, δ): 1.714-1.763 (t, J=6.9 Hz, 3H), 4.194-4.262 (q, J=6.9 Hz 2H), 6.918-6.943 (d, J=7.5 Hz, 1H), 7.009-7.060 (t, J=7.7 Hz, 1H), 7.076-7.126 (t, J=7.3 Hz, 1H), 7.297-7.351 (t, J=7.4 Hz, 1H), 7.456-7.482 (d, J=7.8 Hz, 1H), 7.628-7.654 (d, J=7.8 Hz, 1H), 8.009-8.033 (d, J=7.2 Hz, 1H), 11.153 (s, 1H).

Intermediate 76: 1-ethoxy 9H-9-carbazole carbaldehyde

To a stirred solution of intermediate 75 (4.4 gm, 20.83 mmoles) in dry DMF (30 ml) at 0° C., phosphorous oxychloride (5.9 ml, 62.50 mmoles) was added dropwise and the reaction mixture was allowed to stir at room temperature for 30 min. The reaction mixture was poured in water (50 ml) and extracted with ethyl acetate (3×50 ml). The organic layer was washed with water (3×50 ml) followed by brine (50 ml), dried over Na$_2$SO$_4$ and concentrated to give 5.5 gm of the title product as brown crystalline-solid, IR (Neat, cm$^{-1}$): 652, 753, 953, 1037, 1160, 1220, 1266, 1308, 1335, 1357, 1404, 1428, 1452, 1591, 1693, 1723, and 2936.

$^1$H NMR (300 MHz, DMSO-d$_6$, δ): 1.451-1.496 (t, J=6.9 Hz, 3H), 4.263-4.332 (q, J=6.9 Hz 2H), 7.212-7.237 (d, J=7.5 Hz, 1H), 7.331-7.355 (t, J=7.8 Hz, 1H, 7.417-7.471 (t, J=7.7 Hz, 1H), 7.502-7.557 (t, J=7.5 Hz, 1H), 7.760-7.788 (d, J=7.9 Hz, 1H), 8.139-8.165 (d, J=7.8 Hz, 1H), 8.503-8.530 (d, J=8.1 Hz, 1H), 10.204 (s, 1H).

Intermediate 77: 4-bromo-1-ethoxy 9H-9-carbazole carbaldehyde

To a stirred solution of intermediate 76 (5.5 gm, 23 mmoles) in glacial acetic acid (30 ml) at 0° C., a solution of bromine (1.3 ml, 25.29 mmoles) in glacial acetic acid (15 ml) was added dropwise and the reaction mixture was stirred at the same temperature for 30 min. The reaction mixture was poured in water (60 ml), stirred for 10 min. and the separated solid was filtered. The solid was washed with water (3×100 ml) and dried to give 6.2 gm of the title product as brown crystalline solid.

IR (Neat, cm$^{-1}$): 671, 772, 1020, 1096, 1219, 1246, 1316, 1384, 1594, 2928, and 3368.

$^1$H NMR (300 MHz, DMSO-d$_6$, δ): 1.449-1.495 (t, J=6.9 Hz, 3H), 4.267-4.337 (q, J=6.9 Hz 2H), 7.193-7.222 (d, J=8.7 Hz, 1H), 7.495-7.654 (m, 3H), 8.600-8.628 (d, J=8.4 Hz, 1H), 8.667-8.691 (d, J=7.2 Hz, 1H), 10.244 (s, 1H).

Intermediate 78: 4-bromo-1-ethoxy 9H-carbazole

To a stirred solution of intermediate 77 (6.2 gm, 19.48 mmoles) in ethanol (30 ml), aqueous 6M NaOH soln.(3.5 ml) was added and the reaction mixture was refluxed for 1 hour. Ethanol was evaporated from the reaction mixture under reduced pressure and extracted with ethyl acetate (3×30 ml). The organic layer was washed with water (2×20 ml), dried over Na$_2$SO$_4$ and concentrated to give 1.7 gm of the title product as a thick liquid.

IR (KBr, cm$^{-1}$): 489, 566, 628, 663, 715, 731, 748, 792, 800, 1039, 1093, 1108, 1207, 1229, 1254, 1286, 1326, 1387, 1409, 1451, 1474, 1487, 1571, 2976, and 3378.

$^1$H NMR (300 MHz, DMSO-d$_6$, δ): 1.443-1.490 (t, J=6.9 Hz, 3H), 4.208-4.278 (q, J=6.9 Hz 2H), 6.902-6.930 (d, J=8.4 Hz, 1H), 7.175-7.243 (m, 2H), 7.403-7.453 (t, J=7.3 Hz, 1H), 7.529-7.555 (d, J=7.8 Hz, 1H), 8.494-8.522 (d, J=8.4 Hz, 1H), 11.554 (s, 1H).

Intermediate 79: 1-ethoxy 9H-4-carbazole carbaldehyde

To a stirred solution of intermediate 78(1.5 gm, 5.169 mmoles) in sodium dried ether (30 ml) at room temperature, 2.5M n-BuLi (41.35 mmoles) was added dropwise and the reaction mixture was stirred at the same temperature for 2 hours. The reaction mixture was cooled to 0° C. and dry DMF (3.20 ml 41.35 mmoles) was added and the reaction mixture was stirred at room temperature for 2 hours. Ice pieces were added to the reaction mixture followed by 1N HCl (10 ml) and extracted with ethyl acetate (3×15 ml). The organic layer was washed with brine (15 ml), dried over Na$_2$SO$_4$ and concentrated to give 0.9 gm of crude material which was purified by column chromatography, to give 0.75 gm of the title compound as an off white solid.

IR (KBr, cm$^{-1}$): 505, 566, 578, 633, 667, 710, 740, 777, 788, 882, 944, 1029, 1052, 1106, 1191, 1271, 1292, 1325, 1325, 1391, 1419, 1456, 1469, 1552, 1609, 1623, 1658, 2870, 2931, 2957 and 3197.

$^1$H NMR (300 MHz, DMSO-d$_6$, δ): 1.500-1.547 (t, J=7.0 Hz, 3H), 4.374-4.442 (q, J=6.9 Hz 2H), 7.143-7.230 (m, 2H), 7.409-7.464 (t, J=7.7 Hz, 1H), 7.557-7.585 (d, J=8.4 Hz, 1H), 7.799-7.825 (d, J=7.8 Hz, 1H), 8.993-9.021 (d, J=8.4 Hz, 1H), 10.144 (s, 1H), 11.713 (s, 1H).

Intermediate 80: Methyl-1-ethoxy-9H-4-carbazolecarboxylate derivatives

To a solution of intermediate 79 (0.75 gm, 3.318 mmoles) in a 2:1 mixture of acetone and water (15 ml) at 0° C., sulphamic acid (0.61 gm, 6.276 mmoles) was added followed by a solution of sodium chlorite (0.43 gm, 4.707 mmoles) in water (5 ml) and the reaction mixture was stirred at room temperature for 2 hours. Acetone was evaporated from the reaction mixture under reduced pressureor and extracted with ethyl acetate (2×25 ml).The organic layer was washed with brine (25 ml), dried over Na$_2$SO$_4$ and concentrated to give 0.81 gm of material containing mixture of expected compound and its 6-chloro substituted isomer. To a solution of above mixture (0.8 gm) in dry chloroform (15 ml) thionyl chloride (0.69 ml,) was introduced followed by two drops of dry DMF at 25° C. under anhydrous conditions. After complete conversion of acid to acid chloride, methanol (15 ml) was added to the reaction mixture at 25° C., under nitrogen atmosphere, the reaction mixture was stirred for 15 min. The reaction mixture was adsorbed on silica gel and purified by column chromatography to yield methyl-1-ethoxy-9H-1carbazolecarboxylate (475 mg) as a brown solid and methyl-6-chloro-1-ethoxy-9H-4-carbazolecarboxylate (91 mg) as a brown solid.

Intermediate 80a:
Methyl-1-ethoxy-9H-4-carbazolecarboxylate

IR (KBr, cm$^{-1}$): 491, 524, 595, 637, 743, 758, 779, 953, 1043, 1095, 1127, 1141, 1202, 1228, 1260, 1281, 1308, 1359, 1389, 1406, 1438, 1485, 1513, 1566, 1608, 1621, 1677, 2971 and 3403.
$^1$H NMR (300 MHz, DMSO-d$_6$, δ): 1.479-1.524 (t, J=6.9 Hz, 3H), 3.930 (s, 3H), 4.309-4.377 (q, J=6.9 Hz, 2H), 7.042-7.071 (d, J=8.7 Hz, 1H), 7.107-7.157 (t, J=7.5 Hz, 1H), 7.375-7.425 (t, J=7.5 Hz, 1H), 7.533-7.559 (d, J=7.8 Hz, 1H), 7.778-7.807 (d, J=8.7 Hz, 1H), 8.763-8.790 (d, J=8.1 Hz, 1H), 11.564 (s, 1H).

Intermediate 80b:
Methyl-6-chloro-1-ethoxy-9H-4-carbazolecarboxylate

IR (KBr, cm$^{-1}$): 466, 569, 638, 725, 745, 774, 801, 886, 917, 970, 1026, 1043, 1065, 1104, 1120, 1135, 1184, 1197, 1223, 1259, 1309, 1361, 1390, 1429, 1444, 1459, 1569, 1612, 1725, 2930, 2973, and 3418.
$^1$H NMR (300 MHz, DMSO-d$_6$, δ): 1.475-1.522 (t, J=6.9Hz, 3H), 3.932 (s, 3H), 4.317-4.387 (q, J=6.9 Hz, 2H), 7.089-7.117 (d, J=8.4 Hz, 1H), 7.417-7.453 (dd,J=8.6 Hz, 1H), 7.544-7.573 (d,J=8.7 Hz, 1H), 7.836-7.864 (d, J=8.4 Hz, 1H), 8.891-8.897 (d, J=1.8 Hz, 1H), 11.781 (s, 1H).

Intermediate 81: Methyl-6-chloro-9-(4-fluorobenzyl)-1-methoxy-9H-4-carbazole carboxylate To a solution of intermediate 73b (500 mg 1.727mmoles) in dry DMF (10 ml), under N$_2$ atmosphere, 60% sodium hydride (113.05 mg, 2.591 mmoles) was added at 0° C. and the reaction mixture was stirred at 0° C. for 15 min and at 25° C. for 30 min. then 4-fluorobenzyl bromide (0.22 ml, 1.727 mmoles) was added to the reaction mixture at 0° C., stirred for 15 min at 0° C. and then at 25° C. for 1 hr. The reaction mixture was poured into ice-cold water and acidified with 1N HCl. The compound was extracted with ethyl acetate (2×10 ml), combined the organic layers and washed with water (10 ml) and with brine (10 ml). The organic layer was dried over anhydrous sodium sulphate and concentrated to yield 396 mg of the title compound as creamish solid.
$^1$HNMR(300 MHz,DMSO-d$_6$, δ): 3.943 (s, 3H), 3.968 (s, 3H), 5.932 (s, 2H), 7.045-7.078 (m, 4H), 7.156-7.183 (d, J=8.1 Hz, 1H), 7.481-7.516 (dd, J=8.7 Hz, 1H), 7.705-7.734 (d, J=8.7 Hz, 1H), 7.853-7.880 (d, J=8.1 Hz, 1H), 8.902-8.910 (d, J=2.4 Hz, 1H), Intermediate 82: 6-Chloro-9-(4-fluorobenzyl)-1-methoxy-9H-4-carbazole carboxylic acid To a solution of intermediate 81 (394 mg 0.991mmoles) in 5 mL methanol, 5 mL of 50% sodium hydroxide solution was added and refluxed overnight. Methanol from the reaction mixture was evaporated under reduced pressure, and aqueous layer was acidified with 1N HCl and filtered to yield 324 mg of title compound as off-white solid.

$^1$HNMR(300 MHz,DMSO-d$_6$, δ): 3.961 (s, 3H), 5.931 (s, 2H), 7.049-7.078 (m, 4H), 7.135-7.163 (d, J=8.4 Hz, 1H), 7.469-7.498 (dd, J=8.7 Hz, 1H), 7.687-7.716 (d, J=8.7 Hz, 1H), 7.846-7.874 (d, J=8.4 Hz, 1H), 8.992-8.998 (d, J=1.8 Hz , 1H),

Intermediate 83: 4-Hydroxydibenzothiophene n-Butyllithium (26.25 g, 406 mmols, 175 ml of 2.4M solution in hexane) was added to a stirred solution of dibenzothiophene (25 g, 135.7 mole) in dry THF (200 ml) at 0° C. over a period of 1 hr under dry N$_2$ atmosphere. This reaction mixture was stirred overnight at room temperature and dry oxygen gas was bubbled into the reaction mixture over 5 hrs. This reaction mixture was poured slowly over cold 1N HCl (500 ml). The organic layer was separated and the aqueous layer was extracted with ethyl acetate (3×500 ml). Organic layers were mixed together and concentrated to dryness to get crude product (32 g). The crude product was purified by silica gel column chromatography.
Yield: 9 g (33%). As light brown colour solid.
$^1$H-NMR. (CDCl$_3$, 300 MHz, TMS, δ): 5.30 (s, 1H), 6.90 (d, 1H), 7.40 (t, 1H), 7.50 (m, 2H), 7.80 (d, 1H), 7.85 (m, 1H) and 8.22 (m, 1H).

Intermediate 84: 4-methoxydibenzothiophene

To a solution of intermediate 83 (1.2 g, 6 mmols) in dry acetone (10 ml) was added K$_2$CO$_3$ (1.65 g, 12 mmols) followed by dimethyl sulphate (1.5 g, 12 mmols) and the reaction mixture was refluxed for 6 h and stirred overnight at room temperature to complete the reaction. The reaction mixture was diluted with water and extracted with ethyl acetate. Ethyl acetate layer was washed with water, brine, dried over sodium sulphate and concentrated to get the crude product which was purified by silica gel column chromatography as light yellow colored solid.
Yield: 0.88 g (68.75%).
$^1$H-NMR: (CDCl$_3$, 300 MHz, TMS, δ): 4.03 (s, 3H), 6.92 (d, 1H), 7.24-7.45 (mixed, 3H), 7.78 (d, 1H) 7.87 (m, 1H), 8.12 (m, 1H).

Intermediate 85:
1-bromo4-methoxydibenzothiophene

To a solution of intermediate 84 (0.88 g, 4.1 mmols) in glacial acetic acid (40 ml) was added dropwise a solution of bromine (0.66 g, 4.1 mmols) in acetic acid (10 ml) at room temperature. After 1 hr reaction mixture was poured into ice cold water. The precipitated product was filtered and dried. Crude product was purified by silica gel column chromatography to get a white solid
Yield: 0.88 g (73%),mp.: 108-110° C.
$^1$HNMR: (CDCl$_3$, 300 MHz, TMS, δ): 4.02 (s, 3H), 6.77 (d, 1H), 7.50 (m, 2H), 7.55 (d, 1H), 7.88 (m, 1H), 9.17 (m, 1H).

Intermediate 86:
4-methoxydibenzothiophene-1-carboxylic acid n-Butyllithuim (3.4 mmoles, 1.45 ml of 2.4M solution in hexane) was added to a solution of intermediate 85 (0.8 g, 2.7mmols) in dried ether(30 ml) at 0° C. under N$_2$ atmosphere. After 20 minutes dry CO$_2$ was bubbled into the reaction mixture at the same temperature for 1 hr period. The reaction mixture was poured in ice cooled 1N HCl (100 ml) and extracted with ethyl acetate. The ethyl acetate layer was washed with 5% NaHCO₃ solution (50 ml). The NaHCO₃ layer was then acidified with 1N HCl, white precipitate thus obtained was washed with water and dried to get the pure product Yield: 0.41 g (60%), m.p.: 248-249° C.

¹H-NMR: (CDCl₃, 300 MHz, TMS, δ): 4.11 (s, 3H), 6.94 (d, 1H), 7.25-750 (m, 2H), 7.90 (dd, 1H), 8.15 (d, 1H), 8.92 (dd, 1H).

Intermediate 87: Methyl 4-methoxydibenzothiophene-1-carboxylate

To a solution of intermediate 86 (1.5 g, 5.8 mmols) in dry benzene (25 ml) was added a drop of dry DMF and oxalylchloride (0.75 ml, 8.7 mmols) under N₂ atmosphere. This reaction mixture was stirred overnight at room temperature. To the reaction mixture dry methanol (5 ml) was added and reaction mixture refluxed for 0.5 h. The reaction mixture was concentrated to dryness to get crude product which was purified by silica gel column chromatography using ethyl acetate and petroleum ether gradient Yield: 1.42 gm 1H-NMR: (CDCl₃, 300 MHz, TMS, δ): 4.075 (s, 3H), 4.04 (s, 3H), 6.9 (d, 1H), 7.2-75 (m, 2H), 7.90 (d, 2H), 8.6 (d, 1H).

Intermediate 88: 4-cyclopentyloxydibenzothiophene

To a solution of intermediate 83 (2 g, 9.98 mmols) in dry DMF (10 ml) potassium carbonate (2.8 g, 20 mmols) and cyclopentyl bromide (3.72 g, 25 mmols) was added under nitrogen atmosphere. This reaction mixture was heated at 80° C. for 5 h to complete the reaction. The reaction mixture was quenched with water and extracted with ethyl acetate to get the crude product which was purified by silica gel column chromatography as sticky solid.

Yield: 1.45 g (54%)

¹H-NMR: (CDCl₃, 300 MHz TMS, δ): 1.62-1.70 (m, 2H), 1.80-2.10 (m, 6H), 5.00 (m, 1H), 6.90 (d, 1H), 7.30-7.45 (mixed, 3H), 7.72 (d, 1H), 7.85 (m, 1H) and 8.11 (m, 1H).

Intermediate 89: 1-bromo-4-cyclopentyloxydibenzothiophene

To a solution of intermediate 88 (1.4 g, 5.21 mmols) in glacial acetic acid (40 ml) was added dropwise a solution of bromine (0.26 ml, 5.21 mmols) in acetic acid (20 ml) at room temperature. After 1 hr reaction mixture was poured into ice cold water. The precipitated product was filtered and dried. Crude product was purified by silica gel column chromatography to get a white solid Yield: 1.7 g (77%), white solid, m.p.: 110-112° C.

¹H-NMR: (CDCl₃, 300 MHz, TMS, δ): 1.65-1.70 (m, 2H), 1.82-2.00 (m, 6H), 4.96 (m, 1H), 6.77 (d, 1H), 7.45-7.50 (m, 2H), 7.54 (d, 1H), 7.85 (m, 1H) and 9.15 (m, 1H).

Intermediate 90: 4-cyclopentyloxydibenzothiophene-1-carboxylic acid n-Butyllithuim (3.4 mmoles, 1.45 ml of 2.4M solution in hexane) was added to a solution of intermediate 89 (1 g, 2.87 mmols) in dry ether(30 ml) at 0° C. under N₂ atmosphere. After 20 minutes dry CO₂ was bubbled into the reaction mixture at the same temperature for 1 hr period. The reaction mixture was poured in ice cooled 1 N HCl (100 ml) and extracted with ethyl acetate. The ethyl acetate layer was washed with 5% NaHCO₃ solution (50 ml). The NaHCO₃ layer was then acidified with 1N HCl, white precipitate thus obtained was washed with water and dried to get the pure product Yield: 0.52 g, (58%), white solid, m.p.: 205-206° C.

¹H-NMR: (CDCl₃+1drop DMSO-d₆, 300 MHz, TMS, δ): 1.50-1.60 (m, 2H), 1.69-1.80 (m, 6H), 4.88 (m, 1H), 6.72 (d, 1H), 7.19-7.3 (m, 2H), 7.65-7.68 (dd, 1H), 7.76 (d, 1H), and 8.67 (m, 1H).

Intermediate 91: 4-ethoxy dibenzothiophene

Sodium hydride (50% dispersion, 0.24 g, 0.01 moles, 1 eq) was added to a solution of intermediate 83 (2 g, 0.01 moles, 1 eq) in 10 ml of (dry) DMF at 0° C. for 30-35 minutes and ethyl iodide (3.2 g, 0.02 moles) was added. The reaction mixture was stirred 2 hours at room temperature then the reaction quench with ethyl acetate and washed with water, brine. The organic layer on concentration gave a crude product which was purified by silica gel column chromatography.

Yield: 2 g,

IR (KBr, cm−1): 3685, 3400, 3067, 3019, 2986, 2932, 2400, 1906, 1601, 1570, 1459, 1485, 1475, 1442, 1392, 1306, 1322, 1263, 1216, 1087, 1119, 1052, 755 and 669.

¹H-NMR(CDCl₃, 300 MHz, TMS, δ): 1.52 (t, 3H), 4.25 (q, 2H), 6.88 (d, 1H), 7.34-7.45 (mixed, 3H), 7.73 (d, 1H), 7.82-7.88 (m, 1H), 8.07-8.12 (m, 1H)

Intermediate 92: 1-bromo-4-ethoxy dibenzothiophene

To a solution of intermediate 91 (1.7 g, 7.45 mmols) in glacial acetic acid (40 ml) was added dropwise a solution of bromine (0.38 ml, 7.45 mmols) in acetic acid (10 ml) at room temperature. After 1 hr reaction mixture was poured into ice cold water. The precipitated product was filtered and dried. Crude product was purified by silica gel column chromatography to get a yellow solid. Yield : 2 g, IR (KBr, cm−1): 3330, 2970, 2882, 1557, 1471, 1433, 1394, 1360, 1309, 1294, 1250, 628

¹H-NMR (CDCl₃, 300 MHz, TMS, δ): 1.53 (t, 3H), 4.25 (q, 2H), 6.75 (d, 1H), 7.47-7.50 (m, 2H), 7.56 (d, 1H), 7.85-7.88 (m, 1H), 9.14-9.17 (m, 1H)

Intermediate 93: 4-ethoxy dibenzo thiophene 1-carboxylic acid n-Butyllithuim (6.5 mmols, 2.78 ml of 2.4 M in hexane) was added to a solution of intermediate 92 (1.98 g, 6.51 mmols) in dried ether(30 ml) at 0° C. under N₂ atmosphere. After 20 minute dry CO₂ was bubbled into the reaction mixture at the same temperature for 1 hr period The reaction mixture was poured in ice cooled 1N HCl (100 ml) and extracted with ethyl acetate. The ethyl acetate layer was washed with 5% NaHCO₃ solution (50 ml). The NaHCO₃ layer was then acidified with 1N HCl, white precipitate thus obtained was washed with water and dried to get the pure product.

Yield: 0.7 g, white solid

IR (KBr, cm−1): 3069, 2937, 2978, 2682, 1683, 1583, 1553, 1442, 1392, 1295, 1238, 1271, 1163, 1129, 1116, 1066, 756, 703, 643, 518.

¹H-NMR (DMSO, 300 MHz, TMS, δ): 1.47 (t, 3H), 4.37 (q, 2H), 7.18 (d, 1H), 7.46-7.58 (m, 2H), 7.87 (d, 1H), 8.07 (d, 1H), 8.69 (d, 1H)

Intermediate 94: 4-benzyloxydibenzothiophene sodium hydride (50% dispersion, 0.24 g, 0.01 moles, 1 eq) was added to a solution of intermediate 83 (2 g, 9.9 mmols) in 10 ml of (dry)DMF at 0° C. for 30-35 minutes and benzyl bromide (1.88 g, 9.9 mmols) was added. The reaction mixture was stirred 2 hours at room temperature then the reaction quenched with ethyl actate and washed with water, brine. The organic layer on concentration gave a crude product which was purified by silica gel column chromatography.

Yield: 2.6 g,
$^1$H-NMR(CDCl$_3$, 300 MHz, TMS, δ): 5.29 (s, 2H), 6.94 (d, 1H), 7.31-7.50 (mixed, 8H), 7.75 (d, 1H), 7.85 (m, 1H) and 8.11 (m, 1H)

Intermediate 95: 1-bromo-4-benzyloxy dibenzothiophene

To a solution of intermediate 94 (2.6 g, 8.96 mmols) in glacial acetic acid (40 ml) was added dropwise a solution of bromine (0.46 ml, 8.96 mmols) in acetic acid (10 ml) at room temperature. After 1 hr reaction mixture was poured into ice cold water. The precipitated product was filtered and dried. Crude product was purified by silica gel column chromatography to get a white solid.

Yield: 2.6 g,
$^1$H-NMR (CDCl$_3$, 300 MHz, TMS, δ): 5.28 (s, 2H), 6.79 (d, 1H), 7.32-7.39 (m, 3H), 7.45-7.52 (mixed, 5H), 7.86 (m, 1H) and 9.15 (m, 1H)

Intermediate 96: 4-benzyloxydibenzo thiophene-1-carboxylic acid n-Butyllithuim (5.4 mmols, 2.31 ml of 2.4M in hexane) was added to a solution of intermediate 95 (2 g, 5.42 mmols) in dried ether(30 ml) at 0° C. under N$_2$ atmosphere. After 20 minute dry CO$_2$ was bubbled into the reaction mixture at the same temperature for 1 hr period. The reaction mixture was poured in ice cooled 1N HCl (100 ml) and extracted with ethyl acetate. The ethyl acetate layer was washed with 5% NaHCO$_3$ solution (50 ml). The NaHCO$_3$ layer was then acidified with 1N HCl, white precipitate thus obtained was washed with water and dried to get the pure product Yield 0.5 g,
$^1$H-NMR (CDCl$_3$, 300 MHz, TMS, δ): 5.38 (s, 2H), 6.96 (d, 1H), 7.34-7.43 (mixed, 7H), 7.88 (d, 1H), 8.07 (d, 1H) and 8.89 (d, 1H)

Intermediate 97: 4-Ethyldibenzothiophene n-Butyllithium (108 mmols, 46 ml of 2.4M solution in hexane) was added to a stirred solution of dibenzothiophene (10 g, 54 mmole) in dried THF (150 ml) at 0° C. over a period of 1 hr under dry N$_2$ atmosphere. This reaction mixture was stirred 5 hrs at room temperature then the reaction mixture was cooled to −70° C. and a solution of ethyl iodide in dry THF was added dropwise and stirred at room temperature for over night. This reaction mixture was poured slowly into a cold 1N HCl (200 ml). Organic layer was separated and the aqueous layer was extracted with ethyl acetate (3×500 ml). Organic layers mixed together and concentrated to dryness to get crude product. The crude product was purified by silica gel column chromatography.

Yield: 9.72 g (84.81%) as off white solid.
$^1$H-NMR (DMSO, 300 MHz, TMS, δ): 1.34 (t, 3H), 2.87 (q, 2H), 7.37 (d, 1H), 7.44-7.52 (mixed, 3H), 8.02 (m, 1H), 8.19 (d, 1H) and 8.33 (m, 1H).

Intermediate 98: 6-Ethyl-4-Hydroxydibenzothiophene n-Butyllithium (18.8 mmols, 8.04 ml of 2.4M solution in hexane) was added to a stirred solution of intermediate 97 (2 g, 9.4 mmole) in dried THF (30 ml) at 0° C. over the period of 30 minuted under dry N$_2$ atmosphere. This reaction mixture was stirred overnight at room temperature and dry oxygen gas bubbled in the reaction mixture over 5 hrs. This reaction mixture was poured slowly to the cold 1N HCl (50 ml). Organic layer was separated and the aqueous layer was extracted with ethyl acetate (3×50 ml).

Organic layers mixed together and concentrated to dryness to get crude product (32 g). The crude product was purified by silica gel column chromatography.

Yield: 0.5 g (23%). As light yellow color solid.
$^1$H-NMR: (CDCl$_3$, 300 MHz, TMS, δ): 1.42 (t, 3H), 2,95 (q, 2H), 5.32 (s, 1H), 6.86 (d, 1H), 7.29 (mixed, 2H), 7.41 (t, 1H), 7.75 (d, 1H), 7.97 (d, 1H)

Intermediate 99: 6-Ethyl-4-methoxy-dibenzothiophene

Sodium hydride (50% dispersion, 0.06 g, 2.60 mmols) was added to a solution of intermediate 98 (0.5 g, 2.2 mmols) in 10 ml of (dry)DMF at 0° C. for 30-35 minute and methyl iodide (0.62 g, 4.3 mmols) was added. The reaction mixture was stirred for 4 h at room temperature then the reaction quenched with ethyl acetate and washed with water, brine which on concentration gave crude product which was purified by silica gel column chromatography.

Yield. 0.5 g (97%), off white solid
$^1$H-NMR(CDCl$_3$, 300 MHz, TMS, δ): 1.41 (t, 3H), 2.95 (q, 2H), 4.03 (s, 3H), 6.90 (d, 1H), 7.28 (d, 1H), 7.37-7.45 (m, 2H), 7.74 (d, 1H), 7.97 (d, 1H),

Intermediate 100: 6-Ethyl-4-methoxy-dibenzothiophene-1-carbaldehyde

To a solution of intermediate 99 (0.15 g, 0.61 mmols) in dry dichloromethane (10 ml) was added SnCl$_4$ (0.1 g, 0.418 mmols) followed by dropwise addition of a solution of dichloro(methoxy)methane (0.05 g, 0.478 mmols) in dichlomethane (5 ml) at 0° C. After addition the reaction mixture was stirred at 0° C. for 1 hr. The reaction mixture was diluted with water and extracted with chloroform which on concentration gave a crude product which was purified by silica gel column chromatography.

Yield: 009 g (52%) white solid
$^1$H-NMR(CDCl$_3$, 300 Mz, TMS, δ): 1.43 (t, 3H), 2.98 (q, 2H), 4.13 (s, 3H), 7.02 (d, 1H), 7.37 (d, 1H), 7.47 (t, 1H), 7.99 (d, 1H), 8.96 (d, 1H) and 10.51 (s, 1H)

Intermediate 101: 6-Ethyl-4-methoxy-dibenzothiophene-1-carboxylic acid

To a mixture of the intermediate 100 (0.08 g, 0.29 mmols) in acetone-water (2:1, 50 ml) was added sulphamic acid (0.043 g, 0.44 mmols) followed by addition of sodium chlorite (0.04 g, 0.44 mmols) in 4 portions at 0° C. The reaction mixture was stirred at room temperature for 3 hrs. Acetone was evaporated and reaction mixture was extracted with ethylacetate. Ethyl acetate layer on concentration gave crude product which was purified by silica gel column chromatography.

Yield: 0.05 g (62%) white solid
$^1$H-NMR(CDCl$_3$, 300 MHz, TMS, δ): 1.43 (t, 3H), 2.97 (q, 2H), 4.11 (s, 3H), 6.92(d, 1H), 7.33 (d, 1H), 7.42 (t, 1H), 8.11 (d, 1H) and 8.73 (d, 1H).

Intermediate 102: Methyl 4-hydroxydibenzothiophene 1-carboxylate

Pieces of dry aluminium foil (0.039 g, 1.44 mmols) and Iodine (0.59 g, 4.6 mmols) were refluxed in CS$_2$ till the disappearance of iodine colour. To this solution a solution of intermediate 87 (0.2 g, 0.7 mmols) in CS$_2$ was added dropwise at room temperature with stirring. After addition reaction mixture was refluxed for 1 hr then cooled reaction mixture was poured on crushed ice and extracted with ethyl acetate. Ethyl acetate layer on concentration gave crude product which was purified by silica gel column chromatography.

Yield: 0.17 g (93%), white solid.

$^1$H-NMR: (CDCl$_3$, 300 Mz, TMS, δ): 4.04 (s, 3H), 5.91 (br s, 1H), 6.84 (d, 1H), 7.40-7.50 (p, 2H), 7.77 (d, 1H), 7.87 (d, 1H), and 8.59 (d, 1H)

Intermediate 103: Methyl 4-difluromethoxydibenzothiophene-1-carboxylate

To a solution of intermediate 102 (0.2 g, 4.16 mmols) in dry DMF, NaH (0.2 g 50% dispersion in oil, 4.16 mmols) was added at 0° C. and stirred for 30 min. at 50° C. To this reaction mixture CHF$_2$Cl gas was passed for 2 hrs at room temperature. The reaction mixture was diluted with water and extracted with ethyl acetate. Ethyl acetate layer on concentration gave crude product which was purified on silica gel column chromatography.

Yield: 0.15 g (70%)

$^1$H-NMR. (CDCl$_3$, 300 MHz, TMS, δ): 4.06 (s, 3H), 6.73 (t, J=72.6 Hz, 1H), 7.21 (d, 1H), 7.44-7.50 (m, 2H), 7.78 (d, 1H), 7.87 (d, 1H) and 8.47 (d, 1H)

Intermediate 104: 4-Difluromethoxydibenzothiophene-1-carboxylic acid

The intermediate 103 (0.14 g, 0.5 mmols) was hydrolysed with KOH (0.05 g, 0.99 mmols) in MeOH (5 ml) and water (5 ml) at 50° C. for 2 hrs. MeOH was removed and the reaction mixture was acidified with 1N HCl and extracted with ethyl acetate. Ethyl acetate layer on concentration gave pure product.

Yield. 0.12 g (87%), M.P.: 196-198° C.

$^1$H-NMR: (CDCl$_3$, 300 MHz, TMS, δ): 6.77 (t, J=72 Hz, 1H), 7.26 (d, 1H), 7.45-7.50 (m, 2H), 7.90 (d, 1H), 8.06 (d, 1H) and 8.79 (d, 1H)

The following examples are representative compounds of the invention but should not be construed as limiting in any way.

EXAMPLE 1

N-(3,5-dichloropyrid-4-yl)-4-methoxy dibenzo[b,d]furan-1-carboxamide

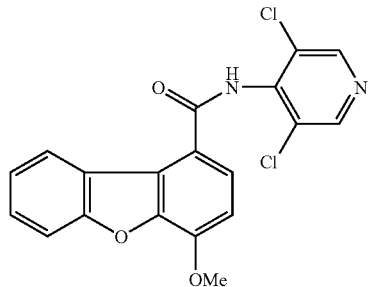

A suspension of intermediate 4 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (9.0 mg, 1.5 equiv., 0.61 mmol, 60% oil dispersion) in DMF (2 ml) was added dropwise a solution of 4-amino-3,5-dichloropyridine (68 mg, 0.41 mmol) in DMF (2 ml) at −10° C. A pre-cooled solution of above acid chloride in THF (2 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent and washing of the resulting crude solid with methanol provided N-(3,5-dichloropyrid-4-yl)-4-methoxy dibenzo[b,d]furan-1-carboxamide as a white solid (15 mg); mp: 302° C.

IR (KBr) 3171, 2974, 1654, 1607, 1491, 1450, 1293, 1202, 1098, 1011, 756 cm$^{-1}$.

$^1$H NMR (300 MHz, DMSO) δ 4.07 (s, 3H), 7.32 (d, 1H, J=8.4 Hz), 7.34 (t, 1H, J=8.4 Hz), 7.52 (t, 1H, J=8.1 Hz), 7.74 (d, 1H, J=8.1 Hz), 7.89 (d, 1H, J=8.4 Hz), 8.41 (d, 1H, J=8.1 Hz), 8.77 (s, 2H), 10.8 (s, 1H).

EXAMPLE 2

N-(3,5-dichloropyrid-4-yl)-4-methoxy dibenzo[b,d]furan-1-carboxamide-N1-oxide

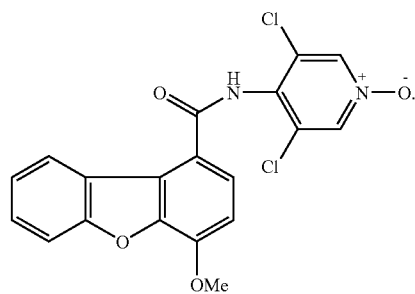

A suspension of N-(3,5-dichloropyrid-4-yl)-4-methoxy dibenzo[b,d]furan-1-carboxamide (200 mg, 0.518 mmol) (example 1) and m-chloroperbenzoic acid (50-55%) (880 mg, 2.5 mmol) in chloroform (10 ml) was refluxed for 2 h. The reaction was cooled and washed with saturated sodium bicarbonate and water. The organic solvent was distilled of in vacuo and the residue was purified by column chromatography using 20% acetone-chloroform as the eluent to give 150 mg of N-(3,5-dichloropyrid-4-yl)-4-methoxy dibenzo[b,d]furan-1-carboxamide-N1-oxide as white solid; mp: 265-270° C.

IR (KBr) 3214, 3060, 3007, 2931, 1655, 1474, 1454, 1282, 1245, 1099, 1011, 751 cm$^{-1}$.

$^1$H NMR (300 MHz, DMSO) δ 4.07 (s, 3H), 7.33 (d, 1H, J=8.4 Hz), 7.35 (t, 1H, J=8.4 Hz), 7.55 (t, 1H, J=8.1 Hz), 7.74 (d, 1H, J=8.1 Hz), 7.88 (d, 1H, J=8.4 Hz), 8.41 (d, 1H, J=8.1 Hz), 8.76 (s, 2H), 10.64 (s, 1H).

EXAMPLE 3

N-(pyrid-4-yl)-4-methoxy dibenzo[b,d]furan-1-carboxamide

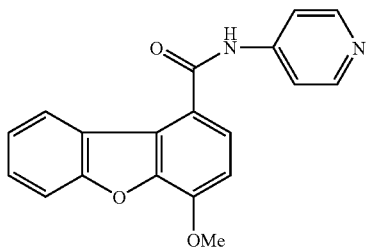

A suspension of intermediate 4 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

A solution of above acid chloride (0.249 mmol) in dry THF (5 ml) was added to a solution of 4-aminopyridine (22 mg, 0.249 mmol) and diisopropylethylamine (50 mg, 0.49 mmol) in dry THF (5 ml) at room temperature. The reaction mixture was stirred at room temperature for 16 h. The reaction mixture was diluted with water (25 ml) and extracted with ethyl acetate (15 ml×3). The ethyl acetate extract was concentrated in vacuo and the residue was purified by silica gel chromatography using 15% acetone-chloroform as the eluent to obtain 20 mg of N-(pyrid4-yl)-4-methoxy dibenzo[b,d]furan-1-carboxamide as a white solid; mp: 215° C.

IR (KBr) 3294, 2923, 2852, 1657, 1585, 1411, 1281, 1096, 814 cm$^{-1}$.

$^1$H NMR (300 MHz, CDCl$_3$) δ 4.15 (s, 3H), 7.04 (d, 1H, J=8.4 Hz), 7.39 (t, 1H, J=8.4 Hz), 7.53 (t, 1H, J=8.4 Hz), 7.65 (m, 4H), 7.93 (brs, 1H), 8.36 (d, 1H, J=7.2 Hz), 8.61 (brs, 2H).

EXAMPLE 4

N(pyrid-4-yl)-4-methoxy dibenzo[b,d]furan-1-carboxamide-N1-oxide

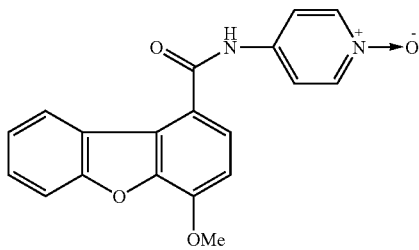

A suspension of N-(pyrid-4-yl)-4-methoxy dibenzo[b,d]furan-1-carboxamide (150 mg, 0.47 mmol) (example 3) and m-chloroperbenzoic acid (50-55%) (406 mg, 2.3 mmol) in chloroform (2.5 ml) was stirred at room temperature for 16 h. Chloroform was evaporated and the resulting solid was washed with saturated sodium bicarbonate solution, water, dried and then purified by column chromatography using 20% acetone-chloroform as the eluent to give 70 mg of N-pyrid-4-yl)-4-methoxy dibenzo[b,d]furan-1-carboxamide-N1-oxide as white solid; nip: 246-251° C.; IR (KBr): 3207, 3116, 3056, 2931, 2840, 2797, 1678, 1626, 1603, 1530, 1485, 1458, 1439, 1391, 1330, 1277, 1214, 1174, 1122, 1099, 1023, 851, 829, 791, 749 cm$^{-1}$.

$^1$H NMR (300 MHz, DMSO) δ 4.07 (s, 3H), 7.32 (d, 1H, J=8.4 Hz), 7.34 (t, 1H, J=8.4 Hz), 7.56 (t, 1H, J=8.4 Hz), 7.65 (m, 2H), 7.84 (d, 2H, J=7.2 Hz), 8.18 (d, 2H, J=7.2 Hz), 8.30 (d, 1H, J=8.4 Hz), 10.96 (s, 1H).

EXAMPLE 5

N-(2-chloropyrid-3-yl)-4-methoxy dibenzo[b,d]furan-1-carboxamide

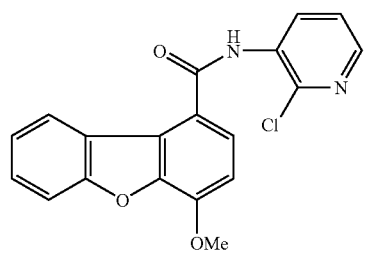

A suspension of intermediate 4 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (41 mg, 2.5 equiv., 1.0 mol, 60% oil dispersion) in DMF (4 ml) was added dropwise a solution of 2-chloro-3-aminopyridine (79 mg, 0.61 mmol) in DMF (4 ml) at −10° C. A pre-cooled solution of above acid chloride in THF (2 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent gave a crude solid which was purified by column chromatography using 5% acetone-chloroform as eluent to give N-(2-chloropyrid-3-yl)-4-methoxy dibenzo[b,d]furan-1-carboxamide as a white solid (30 mg); mp: 192° C.

IR (KBr): 3254, 2924, 1651, 1579, 1525, 1505, 1451, 1389, 1297, 1283, 1202, 1098, 1010, 748 cm$^{-1}$ $^1$H NMR: (300 MHz, DMSO) δ 4.07 (s, 3H), 7.34 (m, 2H), 7.54 (m, 2H), 7.88 (d, 1H, J=8.4 Hz), 7.86 (d, 1H, J=7.86 Hz), 8.20 (d, 1H, J=7.8 Hz), 8.32 (d, 1H, J=4.8 Hz), 10.36 (s, 1H).

EXAMPLE 6

N-(4-fluorophenyl)-4-methoxy dibenzo[b,d]furan-1carboxamide

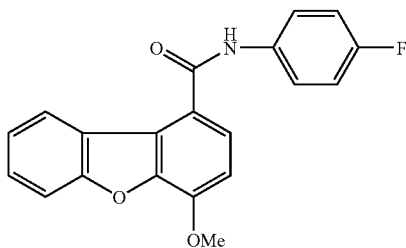

A suspension of intermediate 4 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 4-fluoroaniline (45 mg, 0.406 mmol) and diisopropylethylamine (79 mg, 0.6 mol) in dry THF (5 ml) at room temperature was added above solution of acid chloride (0.406 mmol) in dry THF (5 ml). The reaction mixture was stirred at room temperature for 10-12 h. The reaction mixture was diluted with 5% aqueous hydrochloric acid (10 ml) to precipitate the product The product washed with saturated sodium bicarbonate solution followed by water and petroleum ether. The solid was dried and purified by silica gel chromatography using petroleum ether: ethyl acetate (8:2) as the eluent to obtain 10 mg of N-(4-fluorophenyl)-4-methoxy dibenzo[b,d]furan-1-carboxamide as a white solid; mp: 246° C.

IR (KBr) 3304, 2923, 1646, 1604, 1509, 1406, 1296, 1278, 1096, 823, 831 cm$^{-1}$.

$^1$H NMR (300 MHz, CDCl$_3$) δ 4.11 (s, 3H), 6.99 (d, 1H, J=8.4 Hz), 7.11 (t, 2H, J=8.7 Hz), 7.32 (t, 1H, J=7.8 Hz), 7.5 (t, 1H, J=7.8 Hz), 7.60 (d, 1H, J=8.4 Hz), 7.64 (d, 2H, J=7.2 Hz), 7.65 (d, 1H, J=7.8 Hz), 7.81 (s, 1H), 8.35 (d, 1H, J=7.8 Hz).

EXAMPLE 7

N-(pyrid-3-yl)-4-methoxy dibenzo[b,d]furan-1-carboxamide

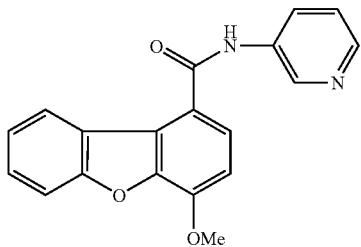

A suspension of intermediate 4 (100 mg, 0.00413 mol) in a mixture of benzene (2 ml) and freshly distilled thionyl chloride (2 ml) was heated to reflux temperature for 4 h The excess thionyl chloride was removed under vacuum to get the corresponding acid chloride.

A solution of acid chloride (0.61 mmol) in dry THF (5 ml) was added to a solution of 3-aminopyridine (57 mg, 0.61 mmol) and diisopropylethylamine (157 mg, 1.32 mmol) in dry THF (5 ml) at room temperature. The reaction mixture was stirred at room temperature for 16 h. The reaction mixture was diluted with water (25 ml) and extracted with ethyl acetate (15 ml×3). The ethyl acetate extract was concentrated in vacuo and the residue was purified by silica gel chromatography using 15% acetone-chloroform as the eluent to obtain 60 mg of N-(pyrid-3-yl)-4-methoxy dibenzo[b,d]furan-1-carboxamide as a white solid; mp: 226° C.

IR (KBr): 3272, 2936, 1646, 1582, 1520, 1484, 1409, 1340, 1286, 1204, 1180, 1117, 1069, 826, 703 cm$^{-1}$.

$^1$H NMR: (300 MHz, DMSO): δ 4.20 (s, 3H), 7.45 (d, 2H, J=8.1 Hz), 7.99 (t, 2H, J=7.2 Hz), 8.27 (d, 1H, J=8.1 Hz), 8.35 (s, 1H), 8.44 (d, 1H, J=6.9), 8.95 (brs, 1H), 9.37 (s, 1H), 10.76 (s, 1H).

EXAMPLE 8

N-(pyrid-3-yl)-4-methoxy dibenzo[b,d]furan-1-carboxamide-N1-oxide

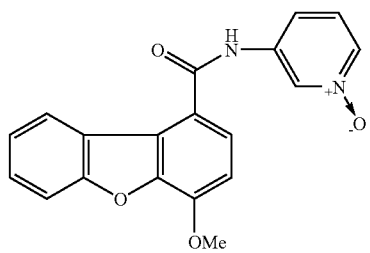

A suspension of N-(pyrid-3-yl)-4-methoxy dibenzo[b,d]furan-1-carboxamide (50 mg, 0.15 mmol) (example 8) and m-chloroperbenzoic acid (50-55%) (135 mg, 0.78 mmol) in chloroform (10 ml) was stirred at room temperature for 16 h. Chloroform was evaporated and the resulting solid was washed with saturated sodium bicarbonate solution, water, dried and then purified by column chromatography using 20% acetone-chloroform as the eluent to give 15 mg of N-(pyrid-3-yl)-4-methoxy dibenzo[b,d]furan-1-carboxamide-N1-oxide as white solid; mp: 239-241° C.

IR (KBr): 2931, 2840, 2797, 2389, 1678, 1626, 1603, 1530, 1511, 1485, 1439, 1395, 1313, 1277, 1294, 1214, 1203, 1174, 1099, 1122, 1036, 851, 749 cm$^{-1}$.

$^1$H NMR: (300 MHz, DMSO): δ 4.06 (s, 3H), 7.29-7.39 (m, 3H), 7.56 (t, 1H, J=7.5 Hz), 7.85 (d, 2H, J=7.5 Hz), 7.94 (t, 1H, J=8.1 Hz), 8.18 (d, 2H, J=7.5 Hz), 8.31 (d, 1H, J=8.4 Hz), 10.96 (s, 1H).

EXAMPLE 9

N-(3,5-dichloropyrid-4-yl)-4-methoxy-8-trifluoromethyl dibenzo[b,d]furan-1-carboxamide

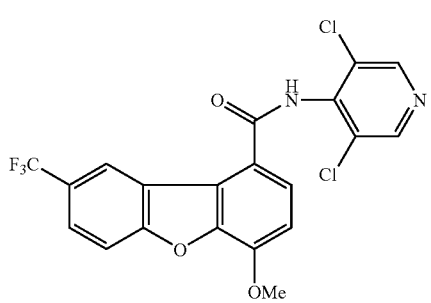

A suspension of intermediate 8 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (27.0 mg, 2.0 equiv., 1.16 mmol, 60% oil dispersion) in DMF (2 ml) was added dropwise a solution of 4-amino-3,5-dichloropyridine (94 mg, 0.58 mmol) in DMF (2 ml) at −10° C. A pre-cooled solution of above acid chloride (0.58 mmol) in THF (2 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. After removal of the organic solvent under vacuo the solid was purified by silica gel chromatography using 12% ethyl acetate: chloroform as the eluent to obtain N-(3,5-dichloropyrid-4-yl)-4-methoxy-8-trifluromethyl dibenzo[b,d]furan-1-carboxamide as a white solid (80 mg); mp: 298° C.

IR (KBr): 3203, 2936, 2848, 1669, 1554, 1489, 1392, 1327, 1286, 1217, 1166, 1117, 1105, 809 cm$^{-1}$.

$^1$H NMR (300 MHz, DMSO) δ 4.11 (s, 3H), 7.44 (d, 1H, J=8.7 Hz), 7.91 (d, 1H, J=8.7 Hz), 8.0 (d, 1H, J=8.7 Hz), 8.8 (s, 2H), 8.87 (s, 1H), 10.94 (s, 1H).

EXAMPLE 10

N-(3,5-dichloropyrid-4-yl)-4-methoxy-8-trifluoromethyl dibenzo[b,d]furan-1-carboxamide-N1-oxide

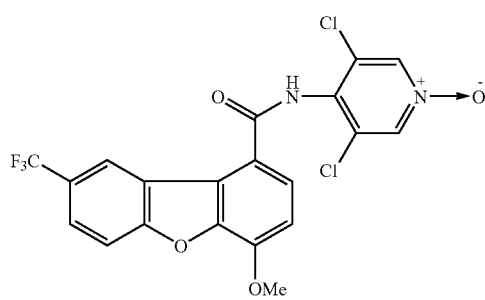

A suspension of N-3,5-dichloropyrid-4-yl)-4-methoxy-8-trifluoromethoxy-dibenzo[b,d]furan-1-carboxamide (70 mg, 0.175 mmol) (example 10) and m-chloroperbenzoic acid (50-55%) (121 mg, 0.703 mmol) in chloroform (5 ml) was stirred at room temperature for 16 h. Chloroform was evaporated and the resulting solid was washed with saturated sodium bicarbonate solution, water, dried and then purified by column chromatography using 25% acetone-chloroform as the eluent to give 18 mg of N-(3,5-dichloropyrid-4-yl)-4-methoxy-8-trifluoromethyl-dibenzo[b,d]furan-1-carboxamide-N1-oxide as white solid; mp: 272° C.

IR (KBr) 3184, 3067, 2934, 1658, 1537, 1479, 1429, 1326, 1284, 1241, 1165, 1107, 896 cm$^{-1}$.

$^1$H NMR (300 MHz, DMSO) δ 4.10 (s, 3H), 7.43 (d, 1H, J=8.7 Hz), 7.91-8.02 (brm, 3H) 8.77 (s, 2H), 8.87 (s, 1H), 10.74 (s, 1H).

EXAMPLE 11

N(pyrid-4-yl)-4-methoxy-8-trifluoromethyl dibenzo[b,d]furan-1-carboxamide

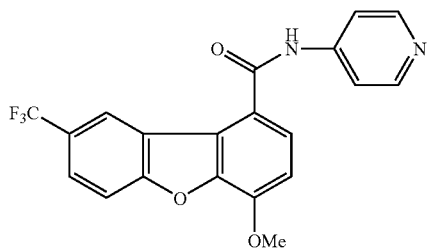

A suspension of intermediate 8 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 4-aminopyridine (52 mg, 0.645 mmol) and diisopropylethylamine (0.3 ml) in dry THF (3 ml) was added a solution of acid chloride (0.645 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 60 mg of N-(pyrid-4-yl)-4-methoxy-8-trifluoromethyl dibenzo[b,d]furan-1-carboxamide as a white solid; mp: 259° C.

IR (KBr) 3308, 2936, 2848, 1660, 1587, 1494, 1411, 1324, 1283, 1207, 1156, 1120, 1104, 818 cm$^{-1}$.

$^1$H NMR (300 MHz, DMSO) δ 4.10 (s, 3H), 7.42 (d, 1H, J=8.4 Hz), 7.81 (d, 2H, J=6.2 Hz), 7.93 (d, 2H, J=8.4 Hz), 8.01 (d, 1H, J=8.4 Hz), 8.51 (d, 2H, J=5.4 Hz), 8.7 (s, 1H), 10.90 (s, 1H).

EXAMPLE 12

N-(3,5-dichloropyrid-4-yl)-4-difluoromethoxy-8-trifluoromethyl dibenzo[b,d]furan-1-carboxamide

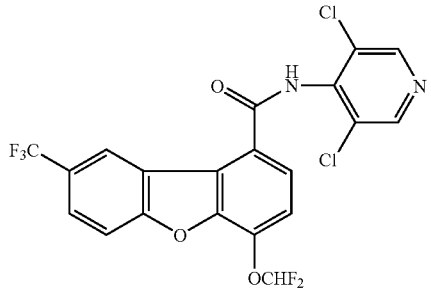

A suspension of intermediate 12 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

A solution of 4-amino-3,5-dichloropyridine (75 mg, 0.46 mmol) in DMF (2.5 ml) was added dropwise to a pre-washed suspension of sodium hydride (44 mg, 2.0 equiv., 0.92 mmol, 60% oil dispersion) in DMF (2.5 ml) at −10° C. A pre-cooled solution of above acid chloride (0.462 mmol) in THF (2 ml) was added, all at once, to the reaction mixture and the contents were stirred at −10° C. for 30 min. The reaction was quenched with brine, diluted with water and extracted with ethyl acetate. The organic extract was washed with water, 5% hydrochloric acid, 5% sodium bicarbonate and brine solution. The organic solvent was distilled off in vacuo and the residue was purified by silica-gel chromatography using 12% ethyl acetate-chloroform as eluent to obtain N-(3,5-dichloropyrid-4-yl)-4-difluoromethoxy-8-trifluoromethyl dibenzo[b,d]furan-1-carboxamide as a white solid (30 mg); mp: 228° C.

IR (KBr) 3200, 2930, 1664, 1555, 1492, 1389, 1325, 1286, 1272, 1168, 1141, 1117, 827 cm$^{-1}$.

$^1$H NMR (300 MHz, DMSO) δ 7.60 (t, 1H, J=72.6 Hz) 7.68 (d, 1H, J=8.4 Hz), 7.98 (d, 2H, J=8.4 Hz), 8.09 (d, 1H, J=8.4 Hz), 8.80 (s, 1H), 8.82 (s, 2H), 11.16 (s, 1H).

EXAMPLE 13

N-(3,5-dichloropyrid-4-yl)-4-difluoromethoxy-trifluoromethyl dibenzo[b,d]furan-1-carboxamide-N1-oxide

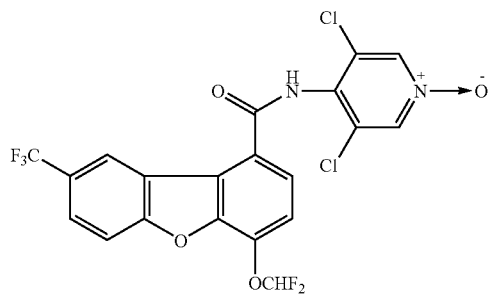

A suspension of N-(3,5-dichloropyrid-4-yl)-4-difluoromethoxy-8-trifluoromethoxy-dibenzo-[b,d]-furan-1-carboxamide (120 mg, 0.244 mmol) (example 13) and m-chloroperbenzoic acid (50-55%) (168 mg, 0.477 mmol) in chloroform (5 ml) was stirred at room temperature 36 h. Chloroform was evaporated and the resulting solid was washed with saturated sodium bicarbonate solution, water, dried and purified by column chromatography using 20% acetone-chloroform as the eluent to give 40 mg of N-3,5-dichloropyrid-4-yl)-4-difluoromethoxy-8-trifluoromethyl-dibenzo[b,d]furan-1-carboxamide-N1oxide as white solid; mp: 249.5° C.

IR (KBr) 3221, 3067, 2927, 2324, 1662, 1539, 1483, 1453, 1359, 1326, 1284, 1240, 1116, 1101, 1056, 1033, 896 cm$^{-1}$.

$^1$H NMR (300 MHz, DMSO) δ 7.60 (t, 1H, J=72 Hz), 7.65 (d, 1H, J=8.4 Hz), 7.99-8.09 (brm, 3H), 8.73 (s, 2H), 8.88 (s, 1H) 11.08 (s, 1H).

EXAMPLE 14

N-(pyrid-4-yl)-4-difluoromethoxy-8-trifluoromethyl dibenzo[b,d]furan-1-carboxamide

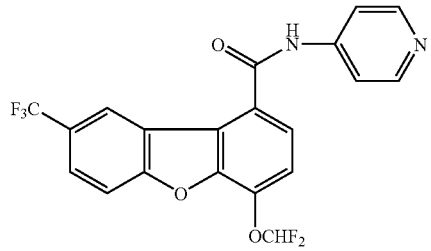

A suspension of intermediate 12 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 4-aminopyridine (65 mg, 0.0.794 mmol) and diisopropylethylamine (0.3 ml) in dry THF (3 ml) was added a solution of above acid chloride (0.645 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 24% acetone-chloroform as the eluent to obtain 45 mg of N-(pyrid-4-yl)-4-difluoromethoxy-8-trifluoromethyl dibenzo[b,d]furan-1-carboxamide as a white solid; mp: 228° C.

IR (KBr) 3245, 3075, 2988, 1685, 1590, 1519, 1508, 1355, 1331, 1297, 1272, 1196, 1120, 1096, 822 cm$^{-1}$.

$^1$H NMR (300 MHz, DMSO) δ 7.60 (t, 1H, J=72.6 Hz) 7.67 (d, 1H, J=8.4 Hz), 7.82 (d, 2H, J=6.2 Hz), 7.95 (dd, 1H, J=8.4 Hz, 1.8 Hz), 8.01 (d, 2H, J=8.7 Hz), 8.52 (d, 2H, J=5.4 Hz), 8.69 (s, 1H), 11.06 (s, 1H).

EXAMPLE 15

N-(pyrid-4-yl)-4-difluoromethoxy-8-trifluoromethyl dibenzo[b,d]furan-1-carboxamide-N1-oxide

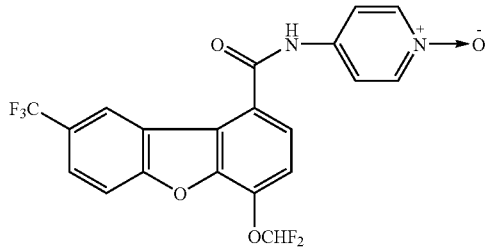

A suspension of N-pyrid-4-yl)-4-difluoromethoxy-8-trifluoromethoxy-dibenzo[b,d]furan-1-carboxamide (100 mg, 0.236 mmol) (example 15) and m-chloroperbenzoic acid (50-55%) (163 mg, 0.947 mmol) in chloroform (5 ml) was stirred at room temperature for 18 h. Chloroform was evaporated and the resulting solid was washed with saturated sodium bicarbonate solution, water, dried and purified by column chromatography using 8% methanol-chloroform as the eluent to give 40 mg of N-(pyrid-4-yl)-4-difluoromethoxy-8-trifluoromethyl-dibenzo[b,d]furan-1-carboxamide-N1-oxide as white solid; mp: 257° C. (dec).

IR (KBr): 2925, 2854, 1692, 1611, 1510, 1487, 1385, 1356, 1322, 1278, 1214, 1197, 1178, 1119, 1055, 1036, 848, 820, 797, 688 cm$^{-1}$.

$^1$H-NMR (300 MHz, DMSO) δ 7.60 (t, 1H, J=72.6 Hz), 7.67 (d, 1H, J=8.4 Hz), 7.85 (d, 2H, J=7.2 Hz), 7.96 (m, 2H), 8.09 (d, 1H, J=8.4 Hz), 8.21 (d, 2H, J=6 Hz), 8.73 (s, 1H), 11.15 (s, 1H).

EXAMPLE 16

N-(pyrid-3-yl)-4-difluoromethoxy-8-trifluoromethyl dibenzo[b,d]furan-1-carboxamide

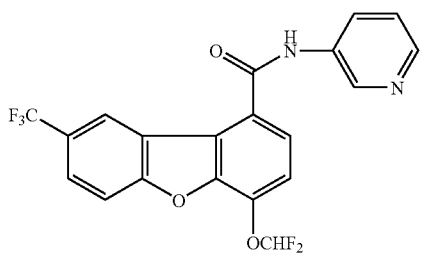

A suspension of intermediate 12 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 3-aminopyridine (26 mg, 0.317 mmol) and diisopropylethylamine (0.2 ml) in dry THF (5 ml) was added a solution of above acid chloride (0.289 mmol) in dry THF (5 ml). The reaction mixture was stirred at room temperature for 12 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 60 mg of N-(pyrid-3-yl)-4-difluoromethoxy-8-trifluoromethyl dibenzo[b,d]furan-1-carboxamide as a white solid; mp: 235-236° C.

IR (KBr): 3273, 1652, 1586, 1529, 1509, 1413, 1423, 1325, 1284, 1270, 1169, 1134, 1121, 1046, 828, 800, 705 cm$^{-1}$.

$^1$H NMR (300 MHz, DMSO) δ; 7.45 (m, 1H), 7.6 (t, 1H, J=85.5 Hz), 7.65 (d, 1H, J=9 Hz), 8.00 (m, 2H, J=6 Hz), 8.1 (d, 1H), 8.25 ((d, 1H), 8.36 (brs, 1H), 8.73 (s, 1H), 8.93 (s, 1H), 10.91 (s, 1H)

EXAMPLE 17

N-(pyrid-3-yl)-4-difluoromethoxy-8-trifluoromethyl dibenzo[b,d]furan-1-carboxamide-N1-oxide

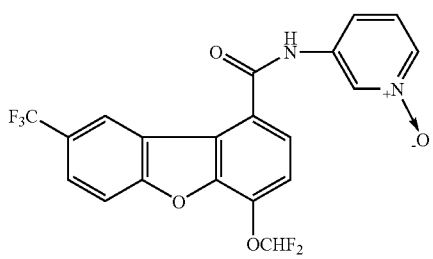

A suspension of N-(pyrid-3-yl)-difluoromethoxy-8-trifluoromethoxy-dibenzo[b,d]-furan-1-carboxamide (40 mg, 0.094 mmol) (example 17) and m-chloroperbenzoic acid (50-55%) (65 mg, 0.379 mmol) in chloroform (5 ml) as stirred at room temperature for 12 h. Chloroform was evaporated and the resulting solid was washed with saturated sodium bicarbonate solution, water, dried and purified by column chromatography using 8% methanol-chloroform as the eluent to give 12 mg of N-(pyrid-3-yl)-4-difluoromethoxy-8-trifluoromethyl dibenzo[b,d]furan-1-carboxamide-N1-oxide as white solid; mp: 225-226° C.

IR (KBr); 3181, 3097, 3030, 2923, 1682, 1578, 1493, 1416, 1385, 1325, 1278, 1205, 1165, 1143, 1118, 1090, 1040, 1053, 849, 824, 672 cm$^{-1}$.

$^1$HNMR (300 MHz, DMSO) δ 7.46 (t, 1H), 7.60 (t, 1H, J=72.6 Hz), 7.69 (q, 2H), 8.01 (m, 4H), 8.73 (s, 1H), 8.83 (s, 1H), 11.03 (s, 1H).

EXAMPLE 18

N-(pyrid-2-yl)-4-difluoromethoxy-8-trifluoromethyl dibenzo[b,d]furan-1-carboxamide

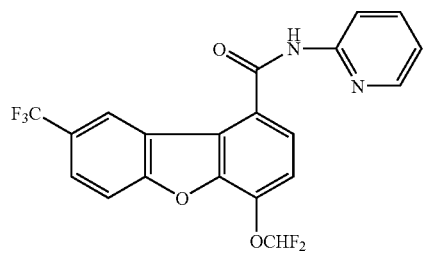

A suspension of intermediate 12 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

A solution of 2-aminopyridine (47 mg, 0.578 mmol) in THF (2.5 ml) was added dropwise to a pre-washed suspension of sodium hydride (27 mg, 2.0 equiv., 0.57 mmol, 60% oil dispersion) in THF (2.5 ml) at −10° C. A pre-cooled solution of above acid chloride (0.289 mmol) in THF (2 ml) was added, all at once, to the reaction mixture and the contents were stirred at 20° C. for 60 min. The reaction was quenched with brine, diluted with water and extracted with ethyl acetate. The organic extract was washed with water, 5% hydrochloric acid, 5% sodium bicarbonate and brine solution. The organic solvent was distilled off in vacuo and the residue was purified by silica-gel chromatography using 5% acetone-chloroform as eluent to obtain N-(pyrid-2-yl)-4-difluoromethoxy-8-trifluoromethyl dibenzo[b,d]furan-1-carboxamide as a white solid (18 mg); mp: 169-170° C.

IR (KBr):3293, 3023, 1655, 1596, 1577, 1529, 1506, 1437, 1399, 1355, 1325, 1315, 1267, 1147, 1113, 1056, 823, 774, 611 cm$^{-1}$.

$^1$HNMR (300 MHz, DMSO) δ 7.22 (t, 1H, J=7.2 Hz), 7.58 (t, 1H, J=77.7), 7.606 (s, 1H), 7.947 (m, 3H), 8.08 (d, 1H, J=8.7 Hz), 8.26 (d, 1H, J=6 Hz), 8.41(d, 1H, J=6 Hz) 8.71 (s, 1H).

EXAMPLE 19

N-(3,5-dichloropyrid-4-yl)-4-difluoromethoxy dibenzo[b,d]furan-1-carboxamide

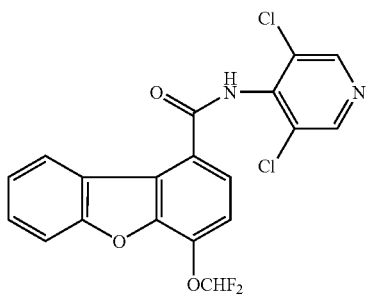

A suspension of intermediate 16 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (29.0 mg, 2.5 equiv., 0.73 mmol, 60% oil dispersion) in DMF (2.5 ml) was added dropwise a solution of 4-amino-3,5-dichloropyridine (47 mg, 0.29 mmol) in DMF (2.5 ml) at −10° C. A pre-cooled solution of above acid chloride in THF (2.5 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. The solvent was evaporated and the resulting crude solid was purified by silica-gel column chromatography using 5% ethyl acetate-chlorofrom as eluent to obtain N-(3,5-dichloropyrid-4-yl)-4-difluoromethoxy dibenzo[b,d]furan-1-carboxamide as a white solid (25 mg); mp: 270° C.

IR (KBr) 3195, 2921, 2851, 1661, 1494, 1381, 1282, 1149, 1029, 755 cm$^{-1}$.

$^1$H NMR (300 Mz, CDCl$_3$) δ 6.93 (t, 1H, J=72 Hz), 7.55 (m, 2H), 7.66 (m, 2H), 7.81 (d, 1H, J=8.4 Hz), 8.47 (d, 1H, J=8.4 Hz), 8.61 (s, 2H).

EXAMPLE 20

N-(pyrid-4-yl)-4-difluoromethoxy dibenzo[b,d]furan-1-carboxamide

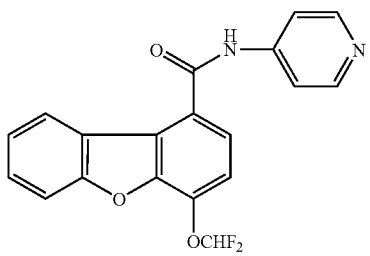

A suspension of intermediate 16 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 4-aminopyridine (42 mg, 0.452 mmol) and diisopropylethyl amine (68 mg, 0.67 mmol) in dry THF (5 ml) was added a solution of above acid chloride (0.452 mmol) in dry THF (5 ml). The reaction mixture was sired at room temperature for 5 h. The reaction mixture was diluted with water (10 ml) and extracted with ethyl acetate (10 ml×3). The ethyl acetate extract was concentrated under reduced pressure and the residue was purified by silica gel chromatography using 15% acetone-chloroform as the eluent to obtain 80 mg of N-(pyrid-4-yl)-4-difluoromethoxy-dibenzo[b,d]furan-1-carboxamide as a white solid; mp: 230° C.

IR (KBr): 3218, 2956, 2879, 1678, 1642, 1549, 1511, 1448, 1397, 1298, 1200, 1130, 993, 828, 754, 645 cm$^{-1}$ $^1$H NMR (300 MHz, DMSO) δ 7.56 (t, 1H, J=72 Hz), 7.45 (t, 1H, J=7.5 Hz), 7.62 (m, 2H), 7.81 (1H, m), 8.20 (1H, d, J=7.8 Hz), 8.52 (1H, d, J=5.4 Hz), 11.04 (1H, s).

EXAMPLE 21

N-(pyrid-4-yl)-4-difluoromethoxy dibenzo[b,d]furan-1-carboxamide-N1-oxide

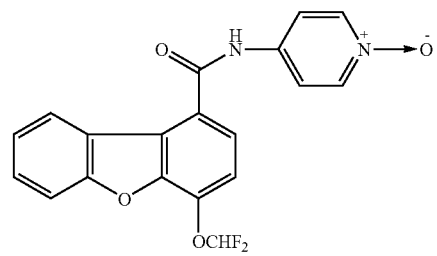

A suspension of N-(pyrid-4-yl)-4-difluoromethoxy-dibenzo[b,d]furan-1-carboxamide (50 mg, 0.14 mmol) (example 21) and m-chloroperbenzoic acid (50-55%) (120 mg, 0.70 mmol) in chloroform (10 ml) was stirred at room temperature for 16 h. Chloroform was evaporated and the resulting solid was stirred in saturated sodium bicarbonate solution, filtered, dried and purified by column chromatography using 40% acetone-chloroform as the eluent to give 30 mg of N-(pyrid-4-yl)-4-difluoromethoxy-dibenzo[b,d]furan-1-carboxamide-N1-oxide as white solid; mp: 244° C.

IR (KBr): −3393, 2790, 1677, 1509, 1487, 1394, 1278, 1198, 1111, 1052, 852, 756 cm$^{-1}$ $^1$H NMR (300 MHz, DMSO) δ 7.42 (t, 1H, J=7.5 Hz), 7.563 (t, 1H, J=72 Hz), 7.62 (m, 2H), 7.72-7.85 (m, 4H), 8.19-8.25 (m, 3H), 11.14 (s, 1H).

EXAMPLE 22

N-(pyrid-3-yl)-4-difluoromethoxy dibenzo[b,d]furan-1-carboxamide

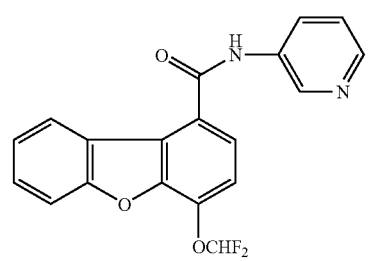

A suspension of intermediate 16 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 3-aminopyridine (42 mg, 0.452 mmol) and diisopropylethylamine (68 mg, 0.679 mmol) in dry THF (5 ml) was added a solution of above acid chloride (0.452 mmol) in dry THF (5 ml). The reaction mixture was stirred at room temperature for 4 h. The reaction mixture was diluted with water (20 ml) and extracted with ethyl acetate (10 ml×3). The ethyl acetate extract was concentrated under reduced pressure and the residue was purified by silica gel chromatography using 15% acetone-chloroform as the eluent to obtain 100 mg of N-(pyrid-3-yl)-4-difluoromethoxy-dibenzo[b,d]furan-1-carboxamide as a white solid; mp: 209-211° C.

IR (KBr): 3210, 2954, 2868, 1671, 1152, 5496, 1509, 1442, 1387, 1292, 1205, 1134, 995, 830, 748, 642 cm$^{-1}$ $^1$H NMR (300 MHz, DMSO) δ 7.56 (t, 1H, J=72 Hz), 7.39 (m, 2H), 7.82 (t, 1H, J=6.0 Hz), 8.261 (1H, m, J=7.2 Hz), 8.35 (1H, d, J=4.5 Hz), 8.95 (1H, s), 10.88 (1H, s).

EXAMPLE 23

N-(pyrid-3-yl)-4-difluoromethoxy dibenzo[b,d]furan-1-carboxamide-N1-oxide

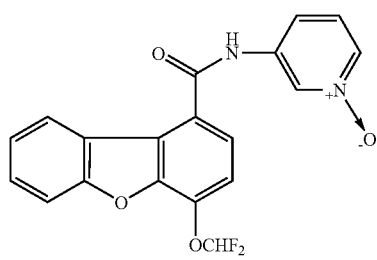

A suspension of N-(pyrid-3-yl)-4-difluoromethoxy-dibenzo[b,d]furan-1-carboxamide (50 mg, 0.14 mmol) (example 23) and m-chloroperbenzoic acid (50-55%) (120 mg, 0.704 mmol) in chloroform (10 ml) was stirred at room temperature for 12 h. Chloroform was evaporated and the resulting solid was stirred in saturated sodium bicarbonate solution, filtered, dried and purified by column chromatography using 40% acetone-chloroform as the eluent to give 25 mg of of N-(pyrid-3-yl)-4-difluoromethoxy-dibenzo[b,d]furan-1-carboxamide-N1-oxide as white solid; mp: 252° C. (dec)

IR (KBr): 3243, 3057, 2921, 1677, 1575, 1450, 1304, 1281, 1198, 1042, 997, 844, 740 cm$^{-1}$ $^1$H NMR (300 MHz, DMSO) δ 7.43 (t, 1H, J=8.1 Hz), 7.56 (t, 1H, J=72 Hz), 7.57-7.70 (m, 4H), 7.79-7.82 (m, 2H), 8.04 (d, 1H, J=5.4 Hz), 8.24 (d, 1H, J=8.4 Hz), 8.86 (s, 1H), 11.01 (s, 1H).

EXAMPLE 24

N-(5-chloropyrid-2-yl)-4-difluoromethoxy dibenzo[b,d]furan-1-carboxamide

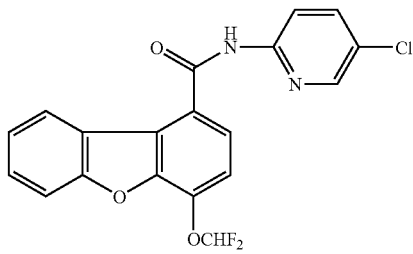

A suspension of intermediate 16 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (28 mg, 2.5 equiv., 0.71 mmol, 60% oil dispersion) in DMF (2.5 ml) was added dropwise a solution of 2-amino-5-chloropyridine (92 mg, 0.71 mmol) in DMF (2.5 ml) at −10° C. A pre-cooled solution of above acid chloride (0.35 mmol) in THF (2.5 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. The solvent was evaporated and the resulting crude solid was purified by silica-gel column chromatography using 20% ethyl acetate-petroleum ether as eluent to obtain N-(5-chloropyrid-2-yl)-4-difluoromethoxy dibenzo[b,d]furan-1-carboxamide as a white solid (10 mg); mp: 155-157° C.

IR (KBr): 3256, 2849, 1659, 1571, 1522, 1503, 1450, 1381, 1249, 1282, 1221, 1197, 1166, 1150, 1132, 1110, 1034, 1011, 754 cm$^{-1}$.

$^1$H NMR: (300 MHz, DMSO): δ 7.32-7.64 (m, 3H), 7.56 (t, 1H, J=72 Hz), 7.79-7.84 (m, 2H.), 8.02 (d, 1H, J=6.3 Hz), 8.22 (d, 1H, J=7.8 Hz), 8.35 (d, 1H, J=9 Hz), 8.45 (s, 1H), 11.38 (s, 1H).

EXAMPLE 25

N-(3,5-dichloropyrid-4-yl)-4-cyclopropylmethoxy dibenzo[b,d]furan-1-carboxamide

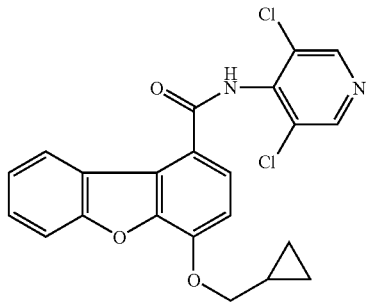

A suspension of intermediate 21 (50 mg, 0.177 mmol) in a mixture of benzene (2 ml) and freshly distilled thionyl chloride (0.5 ml) was heated to reflux temperature for 3 h The excess thionyl chloride was removed under vacuum to get the corresponding acid chloride.

To a pre-washed suspension of sodium hydride (18 mg, 2.5 equiv., 0.443 mmol, 60% oil dispersion) in DMF (2 ml) was added dropwise a solution of 4-amino-3,5-dichloropyridine (28 mg, 0.17 mmol) in DMF (2 ml) at −10° C. A pre-cooled solution of above acid chloride in THF (5 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent and purification of the crude solid by silica gel column chromatography using 10% acetone-chloroform as eluent provided N-(3,5-dichloropyrid-4-yl)-4-cyclopropylmethoxy dibenzo[b,d]furan-1-carboxamide as a white solid (38 mg); mp: 242° C.

IR (KBr) 3202, 2922, 2853, 1665, 1552, 1484, 1396, 1281, 1198, 1095, 903, 835, 750, 672 cm$^{-1}$.

$^1$H NMR (300 MHz, DMSO) 0.452 (m, 2H), 0.66 (m, 2H), 1.38 (m, 1H), 4.18 (d, 2H, J=7.5 Hz), 7.31 (d, 1H, J=9.0 Hz), 7.36 (d, 1H, J=7.5 Hz), 7.55 (t, 1H, J=6.9 Hz), 7.8 (d, 1H, J=8.4 Hz), 7.88 (d, 1H, J=8.4 Hz), 8.42 (d, 1H, J=9.5 Hz), δ 8.78 (s, 1H), δ 10.8 (s, 1H).

EXAMPLE 26

N-(3,5-dichloropyrid-4-yl)-4-cyclopropylmethoxy dibenzo[b,d]furan-1-carboxamide-N1-oxide

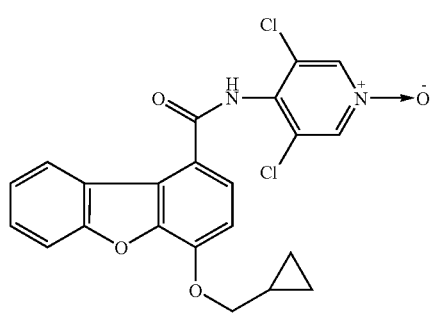

A suspension of N-(3,5-dichloropyrid-4-yl)-4-cyclopropylmethoxy-dibenzo[b,d]furan-1-carboxamide (370 mg, 0.936 mmol) (example 26) and m-chloroperbenzoic acid (50-55%) (1.0 gm, 4.68 mmol) in chloroform (20 ml) was stirred at room temperature for 12 h. The reaction contents were washed with saturated sodium bicarbonate and water. The organic solvent was distilled of in vacuo and the residue was purified by column chromatography using 30% acetone-chloroform as the eluent to give 200 mg of N-(3,5-dichloropyrid-4-yl)-4-cyclopropylmethoxy-dibenzo[b,d]furan-1-carboxamide-N1-oxide as white solid; mp: 263-265° C.

IR (KBr) 3228, 3061, 1662, 1576, 1476, 1395, 1280, 1198, 1097, 895, 750 cm$^{-1}$ $^1$H NMR (300 MHz,CDCl$_3$) δ 0.452 (m, 2H, 0.66 (m, 2H), 1.38 (m, 1H), 4.13 (d, 2H, J=7.5 Hz), 7.21 (d, 1H, J=8.7 Hz), 7.40 (t, 1H, J=7.2 Hz), 7.65 (t, 1H, J=6.9 Hz), 7.79 (d, 1H, J=8.4 Hz), 7.96 (d, 1H, J=8.1 Hz), 8.41 (d, 1H, J=7.2 Hz), 8.75 (d, 2H, J=7.5 Hz), 10.62 (s, 1H).

EXAMPLE 27

N-(pyrid-4-yl)-4-cyclopropylmethoxy dibenzo[b,d]furan-1-carboxamide

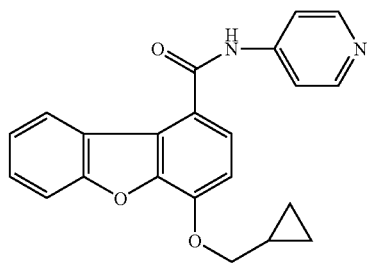

A suspension of intermediate 21 (50 mg, 0.177 mmol) in a mixture of benzene (2 ml) and fleshly distilled thionyl chloride (0.5 ml) was heated to reflux temperature for 3 h. The excess thionyl chloride was removed under vacuum to get the corresponding acid chloride.

To a solution of 4-aminopyridine (33 mg, 0.354 mmol) and diisopropylethylamine (54 mg) in dry THF (3 ml) was added a solution of above acid chloride (0.354 mmol) in dry THF (3 ml). The reaction mixture was stirred at room temperature for 2 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 65 mg of N-(pyridyl)-cyclopropylmethoxy-dibenzo[b,d]furan-1-carboxamide as a white solid; mp: 243-244° C.

IR (KBr) 3278, 2925, 1657, 1583, 1487,1396, 1282, 1195, 1094, 993, 886, 781, 631 cm$^{-1}$ $^1$H NMR (300 MHz, DMSO) δ 0.452 (m, 2H), δ 0.66 (m, 2H), 1.38 (m, 1H), 4.15 (d, 2H, J=6.9 Hz), 7.26 (d, 1H, J=8.4 Hz), 7.37 (t, 1H, J=7.2 Hz), 7.56 (t, 1H, J=6.9 Hz), 7.73-7.81 (m, 4H), 8.29 (d, 1H, J=7.5 Hz), 8.49 (d, 2H, J=6.3 Hz), 10.84 (s, 1H).

EXAMPLE 28

N-(pyrid-4-yl)-4-cyclopropylmethoxy dibenzo[b,d]furan-1-carboxamide-N1-oxide

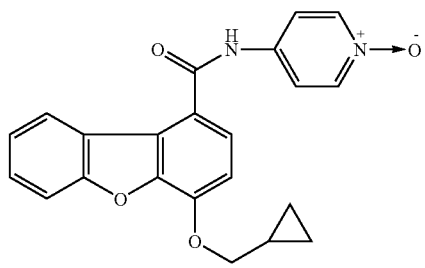

A suspension of N-(pyrid-4-yl)-4-cyclopropylmethoxy-dibenzo[b,d]furan-1-carboxamide (50 mg, 0.139 mmol) (example 28) and m-chloroperbenzoic acid (50-55%) (120 mg, 0.698 mmol) in chloroform (10 ml) was stirred at room temperature for 12-16 h. The reaction contents were washed with saturated sodium bicarbonate and water. The organic solvent was distilled of in vacuo and the residue was purified by column chromatography using 40% acetone-chloroform as the eluent to give 25 mg of N-(pyrid-4-yl)-4-cyclopropylmethoxy-dibenzo[b,d]furan-1-carboxamide-N1-oxide as white solid; mp: 266-268° C.

IR (KBr) 3228, 3061, 1662, 1576, 1476, 1395, 1280, 1198, 1097, 895, 750 cm$^{-1}$ $^1$H NMR (300 MHz, DMSO) δ 0.452 (m, 2H), 0.66 (m, 2H), 1.38 (m, 1H), 4.13 (d, 2H, J=7.5 Hz), 7.21 (d, 1H, J=8.7 Hz), 7.40 (t, 1H, J=7.2 Hz), 7.65 (t, 1H, J=6.9 Hz), 7.79 (d, 1H, J=8.4 Hz), 7.96 (d, 1H, J=8.1 Hz), 8.41 (d, 1H, J=7.2 Hz), 8.75 (d, 2H, J=7.5 Hz), 10.62 (s, 1H).

EXAMPLE 29

N-(pyrid-3-yl)-4-cyclopropylmethoxy dibenzo[b,d]furan-1-carboxamide

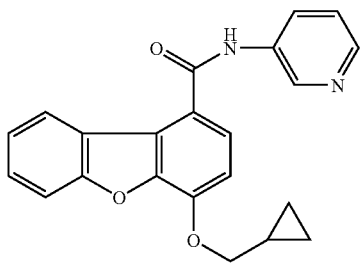

A suspension of intermediate 21 (50 mg, 0.177 mmol) in a mixture of benzene (2 ml) and freshly distilled thionyl chloride (0.5 ml) was heated to reflux temperature for 3 h. The excess thionyl chloride was removed under vacuum to get the corresponding acid chloride.

To a solution of 3-aminopyridine (33 mg, 0.354 mmol) and diisopropylethylamine (0.3 ml) in dry THF (3 ml) was added a solution of above acid chloride (0.0.354 mmol) (in dry THF 3 ml). The reaction mixture was stirred at room temperature for 2 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 70 mg of N-(pyrid-3-yl)-cyclopropylmethoxy-dibenzo[b,d]furan-1-carboxamide as a white solid; mp: 238-240° C.

IR (KBr) 3303, 2927, 2874, 1651, 1526, 1450, 1329, 1288, 1129, 1093, 999, 808, 748 cm$^{-1}$ $^1$H NMR (300 MHz, DMSO) 0.452 (m, 2H), 0.66 (m, 2H), 1.38 (m, 1H), 4.1 (d, 2H, J=7.2 Hz), 7.26 (d, 1H, J=8.4 Hz), 7.33-7.44 (m, 2H), 7.55 (t, 1H, J=8.1 Hz), 7.73-7.80 (m, 2H), 8.24 (d, 1H, J=9.0 Hz), 831-8.33 (m, 2H), 8.92 (s, 1H), 10.68 (s, 1H).

EXAMPLE 30

N-(pyrid-3-yl)cyclopropylmethoxy dibenzo[b,d]furan-1-carboxamide-N1-oxide

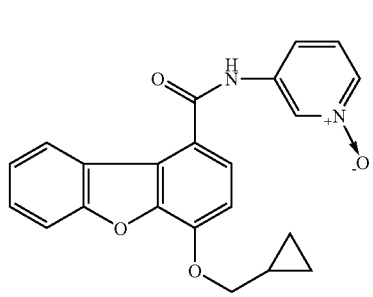

A suspension of N-(pyrid-3-yl)-4-cyclopropylmethoxy-dibenzo[b,d]furan-1-carboxamide (15 mg, 0.139 mmol) (example 30) and m-chloroperbenzoic acid (50-55%) (120 mg, 0.698 mmol) in chloroform (10 ml) was stirred at room temperature for 12 h. The reaction contents were washed with saturated sodium bicarbonate and water. The organic solvent was distilled of in vacuo and the residue was purified by column chromatography using 40% acetone-chloroform as the eluent to give 30 mg of N-(pyrid-3-yl)-4-cyclopropylmethoxy-dibenzo[b,d]furan-1-carboxamide-N-oxide as white solid; mp: 272-275° C.

IR (KBr): 3232, 3069, 2872, 1673, 1571, 1417, 1277, 1154, 1095, 1006, 840, 743 cm$^{-1}$ $^1$H NMR (300 MHz, DMSO) δ 0.452 (m, 2H), 0.66 (m, 2H), 1.38 (m, 1H), 4.13 (d, 2H, J=7.5 Hz), 7.21 (d, 1H, J=8.7 Hz), 7.35-7.58 (m, 2H), 7.68-7.81 (m, 4H), 8.02 (d, 1H, J=6.0 Hz), 8.32 (d, 1H, J=7.8 Hz), 8.86 (s, 1H), 10.82 (s, 1H).

EXAMPLE 31

N-(3,5-dichloropyrid-4-yl)-4-isopropyloxy dibenzo[b,d]furan-1-carboxamide

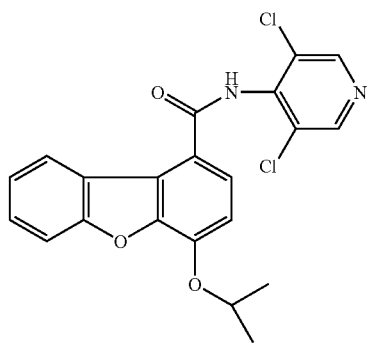

A suspension of intermediate 23 (50 mg, 0.177 mmol) in a mixture of benzene (2 ml) and freshly distilled thionyl chloride (0.5 ml) was heated to reflux temperature for 3 h. The excess thionyl chloride was removed under vacuum to get the corresponding acid chloride.

To a pre-washed suspension of sodium hydride (30.0 mg, 2.0 equiv., 0.74 mmol, 60% oil dispersion) in DMF (3 ml) was added dropwise a solution of 4-amino-3,5-dichloropyridine (60 mg, 0.37 mmol) in DMF (3 ml) at −10° C. A pre-cooled solution of above acid chloride in THF (2 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent and purirication of the crude solid by silica gel column chromatography using 15% ethyl acetate-chloroform as eluent provided N-(3,5-dichloropyrid-4-yl)-4-isopropylmethoxy dibenzo[b,d]furan-1-carboxamide as a white solid (100 mg); mp: 209-211° C.

IR (KBr) 3193, 2973, 1665, 1602, 1555, 1452, 1387, 1279, 1110, 1093, 964, 802, 751, 682 cm$^{-1}$ $^1$H NMR (300 MHz, DMSO) δ 1.43 (d, 6H, J=5.7 Hz), δ 5.06 (m, 1H), 7.35 (t, 1H, J=9.3 Hz), 7.36 (s, 1H), 7.54 (t, 1H, J=6.9 Hz), 7.77 (d, 1H, J=8.1 Hz), 7.8 (d, 1H, J=8.4 Hz), 8.41 (d, 1H, J=7.2 Hz),), 8.78 (s, 1H),), 10.8 (s, 1H).

EXAMPLE 32

N-(3,5-dichloropyrid-4-yl)-4-isopropyloxy dibenzo[b,d]furan-1-carboxamide-N1-oxide

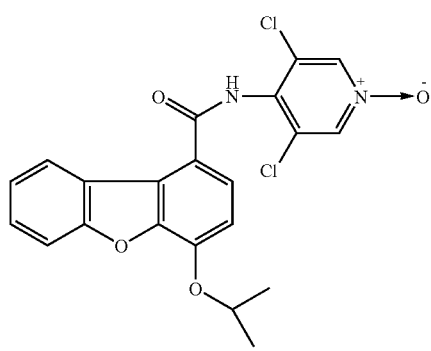

A suspension of N-(3,5-dichloropyrid-4-yl)-4-isopropyloxy-dibenzo[b,d]furan-1-carboxamide (60 mg, 0.144 mmol) (example 32) and m-chloroperbenzoic acid (50-55%) (120 mg, 0.722 mmol) in chloroform (10 ml) was stirred at room temperature for 12 h. The reaction contents were washed with saturated sodium bicarbonate and water. The organic solvent was distilled of in vacuo and the residue was purified by column chromatography using 30% acetone-chloroform as the eluent to give 57 mg of N-(3,5dichlorpyrid-4-yl)-4-isopropyloxy-dibenzo[b,d]furan-1-carboxamide-N1-oxide as white solid; mp: 247-248° C.

IR (KBr) 3213, 2978, 1655, 1574, 1474, 1384, 1280, 1127, 1098, 988, 824, 748 cm$^{-1}$ $^1$H NMR (300 MHz, DMSO) δ 1.41 (d, 6H, J=5.7 Hz), 5.0 (m, 1H), 7.35 (m, 2H), 7.5 (t, 1H, J=6.9 Hz), 7.76 (d, 1H, J=8.4 Hz), 7.85 (d, 1H, J=8.4 Hz), 8.4 (d, 1H, J=7.5 Hz), 8.7 (s, 1H), 10.62 (s, 1H).

EXAMPLE 33

N-(pyrid-4-yl)-4-isopropyloxy dibenzo[b,d]furan-1-carboxamide

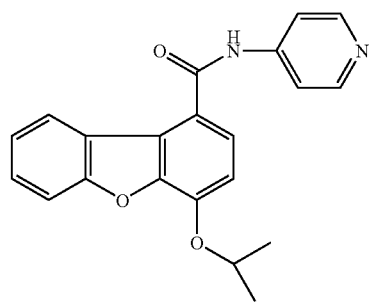

A suspension of intermediate 23 (50 mg, 0.177 mmol) in a mixture of benzene (2 ml) and freshly distilled thionyl chloride (0.5 ml) was heated to reflux temperature for 3 h The excess thionyl chloride was removed under vacuum to get the corresponding acid chloride.

To a solution of 4-aminopyridine (35 mg, 0.37 mmol) and diisopropylethylamine (60 mg. 0.55 mmol) in dry THF (3 ml) was added above solution of acid chloride (0.37 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 90 mg of N-(pyrid-4-yl)-isopropyloxy-dibenzo[b,d]furan-1-carboxamide as a white solid; mp: 151° C. (dec)

IR (KBr) 3278, 2925, 1657, 1583, 1487, 1396, 1282, 1195, 1094, 993, 886, 781, 631 cm$^{-1}$ $^1$H NMR (300 MHz, DMSO) δ 0.452 (m, 2H), 0.66 (m, 2H), 1.38 (m, 1H), 4.15 (d, 2H, J=6.9 Hz), 7.26 (d, 1H, J=8.4 Hz), 7.37 (t, 1H, J=7.2 Hz), 7.56 (t, 1H, J=6.9 Hz), 7.73-7.81 (m, 4H), 8.29 (d, 1H, J=7.5 Hz), 8.49 (d, 2H, J=6.3 Hz), 10.84 (s, 1H).

EXAMPLE 34

N-(pyrid-4-yl)-4-isopropyloxy dibenzo[b,d]furan-1-carboxamide-N1-oxide

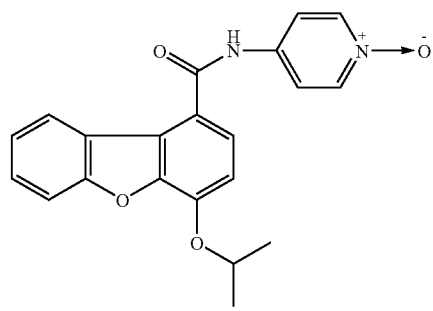

A suspension of N-pyrid-4-yl)-4-isopropyloxy dibenzo[b,d]furan-1-carboxamide (50 mg, 0.144 mmol) (example 34) and m-chloroperbenzoic acid (50-55%) (125 mg, 0.722 mmol) in chloroform (10 ml) was stirred at room temperature for 12 h. The reaction contents were washed with saturated sodium bicarbonate and water. The organic solvent was distilled of in vacuo and the residue was purified by column chromatography using 40% acetone-chloroform as the eluent to give 27 mg of N-pyrid-4-yl)-4-isopropyloxy-dibenzo[b,d]furan-1-carboxamide-N1-oxide as white solid, mp: 247-248° C. (dec)

IR (KBr): 3061, 2918, 2851, 1682, 1594, 1487, 1311, 1293, 1194, 1036, 959, 844, 767 cm$^{-1}$ $^1$H NMR (300 MHz, DMSO) δ 1.43 (d, 6H, J=5.7 Hz), 5.06 (m, 1H), 7.34 (m, 2H), 7.55 (t, 1H, J=6.6 Hz), 7.72-7.86 (m, 5H), 8.18 (d, 2H, J=7.8 Hz), 8.39 (d, 1H, J=7.8 Hz), 10.95 (s, 1H).

EXAMPLE 35

N-(pyrid-3-yl)-4-isopropyloxy dibenzo[b,d]furan-1-carboxamide

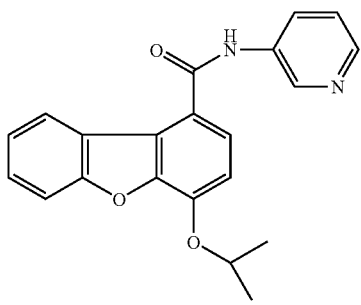

A suspension of intermediate 23 (50 mg, 0.177 mmol) in a mixture of benzene (2 ml) and freshly distilled thionyl chloride (0.5 ml) was heated to reflux temperature for 3 h. The excess thionyl chloride was removed under vacuum to get the corresponding acid chloride.

To a solution of 3-aminopyridine (35 mg, 0.37 mmol) and diisopropylethyl amine (60 mg, 0.55 mmol) in dry THF (3 ml) was added above solution of acid chloride (0.37 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 80 mg of N-(pyrid-3-yl)-isopropyloxy-dibenzo[b,d]furan-1-carboxamide as a white solid; mp: 209-211° C.

IR (KBr): 3283, 2925, 1657, 1525, 1486, 1410, 1293, 1277, 1106, 1092, 994, 884, 788, 671 cm$^{-1}$ $^1$H NMR (300 MHz, DMSO) δ 1.43 (d, 6H, J=5.7 Hz), 5.06 (m, 1H), 7.31-7.45 (m, 3H), 7.45 (t, 1H, J=7.1 Hz), 7.76 (m, 2H), 7.29 (m, 3H), 8.94 (s, 1H), 10.7 (s, 1H).

EXAMPLE 36

N-(pyrid-3-yl)-4-isopropyloxy dibenzo[b,d]furan-1-carboxamide-N1-oxide

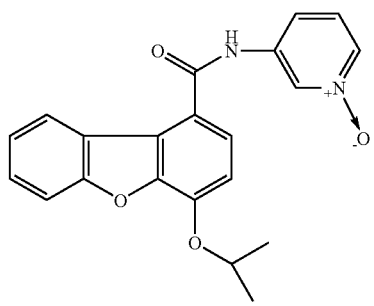

A suspension of N-(pyrid-3-yl)-4isopropyloxy-dibenzo[b,d]furan-1-carboxamide (50 mg, 0.144 mmol) (example 36) and m-chloroperbenzoic acid (50-55%) (125 mg, 0.722 mmol) in chloroform (10 ml) was stirred at room temperature for 12 h. The reaction contents were washed with saturated sodium bicarbonate and water. The organic solvent was distilled off in vacuo and the residue was purified by column chromatography using 40% acetone-chloroform as the eluent to give 30 mg of N-pyrid-3-yl)-4-isopropyloxy-dibenzo[b,d]furan-1-carboxamide-N1-oxide as white solid; mp: 242° C.(dec).

IR (KBr): 3081, 2975, 1683, 1546, 1385, 1278, 1156, 1093, 970, 813, 745 cm$^{-1}$ $^1$H NMR (300 MHz, DMSO) δ 1.43 (d, 6H, J=5.7 Hz), 5.00 (m, 1H), 7.32-7.44 (m, 3H), 7.56 (t, 1H, J=8.1 Hz), 7.68-7.79 (m, 3H), 8.01 (d, 1H, J=5.4 Hz), 8.30 (d, 1H, J=7.8 Hz), 8.62 (s, 1H), 10.82 (s, 1H).

EXAMPLE 37

N-(3,5-dichloropyrid-4-yl)-4-benzyloxy dibenzo[b,d]furan-1-carboxamide

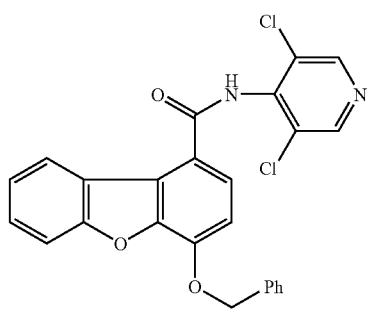

A suspension of intermediate 25 (250 mg, 0.786 mmol) in a mixture of benzene (2 ml) and freshly distilled thionyl chloride (2.0 ml) was heated to reflux temperature for 3 h. The excess thionyl chloride was removed under vacuum to get the corresponding acid chloride.

To a pre-washed suspension of sodium hydride (75 mg, 2.0 equiv., 1.57 mmol, 60% oil dispersion) in DMF (3 ml) was added dropwise a solution of 4-amino-3,5-dichloropyridine (128 mg, 0.78 mmol) in DMF (3 ml) at −10° C. A pre-cooled solution of above acid chloride in THF (5 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution Evaporation of solvent and purification of the crude solid by silica gel column chromatography using 5% ethyl acetate-chloroform as eluent provided N-(3,5-dichloropyrid-4-yl)-4-benzyloxy dibenzo[b,d]furan-1-carboxamide as a white solid (10 mg); mp: 269-270° C. (dec).

IR (KBr): 3376, 3244, 2928, 1664, 1603, 1556, 1484, 1399, 1383, 1278, 1195, 1092, 999, 830, 808, 754 cm$^{-1}$.

$^1$HNMR (300 MHz, DMSO) δ 5.45 (s, 2H), 7.38 (m, 5H), 7.45 (m, 3H), 7.77 (d, 1H, J=9 Hz), 7.86 (d, 1H, J=8.4 Hz), 8.41 (d, 1H, J=9 Hz), 8.77 (s, 2H), 10.81 (s, 1H).

EXAMPLE 38

N-(3,5-dichloropyrid-4-yl)-4-methoxy-8-nitro dibenzo[b,d]furan-1-carboxamide

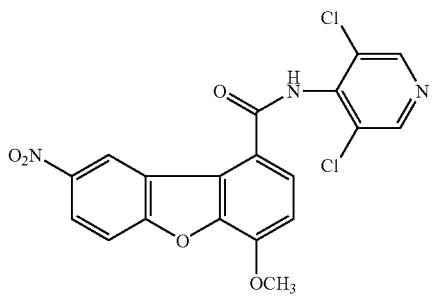

A suspension of intermediate 29 (50 mg, 0.177 mmol) in a mixture of benzene (2 ml) and freshly distilled thionyl chloride (0.5 ml) was heated to reflux temperature for 3 h. The excess thionyl chloride was removed under vacuum to get the corresponding acid chloride.

To a pre-washed suspension of sodium hydride (52 mg, 2.5 equiv., 1.3 mmol, 60% oil dispersion) in DMF (2 ml) was added dropwise a solution of 4-amino-3,5-dichloropyridine (93 mg, 0.52 mmol) in DMF (2 ml) at −10° C. A pre-cooled solution of above acid chloride (0.52 mmol) in THF (2 ml) was added, all at once, to the reaction mixture and the contents were stirred at −10° C. for 30 min. The reaction was quenched with brine, diluted with water and filtered to give a crude solid which was washed with ethanol to give N-(3,5-dichloropyrid-4-yl)-4-methoxy-8-nitro-dibenzo[b,d]furan-1-carboxamide as a white solid (80 mg); mp: 315-317° C.

IR (KBr): 3245, 3092, 2845, 1662, 1614, 1581, 1554, 1519, 1483, 1461, 1439, 1391, 1337, 1282, 1205, 1181, 1067 cm$^{-1}$.

$^1$H NMR (300 MHz, DMSO) δ 4.12 (s, 3H), 7.48 (d, 1H, J=8.1 Hz), 8.03 (d, 1H, J=8.1 Hz), 8.06 (d, 1H, J=8.4 Hz), 8.44 (dd, 1H, J=7.2 Hz), 8.81 (s, 2H). 9.43 (d, 1H, J=1.2 Hz), 10.95 (s, 1H).

EXAMPLE 39

N-(pyrid-4-yl)-4-methoxy-8-nitro dibenzo[b,d]furan-1-carboxamide

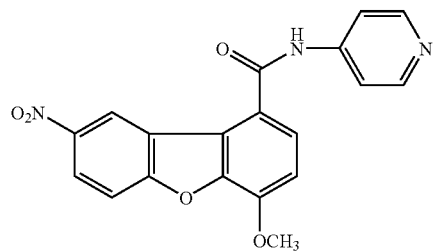

A suspension of intermediate 29 (50 mg, 0.177 mmol) in a mixture of benzene (2 ml) and freshly distilled thionyl chloride (0.5 ml) was heated to reflux temperature for 3 h. The excess thionyl chloride was removed under vacuum to get the corresponding acid chloride.

To a solution of 4-aminopyridine (31 mg, 0.34 mmol) and diisopropylethyl amine (0.3 ml) in dry THF (3 ml) was added a solution of above acid chloride (0.34 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 30 mg of N-(pyrid-4-yl)-4-methoxy-8-nitro-dibenzo[b,d]furan-1-carboxamide as a white solid; mp: 222° C.

IR (KBr): 3272, 2838, 1647, 1522, 1447, 1406, 1296, 1280, 1259, 1174, 1100, 1019 cm$^{-1}$.

$^1$H NMR: (300 MHz, DMSO) δ 4.00 (s, 3H ), 7.22 (m, 3H), 7.50 (t, 1H, J=7.8 Hz), 7.66 (m, 2H), 7.97-7.99 (m, 2H), 8.82-8.84 (m, 2H), 10.85 (s, 1H).

EXAMPLE 40

N-(pyrid-3-yl)-4-methoxy-8-nitro dibenzo[b,d]furan-1-carboxamide

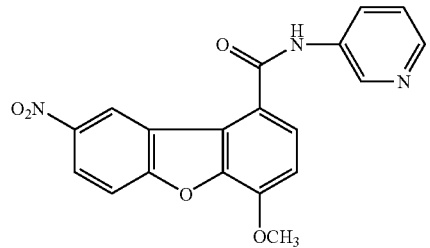

A suspension of intermediate 29 (50 mg, 0.177 mmol) in a mixture of benzene (2 ml) and freshly distilled thionyl chloride (0.5 ml) was heated to reflux temperature for 3 h. The excess thionyl chloride was removed under vacuum to get the corresponding acid chloride.

To a solution of 3-aminopyridine (49 mg, 0.52 mmol) and diisopropylethyl amine (0.3 ml) in dry THF (3 ml) was added a solution of above acid chloride (0.52 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 20 mg of N-(pyrid-3-yl)-methoxy-8-nitro-dibenzo[b,d]furan-1-carboxamide as a white solid; mp: 263-266° C.

IR (KBr): 3273, 3090, 3842, 1647, 1611, 1582, 1520, 1484, 1340, 1286, 1204, 1069, 703 cm$^{-1}$.

$^1$H NMR: (300 Mz, DMSO) δ 4.10 (s, 3H), 7.45 (d, 2H), 7.99 (m, 2H), 8.26 (d, 1H), 8.29 (brs, 1H), 8.46 (d, 1H), 8.95 (brs, 1H), 9.37 (s, 1H), 10.76 (s, 1H).

EXAMPLE 41

N-(3,5-dichloropyrid-4-yl)-4-methoxy-8-chloro-dibenzo[b,d]furan-1-carboxamide

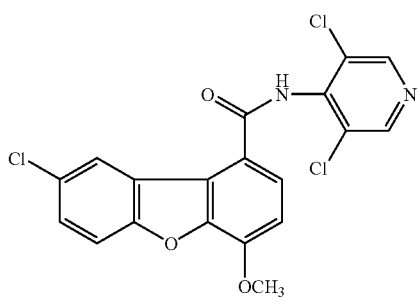

A suspension of intermediate 31 (110 mg, 0.422 mmol) in a mixture of benzene (2 ml) and freshly distilled thionyl chloride (2 ml) was heated to reflux temperature for 3-4 h The excess thionyl chloride was removed under vacuum to get the corresponding acid chloride.

To a pre-washed suspension of sodium hydride (20 mg, 2.0 equiv., 0.844 mmol, 60% oil dispersion) in DMF (3 ml) was added dropwise a solution of 4-amino-3,5-dichloropyridine (68 mg, 0.42 mmol) in DMF (2 ml) at −10° C. A pre-cooled solution of above acid chloride in THF (3 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. The solvent was evaporated and the resulting crude solid was purified by column chromatography using 40% ethyl acetate chloroform as the eluent to obtain 60 mg of N-(3,5-dichloropyrid-4-yl)-4-methoxy-8-chloro-dibenzo[b,d]furan-1-carboxamide as a white solid; mp: 300° C.

IR (KBr): 3173, 2956, 2851, 1660, 1544, 1492, 1454, 1390, 1285, 1257, 1132, 1107, 905, 806, 634 cm$^{-1}$ $^1$H NMR (300 MHz, DMSO) δ 4.05 (s, 3H), 7.38 (d, 2H, J=8.7 Hz), 7.58 (d, 1H, J=9 Hz), 7.80 (d, 1H, J=8.7 Hz), 7.95 (d, 1H, J=8.7 Hz), 8.47 (s, 1H, J=2.4 Hz ), 8.79 (s, 2H), 10.87 (s, 1H).

EXAMPLE 42

N-(3,5-dichloropyrid-4-yl)-4-methoxy-8-bromo-dibenzo[b,d]furan-1-carboxamide

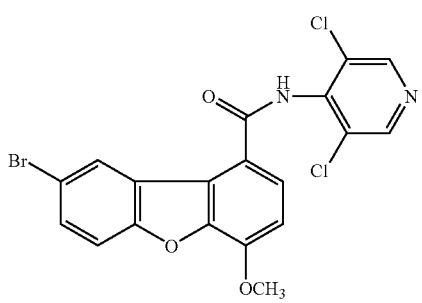

A suspension of intermediate 32 (120 mg, 0.403 mmol) in a mixture of benzene (2 ml) and freshly distilled thionyl chloride (2 ml) was heated to reflux temperature for 3-4 h. The excess thionyl chloride was removed under vacuum to get the corresponding acid chloride.

A solution of 4-amino-3,5-dichloropyridine (68 mg, 0.42 mmol) in DMF (3 ml) at −10° C. was added to a pre-washed suspension of sodium hydride (24 mg, 2.5 equiv., 1.08 mmol, 60% oil dispersion) in DMF (3 ml) dropwise. A pre-cooled solution of above acid chloride in THF (3 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution.The solvent was evaporated and the resulting crude solid was purified by column chromatography using 10% acetone-chloroform as the eluent to obtain 110 mg of N-(3,5-dichloropyrid-4-yl)-4-methoxy-8-bromo-dibenzo[b,d]furan-1-carboxamide as a white solid; mp: 308° C.

IR (KBr): 3144, 3040, 2977, 2944, 2846, 1660, 1542, 1496, 1301, 1282, 1203, 1106, 1018, 914, 803, 726, 662 cm$^{-1}$ $^1$H NMR (300 MHz, DMSO) δ 4.08 (s, 3H), 7.38 (d, 1H, J=8.1 Hz), 7.73 (d, 1H, J=8.7 Hz), 7.76 (d, 1H, J=6.9 Hz), 7.94 (d, 1H, J=8.7 Hz), 8.62 (s, 1H, J=2.1 Hz), 8.79 (s, 2H), 10.87 (s, 1H).

EXAMPLE 43

N-(pyrid-4-yl)-4-methoxy-8-bromo-dibenzo[b,d]furan-1-carboxamide

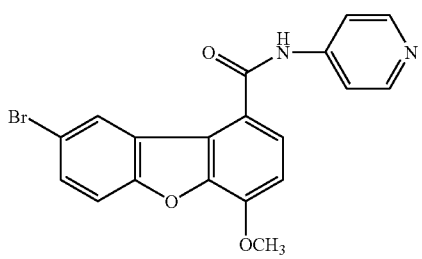

A suspension of intermediate 32 (120 mg, 0.403 mmol) (from step 2 above) in a mixture of benzene (2 ml) and freshly distilled thionyl chloride (2 ml) was heated to reflux temperature for 3-4 h. The excess thionyl chloride was removed under vacuum to get the corresponding acid chloride.

To a solution of 4-aminopyridine (29 mg, 0.310 mmol) and diisopropylethyl amine (59 mg, 0.591 mmol) in dry THF (5 ml) was added a solution of above acid chloride (0.295 mmol) in dry THF (5 ml). The reaction mixture was stirred at room temperature for 2 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 65 mg of N-(pyrid-4-yl)-methoxy-8-bromo-dibenzo[b,d]furan-1-carboxamide as a white solid; mp: 270-273° C.

IR (KBr): 3309, 3037, 2923, 2852, 1660, 1585, 1505, 1410, 1330, 1282, 1256, 1181, 1106, 902, 886, 750, 654 cm$^{-1}$ $^1$H NMR (300 MHz, DMSO) δ 4.07 (s, 1H), 7.35 (d, 1H, J=8.1 Hz), 7.73 (d, 1H), 7.74 (d, 1H, J=6.6 Hz), 7.79 (d, 1H, J=6.7 Hz), 7.85 (d, 1H, J=8.4 Hz), 8.49 (d, 2H, J=6.3 Hz), 8.51 (s, 2H), 10.8 (s, 1H).

EXAMPLE 44

N-(pyrid-3-yl)-4-methoxy-8-bromo-dibenzo[b,d]furan-1-carboxamide

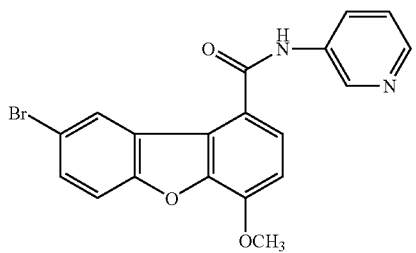

A suspension of intermediate 32 (120 mg, 0.403 mmol) in a mixture of benzene (2 ml) and freshly distilled thionyl chloride (2 ml) was heated to reflux temperature for 3-4 h. The excess thionyl chloride was removed under vacuum to get the corresponding acid chloride.

To a solution of 3-aminopyridine (29 mg, 0.31 mmol) and diisopropylethyl amine (59 mg, 0.591 mmol) in dry THF (5 ml) was added a solution of above acid chloride (0.295 mmol) in dry THF (5 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 30% acetone-chloroform as the eluent to obtain 45 mg of N-pyrid-3-yl)-methoxy-8-bromo-dibenzo[b,d]furan-1-carboxamide as a white solid; mp: 265° C. (dec)

IR (KBr): 3257, 2924, 2853, 1645, 1602, 1525, 1483, 1409, 1390, 1284, 1263, 1107, 1022, 882, 795, 705, 634 cm$^{-1}$ $^1$H NMR (300 MHz, DMSO) δ 4.07 (s, 3H), 7.35 (d, 1H, J=8.4 Hz), 7.41 (t, 1H, J=8.4 Hz), 7.70 (d, 1H, J=8.7 Hz), 7.76 (d, 1H, J=8.7 Hz), 7.86 (d, 1H, J=8.1 Hz), 8.23 (d, 1H, J=3.9 Hz), 8.32 (d, 1H, J=4.5 Hz), 8.55 (s, 1H, J=1.8 Hz), 8.92 (s, 1H, J=2.7 Hz), 10.71 (s, 1H).

EXAMPLE 45

N-(3,5-dichloropyrid-4-yl)-4-methoxy-8-iodo-dibenzo[b,d]furan-1-carboxamide

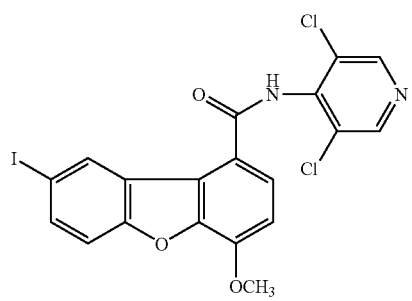

A suspension of intermediate 33 (140 mg, 0.44 mmol) in a mixture of benzene (2 ml) and freshly distilled thionyl chloride (2 ml) was heated to reflux temperature for 3-4 h. The excess thionyl chloride was removed under vacuum to get the corresponding acid chloride.

To a pre-washed suspension of sodium hydride (26 mg, 2.5 equiv., 1.10 mmol, 60% oil dispersion) in DMF (3 ml) was added dropwise a solution of 4-amino-3,5-dichloropyridine (75 mg, 417 mmol) in DMF (2 ml) at −10° C. A pre-cooled solution of above acid chloride in THF (5 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. The ethyl acetate extract was concentrated under reduced pressure and the residue was purified by silica gel chromatography using 20% acetone-chloroform as the eluent to obtain 90 mg N-(3,5-dichloropyrid-4-yl)-4-methoxy-8-iodo-dibenzo[b,d]furan-1-carboxamide as a white solid, mp: 304° C. (dec).

IR (KBr): 3194, 2924, 2853, 1668, 1627, 1552, 1488, 1389, 1286, 1265, 1183, 1107, 893, 808, 778, 658 cm$^{-1}$.

$^1$H NMR (300 MHz, DMSO) δ 4.07 (s, 3H), 7.36 (d, 1H, J=8.7 Hz), 7.61 (d, 1H, J=8.4 Hz), 7.83 (d, 1H, J=8.7 Hz), 7.92 (d, 1H, J=8.4 Hz), 8.79 (s, 2H), 8.81 (s, 1H), 10.86 (s, 1H).

EXAMPLE 46

N-(pyrid-4-yl)-4-methoxy-8-iodo-dibenzo[b,d]furan-1-carboxamide

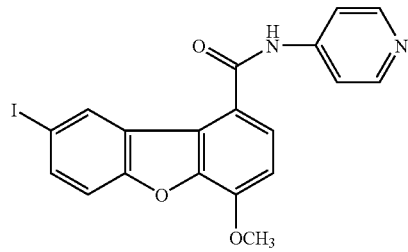

A suspension of intermediate 33 (140 mg, 0.44 mmol) in a mixture of benzene (2 ml) and freshly-distilled thionyl chloride (2 ml) was heated to reflux temperature for 3-4 h The excess thionyl chloride was removed under vacuum to get the corresponding acid chloride.

To a solution of 4-aminopyridine (100 mg, 0.257 mmol) and diisopropylethyl amine (52 mg, 515) in dry THF (5 ml) was added a solution of above acid chloride (0.257 mmol) in dry THF (5 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 30% acetone-chloroform as the eluent to obtain 52 mg of N-(pyrid-4-yl)-methoxy-8-iodo-dibenzo[b,d]furan-1-carboxamide as a white solid; mp: 255-257° C.

IR (KBr): 3292, 2929, 1692, 1659, 1582, 1504, 1410, 1330, 1276, 1200, 1104, 888, 805, 780, 718 cm$^{-1}$ $^1$H NMR (300 MHz, DMSO) δ 4.07 (s, 3H), 7.34 (d, 1H, J=8.4 Hz), 7.62 (d, 1H, J=8.4), 7.79 (d, 1H, J=4.8), 7.85 (d, 1H, J=4.8 Hz), 7.87 (d, 2H), 8.50 (d, 2H, J=5.7 Hz), 8.69 (s, 1H, J=2.1 Hz), 10.86 (s, 1H).

EXAMPLE 47

N-(pyrid-3-yl)-4-methoxy-8-iodo-dibenzo[b,d]furan-1-carboxamide

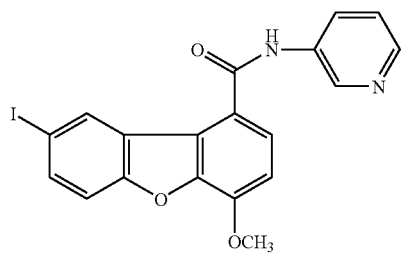

A suspension of intermediate 33 (140 mg, 0.44 mmol) in a mixture of benzene (2 ml) and freshly distilled thionyl chloride (2 ml) was heated to reflux temperature for 3-4 h The excess thionyl chloride was removed under vacuum to get the corresponding acid chloride.

To a solution of 3-aminopyridine (100 mg, 0.257 mmol) and diisopropylethylamine (52 mg, 0.515 mmol) in dry THF (3 ml) was added a solution of above acid chloride (0.257 mmol) in dry THF (3 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 20% acetone-chloroform as the eluent to obtain 64 mg of N-pyrid-3-yl)-methoxy-8-iodo-dibenzo[b,d]furan-1-carboxamide as a white solid; mp: 286-287° C.

IR (KBr): 3256, 2930, 1645, 1599, 1524, 1504, 1408, 1333, 1283, 1266, 1105, 1019, 884, 795, 705 cm$^{-1}$ $^1$H NMR (300 MHz, DMSO) δ 4.07 (s, 3H), 7.34 (d, 1H, J=8.7 Hz), 7.42-7.46 (m, 2H), 7.62 (d, 1H, J=8.7), 7.84 (d, 1H, J=8.7 Hz), 8.26 (d, 1H, J=3.9 Hz), 8.33 (d, 1H, J=4.8 Hz), 8.72 (s, 1H, J=1.2 Hz), 8.92 (s, 1H, J=2.4 Hz), 10.71 (s, 1H).

EXAMPLE 48

N-(4-methylpyrimid-2-yl)-4-methoxy dibenzo[b,d]furan-1-carboxamide

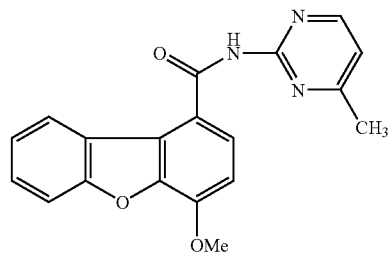

A suspension of intermediate 4 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (82 mg, 2.5 equiv., 2.0 mmol, 60% oil dispersion) in DMF (4 ml) was added dropwise a solution of 2-amino-4-methyl pyrimidine (108 mg, 0.90 mmol) in DMF (4 ml) at −10° C. A pre-cooled solution of above acid chloride (0.826 mmol) in THF (3 ml) was added, all at once, to the reaction mixture and the contents were stirred at −10° C. for 60 min. The reaction was quenched with brine, diluted with water and extracted with ethyl acetate. The organic layer was washed with water, 5% HCl, 5% sodium bicarbonate and brine solution. The ethyl acetate extract was concentrated under reduced pressure and the residue was purified by silica gel chromatography using 15% acetone-chloroform as the eluent to obtain 80 mg N-(4-methylpyrinid-2-yl)-4-methoxy-dibenzo[b,d]furan-1-carboxamide as a white solid; mp; 272-274° C.

IR (KBr)3246, 2927, 2847, 1693, 1629, 1593, 1510, 1438, 1394, 1269, 1175, 1096, 1010, 749 cm$^{-1}$.

$^1$H NMR (300 MHz, DMSO) δ 2.49 (s, 3H), 4.05 (s, 3H), 7.13 (d, 1H, J=8.4 Hz), 7.25 (d, 1H, J=8.4 Hz), 7.33 (t, 1H), 7.54 (t, 1H), 7.72-7.76 (m, 2H), 8.34 (d, 1H, J=7.5 Hz), 8.54 (d, 1H, J=7.5 Hz), 11.05 (s, 1H).

EXAMPLE 49

N-(2,5-dichlorophenyl)-4-methoxy dibenzo[b,d]furan-1-carboxamide

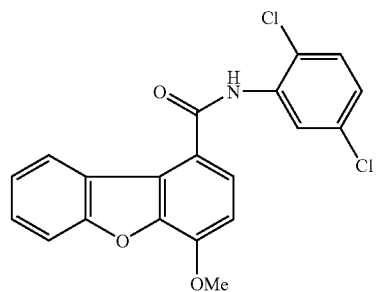

A suspension of intermediate 4 (100 mg, 0.00413 mol) in a mixture of benzene (2 ml) and freshly distilled thionyl chloride (2 ml) was heated to reflux temperature for 4 h. The excess thionyl chloride was removed under vacuum to get the corresponding acid chloride.

To a solution of 2,5-dichloroaniline (117 mg, 0.73 mmol) and diisopropylethyl amine (157 mg, 1.2 mmol) in dry THF (5 ml) was added a solution of acid chloride (0.61 mmol) in dry THF (5 ml). The reaction mixture was stirred at room temperature for 1 h. The reaction mixture was diluted with water (10 ml) and extracted with ethyl acetate (10 ml×3). The ethyl acetate extract was concentrated under reduced pressure and the residue was purified by silica gel chromatography using 30% ethyl acetate-petroleum ether as the eluent to obtain 40 mg of N-(2,5-dichlorophenyl)-methoxy-dibenzo[b,d]furan-1-carboxamide as a white solid; mp: 202° C.

IR (KBr) 3353, 2934, 1665, 1579, 1506, 1452, 1480, 1395, 1280, 1270, 1253, 1148, 1090, 1013, 754 cm$^{-1}$.

$^1$H NMR (300 MHz, DMSO) δ 4.07 (s, 3H), 7.29-7.39 (m, 3H), 7.40-7.75 (m, 4H), 7.87 (d, 1H, J=7.5 Hz), 8.43 (d, 1H, J=7.5 Hz), 10.27 (s, 1H).

EXAMPLE 50a

N-(3,5-dichloropyrid-4-yl)-4-ethoxycarbomethoxy dibenzo[b,d]furan-1-carboxamide

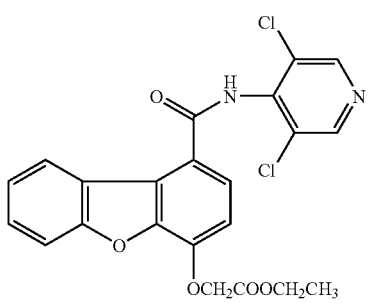

A suspension of intermediate 41 (140 mg, 0.44 mmol) in a mixture of benzene (2 ml) and freshly distilled thionyl chloride (2 ml) was heated to reflux temperature for 3-4 h. The excess thionyl chloride was removed under vacuum to get the corresponding acid chloride.

To a pre-washed suspension of sodium hydride (100 mg, 2.0 equiv., 2.48 mmol, 60% oil dispersion) in DMF (5 ml) was added dropwise a solution of 3,5-dichloro-4-aminopyridine (200 mg, 1.24 mmol) in DMF (5 ml) at −10° C. A pre-cooled solution of above acid chloride in THF (15 ml) was added, all at once, to the reaction mixture and the contents were stirred at −10° C. for 1 h. The reaction was quenched with brine, diluted with water and extracted with ethyl acetate. The organic layer was washed with water, 5% HCl, 5% sodium bicarbonate and brine solution. The solvent was evaporated and the resulting crude solid was purified by silica gel column chromatography using 20% ethyl acetate-chloroform provided N-(3,5-dichloro-pyrid-4-yl)-4-ethoxy-carbomethoxy-dibenzo[b,d]furan-1-carboxamide as a white solid (53a) (30 mg); mp:255-257° C. (dec).

IR (KBr) 3183, 2924, 1743, 1664, 1548, 1489, 1400, 1297, 1196, 1025, 809, 756 cm$^{-1}$.

$^1$H NMR (300 MHz, DMSO) δ 1.23 (t, 3H), 4.22 (q, 2H), 5.16 (s, 2H), 7.30 (d, 1H, J=8.4 Hz), 7.36 (t, 1H, J=8.4 Hz), 7.55 (t, 1H, J=8.4 Hz), 7.77 (d, 1H, J=8.4 Hz), 7.84 (d, 1H, J=8.4 Hz), 8.40 (d, 1H, J=8.4 Hz), 8.77 (s, 2H), 10.84 (s, 1H)

EXAMPLE 50b

N-(3,5-dichloropyrid-4-yl)-4-hydroxycarbomethoxy dibenzo[b,d]furan-1-carboxamide

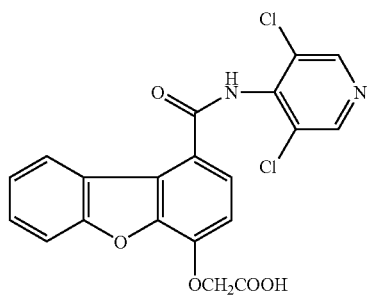

A suspension of intermediate 41 (140 mg, 0.44 mmol) in a mixture of benzene (2 ml) and freshly distilled thionyl chloride (2 ml) was heated to reflux temperature for 3-4 h. The excess thionyl chloride was removed under vacuum to get the corresponding acid chloride.

To a pre-washed suspension of sodium hydride (100 mg, 2.0 equiv., 2.48 mmol, 60% oil dispersion) in DMF (5 ml) was added dropwise a solution of 3,5-dichloro-4-aminopyridine (200 mg, 1.24 mmol) in DMF (5 ml) at −10° C. A pre-cooled solution of above acid chloride in THF (15 ml) was added, all at once, to the reaction mixture and the contents were stirred at −10° C. for 1 h. The reaction was quenched with brine, diluted with water and extracted with ethyl acetate. The organic layer was washed with water, 5% HCl, 5% sodium bicarbonate and brine solution. The solvent was evaporated and the resulting crude solid was purified by silica gel column chromatography using 20% ethyl acetate-chloroform to get the desired product as a white solid (53b) (30 mg); mp: 230° C. (dec).

IR (KBr) 3433, 3128, 2890, 1732, 1632, 1487, 1399, 1297, 1193, 1009, 830, 723 cm$^{-1}$.

$^1$H NMR (300 MHz, DMSO) δ 5.42 (s, 2H), 7.47 (t, 1H, J=7.5 Hz), 7.62 (t, 1H, J=7.5 Hz), 7.79 (d, 1H, J=8.4 Hz), 7.91 (d, 1H, J=8.4 Hz), 7.95 (d, 1H, J=8.4 Hz), 8.22 (d, 1H, J=8.4 Hz), 8.74 (s, 2H), 10.90 (s, 1H).

EXAMPLE 51

N-(3,5-dichloropyrid-4-yl)-4methoxy dibenzo[b,d]furan-2-carboxamide

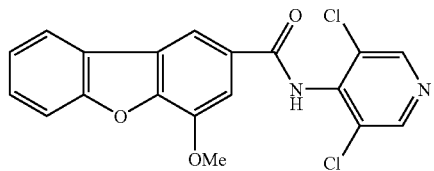

A suspension of intermediate 37 (260 mg, 1.079 mmol) in a mixture of benzene (2 ml) and freshly distilled thionyl chloride (2 ml) was heated to reflux temperature for 3-4 h. The excess thionyl chloride was removed under vacuum to get the corresponding acid chloride.

To a pre-washed suspension of sodium hydride (107 mg, 2.5 equiv., 2.68 mmol, 60% oil dispersion) in DMF (2.5 ml)

was added dropwise a solution of 4-amino-3,5-dichloropyridine (175 mg, 1.074 mmol) in DMF (2.5 ml) at −10° C. A pre-cooled solution of above acid chloride in THF (5 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent and washing of the resulting crude solid with ether provided N-(3,5-dichloropyrid-4-yl)-4-methoxy dibenzo[b,d]furan-2-carboxamide as a white solid (255 mg); mp: 165-166° C.

IR (KBr) 3252, 3060, 2946, 2848, 1665, 1552, 1485, 1398, 1351, 1197, 1099, 812, 749 cm$^{-1}$.

$^1$H NMR (300 MHz, DMSO) δ 4.08 (s, 3H), 7.46 (t, 1H, J=7.8 Hz), 7.58 (t, 1H, J=7.8 Hz), 7.75-7.80 (m, 2H), 8.20 (d, 1H, J=6.9 Hz), 8.43 (s, 1H), 8.77 (s, 2H), 10.76 (s, 1H).

EXAMPLE 52

N-(3,5-dichloropyrid-4-yl)-4-methoxy dibenzo[b,d]furan-3-carboxamide

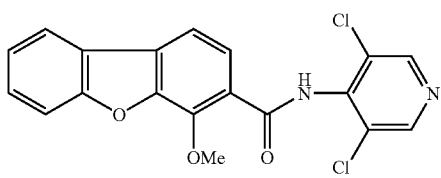

A suspension of intermediate 44 (200 mg, 0.826 mol) in a mixture of benzene (2 ml) and freshly distilled thionyl chloride (2 ml) was heated to reflux temperature for 3 h. The excess thionyl chloride was removed under vacuum to get the corresponding acid chloride.

To a pre-washed suspension of sodium hydride (82 mg, 2.5 equiv., 2.066 mmol, 60% oil dispersion) in DMF (2.5 ml) was added dropwise a solution of 4-amino-3,5-dichloropyridine (134 mg, 0.826 mmol) in DMF (2.5 ml) at −10° C. A pre-cooled solution of above acid chloride (from step 5a) in THF (10 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent and purification of the resulting crude solid by silica gel column chromatography using 5% ethyl acetate-chloroform provided N-(3,5-dichloropyrid-4-yl)-4-methoxy dibenzo[b,d]furan-3-carboxamide as a white solid (230 mg); mp: 176° C. (dec).

IR (KBr) 3301, 2923, 1683, 1629, 1544, 1485, 1315, 1265, 1199, 1095, 906, 886, 750, cm$^{-1}$.

$^1$H NMR (300 MHz, DMSO) δ 4.32 (s, 3H), 7.46 (t, 1H, J=8.4 Hz), 7.58 (t, 1H, J=8.4 Hz), 7.76 (d, 1H, J=8.4 Hz ), 7.84 (d, 1H, J=8.4 Hz), 7.95 (d, 1H, J=8.4 Hz), 8.22 (d, 1H, J=8.4 Hz), 8.74 (s, 2H), 10.49 (s, 1H).

EXAMPLE 53

N4-4-methoxy dibenzo[b,d]furan-1-yl)isonicotinamide

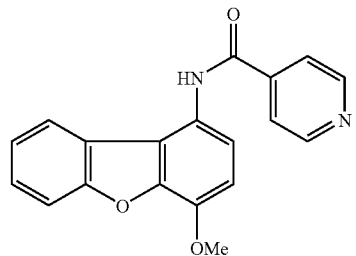

Isonicotinic acid (200 mg, 1.62 mmol) and thionyl chloride (5 ml) was refluxed for 3 h. The excess thionyl chloride was distilled off and a solution of the resulting solid in dry THF (2.5 ml) was added to a solution of intermediate 39 (345 mg, 1.62 mmol) in THF (5 ml) at room temperature. The reaction was stirred at room temperature for 30 min. THF was evaporated, and the residue was partitioned between ethyl acetate (20 ml) and water (10 ml). The ethyl acetate extract was washed with water, concentrated to give 180 mg of crude amide which was purified by silica gel column chromatography using 20% acetone-chloroform as the eluent to give 80 mg of N4-(4-methoxy dibenzo[b,d]furan-1-yl)isonicotinamide as white solid; mp 221° C.

IR (KBr) 3272, 3059, 2838, 1647, 1594, 1522, 1447, 1406, 1296, 1280, 1259, 1174, 1100, 745 cm$^{-1}$.

$^1$H NMR (300 MHz, DMSO) δ 4.00 (s, 3 H), 7.20-7.35 (brm, 3H), 7.50 (t, 1H, J=7.2 Hz), 7.53-7.71 (m, 2H), 7.71 (d, 2H, J=5.1 Hz), 8.82 (d, 2H, J=5.1 Hz), 10.85 (s, 1H).

EXAMPLE 54

N-(3,5-dichloropyrid-4-yl)-4-methoxy dibenzo[b,d]furan-1-sulfonamide

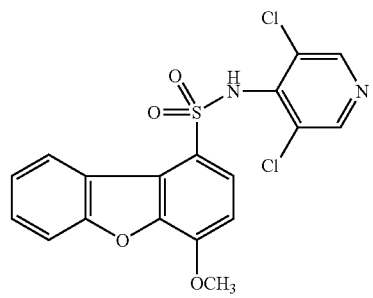

Step 1: 4-methoxy-dibenzo[b,d]furan-1-sulfonyl chloride

Intermediate 40 (400 mg, 1.87 mmol) was dissolved in glacial acetic acid (20 ml) and 17% HCl (10 ml). This solution was cooled to 5° C. and a solution of sodium nitrite (260 mg, 3.74 mmol) in water (5 ml) was added slowly during 10 min. The reaction was stirred for 1 h at 5° C. The reaction mixture was then added to a saturated solution of sulfur dioxide (generated from sodium sulfite and conc. HCl) in acetic acid: benzene (3:2) containing cupric chloride dihydrate (100 mg, 0.513 mmol). The reaction was sired at room temperature for 20 h and then poured water (500 ml) and extracted with ethyl acetate (3×100 ml). The extract was washed with water (5×100 ml) and dried over anhydrous sodium sulfate. The solvent was evaporated to give the product as brown solid (350 mg) which was directly used to make the sulfonamide.

Step 2: N-(3,5-dichloropyrid-4-yl)-4-methoxy dibenzo[b,d]furan-1-sulfonamide

To a pre-washed suspension of sodium hydride (33 mg, 2.0 equiv., 0.827 mmol, 60% oil dispersion) in DMF (2.5 ml) was added dropwise a solution of 4-amino-3,5-dichloropyridine (67 mg, 0.413 mmol) in DMF (2.5 ml) at −10° C. A pre-cooled solution of above sulfonyl chloride (from step 1) in THF (10 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. Evaporation of solvent and purification of the resulting crude solid by silica gel column chromatography using 5% ethyl acetate-chloroform provided N-(3,5-dichloropyrid-4-yl)-4-methoxy dibenzo[b,d]furan-1-sulfonamide as a dark brown solid (25 mg); mp: 242-244° C.

IR (KBr): 2919, 2850, 1628, 1572, 1451, 1392, 1280, 1165, 1097, 952, 889, 752 cm$^{-1}$ $^1$H NMR (300 MHz, DMSO) δ 4.07 (s, 3H), 7.25-7.32 (m, 2H), 7.55 (t, 1H, J=7.8 Hz), 7.74-7.81 (m, 2H), 8.32 (d, 1H, J=7.8 Hz), 8.52 (s, 2H).

EXAMPLE 55

N-(3,5-dichloropyrid-4-yl)-4-methoxy-8-amino-dibenzo[b,d]furan-1-carboxamide

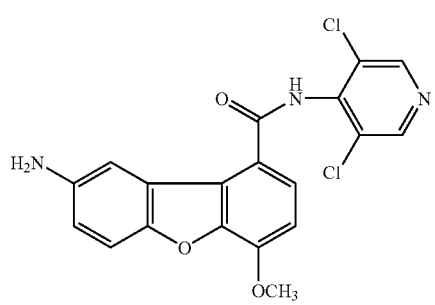

To a suspension of N-(3,5-dichloropyrid-4-yl)-4-methoxy-8-nitro dibenzo[b,d]furan-1-carboxamide (example 38) (4.8 gm, 0.011 mol) in methanol (25 ml) was added activated raney nickel (1.44 gm, 30% w/w) and stirred at reflux for 10 min. Hydrazine hydrate (1.117 gm, 0.022 mol) was added dropwise to the above refluxing reaction mixture. The reaction was refluxed for further 30 min. and filtered through celite bed. The filtrate was concentrated in vaccuo and the residue was purified using silica gel chromatography using 15% acetone in chlroform as the eluent to afford 3.5 gm of N-(3,5-dichloropyrid-4-yl)-4-methoxy-8-amino-dibenzo[b,d]furan-1-carboxamide as white solid. mp: 249° C. (dec).

IR (KBr): 3373, 3300, 2925, 1669, 1605, 1482, 1395, 1281, 1198, 1100, 919, 803 cm−1.

$^1$H NMR (300 MHz, DMSO) δ 4.03 (s, 3H), 5.00 (brs, 2H), 6.79 (d, 1H), 7.24 (d, 1H, J=8.1 Hz), 7.39 (d, 1H, J=9.9 Hz), 7.53 (s, 1H), 7.82 (d, 1H, J=8.1 Hz), 8.75 (s, 2H), 10.69 (s, 1H).

EXAMPLE 56

N-(3,5-dichloropyrid-4-yl)-4-difluoromethoxy-dibenzo[b,d]furan-1-carboxamide-N-oxide

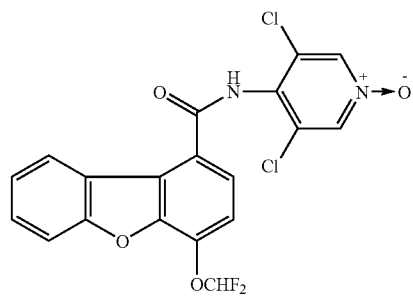

To a stirred solution of N-3,5-dichloropyrid-4-yl)-4-difluoromethoxy-dibenzo[b,d]furan-1-carboxamide (example 19) (800 mg, 0.0018 mol) in chloroform (25 ml) was added 50% m-CPBA (1.63 gm, 0.0094 mol) and the reaction mixture was stirred at room temperature for 48 h The reaction mixture was quenched with 10% aqueous sodium sulfite solution (20 ml) and stirred for 5 minutes. The layers were separated and the organic layer was washed with 1N sodium hydroxide solution (20 ml), water (20 ml) and brine (20 ml). The crude product obtained after evaporation of the solvent was purified by silica gel column chromatography using 30% acetone in chloroform to give 700 mg of the product as white solid, mp ° C.;

IR (KBr): 3218, 3057, 3000, 1659, 1535, 1481, 1452, 1281, 1245, 1219, 1195, 1078, 1033, 831, 754 cm$^{-1}$.

$^1$H NMR (300 MHz, DMSO) δ 7.58 (t, J=72 Hz, 1H), 7.44 (t, 1H), 7.61 (d, 1H), 7.64 (t, 1H), 7.84 (d, 1H), 7.88 (d, 1H), 8.37 (d, 1H), 8.80 (s, 2H), 10.85 (s, 1H).

EXAMPLE 57

N-(3,5dichloropyrid-4-yl)-4-methoxy-8-cyano-dibenzo[b,d]furan-1-carboxamide

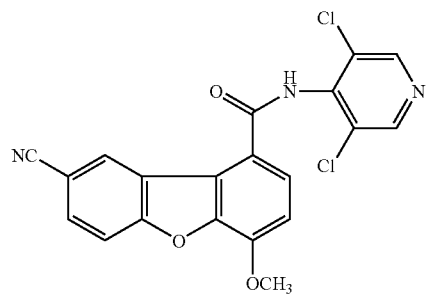

Step 1:
4-methoxy-8-cyano-dibenzo[b,d]furan-1-carboxylic acid

Intermediate 30 (500 mg, 1.99 mmol) was suspended in mixture of concentrated hydrochloric acid: water (1: 1) (20 ml) and stirred at 50° C. for 30 min. The suspension was cooled to 0° C. and a solution of sodium nitrite (161 mg, 2.33 mmol) in water (2 ml) was added dropwise in 15 min. The reaction was stirred for 30 min. at 0-5° C. and then neutralized to neutral pH with saturated sodium carbonate solution The reaction suspension was then added to a pre-cooled solution of CuCN (174 mg, 1.99 mmol) and NaCN (238 mg, 4.86 mmol) in water (10 ml). The reaction was allowed to come to room temperature for 2 h. The reaction mixture was then poured into water (100 ml) and the solid was filtered and then purified by column chromatography using 15% ethyl acetate-chloroform as the eluent to obtain 250 mg of the product as white solid.

$^1$H NMR (300 MHz, DMSO) δ 4.08 (s, 3H), 6.87 (d, 1H), 7.41 (d, 1H, J=6.9 Hz), 8.00-8.12 (m, 2H), 9.29 (s, 1H), 12.25 (brs, 1H).

Step 2: N-(3,5-dichloropyrid-4-yl)-4-methoxy-8-cyano-dibenzo[b,d]furan-1-carboxamide A suspension of 4-methoxy-8-cyano-dibenzo[b,d]furan-1-carboxylic acid (80 mg, 0.299 mmol) (from above step) in a mixture of benzene (2 ml) and freshly distilled thionyl chloride (2 ml) was heated to reflux temperature for 3-4 h. The excess thionyl chloride was removed under vacuum to get the corresponding acid chloride which was subjected the next reaction as such.

To a pre-washed suspension of sodium hydride (29 mg, 2.5 equiv., 0.749 mmol, 60% oil dispersion) in DMF (3 ml) was added dropwise a solution of 4-amino-3,5-dichloropyridine (51 mg, 0.314 mmol) in DMF (2 ml) at −10° C. A pre-cooled solution of above acid chloride (from step 3a) in THF (3 ml) was added, all at once, to the reaction mixture and the contents were stirred at −10° C. for 30 min. The reaction was quenched with brine, diluted with water and extracted with ethyl acetate. The organic layer was washed with water, 5% HCl, 5% sodium bicarbonate and brine solution. The solvent was evaporated to afford a crude solid was purified by column chromatography using 10% ethyl acetate-chloroform as the eluent to obtain 60 mg of N-(3,5-dichloropyrid-4-yl)-4-methoxy-8-chloro-dibenzo[b,d]furan-1-carboxamide as a white solid; mp: >250° C.

IR (KBr): 3183, 3025, 2921, 2226, 1654, 1553, 1488, 1396, 1289, 1185, 1096, 1020, 808 cm$^{-1}$ $^1$H NMR (300 MHz, DMSO) δ 4.11 (s, 3H), 7.50 (d, 1H, J=8.4 Hz), 8.04-8.09 (m, 3H), 8.83 (s, 2H), 8.89 (s, 1H), 10.96 (s, 1H).

EXAMPLE 58

N-(3,5-dichloropyrid-4-yl)-4-difluoromethoxy-8-nitro-dibenzo[b,d]furan-1-carboxamide

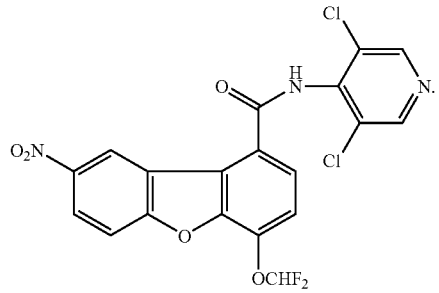

A solution of intermediate 51 (100 mg, 0.30 mmol) (from step 7) in a mixture of benzene (2 ml) and freshly distilled thionyl chloride (2 ml) was heated to reflux temperature for 4 h. The excess thionyl chloride was removed under vacuum to get the corresponding acid chloride To a pre-washed suspension of sodium hydride (25 mg, 60% oil dispersion) in DMF (3 ml) was added dropwise a solution of 4-amino-3,5-dichloropyridine (53 mg, 0.30 mmol) in DMF (2 ml) at −10° C. A pre-cooled solution of above acid chloride (0.30 mmol) in THF (5 ml) was added, all at once, to the reaction mixture and the contents were stirred at −10° C. for 30 min. The reaction was quenched with brine, diluted with water and filtered to give a crude solid which was purified by silica gel chromatography using 10% acetone in chloroform as the eluent to provide 100 mg of N-(3,5-dichloropyrid-4-yl)-4-difluoromethoxy-8-nitro-dibenzo[b,d]furan-1-carboxamide as white solid. mp: >270° C.

IR (KBr): 3213, 2926, 1664, 1555, 1526, 1488, 1339, 1285, 1199, 1090, 904, 823 cm−1.

$^1$H NMR (300 MHz, DMSO) δ 7.63 (t, 1H, J=72 Hz), 7.77 (d, 1H), 8.09 (d, 1H), 8.13 (d, 1H), 8.52 (dd, 1H, J=9.3 Hz, 2.4 Hz), 8.86 (s, 2H), 9.39 (d, 1H, J=2.7 Hz), 11.21 (s, 1H).

EXAMPLE 59

N-(3,5-dichloropyrid-4-yl)-4-difluoromethoxy-8-amino-dibenzo[b,d]furan-1-carboxamide

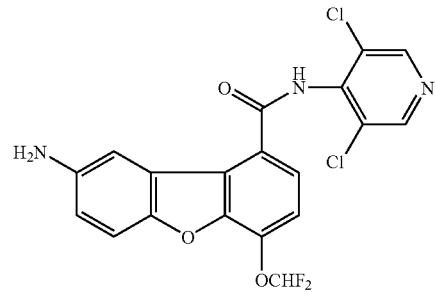

A mixture of N-(3,5-dichloropyrid-4-yl)-4-difluoromethoxy-8-nitro-dibenzo[b,d]furan-1-carboxamide (example 58) (100 mg), methanol (10 ml) and 10% Pd/C (10 mg) was hydrogenated at 60 psi for 12 h. Filteration of the reaction mixture over celite bed and removal of solvent methanol under reduced pressure afforded N-(3,5-dichloropyrid-4-yl)-4-difluoromethoxy-8-amino-dibenzo[b,d]furan-1-carboxamide as white solid. mp: >270° C.

IR (KBr): 3436, 3360, 3185, 2921, 1659, 1555, 1484, 1391, 1292, 1195, 1133, 1055, 910, 811, 674 cm−1.

$^1$H NMR (300 MHz, DMSO) δ 5.14 (brs, 2H), 6.86 (dd, 1H, J=8.7 Hz, 2.4 Hz), 7.53 (t, 1H, J=72 Hz), 7.46-7.51 (m, 2H), 7.80 (d, 1H, J=9.0 Hz), 8.80 (s, 2H), 10.96 (s, 1H).

EXAMPLE 60

3,5-Dichloro-4-(4-ethoxydibenzo[b,d]furan-1-ylcarboxamido)pyridine

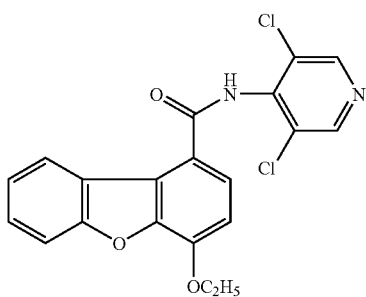

To a stirred and cooled (−10° C.) suspension of 60% sodium hydride (58 mg, 1.4 mmol) in DMF (3 ml) was added 3,5-dichloro-4-aminopyridine (120 mg, 0.70 mmol) and the mixture was stirred for 30 min. The acid chloride, prepared from intermediate 58 (150 mg 0.58 mmol) in THF (5 ml) was added to the reaction mixture in one portion and the mixture was further stirred at the same temperature for 30 min. The reaction mixture was quenched with ice-cold water (25 ml) and extracted with ethyl acetate (3×20 ml). The combined organic extracts were washed with 1N HCl (20 ml), water (20 ml), brine (20 ml) and dried ($Na_2SO_4$). The crude product obtained after evaporation of the solvent was purified by silica gel column chromatography using 50% ethyl acetate in petroleum ether to give 85 mg (36%) of the product as white solid, mp 289-292° C.; IR (KBr) 3207, 2928, 1665, 1488, 1281 cm$^{-1}$. $^1$H NMR (300 MHz, $CDCl_3$) δ 1.61 (t, J=6.9 Hz, 3H), 4.38 (q, J=6.9 Hz, 2H), 7.02 (d, J=8.7 Hz, 1H), 7.30 (t, J=8.2 Hz, 1H), 7.49 (t, J=8.2 Hz, 1H), 7.62 (s, 1H), 7.66 (d, J=8.2 Hz, 1H), 7.76 (d, J=8.7 Hz, 1H), 8.50 (d, J=8.2 Hz, 1H), 8.58 (s, 2H).

EXAMPLE 61

N1-Benzyl-4-cyclopentyloxydibenzo[b,d]furan-1-carboxamide

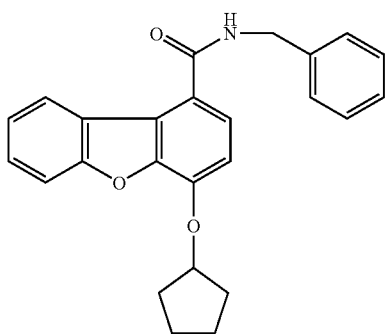

To a stirred solution of benzylamine (30 mg, 0.27 mmol) and triethylamine (0.5 g, 4.9 mmol) in dry dichloromethane (5 ml) was added the acid chloride, prepared from intermediate 60 (40 mg 0.135 mmol) in dichloromethane (5 ml) and the mixture was stirred at room temperature for 30 min. The reaction mixture was quenched with ice-cold water (25 ml) and extracted with dichloromethane (2×20 ml). The combined organic extracts were washed with 1N HCl (20 ml), water (20 ml), brine (20 ml) and dried ($Na_2SO_4$). The crude product obtained after evaporation of the solvent was purified by silica gel column chromatography using 25% ethyl acetate in petroleum ether to give 15 mg (29%) of the product as white solid, mp 172-175° C.; IR (KBr) 3286, 2958, 2869, 1641, 1537, 1293, 1275 cm$^{-1}$, $^1$H NMR (300 MHz, $CDCl_3$) δ 1.59-1.70 (m, 2H), 1.89-1.94 (m, 2H), 2.00-2.04 (m, 4H), 4.75 (d, J=6.3 Hz, 2H), 5.05 (quint., J=4.5 Hz, 1H), 6.33 (brs, 1H), 6.93 (d, J=8.4 Hz, 1H), 7.26-7.49 (m, 7H), 7.62 (d, J=8.1 Hz, 1H), 8.40 (d, J=7.5 Hz, 1H).

EXAMPLE 62

4-(4-Cyclopentyloxydibenzo[b,d]furan-1-ylcarboxamido)pyridine

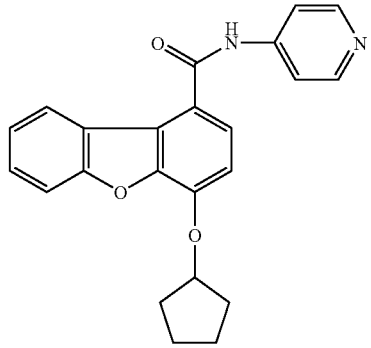

To a stirred solution of 4-aminopyridine (30 mg, 0.32 mmol) and triethylamine (0.5 g, 4.9 mmol) in dry THF (5 ml) was added the acid chloride, prepared from intermediate 60 (50 mg 0.16 mmol) in dry THF (5 ml) and the mixture was stirred at room temperature for 30 min. The reaction mixture was quenched with ice-cold water (25 ml) and extracted with ethyl acetate (2×20 ml). The combined organic extracts were washed with 1N HCl (20 ml), water (20 ml), brine (20 ml) and dried $Na_2SO_4$). The crude product obtained after evaporation of the solvent was purified by silica gel column chromatography using 35% ethyl acetate in petroleum ether to give 23 mg (37%) of the product as white solid, mp 250-253° C.; IR (KBr) 3291, 2964, 2870, 1655, 1586, 1507, 1278 cm$^{-1}$. $^1$H NMR (300 MHz, $CDCl_3$) δ 1.68-1.79 (m, 2H), 1.89-1.94 (m, 2H), 2.02-2.06 (m, 4H), 5.09 (quint., J=4.5 Hz, 1H), 6.99 (d, J=8.4 Hz, 1H), 7.33 (t, J=8.1 Hz, 1H), 7.50 (t, J=7.3 Hz, 1H), 7.59 (d, J=8.4 Hz, 1H), 7.63-7.67 (m, 4H), 7.98 (s, 1H), 8.33 (d, J=7.4 Hz, 1H), 8.57 (d, J=8.4 Hz, 1H).

EXAMPLE 63

3,5-Dichloro-4-(4-cyclopentyloxydibenzo[b,d]furan-1-ylcarboxamido)pyridine

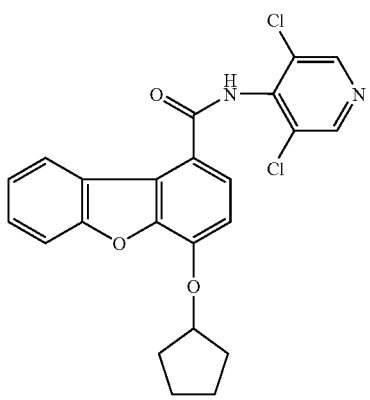

To a stirred and cooled (−10° C.) suspension of 60% sodium hydride (50 mg, 1.4 mmol) in DMF (3 ml) was added 3,5-4chloro-4-aminopyridine (100 mg, 0.70 mmol) and the mixture was stirred for 30 min. The acid chloride, prepared from intermediate 60 (150 mg, 0.50 mmol) in THF (5 ml) was added to the reaction mixture in one portion and the mixture was further stirred at the same temperature for 30 min. The reaction mixture was quenched with ice-cold water (25 ml) and extracted with ethyl acetate (3×20 ml). The combined organic extracts were washed with 1N HCl (20 ml), water (20 ml), brine (20 ml) and dried ($Na_2SO_4$). The crude product was obtained after evaporation of the solvent as white solid 90 mg (40%), mp 284-286° C.;

IR (KBr) 3191, 2953, 1659, 1487, 1277 $cm^{-1}$;

$^1$H NMR (300 MHz, $CDCl_3$) δ 1.70-1.77 (m, 2H), 1.92-2.00 (m, 2H), 2.05-2.11 (m, 4H), 5.13 (quint., J=4.5 Hz, 1H), 7.04 (d, J=8.7 Hz, 1H), 7.32 (t, J=8.5 Hz, 1H), 7.50 (t, J=8.5 Hz, 1H), 7.65 (d, J=8.7 Hz, 1H), 7.69 (s, 1H), 7.78 (d, J=8.7 Hz, 1H), 8.53 (d, J=8.7 Hz, 1H), 8.60 (s, 2H).

EXAMPLE 64

4-(4-Methylsulfanyldibenzo[b,d]furan-1-ylcarboxamido)pyridine

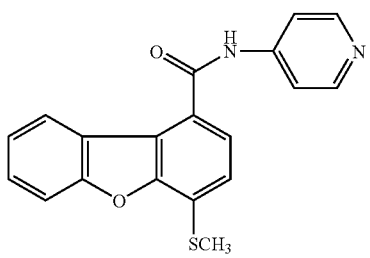

A mixture of intermediate 61 (100 mg, 0.38 mmol), dicyclohexylcarbodimide (88 mg, 0.42 mmol), and dimethylaminopyridine (4 mg, 0.03 mmol) in THF (5 ml) was stirred at room temperature for 5 min. A solution of 4-aminopyridine (40 mg, 0.42 mmol) in THF (2 ml) was added and the mixture stirred at room temperature for 3 h. The mixture was filtered to remove DCU and the filtrate was diluted with ethyl acetate (50 ml) and washed with water (3×50 ml), brine (50 ml) and dried ($Na_2SO_4$). The crude product obtained after evaporation of the solvent was purified by silica gel column chromatography using 3% methanol in chloroform to give 30 mg (23%) of the product as white solid, mp 242-245° C.;

IR (KBr) 3273, 3063, 2925, 1640, 1537, 1445, 1197 $cm^{-1}$.

$^1$H NMR (300 MHz, DMSO-$d_6$) δ 3.02 (s, 3H), 7.44 (t, J=7.8 Hz, 1H), 7.65 (t, J=7.8 Hz, 1H), 7.83-7.87 (m, 3H), 7.97 (dd, J=8.2, 2.1 Hz, 2H), 8.17 (d, J=7.5 Hz, 1H), 8.54 (brs, 2H), 11.22 (s, 1H).

EXAMPLE 65

N3-(4-Methoxydibenzo[b,d]furan-1-yl)nicotinamide

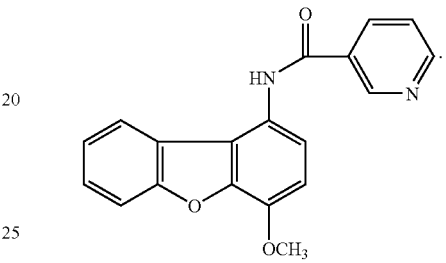

To a stirred and cooled (0° C.) solution of intermediate 40 (100 mg, 0.47 mmol) and triethylamine (95 mg, 0.94 mmol), in dry dichloromethane (10 ml) was added nicotinoyl chloride hydrochloride (80 mg, 0.56 mmol) in dry dichloromethane (5 ml). The cooling bath was removed and the reaction mixture was stirred at room temperature for 12 h. The solvent was removed under reduced pressure and the residue was diluted with EtOAc (30 ml). The EtOAc solution was washed with water (30 ml), brine (20 ml) and dried ($Na_2SO_4$). The crude product obtained after evaporation of the solvent was purified by silica gel column chromatography using 1% methanol in chloroform to give 35 mg (21%) of the product as off-white solid, mp 200-203° C.;

IR (KBr) 3247, 1636, 1523, 1278, 1101 $cm^{-1}$;

$^1$H NMR (300 Mz, $CDCl_3$) δ 4.06 (s, 3H), 6.97 (d, J=8.7 Hz, 1H), 7.29 (t, J=7.2 Hz, 1H), 7.45 (t, J=7.2 Hz, 1H), 7.48 (d, J=8.7 Hz, 1H), 7.57 (d, J=7.2 Hz, 1H), 7.62 (d, J=8.1 Hz, 1H, 7.71 (d, J=7.2 Hz, 1H), 8.30 (brs, 2H), 8.81 (s, 1H), 9.24 (s, 1H).

EXAMPLE 66

N1-Benzyl-4-methoxydibenzo[b,d]furan-1-sulfonamide

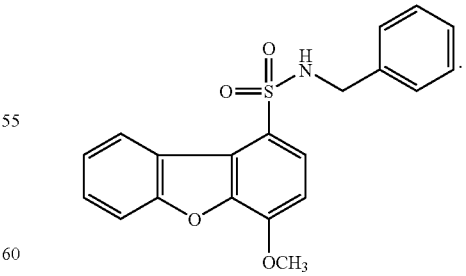

A solution of intermediate 38 (200 mg, 1.08 mmol) in dry chloroform (5 ml) was added in one portion to a stirred and cooled (0° C.) solution of chlorosulfonic acid (118 mg, 1.08 mmol) in dry chloroform (5 ml). The reaction mixture was allowed to warm to room temperature over a period of 1 h.

The solvent was evaporated under reduced pressure to give crude 4-methoxydibenzo[b,d]furan-1-sulfonyl chloride;

To a stirred solution of benzylamine (75 mg, 0.68 mmol) and triethylamine (0.3 g, 2.9 mmol) in dry THF (5 ml) was added the above sulfonyl chloride (100 mg) in dry THF (5 ml) and the mixture was stirred at room temperature for 30 min. The reaction mixture was quenched with ice-cold water (25 ml) and extracted with ethyl acetate (2×20 ml). The combined organic extracts were washed with 1N HCl (20 ml), water (20 ml), brine (20 ml) and dried ($Na_2SO_4$). The crude product obtained after evaporation of the solvent was purified by silica gel column chromatography using 50% ethyl acetate in petroleum ether to give 30 mg (38%) of the product as white solid, mp 180-185° C.;

IR (KBr) 3306, 2929, 2845, 1599, 1573, 1391, 1279, 1159 cm$^{-1}$;

$^1$H NMR (300 MHz, CDCl$_3$) δ 4.06 (d, J=6.3 Hz, 2H), 4.13 (s, 3H), 4.91 (t, J=6.3 Hz, 1H), 6.99-7.02 (m, 3H), 7.08-7.14 (m, 3H), 7.40 (t, J=6.9 Hz, 1H), 7.56 (t, J=6.9 Hz, 1H), 7.68 (d, J=8.7 Hz, 1H), 7.95 (d, 8.7 Hz, 1H), 8.54 (d, J=7.5 Hz, 1H).

EXAMPLE 67

4-(4-Methoxydibenzo[b,d]furan-1-ylsulfonamido)pyridine

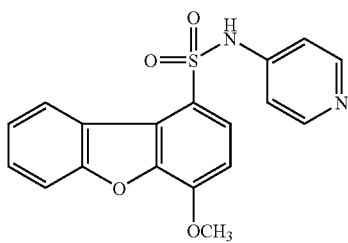

A solution of intermediate 38 (200 mg, 1.08 mmol) in dry chloroform (5 ml) was added in one portion to a stirred and cooled (0° C.) solution of chlorosulfonic acid (118 mg, 1.08 mmol) in dry chloroform (5 ml). The reaction mixture was allowed to warm to room temperature over a period of 1 h. The solvent was evaporated under reduced pressure to give crude 4-methoxydibenzo[b,d]furan-1-sulfonyl chloride; Reaction of 4-aminopyridine (65 mg, 0.70 mmol) with crude 4-methoxydibenzo[b,d]-furan-1-sulfonyl chloride (100 mg) in presence of triethylamine (0.3 g, 2.9 mmol) as described in Example 8 followed by silica gel column chromatography using 10% MeOH in chloroform gave 30 mg (25%) of the product as white solid; IR (KBr) 2920, 2850, 1634, 1481, 1344, 1111, 1093 cm$^{-1}$; $^1$H NMR (300 MHz, DMSO-d$_6$) δ 4.02 (s, 3H), 6.83 (d, J=7.5 Hz, 2H), 7.24 (d, J=8.7 Hz, 1H), 7.39 (t, J=7.2 Hz, 1H), 7.53 (t, J=6.9 Hz, 1H), 7.70 (d, J=8.4 Hz, 1H), 7.87-7.90 (m, 3H), 8.83 (d, J=7.8 Hz, 1H), 12.7 (brs, 1H).

EXAMPLE 68

3,5-Dichloro-4-(4-ethoxydibenzo[b,d]furan-1-ylcarboxamido)pyridine-N-oxide

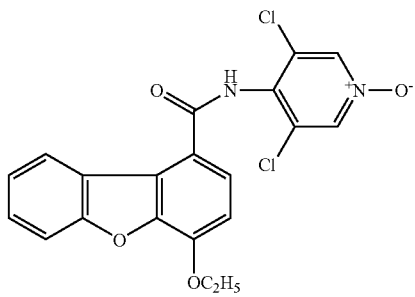

To a stirred solution of 3,5-dichloro-4-(4-ethoxydibenzo[b,d]furan-1-ylcarboxamido)-pyridine (example 60) (40 mg, 0.099 mmol) in chloroform (20 ml) was added 50% m-CPBA (100 mg, 0.29 mmol) and the reaction mixture was refluxed with stirring for 2.5 h. The reaction mixture was quenched with 10% aqueous sodium sulfite solution (20 ml) and stirred for 5 minutes. The layers were separated and the organic layer was washed with 1N sodium hydroxide solution (20 ml), water (20 ml) and brine (20 ml). The crude product obtained after evaporation of the solvent was purified by silica gel column chromatography using 5% methanol in chloroform to give 20 mg (48%) of the product as white solid, mp 265-267° C.;

IR (KBr) 3216, 2924, 2854, 1657, 1475, 1280, 1098 cm$^{-1}$;
$^1$H NMR (300 MHz, CDCl$_3$) δ 1.61 (t, J=6.9 Hz, 3H), 4.38 (q, J=6.9 Hz, 2H), 7.01 (d, J=8.4 Hz, 1H), 7.32 (t, J=8.2 Hz, 1H), 7.50 (t, J=8.2 Hz, 1H), 7.59 (brs, 1H), 7.64 (d, J=8.4 Hz, 1H), 7.72 (d, J=8.4 Hz, 1H), 8.26 (s, 2H), 8.48 (d, J=8.4 Hz, 1H).

EXAMPLE 69

3,5-Dichloro-4-(4-cyclopentyloxydibenzo[b,d]furan-1-ylcarboxamido)pyridine-N-oxide

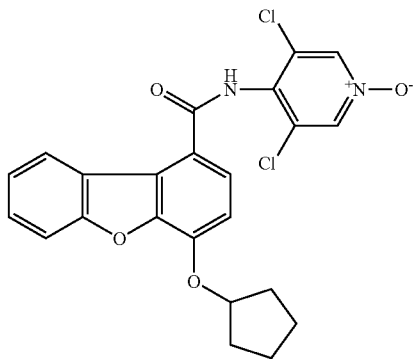

To a stirred solution of 3,5-dichloro-4-(4-cyclopentyloxydibenzo[b,d]furan-1-ylcarboxamido)-pyridine (example 63) (50 mg, 0.113 mmol) in chloroform (20 ml) was added 50% m-CPBA (110 mg, 0.34 mmol) and the reaction mixture was refluxed with stirring for 2.5 h. The reaction mixture was quenched with 10% aqueous sodium sulfite solution (20 ml) and stirred for 5 minutes. The layers were separated and the organic layer was washed with 1N sodium hydroxide solution (20 ml), water (20 ml) and brine (20 ml). The crude product obtained after evaporation of the solvent gave 25 mg (48%) of the product as white solid; mp 255-258° C.;

IR (KBr) 3212, 3185, 2923, 2852, 1657, 1474, 1281, 1242, 1100 cm$^{-1}$;

$^1$H NMR (300 MHz, CDCl$_3$) δ 1.71-1.77 (m, 2H), 1.90-2.02 (m, 2H), 2.03-2.12 (m, 4H), 5.11 (quint, J=4.5 Hz, 1H), 7.00 (d, J=8.7 Hz, 1H), 7.31 (t, J=8.5 Hz, 1H), 7.49 (t, J=8.5 Hz, 1H), 7.60 (s, 1H), 7.63 (d, J=7.8 Hz, 1H), 7.72 (d, J=8.4 Hz, 1H), 8.26 (s, 2H), 8.48 (d, J=8.7 Hz, 1H).

EXAMPLE 70

N-Formyl-1-methoxy-4-[4-methoxyphenylaminosulphonyl]-9H-carbazole

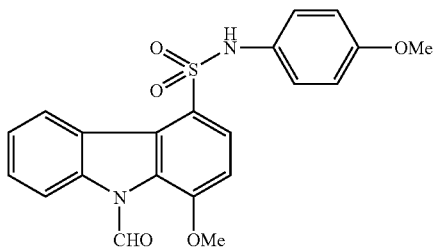

Intermediate 63 (0.2 g, 0.62 mM) was dissolved in 40 ml of chloroform. To it was added p-anisidine (0.21 g, 1.66 mM), 0.19 g triethylamine and the reaction was refluxed for 18 hrs. Solvent was evaporated and the residue was extracted in ethyl acetate. The organic layer was washed with 10% HCl solution, brine and then dried over anhydrous Na$_2$SO$_4$. It was then evaporated to obtain the crude residue which was then purified over silica gel column using ethylacetate-hexane system to obtain the desired compound as beige solid with a yield of 65% (0.16 g); mp 190-192° C.

$^1$H NMR (d$_6$-DMSO, 300 MHz) δ 3.62 (3H, s), 4.08 (3H, s), 6.72-6.91 (4H, m), 7.35 (1H, d, J=8.7 Hz), 7.51 (1H, d of t, J=8.1 Hz, J=1.2 Hz), 7.65 (1H, d of t, J=8.1 Hz, J=1.2 Hz), 7.85 (1H, d, J=8.4 Hz), 8.66 (1H, d, J=8.1 Hz), 8.83 (1H, d, J=7.8 Hz), 10.26 (1H, s), 10.35 (1H, br s).

IR (KBr): 1708, 1574, 1509, 1454, 1393, 1312, 1275, 1167, 1136, 1011 cm$^{-1}$.

EXAMPLE 71

1-methoxy-4-[4-methoxyphenylaminosulphonyl]-9H-carbazole

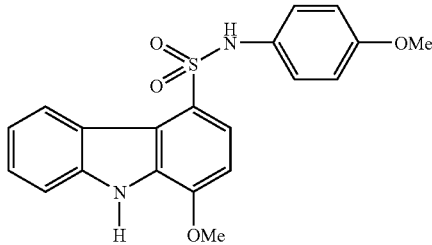

N-Formyl-1-methoxy-4-[4-methoxyphenylaminosulphonyl]-9H-carbazole (example 70) (0.1 g, 0.24 mM) was dissolved in 18 mL of 20% aqueous THF solution. The reaction mixture was cooled to 0° C. in an ice bath. To it was added NaBH$_4$ (0.055 g, 1.45 mM) portion wise. The reaction mixture was stirred overnight Solvent was evaporated and the aqueous layer was extracted with EtOAc. The organic layer was washed with brine and dried over anh. Na$_2$SO$_4$. It was filtered and concentrated to yield the crude product. The crude product was purified over a silica gel column using EtOAc- hexane as a solvent system to yield the desired compound as a white semi-solid with a yield of 66% (0.062 g).

$^1$H NMR (d$_6$-DMSO, 300 MHz) 3.60 (3H, s), 4.04 (3H, s), 6.69 (2H, d, J=9 Hz), 6.85 (2H, d, J=9 Hz), 7.06 (1H, d, J=8.4 Hz), 7.19 (1H, d of t, J=6.9 Hz, J=1.2 Hz), 7.44 (1H, d of t, J=8.1 Hz, J=1.2 Hz), 7.54 (1H, d, J=8.1 Hz), 7.62 (1H, d, J=8.4 Hz), 8.71 (1H, d, J=8.1 Hz), 10.05 (1H, s), 11.85 (1H, s).

IR (KBr): 3342, 2925, 1624, 1566, 1508, 1458, 1402, 1324, 1290, 1153, 1128, 1100, 1011, 963, 804, 753, 672 cm$^{-1}$.

EXAMPLE 72

N-Formyl-1-methoxy-4-[4-methylphenylaminosulphonyl]-9H-carbazole

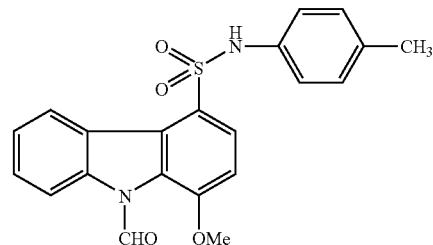

Intermediate 63 (0.2 g, 0.62 mM) was dissolved in 50 ml of chloroform. To it was added p-toludine (0.165 g, 1.54 mM) and 0.16 g triethylamine. The reaction was refluxed for 15 hrs. Solvent was evaporated and the residue was taken up in ethyl acetate. The organic layer was washed with 10% HCl solution, brine and then dried over anh Na$_2$SO$_4$. It was then evaporated to obtain the crude residue which was then purified over silica gel column using ethylacetate-hexane system to obtain the desired compound as beige solid with a yield of 75% (0.18 g); mp 193-199° C.

$^1$H NMR (d$_6$-DMSO, 300 MHz) 2.19 (3H, s), 4.13 (3H, s), 6.9-7.04 (4H, m), 7.42 (1H, d, J=8.7 Hz), 7.57 (1H, t, J=8.4 Hz), 7.7 (1H, t, J=8.4 Hz), 7.94 (1H, d, J=8.7 Hz), 8.70 (1H, d, J=7.8 Hz), 8.89 (1H, d, J=7.8 Hz), 10.3 (1H, s), 10.63 (1H, s).

IR (KBr): 3258, 1706, 1572, 1511, 1451, 1393, 1305, 1273, 1078, 1009, 806 cm$^{-1}$.

EXAMPLE 73

1-methoxy-4-[4-methylphenylaminosulphonyl]-9H-carbazole

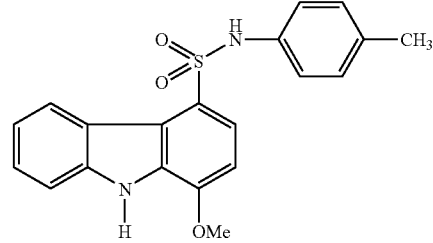

N-Formyl-1-methoxy-4-[4-methylphenylaminosulphonyl]-9H-carbazole (example 72) (0.14 g, 0.35 mM) was dissolved in 15 mL of 20% aqueous THF solution. The reaction mixture was cooled to 0° C. in an ice bath. To it was added NaBH$_4$ (0.08 g, 2.1 mM) portion wise. The reaction mixture was stirred for 4-5 hrs. Solvent was evaporated and the aqueous layer was extracted with EtOAc. The organic layer was washed with brine and dried over anh. Na$_2$SO$_4$. It was filtered and concentrated to yield the desired compound as a white solid with a yield of 99% (0.13 g). mp 199-203° C.

$^1$H NMR (d$_6$-DMSO, 300 MHz) δ 2.11 (3H, s), 4.04 (3H, s), 6.8-6.93 (4H, m), 7.07 (1H, d, J=8.4 Hz), 7.2 (1H, t, J=7.8 Hz), 7.44 (1H, t, J=6.6 Hz), 7.53 (1H, d, J=8.4 Hz), 7.67 (1H, d, J=8.4 Hz), 8.71 (1H, d, J=8.4 Hz), 10.28 (1H, s), 11.86 (1H, s).

IR (KBr): 3393, 1562, 1512, 1322, 1290, 1150, 1100, 813 cm$^{-1}$.

EXAMPLE 74

1-methoxy-4-[4-methylphenylaminosulphonyl-N'-methyl]-9H-carbazole

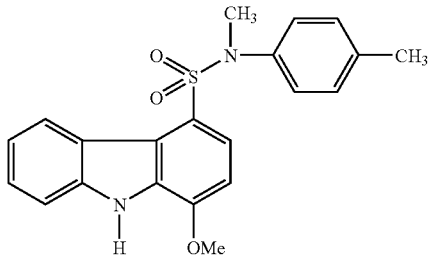

In a 50 ml round bottomed flask was taken 1-methoxy-4-[4-methyl-phenylaminosulphonyl]-9H-carbazole (example 73) (0.095 g, 0.26 mM) dissolved in 10 ml of acetone. To it was added 0.071 g of K$_2$CO$_3$ and methyl iodide (0.146 g, 1.03 mM). The reaction mixture was stirred at room temperature for 4 hrs. The reaction mixture was filtered and the filtrate was concentrated and the obtained residue was purified on a silica gel column. The desired compound was obtained as a white solid with a yield of 76% (0.074 g). mp 184-189° C.

$^1$H NMR (d$_6$-DMSO, 300 Mz) δ 2.2 (3H, s), 3.13 (1H, s), 4.07 (3H, s), 6.93-7.02 (5H, m), 7.09 (1H, d, J=8.4 Hz), 7.38 (1H, t, J=7.2 Hz), 7.50 (2H, d, J=8.1 Hz), 8.29 (1H, d, J=8.1 Hz), 11.88 (1H, s).

IR (KBr): 3350, 2925, 1627, 1563, 1446, 1338, 1269, 1146, 1100, 681, 573 cm$^{-1}$.

EXAMPLE 75

1-methoxy-4-[4-methylphenylaminosulphonyl-N'-methyl]-9methyl carbazole

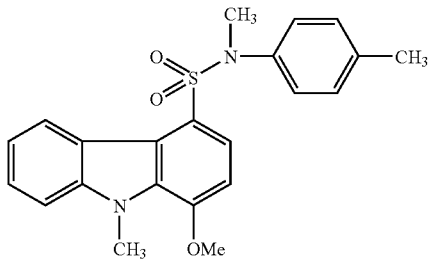

In a 100 ml round bottomed flask was taken 5.2 mg NaH. It was washed with pet ether and to it was added dry THF. The flask was cooled in an ice bath and to it was added a solution of 1-methoxy-4-[4-methylphenylaminosulphonyl-N'-methyl]-9H-carbazole. (example 73) (0.042 g, 0.1 mM) in dry THF. The reaction mixture was stirred for 1 hr and methyl iodide (0.031 g, 0.22 mM) was added. The reaction was stirred further for 48 hrs at room temperature. Reaction mixture was quenched with water and extracted with ethyl acetate. The organic layer was washed with water and brine and dried over anh. Na$_2$SO$_4$. It was then evaporated to obtain the desired compound as a white solid with a yield of 68% (0.029 g); mp 174-180° C.

$^1$H NMR (d$_6$-DMSO, 300 MHz) δ 2.21 (3H, s), 3.15 (1H, s), 4.04 (3H, s), 4.19 (3H, s), 6.96-7.14 (6H, m), 7.45-7.64 (3H, m), 8.4 (1H, d, J=7.8 Hz).

IR (KBr): 2922, 1563, 1508, 1473, 1298, 1268, 1164, 1110, 935, 871, 747 cm$^{-1}$.

EXAMPLE 76

1-methoxy-4-[4-pyridinylaminosulphonyl]-9H-carbazole

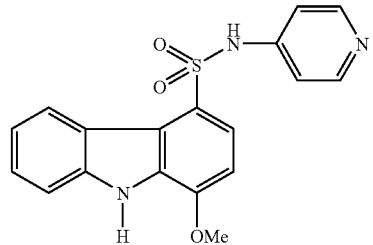

Intermediate 63 (0.2 g, 0.62 mM) was dissolved in 5 ml of pyridine. To it was added 4-aminopyridine (0.35 g, 3.7 mM) and the reaction mixture was heated at 100° C. for three hours. The solvent was evaporated and the residue was purified on a silica gel column using MeOH(CHCl3 to obtain the deformylated desired compound as a white solid with a yield of 41% (0.097 g); mp 311-313° C.

$^1$H NMR (d$_6$-DMSO, 300 MHz) δ 4.03 (3H, s), 6.8 (2H, d, J=6.3 Hz), 7.05 (1H, d, J=8.1 Hz), 7.11 (1H, t, J=7.8 Hz), 7.36 (1H, t, J=7.5 Hz), 7.46 (1H, d, J=7.8 Hz), 7.72-7.9 (3H, m), 8.90 (1H, br s), 11.62 (1H, br s).

IR (KBr): 3452, 2612, 1624, 1568, 1493, 1479, 1342, 1287, 1194, 1114, 960, 933, 778 cm$^{-1}$.

EXAMPLE 77

N4-(2,6-Dichlorophenyl)-1-methoxy-9H-4-carbazolsulphonamide

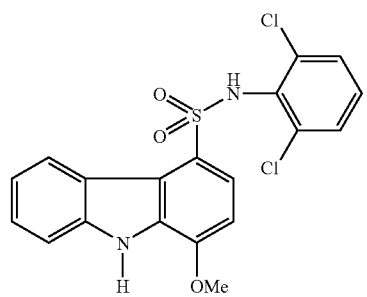

A solution of 4-amino-3,5-dichloropyridine (0.3 g, 1.85 mM) in dry THF was added dropwise to a stirred solution of EtMgBr (1 eq, freshly prepared). To this solution was added intermediate 63 (0.2 g, 0.62 mM) in THF at room temperature. The reaction mixture was refluxed for 18 hrs. The reaction was quenched with aq. NH$_4$Cl and after the standard workup the residue was purified using column chromatography to obtain the desired product as a beige solid with a yield of 15% (0.04 g). mp 201-205° C.

$^1$H NMR (d$_6$-DMSO, 300 MHz) δ 4.07 (3H, s), 7.03-7.09 (2H, m), 7.2-7.26 (1H, m), 7.35-7.42 (3H, m), 7.5-7.58 (2H, m), 8.55 (1H, d, J=8.1 Hz), 9.9 (1H, s), 11.79 (1H, s).

IR (KBr): 3377, 3276, 1627, 1611, 1564, 1444, 1403, 1369, 1322, 1292, 1268, 1156, 1131, 1100, 1014, 957, 884, 785, 675 cm$^{-1}$. MS Obsd & Calcd [M+NH$_4$]438.

EXAMPLE 78

N4-(2,6-Dichlorophenyl)-9-formyl-1-methoxy-9H-4-carbazolsulphonamide

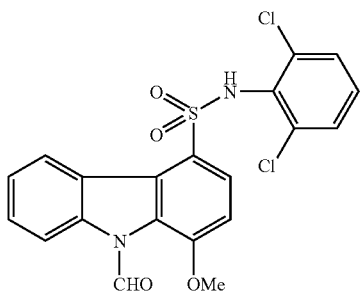

A solution of 4-amino-3,5-dichloropyridine (0.45 g, 2.77 mM) in dry THF was added dropwise to a stirred solution of EtMgBr (1 eq, freshly prepared). To this solution was added intermediate 63 (0.3 g, 0.924 mM) in THF at room temperature. The reaction mixture was stirred for 18 hrs at room temperature. The reaction was quenched with aq. NH$_4$Cl and after the standard workup the residue was purified using column chromatography to obtain the desired product as a beige semi-solid with a yield of 9% (0.04 g).

$^1$H NMR (d$_6$-DMSO, 300 MHz) δ 4.12 (3H, s), 6.90 (1H, t, J=7.2 Hz), 7.22 (1H, d, J=9 Hz), 7.34-7.45 (4H, m), 7.52 (1H, d, J=8.1 Hz), 7.86 (1H, d, J=8.4 Hz), 8.03 (1H, d, J=8.1 Hz), 9.48 (1H, s), 12.05 (1H, s).

IR (KBr): 1697, 1606, 1573, 1509, 1453, 1393, 1308, 1273, 1167, 1134, 1011,984 cm$^{-1}$.

MS Obsd & Calcd [M-H] −447.

EXAMPLE 79

N4-(4-pyridyl)-1-methoxy-9H-4-carbazole carboxamide

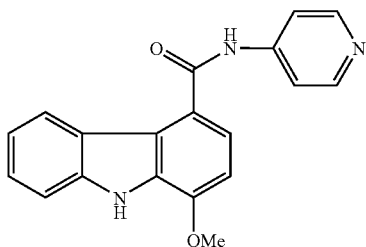

To a stirred solution of intermediate 72 (0.1 gm, 0.4145 mmoles) in dry DMF (5 ml) at room temperature, 4-aminopyridine (0.043 gm, 0.456 moles) was added followed by N-ethyl N'-diethylaminopropyl carbodiimide HCl (0.104 gm, 0.539 mmoles) and DMAP (5.0 mg, 0.04 mmoles).To the above solution triethylamine (0.08 ml, 0.58 mmoles) was added and the reaction mixture was stirred at the same temperature for 15 hours. The reaction mixture was poured in to water (20 ml) and extracted with ethyl acetate (2×20 ml). The organic layer was washed with water (3×20 ml) followed by brine (15 ml), dried over Na$_2$SO$_4$ and concentrated to give 0.1 gm of crude material which was purified by column chromatography, to give 20 mg of the title compound as pale yellow solid, m. p: >250° C.

IR (KBr, cm$^{-1}$): 3413, 2931, 1710, 1662, 1601, 1507, 1414, 1325, 1288, 1178, 1099, 1011 and 700.

$^1$H NMR (300 MHz, DMSO-d$_6$, δ): 4.1 (s, 3H), 7.1 (d, J=8.1 Hz, 2H), 7.4 (t, J=7.5 Hz, 1H), 7.5 (d, J=8.1 Hz, 2H), 8.0 (b s, 2H), 8.2 (d, J=8.4 Hz, 1H), 8.6 (b s, 2H), 11.2 (s, 1H), 11.7 (s, 1H).

EXAMPLE 80

N4-(3,5-dichloro-4-pridyl)-1-methoxy-9H-4-carbazole carboxamide

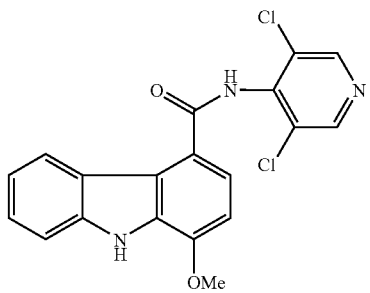

To a solution of intermediate 72 (202 mg, 0.838 mmoles) in dry DMF (5 ml), carbonyldiimidazole (136 mg, 0.838 mmoles) was introduced at 25° C., under nitrogen atmosphere. The reaction mixture was stirred for 4 hrs.

In another two neck round bottom flask 60% sodium hydride (84 mg, 2.095 mmoles) was added to a solution of 3,5 dichloro-4-amino pyridine(136.62 mg, 0.838 mmoles) in dry DMF (3 ml), at −10° C. and stirred for 1 hr, under nitrogen atmosphere. To this solution a solution of starting material-imidazole complex in dry DMF was added at −10° C. The reaction mixture was stirred at −10° C. for 30 min and at 25° C. for 48 hrs under nitrogen atmosphere. To the reaction mixture water (5 ml) was added and neutralized with 1N HCl. The solid precipitated was filtered to yield 20 mg of the title compound as pale brown colored solid, m. p: >250° C.

IR (KBr, cm$^{-1}$): 668, 730, 745, 1014, 1102, 1232, 1268, 1283, 1307, 1402, 1462, 1480, 1546, 1561, 1573, 1660, 2938 and 3185.

$^1$H NMR (300 MHz, DMSO-d$_6$, δ): 4.070 (s, 3H), 7.040-7.127 (m, 2H), 7.340-7.389 (t, J=7.35 Hz, 1H), 7.489-7.516 (d, J=8.1 Hz, 1H), 7.621-7.647 (d, J=7.8 Hz, 1H), 8.368-8.394 (d, J=7.8 Hz, 1H), 8.772 (s, 2H), 10.638 (s, 1H), 11.627 (s, 1H)

EXAMPLE 81

N4-(3,5-dichloro-4-pyridyl)-6-chloro-1-methoxy-9H-4-carbazole carboxamide

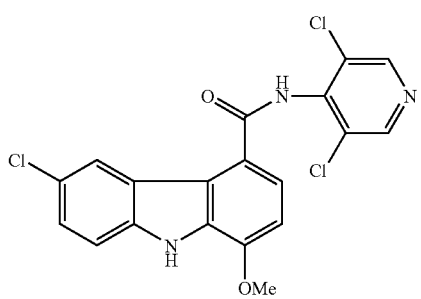

Step 1: 6-chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressure, the residue was acidified with 1N HCl and the precipitated product was filtered, washed with water and dried under vacuum, to give 380 mg of the title product.

IR (KBr, cm$^{-1}$): 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.

$^1$H NMR (300 MHz, DMSO-d$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy 9H-4-carbazole carboxylate

To a suspension of 6-chloro-1-methoxy 9H-4-carbazole carboxylic acid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over Na$_2$SO$_4$ and concentrated to give 0.38 gm of the title product as yellow solid.

IR (KBr, cm$^{-1}$): 3394, 2935, 1746, 1567, 1510, 1347, 1211, 1202, 1100, 951 and 745.

$^1$H NMR (300 MHz, DMSO-d$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: N4-(3,5-dichloro-4-pyridyl)-6-chloro-1-methoxy-9H-4-carbazole carboxamide To a solution of 4-Nitrophenyl-6-chloro-1-methoxy 9H-4-carbazole carboxylate (100 mg, 0.345 mmoles) in dry DMF (5 ml), 3,5-dichloro-4-amino pyridine (56 mg, 0.345 mmoles) was added followed by sodium hydride (60% suspension, 30 mg, 0.7 mmoles) and the reaction mixture was stirred at room temperature for 2 hours. Ice pieces were added to the reaction mixture and diluted with water. The pH of the above emulsion was adjusted to neutral with 1N HCl and the precipitated product was filtered, washed with water, followed by pet ether and dried under vacuum to give 50 mg of the title compound as a pale yellow solid, m. p: >359° C.

IR (KBr, cm$^{-1}$): 3190, 2937, 1660, 1574, 1485, 1463, 1305, 1230, 1114, 1022, 918 and 798.

$^1$H NMR (300 MHz, DMSO-d$_6$, δ): 4.083 (s, 3H), 7.154-7.182 (d, J=8.4 Hz, 1H), 7.383-7.419 (d, J=11.8 Hz, 1H), 7.507-7.536 (d, J=8.7 Hz, 1H), 7.684-7.711 (d, J=8.1 Hz, 1H), 8.462-8.470 (d, J=2.4 Hz, 1H), 8.792 (s, 2H), 10.701 (s, 1H), 11.855 (s, 1H).

EXAMPLE 82

N4-(3,5-dichloro-4-pyridyl)-9-benzyl-6-chloro-1-methoxy-9H-4-carbazole carboxamide

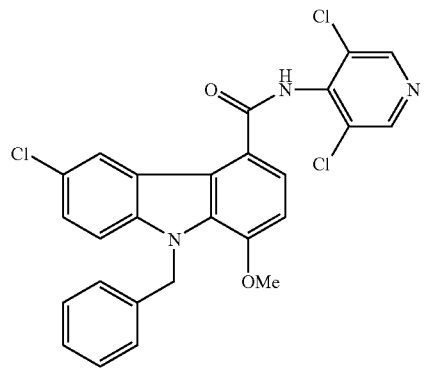

Step 1: 6-chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressure, the residue was acidified with 1N HCl and the precipitated product was filtered, washed with water and dried under vacuum, to give 380 mg of the title product.

IR (KBr, cm$^{-1}$): 565, 589, 631, 657, 745, 791, 885, 919, 989, 1015, 1066, 1111, 1269,1 291, 1305, 1371, 1418, 1461, 1567, 1613, 1625, 1684, 2623, 2849, 2939 and 3461.

$^1$H NMR (300 MHz, DMSO-d$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy 9H-4-carbazole carboxylate

To a suspension of 6-chloro-1-methoxy 9H-4-carbazole carboxylic acid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over $Na_2SO_4$ and concentrated to give 0.38 gm of the title product as yellow solid.

IR (KBr, $cm^{-1}$): 3394, 2935, 1746, 1567, 1510, 1347, 1211, 1202, 1100, 951 and 745.
$^1$H NMR (300 MHz, DMSO-$d_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 9-benzyl-6-chloro-1-methoxy-4-carbazole carboxylate

To a solution of 4-Nitrophenyl-6-chloro-1-methoxy-9H-4-carbazole carboxylate (0.38 gm, 0.958 mmoles) in dry DMF (10 ml) under nitrogen atmosphere at 0° C., sodium hydride (60% suspension, 60 mg, 1.44 mmoles) was added and the reaction mixture was stirred at room temperature for 30 min. The reaction mixture was cooled to 0° C., benzyl bromide (0.12 ml, 0.958 mmoles) was added and the reaction mixture was stirred at room temperature for 2 hours. Ice pieces were added to the reaction mixture followed by water (20 ml) and extracted with ethyl acetate (2×15 ml). The organic layer was washed with water (3×20 ml), brine (20 ml), dried over $Na_2SO_4$ and concentrated. The crude material was purified by column chromatography to give 130 mg of the title compound.

IR (KBr, $cm^{-1}$): 3436, 3129, 2968, 1728, 1522, 1353, 1208, 1132, 1042, 937 and 695.
$^1$H NMR (300 MHz, DMSO-$d_6$, δ): 4.032 (s, 3H), 6.016 (s, 2H), 7.026-7.049 (d, J=6.9 Hz, 2H), 7.186-7.312 (m, 4H), 7.509-7.546 (dd, J=8.7 Hz, 1H), 7.707-7.769 (m, 3H), 8.24-8.268 (d, J=8.4 Hz, 1H), 8.39-8.42 (d, J=9.0 Hz, 2H), 8.898-8.905 (d, J=2.1 Hz, 1H).

Step 4: N4-(3,5-dichloro-4-pyridyl)-9-benzyl-6-chloro-1-methoxy-9H-4-carbazole carboxamide To a solution of 4-Nitrophenyl 9-benzyl-6-chloro-1-methoxy-4-carbazole carboxylate (124 mg, 0.255 mmoles) in dry DMF (3 ml) under nitrogen atmosphere, 3,5-dichloro-4-amino pyridine (41.5 mg, 0.255 mmoles) was added followed by sodium hydride (60% suspension, 16.7 mg, 0.382 mmoles) and the reaction mixture was stirred at room temperature for one hour. Ice pieces were added to the reaction mixture, diluted with water (15 ml) and neutralized with 1N HCl. The precipitated product was filtered, washed with water, dried and purified by column chromatography to give 60 mg of the title compound as an off white solid, m. p: 210-213° C.

IR (KBr, $cm^{-1}$): 3193, 2923, 1658, 1482, 1462, 1255, 1128, 1073, 1020, 795 and 703.
$^1$H NMR (300 MHz, DMSO-$d_6$, δ): 3.97 (s, 3H), 5.96 (s, 2H), 7.032-7.06 (d, J=8.4 Hz, 2H), 7.165-7.229 (m, 5H), 7.429-7.466 (dd, J=9.9 Hz, 1H), 7.641-7.669 (d, J=8.4 Hz, 1H), 8.441-8.447 (d, J=1.8 Hz, 1H), 8.802 (s, 2H), 10.81 (s, 1H).

EXAMPLE 83

N4-(3,5-dichloro-4-pyridyl)-6-chloro-9-cyclohexylmethyl-1-methoxy-9H-4-carbazole carboxamide

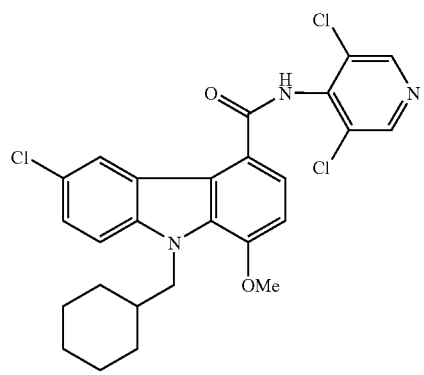

Step 1: 6-chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressure, the residue was acidified with 1N HCl and the precipitated product was filtered, washed with water and dried under vacuum, to give 380 mg of the title product.

IR (KBr, $cm^{-1}$): 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.
$^1$H NMR (300 MHz, DMSO-$d_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d, J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy 9H-4-carbazole carboxylate

To a suspension of 6-chloro-1-methoxy 9H-4-carbazole carboxylic acid (375 mg, 1.36 mmoles) in dry chloroform (15 ml), thionyl chloride (0.3 ml 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over $Na_2SO_4$ and concentrated to give 0.38 gm of the title product as yellow solid.

IR (KBr, cm$^{-1}$):3394, 2935, 1746, 1567, 1510, 1347, 1211, 1202, 1100, 951 and 745.

$^1$H NMR (300 MHz, DMSO-d$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 6-chloro-9-cyclohexylmethyl-1-methoxy-4-carbazole carboxylate To a solution of 4-Nitrophenyl 6-chloro-9H-1-methoxy-4-carbazole carboxylate (200 mg, 0.69 mmoles) in dry DMF (10 ml) under nitrogen atmosphere, at 0° C., sodium hydride (60% suspension, 42 mg, 1.036 mmoles) was added and the reaction mixture was stirred at room temperature for 30 min. The reaction mixture was cooled to 0° C., cyclohexyl methyl bromide (0.096 ml, 0.69 mmoles) was added and the reaction mixture was stirred at room temperature for 24 hours. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over Na$_2$SO$_4$ and concentrated. The crude material was purified by column chromatography to give 60 mg of the title compound.

$^1$H NMR (300 MHz, DMSO-d$_6$, δ): 1.082 (m, 6H), 1.381-1.397 (b, 2H), 1.565-1.626 (b, 2H), 1.81 (b, 1H), 4.011 (s, 3H), 4.541-4.564 (d, J=6.9 Hz, 2H), 7.258-7.286 (d, J=8.4 Hz, 1H), 7.5-7.536 (dd, J=8.7 Hz, 1H), 7.682-7.711 (d, J=8.7 Hz, 2H), 7.736-7.767 (d, J=8.7 Hz, 1H), 8.2-8.226 (d, J=8.1 Hz, 1H), 8.374-8.403 (d, J=8.7 Hz, 2H), 8.857-8.863 (d, J=1.8 Hz, 1H).

Step 4: N4-(3,5-dichloro-4-pyridyl)-6-chloro-9-cyclohexylmethyl-1-methoxy-9H-4-carbazole carboxamide To a solution of 4-Nitrophenyl 9-cyclohexyl methyl-6-chloro-1-methoxy-4-carbazole carboxylate (55 mg, 0.1116 mmoles) in dry DMF (3 ml) under nitrogen atmosphere, 3,5-dichloro-4-amino pyridine (18.2 mg, 0.1116 mmoles) was added followed by sodium hydride (60% suspension, 9.0 mg, 0.2233 mmoles) and the reaction mixture was stirred at room temperature for one hour. Ice pieces were added to the reaction mixture, diluted with water (15 ml) and neutralized with 1N HCl. The precipitated product was filtered, washed with water and dried under vacuum to give 38 mg of the title compound as an off white solid, m. p: 247-249° C.

$^1$H NMR (300 MHz, DMSO-d$_6$, δ): 1.08 (m, 6H), 1.381-1.397 (b, 2H), 1.565-1.626 (b, 2H), 1.81 (b, 1H), 4.056 (s, 3H), 4.507-4.532 (d, J=7.5 Hz, 2H), 7.183-7.211 (d, J=8.4 Hz, 1H), 7.44-7.477 (dd, J=8.7 Hz, 1H), 7.611-7.637 (d, J=7.8 Hz, 1H), 7.684-7.713 (d, J=8.7 Hz, 1H), 8.415-8.421 (d, J=1.8 Hz, 1H), 8.803 (s, 2H), 10.784 (s, 1H).

EXAMPLE 84

N4-(3,5-dichloro-4-pyridyl)-6-chloro-9-(4-fluorobenzyl)-1-methoxy-9H-4-carbazole carboxamide

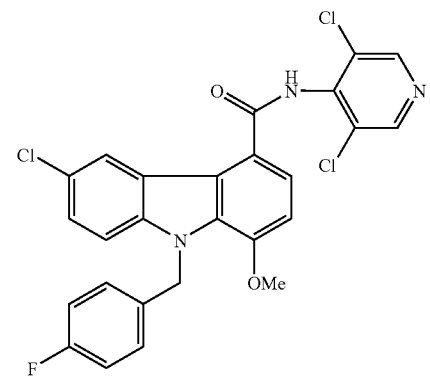

Step 1: 6-chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressureor, the residue was acidified with 1N HCl and the precipitated product was filtered, washed with water and dried under vacuum, to give 380 mg of the title product.

IR (KBr, cm$^{-1}$): 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.

$^1$H NMR (300 MHz, DMSO-d$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d, J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy 9H-4-carbazole carboxylate

To a suspension of 6-chloro-1-methoxy 9H-4-carbazole carboxylic acid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over Na$_2$SO$_4$ and concentrated to give 0.38 gm of the title product as yellow solid.

IR (Br, cm$^{-1}$): 3394, 2935, 1746, 1567, 1510, 1347, 1211, 1202, 1100, 951 and 745.

$^1$H NMR (300 MHz, DMSO-d$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 6-chloro-9-(4-fluoro benzyl)-1-methoxy-4-carbazole carboxylate To a solution of 4-Nitrophenyl 6-chloro-9H-1-methoxy-4-carbazole carboxylate (200 mg, 0.69 mmoles) in dry DMF (10 ml) under nitrogen atmosphere, at 0° C., sodium hydride (60% suspension, 42 mg, 1.036 rnmoles) was added and the reaction mixture was stirred at room temperature for 30 min. The reaction mixture was cooled to 0° C., 4-fluoro benzyl-bromide (0.086 ml, 0.69 mmoles) was added and stirred the reaction mixture at room temperature for 30 min. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over $Na_2SO_4$ and concentrated. The crude material was diluted with ethyl acetate (20 ml) and allowed to stand at 10° C. for 10 min. The separated solid flakes were filtered, washed with pet ether and dried to give 176 mg of the title compound.

IR (KBr, cm$^{-1}$): 2933, 1727, 1567, 1510, 1456, 1342, 1244, 1178, 1130, 1042, 1013, 803 and 743.

$^1$H NMR (300 MHz, DMSO-d$_6$, δ): 4.031 (s, 3H), 5.983 (s, 2H), 7.065-7.089 (d, J=7.2 Hz, 4H), 7.274-7.303 (d, J=8.7 Hz, 1H), 7.51-7.547 (dd, J=9.0 Hz, 1H), 7.693-7.724 (d, J=9.3 Hz, 2H), 7.757-7.786 (d, J=8.7 Hz, 1H), 8.228-8.257 (d, J=8.7 Hz, 1H), 8.379-8.408 (d, J=8.7 Hz, 2H), 8.886-8.893 (d, J=2.1 Hz, 1H).

Step 4: N4-3,5-dichloro-4-pyridyl)-6-chloro-9-(4-fluorobenzyl)-1-methoxy-9H-4-carbazole carboxamide To a solution of 4-Nitrophenyl 9-(4-fluoro benzyl)-6-chloro-1-methoxy-4-carbazole carboxylate (170 mg, 0.4276 mmoles) in dry DMF (6 ml) under nitrogen atmosphere, 3,5-dichloro-4-amino pyridine (69.7 mg, 0.1116 mmoles) was added followed by sodium hydride (60% suspension, 37.0 mg, 0.8553 mmoles) and the reaction mixture was stirred at room temperature for two hours. Ice pieces were added to the reaction mixture, diluted with water (15 ml) and neutralized with 1N HCl. The precipitated product was filtered, washed with water and dried under vacuum to give 100 mg of the title compound as an off white solid, m. p: 249-250° C.

IR (KBr, cm$^{-1}$): 3189, 2938, 1651, 1509, 1488, 1462, 1399, 1310, 1272, 1256, 1222, 1133, 1019, 815 and 795.

$^1$H NMR (300 MHz, DMSO-d$_6$, δ): 3.984 (s, 3H), 5.94 (s, 2H), 7.065-7.104 (m, 4H), 7.206-7.234 (d, J=8.4 Hz, 1H), 7.446-7.482 (dd, J=8.7 Hz, 1H), 7.648-7.674 (d, J=7.8 Hz, 1H), 7.705-7.734 (d, J=8.7 Hz, 1H), 8.444-8.451 (d, J=2.1 Hz, 1H), 8.805 (s, 2H), 10.81 (s, 1H).

EXAMPLE 85

N4-(3,5-dichloro-4-pyridyl)-6-chloro-9-(4-methoxy-benzyl)-1-methoxy-9H-4-carbazolecarboxamide

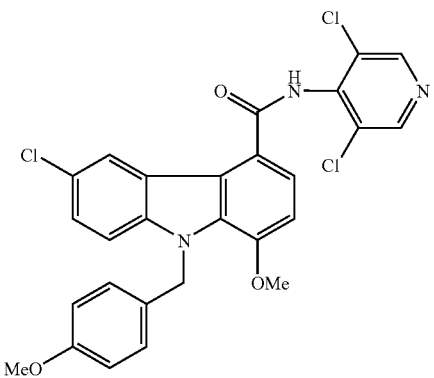

Step 1: 6-chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressure, the residue was acidified with 1N HCl and the precipitated product was filtered, washed with water and dried under vacuum, to give 380 mg of the title product IR (KBr, cm$^{-1}$): 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.

$^1$H NMR (300 MHz, DMSO-d$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d, J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy 9H-4-carbazole carboxylate

To a suspension of 6-chloro-1-methoxy 9H-4-carbazole carboxylicacid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over $Na_2SO_4$ and concentrated to give 0.38 gm of the title product as yellow solid.

IR (KBr, cm$^{-1}$): 3394, 2935, 1746, 1567, 1510, 1347, 1211, 1202, 1100, 951 and 745.

$^1$H NMR (300 MHz, DMSO-d$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 6-chloro-9-(4-methoxy benzyl)-1-methoxy-4-carbazole carboxylate To a solution of 4-Nitrophenyl 6-chloro-9H-1-methoxy-4-carbazole carboxylate (200 mg, 0.69 mmoles) in dry DMF (10 ml) under nitrogen atmosphere, at 0° C., sodium hydride (60% suspension, 42 mg, 1.036 mmoles) was added and the reaction mixture was stirred at room temperature for 30 min. The reaction mixture was cooled to 0° C., 4-methoxy benzylchloride (0.094 ml, 0.69 mmoles) was added and stirred the reaction mixture at room temperature for 30 min The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over $Na_2SO_4$ and concentrated. The crude material was diluted with ethyl acetate (20 ml) and allowed to stand at 10° C. for 10 min The separated solid flakes were filtered, washed with pet ether and dried to give 100 mg of the title compound.

IR (KBr, $cm^{-1}$): 3434, 2837, 1726, 1565, 1523, 1514, 1461, 1353, 1252, 1172, 1133, 1040, 1012 and 804.

$^1$H NMR (300 MHz, DMSO-$d_6$, δ): 3.653 (s, 3H), 4.064 (s, 3H), 5.926 (s, 2H), 6.774-6.803 (d, J=8.7 Hz, 2H), 6.996-7.026 (d, J=9.0 Hz, 2H), 7.281-7.308 (d, J=8.1 Hz, 1H), 7.50-7.536 (dd, J=8.7 Hz, 1H), 7.692-7.723 (d, J=9.3 Hz, 2H), 7.752-7.781 (d, J=8.7 Hz, 1H), 8.225-8.252 (d, J=8.1 Hz, 1H), 8.377-8.408 (d, J=9.3 Hz, 2H), 8.871-8.880 (d, J=2.7 Hz, 1H).

Step 4: N4-(3,5-dichloro-4-pyridyl)-6-chloro-9-4-methoxy benzyl)-1-methoxy-9H-4-carbazole carboxamide To a solution of 4-Nitrophenyl 9-(4-methoxy benzyl)-6-chloro-1-methoxy-4-carbazole carboxylate (95 mg, 0.232 mmoles) in dry DMF (5 ml) under nitrogen atmosphere, 3,5-dichloro-4-amino pyridine (37.8 mg, 0.232 mmoles) was added followed by sodium hydride (60% suspension, 20.0 mg, 0.464 mmoles) and the reaction mixture was stirred at room temperature for two hours. Ice pieces were added to the reaction mixture, diluted with water (15 ml) and neutralized with 1N HCl. The precipitated product was filtered, washed with water and dried under vacuum to give 60 mg of the title compound as an off white solid, m. p: 257-258° C.

IR (KBr, $cm^{-1}$): 3240, 2933, 1666, 1512, 1478, 1461, 1304, 1255, 1128, 1019 and 795.

$^1$H NMR (300 MHz, DMSO-$d_6$, δ): 3.649 (s, 3H), 4.017 (s, 3H), 5.883 (s, 2H), 6.772-6.801 (d, J=8.7 Hz, 2H), 7.018-7.045 (d, J=8.1 Hz, 2H), 7.209-7.237 (d, J=8.4 Hz, 1H), 7.433-7.469 (dd, J=8.4 Hz, 1H), 7.64-7.667 (d, J=8.1 Hz, 1H), 7.698-7.728 (d, J=9.0 Hz, 1H), 8.428-8.434 (d, J=1.8 Hz, 1H), 8.803 (s, 2H), 10.805 (s, 1H).

EXAMPLE 86

N4-(3,5-dichloro-4-pyridyl)-9-(4-fluorobenzyl)-1-methoxy-9H-4-carbazole carboxamide

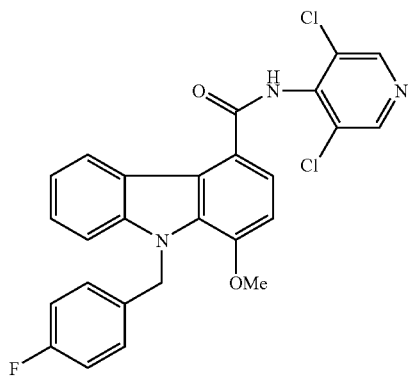

Step 1: 1-methoxy 9H-4-carbazole carboxylic acid

To a solution of intermediate 73a (800 mg, 2.7 mmoles) in methanol (25 ml), an aqueous (10 ml) solution of sodium hydroxide (220 mg, 5.4 mmoles) was added and the reaction mixture was refluxed for 6 hours. Methanol was evaporated from the reaction mixture under reduced pressureor, acidified the residue with 1N HCl and the precipitated product was filtered, washed with water and dried under vacuum, to give 780 mg of the title product.

$^1$H NMR (300 MHz, DMSO-$d_6$, δ): 4.21 (s, 3H), 7.0-7.1 (d, J=8.4 Hz, 1H), 7.1-7.2 (t, J=7.2 Hz, 1H), 7.4 (t, J=7.5 Hz, 1H), 7.5 (d, J=8.1 Hz, 1H), 7.8 (d, J=8.4 Hz, 1H), 8.9 (d, J=8.1 Hz, 1H), 11.6 (s, 1H), 12.6 (s, 1H).

Step 2: 4-Nitrophenyl-1-methoxy 9H-4-carbazole carboxylate

To a suspension of 1-methoxy 9H-4-carbazole carboxylic acid (800 mg, 3.3 mmoles) in dry chloroform (15 ml), thionyl chloride (0.73 ml, 9.95 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (25 ml) was added followed by 4-nitrophenol (461 mg, 3.3 mmoles) and triethylamine (0.466 ml, 3.3 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over $Na_2SO_4$ and concentrated to give 0.9 g of the title product as yellow solid.

IR (KBr, $cm^{-1}$): 3388, 2925, 1744, 1567, 1510, 1350, 1205, 1085, 951 and 749.

$^1$H NMR (300 MHz, DMSO-$d_6$, δ): 4.127 (s, 3H), 7.1-7.151 (t, J=7.8 Hz, 1H), 7.191-7.220 (d, J=8.7 Hz, 1H), 7.404-7.454 (t, J=7.8 Hz, 1H), 7.546-7.572 (d, J=7.8 Hz, 1H), 7.678-7.703 (d, J=7.5 Hz, 2H), 8.158-8.186 (d, J=8.4 Hz, 1H), 8.371-8.396 (d, J=7.5 Hz, 2H), 8.760-8.788 (d, J=8.4 Hz, 1H), 11.85 (s, 1H).

Step 3: 4-Nitrophenyl-9-(4-fluoro benzyl)-1-methoxy-4-carbazole carboxylate

To a solution of 4-Nitrophenyl-9H-1-methoxy-4-carbazole carboxylate (130 mg, 0.36 mmoles) in dry DMF (6 ml) under nitrogen atmosphere, at 0° C., sodium hydride (60% suspension, 20 mg, 0.503 mmoles) was added and the reaction mixture was stirred at room temperature for 30 min. the reaction mixture was cooled to 0° C., 4-fluoro benzylbromide (0.045 ml, 0.36 mmoles) was added and stirred the reaction mixture at room temperature for 30 min. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over $Na_2SO_4$ and concentrated. The crude material was diluted with ethyl acetate (20 ml) and allowed to stand at 10° C. for 10 min. The separated solid flakes were filtered, washed with pet ether and dried to give 150 mg of the title compound.

IR (KBr, $cm^{-1}$): 3398, 2924, 1742, 1513, 1457, 1344, 1215, 1047, 1011, 924 and 744.

$^1$H NMR (300 MHz, DMSO-$d_6$, δ): 4.023 (s, 3H), 5.974 (s, 2H), 7.058-7.099 (m, 4H), 7.161-7.209 (t, J=7.2 Hz, 1H), 7.461-7.510 (t, J=7.2 Hz, 1H), 7.684-7.715 (d, J=9.3 Hz, 2H), 8.017-8.049 (d, J=9.6 Hz, 1H), 8.165-8.194 (d, J=8.7 Hz, 2H), 8.368-8.399 (d, J=9.3 Hz, 2H), 8.785-8.811 (d, J=7.8 Hz, 1H).

Step 4: N4-(3,5-dichloro-4-pyridyl)-9-(4-fluorobenzyl)-1-methoxy-9H-4-carbazole carboxamide To a solution of 4-Nitrophenyl 9-(4-fluoro benzyl)-1-methoxy-9H-4-carbazole carboxylate (50 mg, 0.106 mmoles) in dry DMF (4 ml) under nitrogen atmosphere, 3,5dichloro-4-amino pyridine (17.34 mg, 0.106 mmoles) was added followed by sodium hydride (60% suspension, 8.5 mg, 0.212 mmoles) and the reaction mixture was stirred at room temperature for two hours. Ice pieces were added to the reaction mixture, diluted with water (15 ml) and neutralized with 1N HCl. The precipitated product was filtered, washed with water and dried under vacuum to give 15 mg of the title compound as an off white solid, m.p: 222-225° C.

IR (KBr, $cm^{-1}$): 3503, 3207, 1662, 1509, 1483, 1462, 1403, 1319, 1257, 1221, 1118, 1014, 820 and 749.

$^1$H NMR (300 MHz, DMSO-$d_6$, δ): 3.974 (s, 3H), 5.934 (s, 2H), 7.057-7.183 (m, 6H), 7.396-7.445 (t, J=7.5 Hz, 1H), 7.594-7.622 (d, J=7.8 Hz, 1H), 7.635-7.663 (d, J=8.4 Hz, 1H), 8.348-8.374 (d, J=7.8 Hz, 1H), 8.780 (s, 2H), 10.738 (s, 1H).

EXAMPLE 87

N4-(4-pyridyl)-9-(4-fluorobenzyl)-1-methoxy-9H-4-carbazole carboxamide

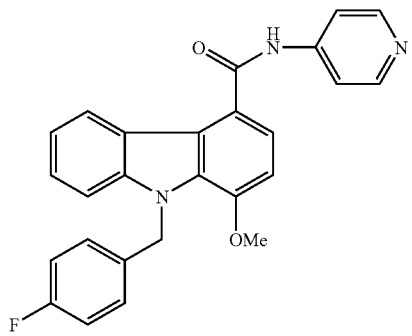

Step 1: Methyl 9-(4-fluoro benzyl)-1-methoxy-4-carbazole carboxylate

To a solution of intermediate 73a (400 mg, 1.568 mmoles) in dry DMF (15 ml) under nitrogen atmosphere, at 0° C., sodium hydride (60% suspension, 88 mg, 2.19 mmoles) was added and the reaction mixture was stirred at room temperature for 30 min. The reaction mixture was cooled to 0° C., 4-fluoro benzylbromide (0.2 ml, 1.568 mmoles) was added and stirred the reaction mixture at room temperature for 30 min. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over $Na_2SO_4$ and concentrated to give 500 mg of the title compound.

$^1$H NMR (300 MHz, DMSO-$d_6$, δ): 3.942 (s, 3H), 3.965 (s, 3H), 5.929 (s, 2H), 7.045-7.141 (m, 5H), 7.170-7.219 (t, J=7.5 Hz, 1H), 7.433-7.485 (t, J=7.2 Hz, 1H), 7.643-7.671 (d, J=8.4 Hz, 1H), 7.780-7.807 (d, J=8.1 Hz, 1H), 8.748-8.774 (d, J=7.8 Hz, 1H).

Step 2: 9-(4-fluoro benzyl)-1-methoxy-4-carbazole carboxylic acid

To a solution of 9-(4-fluoro benzyl)-1-methoxy-4-carbazole carboxylic acid methyl ester (490 mg, 1.35 mmoles) in methanol (15 ml), an aqueous (10 ml) solution of sodium hydroxide (108 mg, 2.7 mmoles) was added and the reaction mixture was refluxed for 6 hours. Methanol was evaporated from the reaction mixture under reduced pressure, acidified the residue with 1N HCl and the precipitated product was filtered washed with water and dried under vacuum, to give 420 mg of the title product IR (KBr, $cm^{-1}$): 3436, 2839, 1689, 1565, 1462, 1277, 1260, 1217, 1012 and 740.

$^1$H NMR (300 MHz, DMSO-$d_6$, δ): 3.955 (s, 3H), 5.924 (s, 2H), 7.014-7.105 (m, 5H), 7.152-7.203 (t, J=7.5 Hz, 1H), 7.417-7.466 (t, J=7.5 Hz, 1H), 7.622-7.650 (d, J=8.4 Hz, 1H), 7.784-7.814 (d, J=9.0 Hz, 1H), 8.876-8.902 (d, J=7.8 Hz, 1H), 12.751 b s, 1H).

Step 3: N4-(4-pyridyl)-9-4-fluorobenzyl)-1-methoxy 9H-4-carbazole carboxamide

To a suspension of 9-(4-fluoro benzyl)-1-methoxy 9H-4-carbazole carboxylicacid (100 mg, 0.286 mmoles) in dry chloroform (15 ml), thionyl chloride (0.063 ml, 0.86 mmoles) was added followed by 2 drops of dry DMF and the reaction mixture was sired under nitrogen atmosphere for two hours. Solvent and the excess thionyl chloride were evaporated from the reaction mixture and dried under vacuum. To this residue, dry chloroform (15 ml) was added followed by 4-aminopyridine (27 mg, 0.286 mmoles) and triethylamine (0.06 ml, 0.43 mmoles) were added and the reaction mixture was stirred under nitrogen atmosphere for 17 hours. The reaction mixture was diluted with chloroform (30 ml) and washed with water (2×10 ml). The organic layer was washed with brine (20 ml), dried over $Na_2SO_4$ and concentrated to give 45 mg of the title product as pale yellow solid, m.p: 230-232° C.

IR (KBr, $cm^{-1}$): 3306, 2964, 1682, 1594, 1509, 1462, 1328, 1296, 1256, 1209, 1114, 1015, 827 and 745.

$^1$H NMR (300 MHz, DMSO-$_6$, δ): 3.968 (s, 3H), 5.924 (s, 2H), 7.063-7.160 (m, 6H), 7.431-7.458 (m, 2H), 7.653-7.681 (d, J=8.4 Hz, 1H), 7.786-7.804 (d, J=5.4 Hz, 2H), 8.122-8.149 (d, J=8.7 Hz, 2H), 10.868 (s, 1H).

EXAMPLE 88

N4-(3,5-dichloro-4-pyridyl)-9-benzyl-1-methoxy-9H-4-carbazolecarboxamide

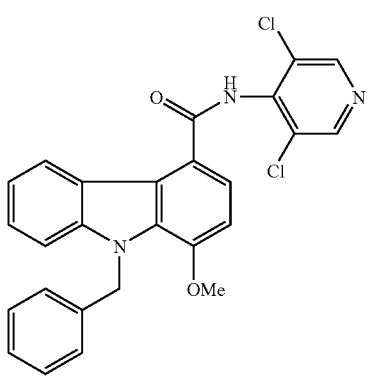

Step 1: Methyl-9-benzyl-1-methoxy-9H-4-carbazolecarboxylate

To a solution of intermediate 73a (417 mg, 1.635 mmoles) in dry DMF (10 ml), under $N_2$ atmosphere, 60% sodium hydride (107.04 mg, 2.453 mmoles) was added at 0° C. and the reaction mixture was stirred at 0° C. for 15 min and at 25° C. for 30 min. then benzyl bromide (0.22 ml, 1.799 mmoles) was added to the reaction mixture at 0° C., stirred for 15 min at 0° C. and then at 25° C. for 1 hr.

The reaction mixture was poured into ice-cold water and acidified with 1N HCl. The compound was extracted with ethyl acetate (3×10 ml), combined the organic layers and washed with water (10 ml) and with brine (10 ml). The organic layer was dried over anhydrous sodium sulphate and concentrated to yield 624 mg of the title compound as a white solid.

IR (KBr,$cm^{-1}$): 669, 758, 768, 1018, 1087, 1120, 1216, 1252, 1301, 1319, 1435, 1453, 1461, 1522, 1570, 1595, 1710, 2400, 2855, 2928, 3019 and 3400

$^1$H NMR (300 MHz, DMSO-$d_6$, δ): 3.943 (s, 3H), 3.953 (s, 3H), 5.950 (s, 2H), 7.031-7.052 (d, J=6.3 Hz, 2H), 7.138-7.347 (m, 5H), 7.411-7.476 (t, J=8.7 Hz, 1H), 7.614-7.641(d, J=8.1 Hz, 1H), 7.778-7.806 (d, J=8.4 Hz, 1H), 8.748-8.776 (d, J=8.4 Hz, 1H)

Step 2:
9-benzyl-1-methoxy-9H-4-carbazolecarboxylic acid

To a solution of methyl-9-benzyl-1-methoxy-9H-4-carbazolecarboxylate (612 mg, 1.773 mmoles) aqueous sodium hydroxide (71mg, 1.773 mmoles) was added and the reaction mixture was refluxed for 1 hr. Methanol was evaporated under reduced pressure, the reaction mixture was acidified with 1N HCl and filtered to yield 430 mg of title compound as off-white solid.

IR (KBr,$cm^{-1}$): 522, 584, 629, 679, 695, 729, 742, 785, 1015, 1072, 1089, 1122, 1221, 1246, 1263, 1303, 1320, 1358, 1413, 1443, 1452, 1462, 1564, 1592, 1671, 1860, 2619, 2854, 2933 and 3030

$^1$H NMR (300 MHz,DMSO-$d_6$, δ): 3.945 (s, 3H), 5.947 (s, 2H), 7.032-7.055 (d, J=6.9 Hz, 2H), 7.149-7.347 (m, 5H), 7.403-7.455 (t, J=7.8 Hz, 1H), 7.594-7.620 (d, J=7.8 Hz, 1H), 7.783-7.810 (d, J=8.1 Hz, 1H), 8.875-8.902 (d, J=8.1 Hz, 1H)

Step 3: 4-nitrophenyl-9-benzyl-1-methoxy-9H-4-carbazolecarboxylate

To a solution of 9-benzyl-1-methoxy-9H-4-carbazolecarboxylic acid (430 mg, 1.299 moles) in dry chloroform (10 ml), thionyl chloride (0.28 ml, 3.90 mmoles) was introduced followed by two drops of dry DMF at 25° C. under anhydrous conditions.

After complete conversion of acid to acid chloride, chloroform and thionyl chloride were evaporated under reduced pressure to give yellow colored solid acid chloride, it was flushed with nitrogen to remove traces of thionyl chloride and then dissolved in dry chloroform (10 ml). p-nitrophenol (181 mg, 1.299 mmoles) and triethyl amine (0.24 ml, 1.688 mmoles) was added to the reaction mixture at 25° C., under nitrogen atmosphere, the reaction mixture was stirred for half an hour. The reaction mixture was diluted with chloroform (10 ml) and washed with water (15 ml) followed by brine (10 ml). The organic layer was dried over anhydrous sodium sulphate and concentrated to give 420 mg of the crude compound which was purified by column chromatography to yield 239 mg of the title compound as yellow solid.

IR (KBr, $cm^{-1}$): 554, 567, 647, 679, 695, 732, 745, 781,8 08, 861, 936, 1011, 1026, 1050, 1121, 1177, 1205, 1244, 1270, 1303, 1318, 1345, 1406, 1463, 1491, 1522, 1562, 1591, 1613, 1731, 2854, 2924, 2956 and 3433

$^1$H NMR (300 MHz,DMSO-$d_6$, δ): 4.020 (s, 3H), 6.002 (s, 2H), 7.040-7.063 (d, J=6.9 Hz, 2H), 7.188-7.258 (m, 5H), 7.455-7.505 (t, J=7.5 Hz, 1H), 7.669-7.721 (m, 3H), 8.171-8.199 (d, J=8.4 Hz, 1H) 8.376-8.403 (d, J=8.1 Hz, 2H), 8.793-8.821 (d, J=8.4 Hz, 1H)

Step 4: N4-(3,5-dichloro-4-pyridyl)-9-benzyl-1-methoxy-9H-4-carbazolecarboxamide To a solution of 4-nitrophenyl-9-benzyl-1-methoxy-9H-4-carbazolecarboxylate (229 mg, 0.506 mmoles) and 3,5-dichloro-4-aminopyridine (82.53 mg, 0.506 mmoles) in dry DMF (10 ml), under N₂ atmosphere, 60% sodium hydride (44.19 mg, 1.012 mmoles) was added at 25° C. and the reaction mixture was stirred overnight. The reaction mixture was poured into ice-cold water and neutralized with 1N HCl. The compound was extracted with chloroform (2×15ml), combined the organic layers and washed with water (3×15 ml) and with brine (15 ml). The organic layer was dried over anhydrous sodium sulphate and concentrated to give 200 mg of the crude compound which was purified by column chromatography to yield 139 mg of the title compound as light brown colored solid, m.p: 215-217° C.

IR (KBr, cm⁻¹): 747, 1015, 1256, 1451, 1653, 1815 and 3217.

¹H NMR (300 MHz, DMSO-$d_6$, δ): 3.97 (s, 3H), 5.96 (s, 2H), 7.05-7.23 (m, 7H), 7.39-7.44 (m, 1H), 7.60-7.64 (d, J=8.1 Hz, 2H), 8.36-8.38 (d, J=7.8 Hz, 1H), 8.79 (S, 2H), 10.75 (s, 1H).

EXAMPLE 89

N4-(3,5-dichloro-4-pyridyl)-9-benzyl-1ethoxy-9H-4-carbazolecarboxamide

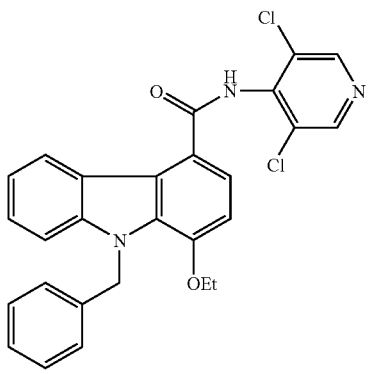

Step 1:
Methyl-9-benzyl-1-ethoxy-9H-4-carbazolecarboxylate

To a solution of intermediate 80a (469 mg, 1.740 mmoles) in dry DMF (10 ml), under N₂ atmosphere, 60% sodium hydride (113.88 mg, 2.610 mmoles) was added at 0° C. and the reaction mixture was stirred at 0° C. for 15 min and at 25° C. for 30 min. then benzyl bromide (0.23 ml, 1.914 mmoles) was added to the reaction mixture at 0° C., stirred for 15 min at 0° C. and then at 25° C. for 1 hr. The reaction mixture was poured into ice-cold water and acidified with 1N HCl. The compound was extracted with ethyl acetate (3×10 ml), combined the organic layers and washed with water (10 ml) and with brine (10 ml). The organic layer was dried over anhydrous sodium sulphate and concentrated to yield 730 mg of the title compound as brown solid.

IR (KBr, cm⁻¹): 553, 577, 639, 697, 735, 748, 945, 1026, 1085, 1120, 1154, 1210, 1252, 1272, 1301, 1325, 1394, 1407, 1435, 1452, 1464, 1567, 1711 and 2925.

¹HNMR(300 MHz,DMSO-$_6$, δ): 1.248-1.295 (t, J=6.9 Hz, 3H), 3.942 (s, 3H), 4.169-4.237 (q, J=6.9 Hz, 2H), 5.974 (s, 2H), 6.992-7.014 (d, J=6.6 Hz, 1H), 7.071-7.099 (d, J=8.4 Hz, 1H), 7.152-7.240 (m, 5H), 7.425-7.474 (t, J=7.4 Hz, 1H), 7.611-7.638 (d, J=8.1 Hz, 1H), 7.758-7.786 (d, J=8.4 Hz, 1H), 8.763-8.789 (d, J=7.8 Hz, 1H)

Step 2:
9-Benzyl-1-ethoxy-9H-4-carbazolecarboxylic acid

To a solution of methyl-9-benzyl-1-ethoxy-9H-4-carbazolecarboxylate (728 mg, 2.027 mmoles), in methanol (10 ml), aqueous sodium hydroxide (81 mg, 2.027 mmoles) was added and the reaction mixture was refluxed for 1 hr. Methanol was evaporated under reduced pressure, the reaction mixture was acidified with 1N HCl and filtered to yield 599 mg of title compound as an off-white solid.

IR (KBr, cm⁻¹): 522, 638, 694, 729, 743, 786, 815, 833, 956, 1027, 1086, 1122, 1161, 1221, 1245, 1263, 1299, 1322, 1364, 1395, 1414, 1442, 1451, 1462, 1565, 1588, 1673, 1867, 2625 and 2924.

¹H NMR(300 MHz, DMSO-$d_6$, δ): 1.251-1.297 (t, J=6.9 Hz, 3H), 4.166-4.211 (q, J=6.9 Hz, 2H), 5.974 (s, 2H), 6.998-7.022 (d, J=7.2 Hz, 1H), 7.050-7.079 (d,J=8.7 Hz, 1H), 7.152-7.221 (m, 5H), 7.406-7.458 (t, J=7.8 Hz, 1H), 7.589-7.617 (d, J=8.4 Hz, 1H), 7.763-7.789 (d, J=7.8 Hz, 1H), 8.891-8.919 (d, J=8.4 Hz, 1H)

Step 3: 4-Nitrophenyl-9-benzyl-1-ethoxy-9H-4-carbazolecarboxylate

To a solution of 9-benzyl-1-ethoxy-9H-4-carbazolecarboxylic acid (593 mg, 1.718 moles) in dry chloroform (15 ml), thionyl chloride (0.38 ml, 5.154 mmoles) was introduced followed by two drops of dry DMF at 25° C. under anhydrous conditions.

After complete conversion of acid to acid chloride, chloroform and thionyl chloride were evaporated under reduced pressure to give yellow colored solid acid chloride, it was flushed with nitrogen to remove traces of thionyl chloride and then dissolved in dry chloroform (15 ml). p-nitrophenol (239 mg, 1.718 mmoles) and triethyl amine (0.36 ml, 2.577 mmoles) was added to the reaction mixture at 25° C., under nitrogen atmosphere, the reaction mixture was stirred for half an hour. The reaction mixture was diluted with chloroform (10 ml) and washed with water (15 ml) followed by brine (10 ml). The organic layer was dried over anhydrous sodium sulphate and concentrated to give 520 mg of the crude compound which was purified by column chromatography to yield 136 mg of the title compound as yellow solid.

IR (KBr, cm⁻¹): 614, 648, 685, 700, 745, 833, 916, 948, 1009, 1029, 1053, 1117, 1132, 1148, 1214, 1252, 1319, 1274, 1345, 1392, 1404, 1453, 1487, 1522, 1560, 1591, 1613, 1730, 2932 and 2973.

¹H NMR(300 MHz,DMSO-$_6$, δ): 1.277-1.324 (t, J=7.1 Hz, 3H), 4.237-4.307 (q, J=7.1 Hz, 2H), 6.022 (s, 2H), 6.993-7.014 (d, J=6.3 Hz, 2H), 7.157-7.261 (m, 5H), 7.450-7.5 (t, J=7.3 Hz, 1H), 7.661-7.716 (m, 3H), 8.147-8.176 (d, J=8.7 Hz, 1H), 8.369-8.4 (d, J=7.1 Hz, 2H), 8.803-8.829 (d, J=7.8 Hz, 1H)

Step 4: N4-(3,5-dichloro-4-pyridyl)-9-benzyl-1-ethoxy-9H-4-carbazolecarboxamide

To a solution of 4-nitrophenyl-9-benzyl-1-ethoxy-9H-4-carbazolecarboxylate (123 mg, 0.264 mmoles) and 3,5 dichloro-4-aminopyridine (43 mg, 0.264 mmoles) in dry DMF (5 ml), under N₂ atmosphere, 60% sodium hydride (23.02 mg, 0.528) was added at 25° C. and the reaction mixture was stirred overnight. The reaction mixture was poured into ice-cold water and neutralized with 1N HCl. The compound was extracted with chloroform (3×15 ml), combined the organic layers and washed with water (3×15 ml)

and with brine (15 ml). The organic layer was dried over anhydrous sodium sulphate and concentrated to IR (KBr, cm⁻): 748, 1120, 1255, 1452, 1463, 1485, 1572, 1659, 2927 and 3210.

⁻¹H NMR (300 MHz, DMSO-$d_6$, δ): 1.232-1.319 (t, J=6.75 Hz, 3H), 4.184-4.252 (q, J=6.9 Hz 2H), 5.983 (s, 2H), 7.016-7.251 (m, 7H), 7.386-7.435 (t, J=7.35 Hz, 1H), 7.578-7.635 (t, J=8.55 Hz, 2H), 8.360-8.386 (d, J=7.8 Hz, 1H), 8.780 (s, 2H), 10.737 (s, 1H)

EXAMPLE 90

N4-(3,5-dichloro-4-pyridyl)-9-benzyl-6-chloro-1-ethoxy-9H-4-carbazolecarboxamide

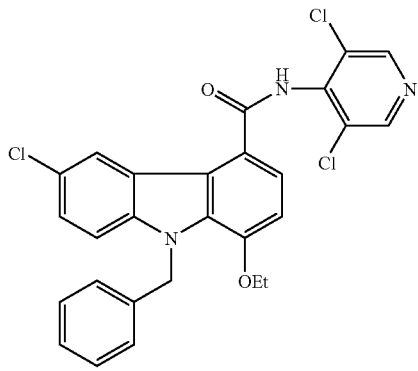

Step 1: Methyl-9-benzyl-6-chloro-1-ethoxy-9H-4-carbazolecarboxylate

To a solution of intermediate 80b (86 mg, 0.283 mmoles) in dry DMF (3 ml), under $N_2$ atmosphere, 60% sodium hydride (18.55 mg, 0.425 mmoles) was added at 0° C. and the reaction mixture was stirred at 0° C. for 15 min and at 25° C. for 30 min. then benzyl bromide (0.04 ml, 0.315 mmoles) was added to the reaction mixture at 0° C., stirred for 15 min at 0° C. and then at 25° C. for 1 hr. The reaction mixture was poured into ice-cold water and acidified with 1N HCl. The compound was extracted with ethyl acetate (2×10 ml), combined the organic layers and washed with water (10 ml) and with brine (10 ml). The organic layer was dried over anhydrous sodium sulphate and concentrated to yield 114 mg of the title compound as a brown solid.

IR (KBr, cm⁻¹): 456, 554, 613, 640, 695, 730, 749, 783, 845, 897, 967, 1035, 1071, 1093, 1129, 1189, 1212, 1259, 1308, 1379, 1394, 1435, 1451, 1495, 1568, 1591, 1706, 2854 and 2925.

¹HNMR(300 MHz,DMSO-$d_6$, δ): 1.228-1.293 (t, J=6.9 Hz, 3H), 3.945 (s, 3H), 4.177-4.246 (q, J=6.9 Hz, 2H), 5.979 (s, 2H), 6.970-6.992 (d, J=6.6 Hz, 1H), 7.117-7.250 (m, 5H), 7.471-7.507 (dd, J=8.9 Hz, 1H), 7.674-7.705 (d, J=9.3 Hz, 1H), 7.835-7.862 (d, J=8.1 Hz, 1H), 8.919-8.925 (d, J=1.8 Hz, 1H)

Step 2: 9-Benzyl-6-chloro-1-ethoxy-9H-4-carbazolecarboxylic acid

To a solution of methyl-9-benzyl-6-chloro-1-ethoxy-9H-4-carbazolecarboxylate (110 mg, 0.280 mmoles) aqueous sodium hydroxide (11.18 mg, 0.280 mmoles) was added and the reaction mixture was refluxed for 1 hr. Methanol was evaporated under reduced pressure, the reaction mixture was acidified with 1N HCl and filtered to yield 98 mg of title compound as off-white solid.

IR (KBr, cm⁻¹): 527, 557, 640, 658, 693, 729, 752, 785, 817, 847, 892, 918, 1032, 1072, 1093, 1129, 1267, 1307, 1324, 1365, 1392, 1416, 1450, 1496, 1567, 1590, 1678 and 2924.

¹H NMR(300 MHz,DMSO-$d_6$, δ): 1.222-1.290 (t, J=6.9 Hz, 3H), 4.168-4.237 (q, J=6.9 Hz, 2H), 5.974 (s, 2H), 6.975-7.001 (d, J=7.1 Hz, 1H), 7.092-7.251 (m, 5H), 7.450-7.487 (dd, J=8.7 Hz, 1H), 7.653-7.682 (d, J=8.7 Hz, 1H), 7.827-7.854 (d, J=8.1 Hz, 1H), 9.0-9.008 (d, J=2.4 Hz, 1H), 12.823 (bs, 1H).

Step 3: Preparation of 4-nitrophenyl-9-benzyl-6-chlor-1-ethoxy-9H-4-carbazole carboxylate To a solution of 9-benzyl-6-chloro-1-ethoxy-9H-4-carbazolecarboxylic acid (91 mg, 0.240 moles) in dry chloroform (10 ml), thionyl chloride (0.053 ml, 0.719 mmoles) was introduced followed by two drops of dry DMF at 25° C. under anhydrous conditions. After complete conversion of acid to acid chloride, chloroform and thionyl chloride were evaporated under reduced pressure to give yellow colored solid acid chloride, it was flushed with nitrogen to remove traces of thionyl chloride and then dissolved in dry chloroform (10 ml). p-nitrophenol (33.34 mg, 0.240 mmoles) and triethyl amine (0.05 ml, 0.360 mmoles) was added to the reaction mixture at 25° C., under nitrogen atmosphere, the reaction mixture was stirred for half an hour. The reaction mixture was diluted with chloroform (10 ml) and washed with water (15 ml) followed by brine (10 ml). The organic layer was dried over anhydrous sodium sulphate and concentrated to give 55 mg of the crude compound which was purified by column chromatography to yield 33 mg of the title compound as a yellow solid.

IR (KBr, cm⁻¹): 496, 642, 696, 736, 805, 844, 881, 897, 915, 962, 1026, 1051, 1129, 1155, 1195, 1214, 1247, 1290, .1324, 1346, 1392, 1451, 1491, 1523, 1562, 1592, 1615, 1722, and 2924.

¹HNMR(300 MHz, DMSO-$d_6$, δ): 1.232-1.295 (t, J=6.9 Hz, 3H), 4.267-4.289 (q, J=6.9 Hz, 2H), 6.026 (s, 2H), 6.879-6.909 (d, J=9.0 Hz, 2H), 6.967-6.990 (d, J=6.9 Hz, 1H), 7.172-7.264 (m, 3H), 7.495-7.533 (dd, J=8.9 Hz, 1H), 7.692-7.755 (m, 3H), 8.077-8.108 (d, J=9.3 Hz, 2H), 8.374-8.405 (d, J=9.3 Hz, 1H), 8.897-8.904 (d, J=2.1 Hz, 1H).

Step 4: N4-(3,5-dichloro-4-pyridyl)-9-benzyl-6-chloro-1-ethoxy-9H-4-carbazolecarboxamide To a solution of 4-nitrophenyl 9-benzyl-6-chloro-1-ethoxy-9H-4-carbazolecarboxylate (31 mg, 0.062 mmoles) and 3,5 dichloro-4-aminopyridine (10.1 mg, 0.062 mmoles) in dry DMF (3 ml), under $N_2$ atmosphere, 60% sodium hydride (5.40 mg, 0.124 mmoles) was added at 25° C. and the reaction mixture was stirred overnight. The reaction mixture was poured into ice-cold water and neutralized with 1N HCl. The compound was extracted with chloroform (3×10 ml), combined the organic layers and washed with water (3×10 ml) and with brine (10 ml). The organic layer was dried over anhydrous sodium sulphate and concentrated to give 22.5 mg of the title compound as an off-white crystalline solid. m. p: 221-223° C.

IR (KBr, cm⁻¹): 795, 1133, 1259, 1269, 1452, 1463, 1487, 1570, 1650, 2924 and 3178.

¹H NMR (300 MHz, DMSO-$d_6$, δ): 1.269-1.314 (t, J=6.75 Hz, 3H), 4.187-4.255 (q, J=6.75 Hz 2H), 5.981 (s, 2H), 6.993-7.014 (d, J=6.3 Hz 2H), 7.165-7.255 (m, 4H), 7.429-7.464 (dd, J=8.7 Hz, 1H), 7.622-7.700 (m, 2H), 8.446-8.452 (d, J=1.8 Hz, 1H), 8.798(s, 2H), 10.803 (s, 1H)

EXAMPLE 91

N4-(4-pyridyl)-9-benzyl-1-ethoxy-9H-4-carbazolecarboxamide

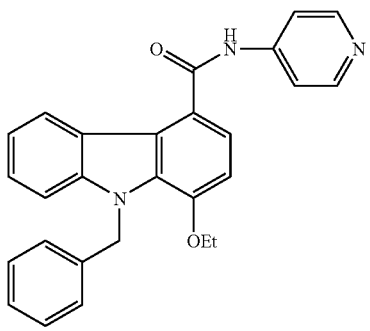

Step 1:
Methyl-9-benzyl-1-ethoxy-9H-4-carbazolecarboxylate

To a solution of intermediate 80a (469 mg, 1.740 mmoles) in dry DMF (10 ml), under $N_2$ atmosphere, 60% sodium hydride (113.88 mg, 2.610 mmoles) was added at 0° C. and the reaction mixture was stirred at 0° C. for 15 min and at 25° C. for 30 min. then benzyl bromide (0.23 ml, 1.914 mmoles) was added to the reaction mixture at 0° C., stirred for 15 min at 0° C. and then at 25° C. for 1 hr. The reaction mixture was poured into ice-cold water and acidified with 1N HCl. The compound was extracted with ethyl acetate (3×10 ml), combined the organic layers and washed with water (10 ml) and with brine (10 ml). The organic layer was dried over anhydrous sodium sulphate and concentrated to yield 730 mg of the title compound as a brown solid.

IR (KBr, cm$^{-1}$): 553, 577, 639, 697, 735, 748, 945, 1026, 1085, 1120, 1154, 1210, 1252, 1272, 1301, 1325, 1394, 1407, 1435, 1452, 1464, 1567, 1711 and 2925.

$^1$HNMR(300 MHz,DMSO-d$_6$, δ): 1.248-1.295 (t, J=6.9 Hz, 3H), 3.942 (s, 3H), 4.169-4.237 (q, J=6.9 Hz, 2H), 5.974 (s, 2H), 6.992-7.014 (d, J=6.6 Hz, 1H), 7.071-7.099 (d, J=8.4 Hz, 1H), 7.152-7.240 (m, 5H), 7.425-7.474 (t, J=7.4 Hz, 1H), 7.611-7.638 (d, J=8.1 Hz, 1H), 7.758-7.786 (d, J=8.4 Hz, 1H), 8.763-8.789 (d, J=7.8 Hz, 1H)

Step 2:
9-Benzyl-1-ethoxy-9H-4-carbazolecarboxylic acid

To a solution of methyl-9-benzyl-1-ethoxy-9H-4-carbazolecarboxylate (728 mg, 2.027 mmoles) aqueous sodium hydroxide (81 mg, 2.027 mmoles) was added and the reaction mixture was refluxed for 1 hr. Methanol was evaporated under reduced pressure, the reaction mixture was acidified with 1N HCl and filtered to yield 599 mg of title compound as an off-white solid.

IR (KBr, cm$^{-1}$): 522, 638, 694, 729, 743, 786, 815, 833, 956, 1027, 1086, 1122, 1161, 1221, 1245, 1263, 1299, 1322, 1364, 1395, 1414, 1442, 1451, 1462, 1565, 1588, 1673, 1867, 2625 and 2924.

$^1$H NMR(300 MHz, DMSO-d$_6$, δ): 1.251-1297 (t, J=6.9 Hz, 3H), 4.166-4.211 (q, J=6.9 Hz, 2H), 5.974 (s, 2H), 6.998-7.022 (d, J=7.2 Hz 1H), 7.050-7.079 (d, J=8.7,1H), 7.152-7.221 (m, 5H), 7.406-7.458 (t, J=7.8 Hz, 1H), 7.589-7.617 (d, J=8.4 Hz, 1H), 7.763-7.789 (d, J=7.8 Hz, 1H), 8.891-8.919 (d, J=8.4 Hz, 1H)

Step 3: N4-(4-pyridyl)-9-benzyl-1-ethoxy-9H-4-carbazolecarboxamide

To a solution of 9-benzyl-1-ethoxy-9H-4-carbazolecarboxylic acid (57 mg, 0.165 moles) in dry chloroform (5 ml), thionyl chloride (0.04 ml, 0.495 mmoles) was introduced followed by two drops of dry DMF at 25° C. under anhydrous conditions.

After complete conversion of acid to acid chloride, chloroform and thionyl chloride were evaporated under reduced pressure to give yellow colored solid acid chloride, it was flushed with nitrogen to remove traces of thionyl chloride and then dissolved in dry chloroform (5 ml). 4-amino pyridine (15.54 mg, 0.165 mmoles) and triethyl amine (0.04 ml 0.248 mmoles) was added to the reaction mixture at 25° C., under nitrogen atmosphere, the reaction mixture was stirred overnight.

The reaction mixture was diluted with chloroform (10 ml) and washed with water (15 ml) followed by brine (5 ml). The organic layer was dried over anhydrous sodium sulphate and concentrated to give 90 mg of the crude compound which was purified by column chromatography to yield 74 mg of the title compound as an off-white solid, m.p: 242-244° C.

IR (KBr, cm$^-$): 733, 747, 1116, 1207, 1257, 1294, 1328, 1510, 1572, 1594, 1689, 2923 and 3222.

$^1$H NMR (300 MHz, DMSO-d$_6$, δ): 1.266-1.313 (t, J=7.05 Hz, 3H), 4.176-4.244 (q, J=6.75 Hz 2H), 5.976 (s, 2H), 7.024-7.256 (m, 7H), 7.388 (s, 1H), 7.409-7.435 (d, J=7.8 Hz, 1H), 7.622-7.650 (d, J=8.4 Hz, 1H), 7.789-7.809 (d, J=6 Hz, 2H), 8.139-8.165 (d, J=7.8 Hz, 1H), 8.475-8.493 (d, J=5.4 Hz, 2H), 10.867 (s, 1H)

EXAMPLE 92

N4-(3-pyridyl)-6-chloro-9-(4-fluorobenzyl)-1-methoxy-9H-4-carbazolecarboxamide

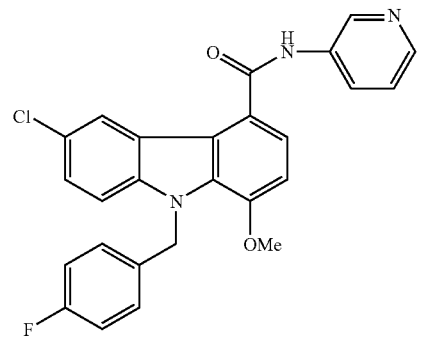

To a solution of intermediate 82 (100 mg, 0.251 mmoles) in dry chloroform (5 ml), thionyl chloride (0.06 ml, 0.754 mmoles) was introduced followed by two drops of dry DMF at 25° C. under anhydrous conditions. After complete conversion of acid to acid chloride, chloroform and thionyl chloride were evaporated under reduced pressure to give yellow colored solid acid chloride, it was flushed with nitrogen to remove traces of thionyl chloride and then dissolved in dry chloroform (5 ml). 3-amino pyridine (23.67 mg, 0.251mmoles) and triethyl amine (0.053 ml) were added to the reaction mixture at 25° C., under nitrogen atmosphere. The reaction mixture was stirred overnight. The reaction mixture was diluted with chloroform (10 ml) and washed with water (15 ml) followed by brine (5 ml). The organic layer was dried over anhydrous sodium sulphate and concentrated to give 110 mg of the crude compound which was purified by column chromatography to yield 87 mg of the title compound as a pale yellow colored solid, m. p: 224-228° C.

IR (KBr, cm$^{-1}$): 711, 795, 1127, 1266, 1255, 1273, 1377, 1403, 1459, 1483, 1509, 1573, 1585, 1645, 1740, 2850, 2920, 2955 and 3267.

$^1$H NMR (300 MHz, DMSO-$_6$, δ): 3.971 (s, 3H), 5.937 (s, 2H), 7.063-7.094 (m, 4H), 7.179-7.205 (d, J=7.8 Hz, 1H), 7.413-7.473 (m, 2H), 7.532-7.560 (d, J=8.4 Hz, 1H), 7.709-7.737 (d, J=8.4 Hz, 1H), 8.260-8.336 (m, 3H), 8.929 (s, 1H), 10.718(s, 1H).

EXAMPLE 93

N4-(4-pyridyl)-6-chloro-9-(4-fluorobenzyl)-1-methoxy-9H -4-carbazolecarboxamide

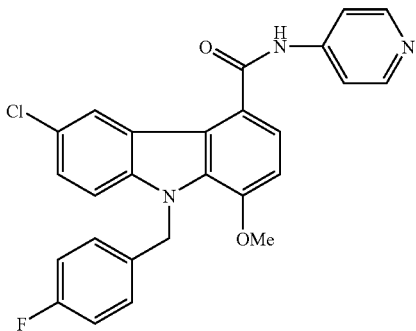

To a solution of intermediate 82 (100 mg, 0.251 mmoles) in dry chloroform (5 ml), thionyl chloride (0.06 ml, 0.754 mmoles) was introduced followed by two drops of dry DMF at 25° C. under anhydrous conditions. After complete conversion of acid to acid chloride, chloroform and thionyl chloride were evaporated under reduced pressure to give a yellow colored solid acid chloride, it was flushed with nitrogen to remove traces of thionyl chloride and then dissolved in dry chloroform (5 ml). 4-amino pyridine (23.67 mg, 0.251 mmoles) and triethyl amine (0.053 ml) was added to the reaction mixture at 25° C., under nitrogen atmosphere. The reaction mixture was stirred overnight. The reaction mixture was diluted with chloroform (10 ml) and washed with water (15 ml) followed by brine (5 ml). The organic layer was dried over anhydrous sodium sulphate and concentrated to give 100 mg of the crude compound which was crystallized from chloroform-pet ether to yield 73 mg of the title compound as a white solid, m. p: 241-245° C.

IR (KBr, cm$^{-1}$): 757, 779, 798, 818, 1129, 1216, 1253, 1277, 1329, 1411, 1459, 1487, 1506, 1585, 1670, 2941, and 3371.

$^1$H NMR (300 MHz, DMSO-d$_6$, δ): 3.975 (s, 3H), 5.939 (s, 2H), 7.064-7.095 (m, 4H), 7.181-7.209 (d, J=8.4 Hz, 1H), 7.454-7.556 (m, 2H), 7.717-7.807 (m, 3H), 8.235 (s, 1H), 8.494-8.511 (d, J=5.1 Hz, 2H), 10.882 (s, 1H).

EXAMPLE 94

N4-(3,5dichloro-4-pyridyl)-8-chloro-9-cyclohexylmethyl-1-methoxy-9H-4-carbazole carboxamide

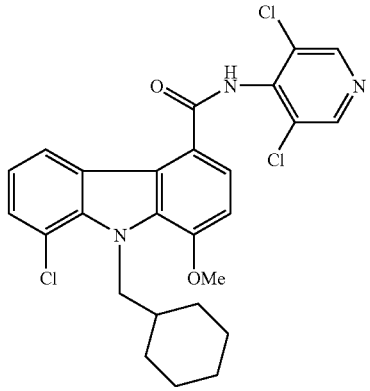

Step 1: Methyl-8-chloro-1-methoxy-9H-4-carbazole carboxylate

To a solution of intermediate 73c (530 mg 1.237 mmoles) in dry chloroform (20 mL) thionyl chloride (0.18 mL 2.5009 mmoles), was added followed by a drop of DMF and the reaction mixture was stirred at 25° C. under nitrogen atmosphere for 1 hr, to this added 10 mL methanol and stirred for 10 minutes. Solvent from the reaction mixture was evaporated under reduced pressure, diluted with ethyl acetate (100 mL) and washed with saturated solution of sodium bicarbonate (2×50 mL), with brine (2×50 mL), dried over sodium sulfate and concentrated to give 540 mg of the title compound.

$^1$H NMR (300 MHz, DMSO-d$_6$, δ):3.937 (s, 3H), 4.073 (s, 3H) 7.13-7.18 (m, 2H), 7.48-7.51 (m, 1H) 7.856-7.88 (d, J=8.4 Hz, 1H) 8.761-8.789 (d, J=8.4 Hz, 1H), 11.78 (s 1H)

Step 2: Methyl-8-chloro-9-cyclohexylmethyl-1-methoxy-9H-4-carbazole carboxylate

To a suspension of sodium hydride 55% (106.5 mg 2.6632) in dry DMF (5 mL), methyl-8-chloro-1-methoxy-9H-4-carboxylate (257 mg 0.8877 mmoles) was added at 0° C. under nitrogen atmosphere and stirred for 1 hr at 25° C. Cooled the reaction mixture to 0° C. and added cycloxylmethyl bromide (0.124 mL 0.8877 mmoles). The reaction mixture was stirred for 2 hrs at 25° C. The reaction mixture was quenched with ice cold water (50 mL) and extracted with ethyl acetate (2×30 mL), the organic layer was washed with water (2×50 mL), brine (2×25 mL), dried over sodium sulfate and concentrated to give 174 mg of the title compound.

IR (KBR, cm$^{-1}$): 650, 678, 728, 772, 1026, 1248, 1294, 1571, 1720, 2922 and 3425.

$^1$H NMR (300 MHz, DMSO-d$_6$, δ): 0.942 (m, 7H) 1.527 (m, 4H), 3.935 (s, 3H), 4.058 (s, 3H), 5.008-5.032 (d, J=7.2 Hz, 2H), 7.155-7.207 (m, 2H), 7.755-7.782 (d, J=8.1 Hz, 1H), 7.503-7.527 (d, J=8.1 Hz, 1H), 8.665-8.692 (d, J=8.1 Hz, 1H).

Step 3: 8-Chloro-9-cyclohexylmethyl-1-methoxy-9H-4-carbazole carboxylic acid

To a solution of methyl-8-chloro-9-cyclohexylmethyl-1-methoxy-9H-4-carbazole carboxylate (95 mg 0.2464 mmoles) in 5 mL methanol, 2 mL of 10% sodium hydroxide solution was added and refluxed for 3 hrs. Methanol from the reaction mixture was evaporated under reduced pressure, diluted with ethyl acetate (50 mL) and washed with 10% sodium hydroxide solution (2×20 mL), this aqueous layer was acidified with 1N HCl and extracted with ethyl acetate (2×25 mL), dried over sodium sulfate and concentrated to give 90 mg of the title compound.

$^1$H NMR (300 MHz, DMSO-$_6$, δ): 0.943 (m, 7H), 1.529 (m, 4H), 4.049 (s, 3H), 5.006-5.030 (d, J=7.2 Hz, 2H), 7.136-7.195 (t, J=8.8 Hz, 2H) 7.479-7.508 (d, J=7.8 Hz, 1H), 7.479-7.508 (d, J=8.1 Hz, 1H), 8.824-8.855 (d, J=8.1 Hz, 1H), 12.9 (bs, 1H).

Step 4: 4-Nitrophenyl-8-chloro-9-cyclohexylmethyl-1-methoxy-9H-4-carbazole carboxylate To a solution of 8-chloro-9-cyclohexylmethyl-1-methoxy-9H-4-carbazole carboxylicacid (82 mg, 0.2126 mmoles) in 10 mL dry chloroform, thionyl chloride (0.047 mL, 1.765 mmoles) was added followed by a drop of DMF. The reaction mixture was stirred for 1 hr at 25° C. under nitrogen atmosphere. To the reaction mixture 4-nitrophenol (29.6 mg, 0.2126 mmoles) was added and the reaction mixture was allowed to stirred for 2 hrs. The reaction mixture was quenched in ice cold water (50 mL) and extracted with ethyl acetate (2×25 ml). Ethyl acetate layer was washed with sodium bicarbonate solution (2×20 mL), 1N HCl (2×20 mL) and with brine (30 mL), dried over sodium sulphate and concentrated to give 50 mg of title compound.

IR (KBR, cm$^{-1}$): 765, 811, 939, 1209, 1345, 1520, 1590, 1744, 2924, 3434, $^1$H NMR (300 MHz, DMSO-d$_6$, δ): 0.951 (m, 7H), 1.531 (m, 4H), 4.057 (s, 3H), 5.009-5.034 (d, J=7.5 Hz, 2H), 7.156-7.256 (m, 5H), 7.75-7.77 (d, J=8.4 Hz, 2H), 8.665-8.694 (d, J=7.8 Hz, 2H)

Step 5: N4-(3,5-dichloro-4-pyridyl) 8-chloro-9-cyclohexylmethyl-1-methoxy-9H-4-carboxamide To a solution of 4-nitrophenyl-8-chloro-9-cyclohexylmethyl-1-methoxy-9H-4-carbazole car-boxylate (44 mg, 0.0919 mmoles) and 3,5-dichloro-4-aminopyridine (21.6 mg, 0.1329 mmoles) in dry DMF (5 ml) at 25° C. under nitrogen atmosphere, sodium hydride 55% (5 mg 0.1195 mmoles) was added and stirred for 1 hr at room temperature. The reaction mixture was quenched in ice cold water (25 mL) and extracted with ethyl acetate (2×25 mL), ethyl acetate layer was washed with bicarbonate (2×25 mL), with 1N HCl (2×25 mL) and with brine (25 mL), dried over sodium sulphate and concentrated to give 20 mg of the title compound.

$^1$H NMR (300 MHz, DMSO-d$_6$, δ): 0.986-1.016 (m, 7H), 1.55 (m, 4H), 4.069 (s, 3H) 5.014-5.039 (d, J=7.5 Hz, 2H), 7.109-7.619 (m, 2H), 7.469-7.492 (d, J=6.9 Hz, 1H), 7.591-7.619 (d, J=8.4 Hz, 1H), 8.316-8.338 (d, J=6.6 Hz, 1H), 8.789 (s, 2H), 10.874 (bs, 1H)

EXAMPLE 95

N4-(3,5dichloro-4pyridyl)-8-chloro-9-(4-Fluorobenzyl)-1-methoxy-9H-4-carbazole carboxamide

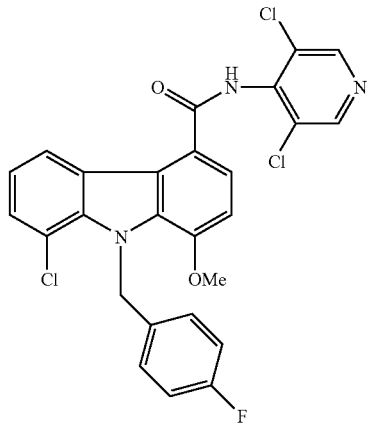

Step 1: Methyl-8-chloro-9-(4-Fluoro benzyl)-1-methoxy-9H-4-carbazole carboxylate To a suspension of sodium hydride 55% (109 mg, 2.76 mmoles) in dry DMF (10 ml), intermediate 73c (265 mg, 0.9153 mmoles) was added at 0° C. under nitrogen atmosphere and stirred for 1 hr at 25° C. Cooled the reaction mixture to 0° C. and 4-fluro benzyl bromide (0.114 mL, 0.915 mmoles) was added. The reaction mixture was stirred for 2 hrs at 25° C., quenched with ice cold water (50 mL) and extracted with ethyl acetate (2×30 mL). The organic layer was washed with water (2×50 mL), brine (2×25 mL), dried over sodium sulfate and concentrated to give 150 mg of the title compound.

IR (KBR, cm$^{-1}$): 637, 729, 773, 872, 1090, 1259, 1295, 1398, 1508, 1706, $^1$H NMR (300 MHz, DMSO-d$_6$, δ): 3.921 (s, 3H), 3.940 (s, 3H), 6.317 (s, 2H), 6.886-6.915 (t, J=8.7 Hz, 2H), 6.996-7.055 (t, J=8.8 Hz, 2H), 7.144-7.234 (m, 2H), 7.492-7.518 (d, J=7.8 Hz, 1H) 7.718-7.809 (d J=8.4 Hz, 1H), 8.704-8.730 (d, J=7.8 Hz, 1H)

Step 2: 8-Chloro-9-(4-Fluoro benzyl)-1-methoxy-9H-4-carbazole carboxylic acid

To a solution of methyl-8-chloro-9-4-Fluorobenzyl)-1-methoxy-9H-4-carbazole carboxylate (150 mg, 0.377 mmoles) in 10 mL methanol, 2 mL of 10% sodium hydroxide solution was added and refluxed for 3 hrs. Methanol from the reaction mixture was evaporated under reduced pressure, diluted with ethyl acetate (50 mL) and washed with 10% sodium hydroxide solution (2×20 mL), this aqueous layer was acidified with 1N HCl and extracted with ethyl acetate (2×30 mL), dried over sodium sulfate and concentrated to give 135 mg of the title compound.

IR (KBR, cm$^{-1}$): 661, 726, 774, 1029, 1128, 1256, 1412, 1510, 1568, 1693, 3480.

$^1$H NMR (300 MHz, DMSO-d$_6$, δ): 3.914 (s, 3H), 6.316 (s, 2H), 6.889-6.936 (t, J=7.0 Hz, 2H), 6.996-7.055 (t, J=8.8 Hz, 2H), 7.123-7.222 (m, 2H), 7.477-7.50 (d, J=6.9 Hz, 1H), 7.797-7.825 (d, J=8.4 Hz, 1H), 8.865-8.889 (d, J=7.2 Hz, 1H), 12.93 (bs, 1H).

Step 3: 4-nitrophenyl-8-chloro-9-(4-Fluorobenzyl-1-methoxy-9H-4-carbazole carboxylate To a solution of 8-chloro-9-(4-Fluorobenzyl)-1-methoxy-9H-4-carbazole carboxylic acid (130 mg, 0.327 mmoles) in 10 mL dry chloroform, thionyl chloride (0.071 mL, 0.981 mmoles) was added followed by a drop of DMF. The reaction mixture was stirred for 1 hr at 25° C. under nitrogen atmosphere. To the reaction mixture, 4-nitrophenol (45.5 mg, 0.3272 mmoles) was added and the reaction mixture was stirred for 2 hrs. The reaction mixture was quenched in ice cold water (50 mL) and extracted with ethyl acetate (2×25 ml). Ethyl acetate layer was washed with sodium bicarbonate solution (2×25 mL), 1N HCl (2×25 mL) and with brine, dried over sodium sulphate and concentrated to give 150 mg of the title compound.

IR (KBR, cm$^{31\ 1}$): 496, 726, 888, 1054, 1081, 1135, 1197, 1347, 1518, 1591, 1722, $^1$H NMR (300 MHz, DMSO-d$_6$, δ): 3.926 (s, 3H), 6.324 (s, 2H), 6.892-6.940 (t, J=7.2 Hz, 2H), 7.003-7.061 (t, J=8.7 Hz, 2H), 7.149-7.238 (m, 2H), 7.494-7.532 (d, J=7.8 Hz, 1H), 7.778-7.806 (d, J=8.4 Hz, 1H) 8.711-8.737 (d, J=7.8 Hz, 1H).

Step 4: N4-(3,5-dichloro-4-pyridyl)-8-chloro-9-(4Fluorobenzyl)-1-methoxy-9H-4-carbazole carboxamide To a solution of 4-nitrophenyl-8-chloro-9-(4-Fluorobenzyl)-1-methoxy-9H-4-carbazole carboxylate (100 mg, 0.1982 mmoles) and 3,5-dichloro 4-amino pyridine (32.3 mg, 0.1982 mmoles) in dry DMF (7 mL), at 25° C. under nitrogen atmosphere, sodium hydride 55% (10.3 mg, 0.2576 mmoles) was added and stirred for 1 hr. The reaction mixtre was quenched in ice cold water (25 mL) and extracted with ethyl acetate (2×25 mL). The organic layer was washed with bicarbonate (2×25 mL), followed by 1N HCl (2×25 mL) and with brine (25 mL), dried over sodium sulphate and concentrated to give the 70 mg of the title compound.

IR (KBR, cm$^{-1}$): 676, 782, 875, 1032, 1217, 1255, 1400, 1492, 1556, 1668, 2926, 3194.

$^1$H NMR (300 MHz, DMSO-d$_6$, δ): 3.94 (s, 3H), 6.34 (s, 2H), 6.923-6.970 (t, J=8.5 Hz, 2H), 7.024-7.053 (t, J=7.4 Hz, 2H), 7.083-7.234 (m, 2H), 7.463-7.4859 (d, J=6.69 Hz, 1H), 7.622-7.650 (d, J=8.4 Hz, 1H), 8.345-8.369 (d, J=7.3 Hz, 1H), 8.793 (s, 2H), 10.865 (s, 1H).

EXAMPLE 96

N4-(3,5-dichloro-4-pyridyl)-6-chloro-1-methoxy-9-methyl-9H-4-carbazole carboxamide

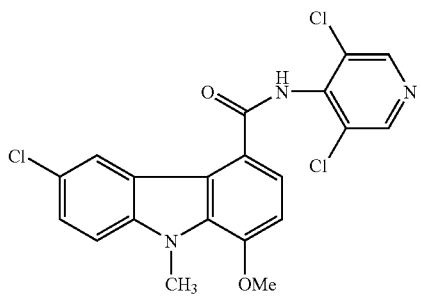

Step 1: Methyl-6-chloro-1-methoxy-9-methyl-9H-4-carbazole carboxylate

To a solution of intermediate 73b (400 mg, 1.3817 mmoles) in dry DMF (7 mL), sodium hydride 55% (71.8 mg, 1.796 mmoles) was added at 0° C. and stirred for 1 hr at 25° C. under nitrogen atmosphere. Methyl iodide (0.17 mL, 2.763 mmoles) was added to the reaction mixture at 0° C. and the reaction mixture was stirred at 25° C. for 1 hr. Reaction mixture was quenched with ice cold water (100 mL) and extracted with ethyl acetate (2×50 mL), washed with brine (2×50 mL), dried over sodium sulfate and concentrated to give 400 mg of the title compound.

IR (KBR, cm$^{-1}$): 625, 849, 1066, 1088, 1250, 1567, 1595, 1712.

$^1$H NMR (300 MHz, DMSO-d$_6$, δ): 3.934 (s, 3H), 4.033 (s, 3H), 4.150 (s, 3H), 7.118-7.146 (d, J=8.4 Hz, 1H), 7.498-7.534 (dd, J=8.8 Hz, 2H), 7.630-7.661 (d, J=9.3 Hz, 2H), 8.883-8.889 (d, J=1.8 Hz, 1H).

Step 2: 6-Chloro-1-methoxy-9-methyl-9H-4-carbazole carboxylicacid

To a solution of methyl-6-chloro-1-methoxy-9-methyl-9H-4-carbazole carboxylate (390 mg 1.285 mmoles) in 20 mL methanol, 5 mL of 10% sodium hydroxide solution was added and stirred for 3 hrs. Methanol from the reaction mixture was evaporated under reduced pressure, diluted with ethyl acetate (5 mL) and washed with 10% sodium hydroxide solution (2×2 mL). This aqueous layer is acidified with 1N HCl and extracted with ethyl acetate (2×25 mL), dried over sodium sulfate and concentrated to give 350 of the title compound IR (KBR, cm$^{-1}$): 629, 744, 784, 1017, 1117, 1268, 1449, 1567, 1683, 2942.

$^1$H NMR (300 MHz, DMSO-d$_6$, δ): 4.03 (s, 3H), 4.156 (s, 3H), 7.109-7.138 (d, J=8.7 Hz, 1H), 7.487-7.524 (d, J=9.6 Hz, 1H), 7.625-7.654 (d, J=8.7 Hz, 1H), 7.817-7.845 (d, J=8.4 Hz, 1H), 8.972-8.979 (d, J=2.1 Hz, 1H)

Step 3: 4-Nitrophenyl-6-chloro-1-methoxy-9-methyl-9H-4-carbazole carboxylate To a solution of 6-chloro-1-methoxy-9-methyl-9H-4-carbazole carboxylic acid (350 mg, 1.372 mmoles) in 15 mL dry chloroform, under nitrogen atmosphere, thionyl chloride (0.150 mL, 2.058 mmoles) was added followed by a drop of dry DMF and stirred at 25° C. for 1 hr. To this, 4-nitrophenol (190 mg, 1.372 mmoles) was added followed by triethyl amine (0.25 mL, 1.784 mmoles) and stirred the reaction mixture for 2 hr at 25° C. Chloroform from the reaction mixture was evaporated and diluted the residue with ethyl acetate (50 mL). The organic layer was washed with 1% sodium hydroxide solution (20 mL), 1N HCl (25 mL), brine (50 ML), dried over sodium sulfate and concentrated to give 200 mg of the title compound.

IR (KBR, cm$^{-1}$): 610, 744, 786, 943, 1020, 1048, 1212, 1249, 1306, 1347, 1519, 1748, $^1$H NMR (300 MHz, DMSO-d$_6$, δ): 4.107 (s, 3H), 4.211 (s, 3H), 7.256-7.286 (d, J=9 Hz, 1H), 7.537-7.575 (dd, J=8.8 Hz, 1H), 7.692-7.729 (m, 3H) 8.208-8.231 (d, J=8.1 Hz, 1H), 8.374-8.405 (d, J=39.3 Hz, 2H), 8.868-8.876 (d, J=3 Hz, 1H).

Step 4: N4-(3,5-dichloro-4-pyridyl)-6-chloro-1-methoxy-9-methyl-9H-4-carbazole carboxamide To a solution of 4-nitrophenyl-6-chloro-1-methoxy-9-methyl-9H-4-carbazole carboxylate (160 mg, 0.4255 mmoles), and 3,5-dichloro-4-amino pyridine (69.36 mg, 0.4255 mmoles) in dry DMF (7 mL) at 25° C., sodium hydride 55% (34 mg, 0.8510 mmoles) was added and stirred under nitrogen atmosphere for 1 hr. The reaction mixture was quenched in ice cold water (25 mL) and extracted with ethyl acetate (2×25 mL). The organic layer was washed with bicarbonate (2×25 mL), followed by 1N HCl (2×25 mL) and with brine (25 mL), dried over sodium sulphate and concentrated to give the 90 mg of the title compound.

$^1$H NMR (300 MHz, DMSO-d$_6$, δ): 4.046 (s, 3H), 4.172 (s, 3H), 7.175-7.203 (d, J=8.4 Hz, 1H), 7.5 (m, 1H) 7.615-7.667 (t, 7.8 Hz, 2H), 8.429-8.436 (d, J=2.1 Hz, 1H), 8.758 (s, 2H) 10.769 (s, 1H).

EXAMPLE 97

N4-(3,5-dichloro-4-pyridyl-N-oxide)-6-chloro-9-(4-fluorobenzyl)-1-methoxy-9H-4-carbazolecarboxamide

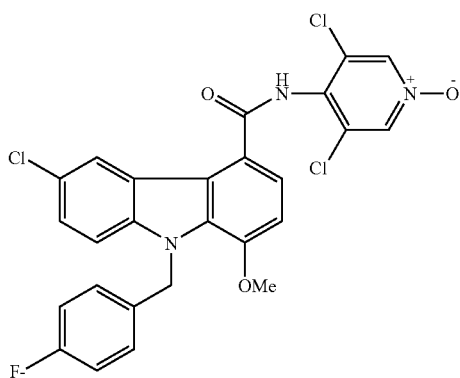

Step 1: 6-Chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressureor, the residue was acidified with 1N HCl and the precipitated product was filtered, washed with water and dried under vacuum, to give 380 mg of the title product.

IR (KBR, cm$^{-1}$): 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.

$^1$H NMR (300 MHz, DMSO-$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d, J=8.4 Hz, 1H), 8.96-8.967 (d, J=2.4 Hz, 1H), 11.84 (s, 1H), 12.8 (b s, 1H).

Step 2: 4-Nitrophenyl -6chloro-1-methoxy 9H-4-carbazole carboxylate

To a suspension of 6-chloro-1-methoxy-9H-4-carbazole carboxylic acid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over Na$_2$SO$_4$ and concentrated to give 0.38 gm of the title product as a yellow solid.

IR (KBr, cm$^{-1}$): 3394, 2935, 1746, 1567, 1510, 1347, 1211, 1202, 1100, 951 and 745.

$^1$H NMR (300 MHz, DMSO-$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 6-chloro-9-(4-fluoro benzyl)-1-methoxy-4-carbazole carboxylate To a solution of 4-Nitrophenyl 6-chloro-9H-4-methoxy-4-carbazole carboxylate (200 mg, 0.69 mmoles) in dry DMF (10 ml) under nitrogen atmosphere, at 0° C., sodium hydride (60% suspension, 42 mg, 1.036 mmoles) was added and the reaction mixture was stirred at room temperature for 30 min. The reaction mixture was cooled to 0° C., 4-fluoro benzylbromide (0.086 ml, 0.69 mmoles) was added and stirred the reaction mixture at room temperature for 30 min. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over Na$_2$SO$_4$ and concentrated. The crude material was diluted with ethyl acetate (20 ml) and allowed to stand at 10° C. for 10 min. The separated solid flakes were filtered, washed with pet ether and dried to give 176 mg of the title compound.

IR (KBr, cm$^{-1}$): 2933, 1727, 1567, 1510, 1456, 1342, 1244, 1178, 1130, 1042, 1013, 803 and 743.

$^1$H NMR (300 MHz, DMSO-d$_6$, δ): 4.031 (s, 3H), 5.983 (s, 2H), 7.065-7.089 (d, J=7.2 Hz, 4H), 7.2747.303 (d, J=8.7 Hz, 1H), 7.51-7.547 (dd, J=9.0 Hz, 1H), 7.693-7.724 (d, J=9.3 Hz, 2H), 7.757-7.786 (d, J=8.7 Hz, 1H), 8.228-8.257 (d, J=8.7 Hz, 1H), 8.379-8.408 (d, J=8.7 Hz, 2H), 8.886-8.893 (d, J=2.1 Hz, 1H).

Step 4: N4-3,5-dichloro-4-pyridyl N-oxide)-6-chloro-9-(4-fluorobenzyl)-1-methoxy-9H-4-carbazolecarboxamide To a solution of 4-nitrophenyl-6-chloro-9-(4-fluorobenzyl)-1-methoxy-9H-4-carbazole-carboxylate (100 mg, 0.198 mmoles) and 3,5 dichloro-4-aminopyridyl N-oxide (35.5 mg, 0.198 mmoles) in dry DMF (5 ml), under N$_2$ atmosphere, 60% sodium hydride (17.29 mg, 0.396 mmoles) was added at 25° C. and the reaction mixture was stirred overnight. The reaction mixture was poured into ice-cold water and neutralized with 1N HCl. The compound was extracted with chloroform (3×10 ml), combined the organic layers and washed with water (3×10 ml) and with brine (10 ml). The organic layer was dried over anhydrous sodium sulphate and concentrated to give 110 mg of the crude compound which was purified by column chromatography to yield 65 mg of the title compound as Creamish white solid, m. p: 277-277.5° C.

IR (KBr, cm$^{-1}$): 524, 764, 792, 832, 1016, 1096, 1132, 1233, 1260, 1308, 1422, 1464, 1486, 1509, 1568, 1596, 1647, 2928, 3256 and 3434

$^1$H NMR (300 MHz, DMSO-d$_6$, δ): 3.973 (s, 3H), 5.931 (s, 2H), 7.055-7.093 (m, 3H), 7.185-7.213 (d, J=8.4 Hz, 1H), 7.436-7.472 (dd, J=8.9 Hz, 1H), 7.615-7.642 (d, J=8.1 Hz, 1H), 7.695-7.725 (d, J=9 Hz, 1H), 8.294 (s, 1H), 8.424-8.431 (d, J=2.1 Hz, 1H), 8.763 (s, 2H), 10.617 (s, 1H)

EXAMPLE 98

N4-(3,5-dichloro-4-pyridyl-N-oxide)-6-chloro-9-(4-methoxybenzyl)-1-methoxy-9H-4-carba-zolecarboxamide

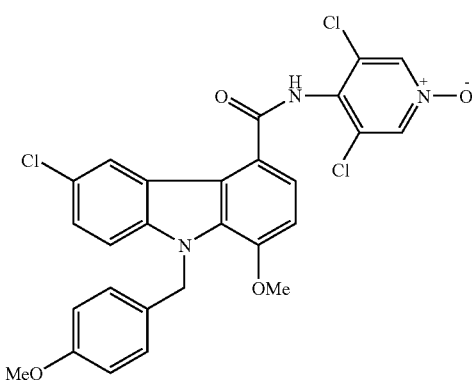

Step 1: 6-Chloro-1-methoxy 9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressureor, the residue was acidified with 1N HCl and the precipitated product was filtered, washed with water and dried under vacuum, to give 380 mg of the title product.

IR (KBR, cm$^{-1}$: 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.

$^1$H NMR (300 MHz, DMSO-d$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d, J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy-9H-4-carbazole carboxylate

To a suspension of 6-chloro-1-methoxy-9H-4-carbazole carboxylic acid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over Na$_2$SO$_4$ and concentrated to give 0.38 gm of the title product as yellow solid.

IR (KBr, cm$^{-1}$): 3394, 2935, 1746, 1567, 1510, 1347, 1211, 1202, 1100, 951 and 745.

$^1$H NMR (300 MHz, DMSO-d$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 6-chloro-9-(4-methoxy benzyl)-1-methoxy-4-carbazole carboxylate To a solution of 4-nitrophenyl 6chloro-9H-1-methoxy-4-carbazole carboxylate (200 mg, 0.69 mmoles) in dry DMF (10 ml) under nitrogen atmosphere, at 0° C., sodium hydride (60% suspension, 42 mg, 1.036 mmoles) was added and the reaction mixture was stirred at room temperature for 30 min. The reaction mixture was cooled to 0° C., 4-methoxy benzylchloride (0.094 ml, 0.69 mmoles) was added and stirred the reaction mixture at room temperature for 30 min. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over Na$_2$SO$_4$ and concentrated. The crude material was diluted with ethyl acetate (20 ml) and allowed to stand at 10° C. for 10 min. The separated solid flakes were filtered, washed with pet ether and dried to give 100 mg of the title compound.

IR (KBr, cm$^{-1}$): 3434, 2837, 1726, 1565, 1523, 1514, 1461, 1353, 1252, 1172, 1133, 1040, 1012 and 804.

$^1$H NMR (300 MHz, DMSO-$_6$, δ): 3.653 (s, 3H), 4.064 (s, 3H), 5.926 (s, 2H), 6.774-6.803 (d, J=8.7 Hz, 2H), 6.996-7.026 (d, J=9.0 Hz, 2H), 7.281-7.308 (d, J=8.1 Hz, 1H), 7.50-7.536 (dd, J=8.7 Hz, 1H), 7.692-7.723 (d, J=9.3 Hz, 2H), 7.752-7.781 (d, J=8.7 Hz, 1H), 8.225-8.252 (d, J=8.1 Hz, 1H), 8.377-8.408 (d, J=9.3 Hz, 2H), 8.871-8.880 (d, J=2.7 Hz, 1H).

Step 4: N4-(3,5-dichloro-4-pyridyl-N-oxide)-6-chloro-9-(4-methoxybenzyl)-1-methoxy-9H-4-carbazolecarboxamide To a solution of 4-nitrophenyl 6-chloro-9-(4-methoxybenzyl)-1-methoxy-9H-4-carbazolecarboxylate (73 mg, 0.141 mmoles) and 3,5 dichloro-4-aminopyridyl N-oxide (25.29 mg, 0.141 mmoles) in dry DMF (5 ml), under N$_2$ atmosphere, 60% sodium hydride (12.33 mg, 0.283 mmoles) was added at 25° C. and the reaction mixture was stirred overnight. The reaction mixture was poured into ice-cold water and neutralized with 1N HCl. The compound was extracted with chloroform (3×10 ml), combined the organic layers and washed with water (3×10 ml) and with brine (10 ml). The organic layer was dried over anhydrous sodium sulphate and concentrated to give 70 mg of the crude compound which was purified by column chromatography to yield 33 mg of the title compound as a pale yellow solid, m. p: 247.8-248.5° C.

$^1$H NMR (300 MHz, DMSO-d$_6$, δ): 3.641 (s, 3H), 4.005 (s, 3H), 5.873 (s, 2H), 6.762-6.791 (d, J=8.7 Hz, 2H), 7.006-7.034 (d, J=8.4 Hz, 2H), 7.190-7.218 (d, J=8.4 Hz, 1H), 7.425-7.462 (dd, J=8.9 Hz, 1H), 7.608-7.636 (d, J=8.4 Hz, 1H), 7.690-7.719 (d, J=8.7 Hz, 1H), 8.402-8.410 (d, J=2.4 Hz, 1H), 8.766 (s, 2H), 10.608 (s, 1H)

EXAMPLE 99

N4-(3,5-dichloro-4-pyridyl-N-oxide)-6-chloro-9-cyclohexylmethyl-1-methoxy-9-H-4-carbazolecarboxamide

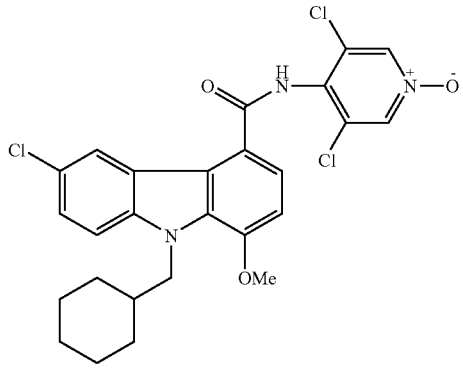

Step 1: 6-Chloro-1-methoxy-9H-4-carbazole carboxylic acid

To a solution of intermediate 73b (400 mg, 1.38 mmoles) in methanol (15 ml), an aqueous (5 ml) solution of sodium hydroxide (110 mg, 2.76 mmoles) was added and the reaction mixture was refluxed for 6 hours. Methanol was evaporated from the reaction mixture under reduced pressureor, the residue was acidified with 1N HCl and the precipitated product was filtered, washed with water and dried under vacuum, to give 380 mg of the title product.

IR (KBR, cm$^{-1}$): 565, 589, 631, 657, 745, 791, 885, 919, 989, 1015, 1066, 1111, 1269, 1291, 1305, 1371, 1418, 1461, 1567, 1613, 1625, 1684, 2623, 2849, 2939 and 3461.

$^1$H NMR (300 MHz, DMSO-d$_6$, δ): 4.065 (s, 3H), 7.087-7.115 (d, J=8.4 Hz, 1H), 7.399-7.437 (d, J=11.4 Hz, 1H), 7.505-7.534 (d, J=8.7 Hz, 1H), 7.5-7.877 (d, J=8.4 Hz, 1H), 8.96-8.967 (d, J=2.4 Hz, 1H), 11.84 (s, 1H), 12.8 (b s, 1H).

Step 2: 4-Nitrophenyl-6-chloro-1-methoxy 9H-4-carbazole carboxylate

To a suspension of 6-chloro-1-methoxy 9H-4-carbazole carboxylic acid (375 mg, 1.36 mmoles) in dry chloroform (15 ml), thionyl chloride (0.3 ml, 4.08 mmoles) was added followed by 2 drops of dry DMF and stirred the reaction mixture under nitrogen atmosphere for two hours. Solvent and the excess thionyl chloride were evaporated from the reaction mixture and dried under vacuum. To this residue, dry chloroform (15 ml) was added followed by 4-nitrophenol (190 mg, 1.36 mmoles) and triethylamine (0.29 ml, 2.04 mmoles) were added and the reaction mixture was stirred under nitrogen atmosphere for 2 hours. The reaction mixture was diluted with chloroform (30 ml) and washed with 1N HCl. The organic layer was washed with brine (20 ml), dried over Na$_2$SO$_4$ and concentrated to give 0.38 gm of the title product as a yellow solid.

IR (KBr, cm$^{-1}$): 3394, 2935, 1746, 1567, 1510, 1347, 1211, 1202, 1100, 951 and 745.

$^1$H NMR (300 MHz, DMSO-$_6$, δ): 4.13 (s, 3H), 7.225-7.255 (d, J=9.0 Hz, 1H), 7.438-7.476 (d, J=11.4 Hz, 1H), 7.552-7.581 (d, J=8.7 Hz, 1H), 7.679-7.708 (d, J=8.7 Hz, 1H), 8.204-8.231 (d, J=8.1 Hz, 1H), 8.364-8.395 (d, J=9.3 Hz, 1H), 8.832-8.839 (d, J=2.1 Hz, 1H), 12.06 (s, 1H).

Step 3: 4-Nitrophenyl 6-chloro-9-cyclohexylmethyl-1-methoxy-4-carbazole carboxylate To a solution of 4-nitrophenyl 6-chloro-9H-1-methoxy-4-carbazole carboxylate (200 mg, 0.69 mmoles) in dry DMF (10 ml) under nitrogen atmosphere, at 0° C., sodium hydride (60% suspension, 42 mg, 1.036 mmoles) was added and the reaction mixture was stirred at room temperature for 30 min. The reaction mixture was cooled to 0° C., cyclohexyl methyl bromide (0.096 ml, 0.69 mmoles) was added and the reaction mixture was stirred at room temperature for 24 hours. The reaction mixture was diluted with ethyl acetate (25 ml), added 1N HCl (15 ml), shaken and separated the layers. The aqueous layer was extracted with ethyl acetate (20 ml), combined the organic layers, washed with water (3×15 ml), dried over Na$_2$SO$_4$ and concentrated. The crude material was purified by column chromatography to give 60 mg of the title compound.

$^1$H NMR (300 MHz, DMSO-d$_6$, δ): 1.082 (m, 6H), 1.381-1.397 (b, 2H), 1.565-1.626 (b, 2H), 1.81 (b, 1H), 4.011 (s, 3H), 4.541-4.564 (d, J=6.9 Hz, 2H), 7.258-7.286 (d, J=8.4 Hz, 1H), 7.5-7.536 (dd, J=8.7 Hz, 1H), 7.682-7.711 (d, J=8.7 Hz, 2H), 7.736-7.767 (d, J=8.7 Hz, 1H), 8.2-8.226 (d, J=8.1 Hz, 1H), 8.374-8.403 (d, J=8.7 Hz, 2H), 8.857-8.863 (d, J=1.8 Hz, 1H).

Step 4: N4-(3,5-dichloro-4-pyridyl-N-oxide)-6-chloro-9-cyclohexylmethyl-1-methoxy-9H-4-carbazolecarboxamide To a solution of 4-nitrophenyl-6-chloro-9-cylclohexylmethyl-1-methoxy-9H-4-carbazolecar-boxylate (72 mg, 0.146 mmoles) and 3,5-dichloro-4-aminopyridyl-N-oxide (26.29 mg, 0.146 mmoles) in dry DMF (5 ml), under N$_2$ atmosphere, 60% sodium hydride (12.75 mg, 0.292 mmoles) was added at 25° C. and the reaction mixture was stirred overnight. The reaction mixture was poured into ice-cold water and neutralized with 1N HCl. The compound was extracted with chloroform (3×10 ml), combined the organic layers and washed with water (3×10 ml) and with brine (10 ml). The organic layer was dried over anhydrous sodium sulphate and concentrated to give 50 mg of the crude compound which was purified by column chromatography to yield 38 mg of the title compound as a creamish white solid, m. p: 268.8-268.9° C.

IR (KBr,cm$^{-1}$): 525, 649, 748, 788, 798, 830, 895, 1018, 1096, 1127, 1174, 1211, 1234, 1249, 1304, 1422, 1467, 1481, 1529, 1568, 1598, 1662, 852, 2926, 3110 and 3310

$^1$H NMR (300 MHz, DMSO-d$_6$, δ): 1.074-1.618 (m, 11H), 4.045 (s, 3H), 4.497-4.520 (d, J=6.9 Hz, 2H), 7.163-7.190 (d, J=8.1 Hz, 1H), 7.431-7.467 (dd, J=8.7 Hz, 1H), 7.579-7.606 (d, J=8.1 Hz, 1H), 7.672-7.701 (d, J=8.7 Hz, 1H), 8.394-8.401 (d, J=2.1 Hz, 1H), 8.761 (s, 2H), 10.589 (s, 1H)

EXAMPLE 100

N4-3,5-dichloro-4-pyridyl)-9-methyl-1-methoxy-9H-4-carbazolecarboxamide

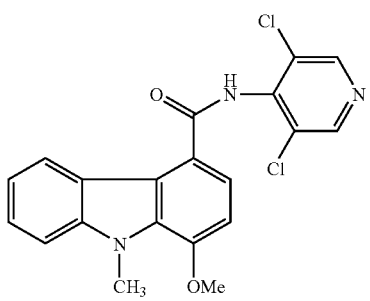

Step 1: 1-Methoxy-9-methyl-9H-4-carbazole carbaldehyde

To a suspension of sodium hydride (55% suspension, 0.266 gm, 6.66 mnmoles) in dry DMF (15 mL), intermediate 71 (1 gm, 4.44 mmoles) was added at 0° C. and stirred for 1 hr at 25° C. The reaction mixture was cooled to 0° C. and added slowly methyl iodide (0.55 mL 8.88 mmoles). This reaction mixture was stirred at 25° C. for 1 hr. The reaction mixture was quenched in ice cold water slowly (100 mL) and extracted with ethyl acetate (2×50 mL). The organic layer was washed with water (3×50 mL), followed by brine (2×50 mL), dried over sodium sulphate and concentrated to give 0.875 gm of the title compound.

$^1$H NMR (300 MHz, DMSO-$d_6$, δ): 4.095 (s, 3H), 4.187 (s, 3H), 7.284-7.203 (m, 2H), 7.8 (t, J=8.0 Hz, 1H), 8.4 (d, 3H), 10.175 (s, 1H)

Step 2: 1-Methoxy-9-methyl-9H-4-carbazole carboxylic acid

To a solution of 1-methoxy-9-methyl 9H-4-carbazolecarbaldehyde (100 mg 0.4184 mmoles) in a mixture of 8 mL acetone and 4 mL water, sulfamic acid (48.7 mg 0.502 mmoles) was added followed by a solution of sodium chlorite (37.8 mg, 0.4184 mmoles) in 2 mL water and the reaction mixture was stirred at 25° C. for 4 hrs. Acetone from the reaction mixture was evaporated under reduced pressure, diluted with ethyl acetate 30 mL. Organic layer was separated and basified with freshly prepared sodium bicarbonate solution and separated the aqueous layer and acidified with 1N HCl and extracted with ethyl acetate (2×25 mL). Ethyl acetate layer was washed with brine (2×20 mL), dried over sodium sulfate and concerted to give 95 mg of the tide compound.

$^1$H NMR (300 MHz, DMSO-$d_6$, δ): 4.028 (s, 3H), 4.161 (s, 3H), 7.196-7.070 (m, 2H,) 7.632-7.456 (m, 2H), 8.4 (d, 1H), 8.1 (d 1H).

Step 3: 4-Nitrophenyl-1-methoxy-9-methyl-9H-4-carbazole carboxylate

To a solution of 1-methoxy-9methyl 9H-4-carbazolecarboxylic acid (150 mg 0.588 mmoles) in 10 mL dry chloroform thionyl chloride (210 mg 1.765 mmoles) was added followed by a drop of DMF. The reaction mixture was stirred for 1 hr at 25° C. under nitrogen atmosphere. To the reaction mixture added 4-nitrophenol (82 mg 0.588 mmoles) followed by triethyl amine (77.2 mg 0.764 mmoles) and the reaction mixture was allowed to stirred for 2 hrs. The reaction mixture was quenched in ice cold water 50 mL and extracted with ethyl acetate (2×25 ml). Ethyl acetate layer was washed with sodium bicarbonate solution (2×20 mL), followed by water (1×25 mL), 1N HCl (2×20 mL) and with brine, dried over sodium sulphate and concentrated to give 100 mg of the title compound.

$^1$H NMR (300 MHz, DMSO-$d_6$, δ): 4.09 (s 3H), 4.20 (s 3H), 7.15-7.24 (m 2H), 7.50-7.54 (t, J=8.0 Hz, 1H), 7.64-7.71 (m 3H), 8.14-8.17 (J=8.7 Hz, 1H), 8.36-8.40 (d, J=7.2 Hz, 2H), 8.77-8.79 (d, J=7.8 Hz, 1H).

Step 4: N4-(3,5-dichloro-4-pyridyl)-1-methoxy-9-methyl-9H-4-carbazole carboxamide To a solution of 4-nitrophenyl-1-methoxy-9-methyl 9H-4-carbazolecarboxylate (50 mg 0.1329 mmoles) and 3,5-dichloro 4-amino pyridine (21.6 mg, 0.1329 mmoles) in dry DMF (5 ml) at 25° C. under nitrogen atmosphere, sodium hydride 55% (7 mg 0.1728 mmoles) was added and stirred at room temperature for 1 hr. The reaction mixture was quenched in ice cold water (25 mL) and extracted with ethyl acetate (2×25 mL), ethyl acetate layer was washed with bicarbonate (2×25 mL), with 1N HCl (2×25 mL) and with brine (25 mL), dried over sodium sulphate and concentrated to give 20 mg of the title compound.

$^1$H NMR (300 MHz, DMSO-$d_6$, δ): 4.043 (s, 3H), 7.174 (s, 3H), 7.099-7.159 (m, 2H) 7.45-7.49 (t, J=7.2 Hz, 1H) 7.568-7.607 (m, 2H) 8.343-8.369 (d, J=7.8 Hz, 1H) 8.77 (s, 2H), 10.699 (s 1H).

EXAMPLE 101

3,5Dichloro-4-(4-methoxydibenzo[b,d]-thiophen-1-ylcarboxamido)pyridine

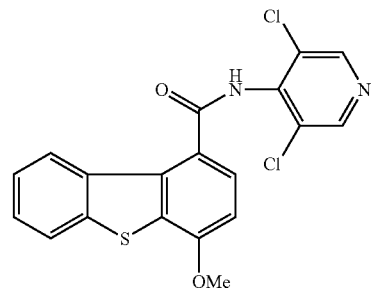

Sodium hydride (0.66 mmols, 36 mg of 50% dispersed in oil) was added to a stirred dry DMF solution of 3,5-dichloro-4-aminopyridine (0.083 g, 0.5 mmols) at −10° C. After 30 minutes dry THF (5 ml) solution of the acid chloride of intermediate 86 (0.46 mmols) was added to the reaction mixture at 0° C. The reaction mixture was stirred 3 hrs at room temperature and poured in ice-water mixture to get precipitate. The precipitated product was filtered, washed with water and dried which was further purified by silica get column chromatography to get white solid.

Yield: 0.078 g, (46%), m.p.: 286-287° C.

IR (KBr, cm−1): 3434, 3192, 2926, 1665, 1567, 1554, 1483, 1287, 1265, 1111, 1066, 1016 and 811.84 cm−1.

¹H-NMR: (CDCl₃, 300 MHz, TMS, δ): 4.09 (s, 3H), 6.92 (d, 1H), 7.38 (t, 1H), 7.47 (t, 1H), 7.63 (s, 1H), 7.78 (d, 1H), 7.88 (d, 1H), 8.52 (d, 1H) and 8.60 (s, 2H).

EXAMPLE 102

3,5-Dichloro-4-(4-cyclopentyloxydibenzo[b,d]-thiophen-1-ylcarboxamido)pyridine

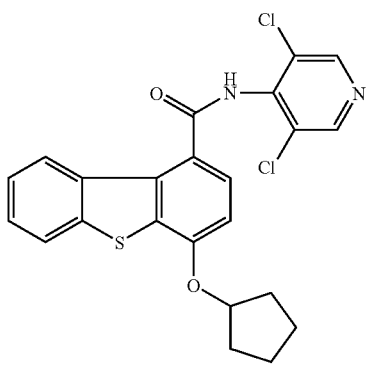

Sodium hydride (0.66 mmols, 36 mg of 50% dispersed in oil) was added to a stred dry DMF solution of 3,5-dichloro-4-aminopyridine (0.083 g, 0.5 mmols) at −10° C. After 30 minutes dry THF (5 ml) solution of the acid chloride of intermediate 90 (0.25 g, 0.8 mmols) was added to the reaction mixture at 0° C. The reaction mix was stirred 3 hrs at room temperature and poured in ice-water mixture to get precipitate. The precipitated product was filtered a washed with water and dried which was further purified by silica gel column chromatography to yield a white solid.

yield: 0.16 g ((44%), white solid, m.p.: 285-286° C.

IR (KBr, cm−1): 3433, 3198, 2955, 1665, 1554, 1481, 1441, 1400, 1286, 1262, 1167, 1104, 1061, 985, and 820

¹H-NMR: (CDCl₃ + DMSO-d₆, 300 MHz, TMS, δ): 1.60-2.04 (m, 8H), 5.05 (m, 1H), 6.90 (d, 1H), 7.20-7.47 (m, 2H), 7.63 (s, 1H), 7.74 (d, 1H), 7.85 (d, 1H), 8.50 (d, 1H) and 8.60 (s, 2H).

EXAMPLE 103

N1 (4-methoxyphenyl)-4-methoxydibenzo[b,d]thiophene-1-carboxamide

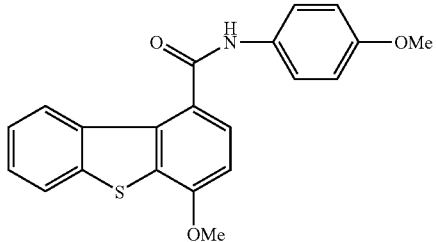

Sodium hydride (0.66 mmols, 36 mg of 50% dispersed in oil) was added to a stirred dry DMF solution of 4-methoxyaniline (0.1 g, 0.852 mmol) at −10° C. After 30 minutes dry THF (5 ml) solution of the acid chloride of intermediate 86 (0.2 g, 0.775 mmol) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to yield a white solid.

Yield: 0.18 g (64%), m.p.: 252-253° C.

IR (KBr, cm−1): 3297, 3048, 3012, 2938, 2836, 1644, 1614, 1599, 1555, 1568, 1525, 1512, 1439, 1408, 1293, 1262, 1245, 1182, 1173, 1109, 1066, 1031, 1016, 821, 789 and 733

¹H-NMR: (CDCl₃, 300 MHz, TMS, δ): 3.8 (s, 3H), 4.05 (s, 3H), 6.80-6.90 (fused t, 3H), 7.30 (t, 1H), 7.45 (t, 1H), 7.60 (m, 4H0, 7.87 (d, 1H) and 8.30 (d, 1H).

EXAMPLE 104

N1-(4-methoxyphenyl)-4-methoxydibenzo[b,d]thiophene-1-carboxamide-5,5-dioxide

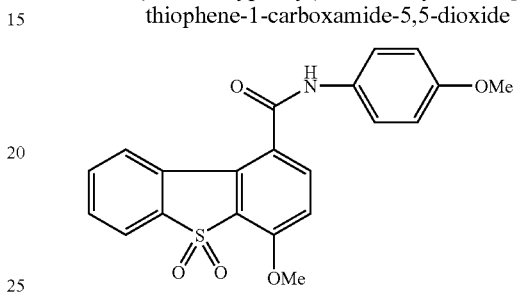

To a dichloromethane (10 ml) solution of N1 (4-methoxyphenyl)-4-methoxydibenzo-[b,d]thiophene-1-carboxamide (example 103), (0.07 g, 0.192 mmols ), 3-chloro-per-benzoic acid (0. 173 g, 0.768 mmols, 50% dispersion in water) was added in portions. This reaction mixture was stirred at room temperature for 2 hrs. CH₂Cl₂ was removed from reaction mixture and it was triturated with 5% NaHCO₃ solution to get solid product. The product was filtered and washed thoroughly with water and dried.

Yield: 0.04 g (52%), m.p.: 289-290° C.

IR (KBr, cm−1): 3356, 3084, 2926, 2848, 1676, 1599, 1561, 1536, 1509, 1497, 1462, 1292, 1254, 1235, 1160, 1136, 1059, 1034, 1013, 926, 871, 829, 755, 732, 635 and 624

¹H-NMR: (CDCl₃, 300 MHz, TMS, δ): 3.83 (s, 3H), 4.05 (s, 3H), 6.90-6.99 (mixed d, 3H), 7.50-7.58 (m, 3H), 7.61(s, 1H), 7.66 (d, 1H), 7.82 (m, 1H), 7.95 (m, 1H).

EXAMPLE 105

N1-(4-chlorophenyl)-4-methoxydibenzo[b,d]thiophene-1-carboxamide

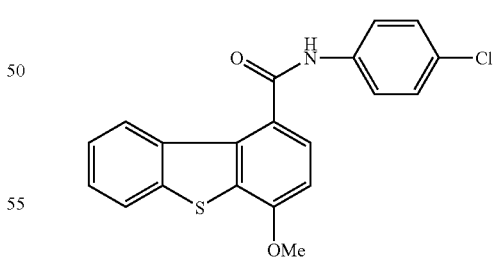

Sodium hydride (0.66 mmols, 36 mg of 50% dispersed in oil) was added to a stirred dry DMF solution of 4-chloroaniline (0.11 g, 0.85 mmol) at −10° C. After 30 minutes dry THF (5 ml) solution of the acid chloride of intermediate 86 (0.2 g, 0.775 mmol) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to yield a white solid.

Yield: 0.07 g (17%), m.p.: 269-270° C.

IR (KBr, cm−1): 3288, 2923, 1651, 1590, 1568,1556, 1514, 1495, 1395, 1304, 1288, 1257, 1108, 1064, 1013, 823, 766, and 733.

$^1$H-NMR: (CDCl$_3$, 300 MHz, TMS, δ): 4.00 (s, 3H), 6.20 (d, 1H), 7.30 (mixed d, 3H), 7.40 (t, 1H), 7.58 (d, 1H), 7.60 (m, 3H), 7.85 (d, 1H), 8.25 (d, 1H).

EXAMPLE 106

4-(4-methoxydibenzo[b,d]thiophene-1-ylcarboxamido)pyridine

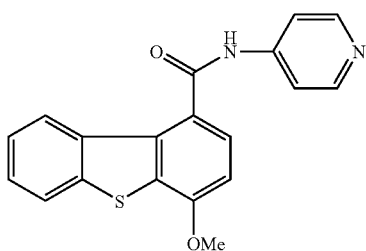

Sodium hydride (0.66 mmols, 36 mg of 50% dispersed in oil) was added to a stirred dry DMF solution of 4-aminopyridine (0.087 g, 0.92 mmols) at −10° C. After 30 minutes dry THF (5 ml) solution of the acid chloride of intermediate 86 (0.2 g, 0.775 mmol) was added to the reaction mixture at 0° C. The reaction mixture was stirred 3 hrs at room temperature and poured in ice-water mixture to get a precipitate. The precipitated product was filtered a washed with water and dried which was further purified by silica gel column chromatography to yield a white solid.

Yield: 0.04 g (26%), m.p.: 246-248° C.

IR (KBr, cm−1): 3290, 2925, 1656, 1584, 1567, 1509, 1410, 1330, 1283, 1261, 1211, 1109, 1064, 1010, and 816.

$^1$H-NMR: (CDCl$_3$, 300 MHz, TMS, δ): 4.07 (s, 3H), 6.91 (d, 1H), 7.36 (t, 1H), 7.44 (t, 1H), 7.57-7.63 (mixed d, 3H), 7.85 (s, 1H), 7.89 (d, 1H) 8.20 (d, 1H) and 8.56 (d, 1H).

EXAMPLE 107

4-(4-Cyclopentyloxydibenzo[b,d]thiophene-1-yl-carboxamido)pyridine

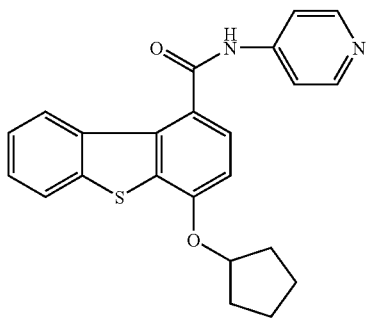

Sodium hydride (0.66 mmols, 36 mg of 50% dispersed in oil) was added to a stirred dry DMF solution of 4-aminopyridine (0.027 g, 0.28 mmols) at −10° C. After 30 minutes dry THF (5 ml) solution of the acid chloride of intermediate 90 (0.08 g, 0.25 mmols) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to yield a white solid.

Yield: 0.025 g (25%), light yellow solid, m.p.: 254-256° C.

IR (KBr, cm−1): 3288, 2958, 1655, 1585, 1565, 1510, 1440, 1415, 1329, 1286, 1260, 1166, 1105, 1060, 984, and 823.

$^1$H-NMR: (CDCl$_3$, 300 MHz, TMS, δ): 1.70-2.03 (m, 8H), 5.00 (m, 1H), 6.89 (d, 1H) 7.34 (t, 1H), 7.44 (t, 1H), 7.55-7.65 (mixed, 3H), 7.85-7.89 (mixed, 3H), 8.20 (d, 8.56 (s, 1H).

EXAMPLE 108

3,5Dichloro-4-(4-cyclopentyloxydibenzo[b,d]-thiophen-5,5-dioxide-1-ylcarbox-amido)pyridine-N-oxide

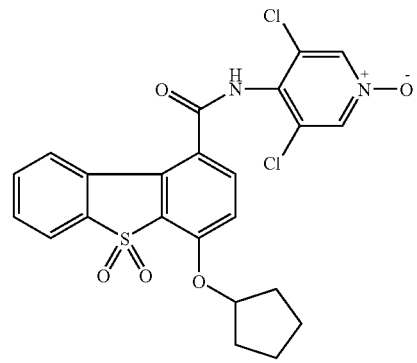

To a dichloromethane (10 ml) solution of 3,5-dichloro-4-(4-cyclopentyloxy-dibenzo-[b,d]-1-ylcarboxamido)pyridine (example 102) (0.055 g, 0,12 mmols) 3-chloro-per-benzoic acid (0.24 mmols, 0.083 g of 50-80% dispersion in water) was added in portions. This reaction mixture was stirred at room temperature for 2 hrs. CH$_2$Cl$_2$ was removed from reaction mixture and it was triturated with 5% NaHCO$_3$ solution to get solid product The product was filtered and washed thoroughly with water and dried.

Yield: 0.30 g (32%), m.p.: 288° C. (dec.)

IR (KBr, cm−1): 3431, 3099, 2967, 2940, 2872, 1674, 1602, 1565, 1532, 1492, 1466, 1449, 1310, 1292, 1266, 1231, 1160, 1137, 1096, 1090, 988, 976, 833, and 766

$^1$H-NMR: (DMSO-d$_6$, 300 MHz, TMS, δ): 1.63-1.96 (m, 8ll), 5.19 (m, 1H), 7.44 (d, 1H), 7.65-7.77 (m, 2H), 7.85 (d, 1H), 7.93 (d, 1H), 8.06 (d, 1H), 8.76 (s, 2H) and 11.05 (s, H).

EXAMPLE 109

3,5-Dichloro-4-(4-methoxydibenzo[b,d]-thiophen-5,5-dioxide-1-yl-carboxamido)pyridine-N-oxide

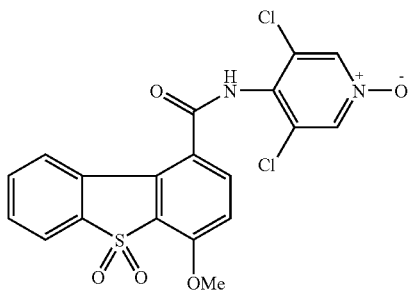

To a dichloromethane (10 ml) solution of 3,5-Dichloro-4-(4-methoxydibenzo[b,d]-thiophen-1-ylcarboxamido)pyridine (example 102) (0.05 g, 0.12 mmols) 3-chloro-perbenzoic acid (0.24 mmols, 0.083 g of 50-80% dispersion in water) was added in portions. This reaction mixture was stirred at room temperature for 2 hrs. CH$_2$Cl$_2$ was removed from reaction mixture and it was triturated with 5% NaHCO$_3$ solution to get solid product. The product was filtered and washed thoroughly with water and dried.

Yield: 0.02 g (28.2%), m.p.: 243° C. (dec.)

IR (KBr, cm−1): 3399, 3246, 3106, 2925, 1684, 1600, 1564, 1493, 1465, 1299, 1268, 1233, 1160, 1136, 1089, 990, 834, 764, 732, 639.

$^1$H-NMR: (DMSO-d$_6$, 300 MHz, TMS, δ): 4.05 (s, 3H), 7.44 (d, 1H), 7.68 (t, 1H), 7.75 (t, 1H), 7.88 (d, 1H), 7.98 (d, 1H), 8.08 (d, 1H), 8.77 (s, 2H) and 11.08 (s, 1H).

EXAMPLE 110

3,5 Dichloro-4-(4-methoxydibenzo[b,d]-thiophen-5,5dioxide-1-yl-carboxamido)pyridine

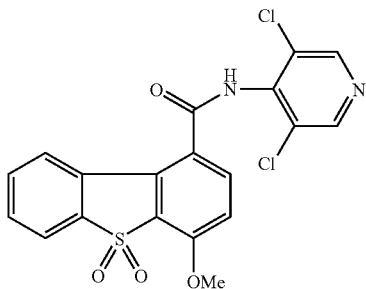

Step 1:
4-Methoxydibenzo[b,d]thiophene-1-carboxylic acid-5,5-dioxide

To a solution of intermediate 86 (0.1 g, 0.38 mmols) in dichloromethane (5 ml) was added 3-chloroperbenzoic acid (0.8 mmols, 0.3 g 50-80% in water) and stirred for 3 hrs at room temperature. Dichloromethane was removed and the crude product thus obtained was purified by silica gel column chromatography to get white solid product.

Yield: 0.06 g (54%)

$^1$H-NMR: (CDCl$_3$+1 drop DMSO-d$_6$, 300 MHz, TMS, δ): 3.98 (s, 3H), 6.92 (d, 1H) 7.41-7.52 (m, 2H), 7.69 (d, 1H), 7.93 (d, 1H) and 8.42 (d, 1H)

Step 2: 3,5-Dichloro-4-(4-methoxydibenzo[b,d]thiophen-5,5-dioxide-1-yl-carboxamido)pyridine To a solution of the 4-methoxydibenzo[b,d]thiophene-1-carboxylic acid-5,5-dioxide (0.06 g, 0.2 mmols) in dry DMF (2 ml) under N$_2$ atmosphere N,N'-carbonyldiimidazole (0.039 g, 0.24 mmols) was added and this reaction mixture was stirred for 2 hrs at room temperature. This reaction mixture was then added to a stirring solution of 4-amino-3,5-dichloropyridine (0.048 g, 0.29 mmols) in dry DMF (2 ml) and NaH (0.29 mmols, 0.021 g of 50% dispersion in oil) at 0° C. After the addition this reaction mixture was stirred overnight at room temperature. The reaction mixture was quenched with water and extracted with ethyl acetate. Ethyl acetate layer was washed with water, dried over sodium sulphate and contrated to get the crude product which was purified by silica gel column chromatography to to white solid product.

Yield: 0.0.27 g (30%), m.p.: 250° C. (dec.)

IR (KBr, cm−1): 3433, 3267, 2927, 1673, 1600, 1553, 1495, 1464, 1400, 1305, 1281, 1161, 1138, 1032, 1011, 889, 822, 766, 749, 732

$^1$H-NMR: (DMSO-d$_6$, 300 MHz, TMS, δ): 4.06 (s, 3H), 7.45 (d, 1H), 7.76-7.75 (m, 2H), 7.88 (d, 1H), 7.98 (d, 1H), 8.09 (d, 1H), 8.80 (s, 2H) and 11.28 (s, 1H)

EXAMPLE 111

3,5 Dichloro-4-(4-difluoromethoxydibenzo[b,d]-thiophen-1-ylcarboxamido)pyridine

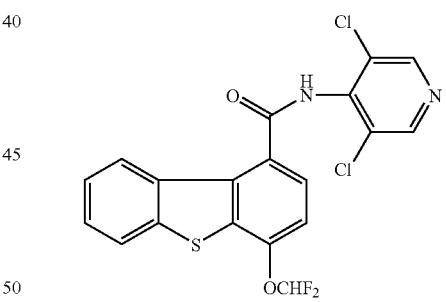

To a solution of intermediate 104 (0.1 g, 0.36 mmols) in dry DMF (5 ml) was added 1,1'-carbonyldiimidazole (0.135 g, 0.882 mmols) under N$_2$ atmosphere and reaction mixture was stirred for 2 hrs at room temperature. In another flask sodium hydride (1.10 mmols, 0.052 g of 50% dispersion in oil) was added to 3,5-dichloro-4-aminopyridine (0.178 g, 1.10 mmols) in dry DMF at room temperature and stirred for 30 minutes under nitrogen. To this reaction mixture the above imidazole intermediate reaction mixture was added dropwise. After addition the reaction mixture was stirred overnight. The reaction mixture was diluted with ethyl acetate and ethyl acetate layer washed with water, brine and concentrated under vacuo to give the crude product which was purified by column chromatography.

Yield: 0.1 g (85%) white solid, M.P.: 249-251° C.

IR (KBr, cm−1): 3433, 3183, 2927, 1661, 1556, 1499, 1483, 1402, 1386, 1286, 1254, 1124, 1091, 1066, 1049, 822, 757 and 715.

$^1$H-NMR: (CDCl$_3$, 300 MHz, TMS, δ): 6.74 (t, J=72.6 Hz, 1H), 7.27 (d, 1H), 7.41 (t, 1H), 7.50 (t, 1H), 7.72 (fused s, 1H), 7.73 (fused d, 1H), 7.78 (fused d, 1H), 8.46 (d, 1H) and 8.60 (s, 2H).

EXAMPLE 112

N1-(4-methoxyphenyl)-4-methoxydibenzo[b,d]thiophene-1-sulfonamide

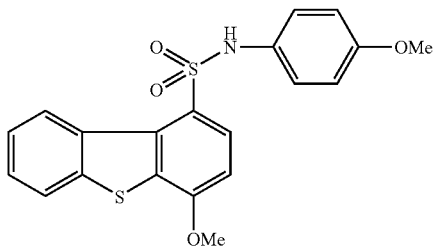

Step 1:
4-Methoxy-dibenzo[b,d]thiophene-1-sulfonic acid

To a chloroform (25 ml) solution of intermediate 84 (0.5 g, 2.33 mmols) was added dropwise chlorosulfonic acid (0.54 g, 4.76 mmols) at −10° C. and the reaction mixture was stirred for 1 hr. The reaction mixture was poured slowly to crushed ice which gave a precipitate which dissolved when ice melted. The water was evaporated to complete dryness which gave desired product.

Yield: 0.36 g $^1$H-NMR (CD$_3$OD, 300 MHz, TMS, δ): 4.05 (S, 3H), 7.01 (d, 1H), 7.40 (m, 2H), 7.84-7.87 (m, 1H), 8.17 (d, 1H), 9.41-9.44 (m, 1H).

Step 2: N1-(4-methoxyphenyl)-4-methoxydibenzo[b,d]thiophene-1-sulfonamide

To 4-methoxy-dibenzo[b,d]thiophene-1-sulfonic acid (0.1 g, 0.3 mmols) form step 1, was added thionyl chloride (5 ml) and refluxed for 2 hrs. Thionyl chloride was then evaporated and the residue was dissolved in dry acetone (20 ml). To the acetone solution 4-aminopyridine (0.044 g, 0.36 mmols) followed by pyridine (2 ml) and DMAP (0.005 g) was added. The reaction mixture was allowed to stirred at room temperature for over night. The reaction mixture was then added to water and extracted with ethyl acetate. Ethyl acetate layer on concentration gave crude product which was purified over silica gel column chromatography to get pure product.

Yield: 0.035 g, of a brownish color solid, m.p.: 158-161° C.

$^1$H-NMR (CDCl$_3$, 300 MHz, TMS, δ): 3.65 (s, 3H), 4.05 (s, 3H), 6.57 (d, 2H), 6.65 (s, 1H), 6.68 (t, 2H), 6.81 (d, 1H), 7.57 (m, 2H), 7.96 (m, 1H), 8.02 (d, 1H), 9.02 (m, 1H).

EXAMPLE 113

2-(4-Methoxydibenzo[b,d]thiophen-1-ylcarboxamido)-pyridine

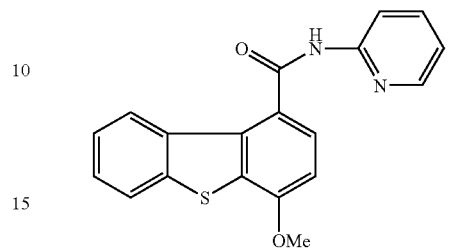

Sodium hydride (0.66 mmols, 36 mg of 50% dispersed in oil) was added to a stirred dry DMF solution of 2-aminopyridine (0.080 g, 0.92 mmols) at −10° C. After 30 minutes dry THF (5 ml) solution of the acid chloride of intermediate 86 (0.2 g, 0.77 mmols) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to yield a white solid.

Yield: 0.03 g (19.5%), Yellow solid, m.p.: 182-184° C.

IR (KBr, cm−1): 3401, 3019, 2926, 2400, 1679, 1576, 1513, 1491, 1432, 1296, 1259, 1215, 1110, 1066, 1018, 929, 759, 669.

$^1$H-NMR: (CDCl$_3$, 300 MHz, TMS, δ): 4.07 (s, 3H), 6.89 (d, 1H), 7.04-7.08 (m, 1H), 7.35 (t, 1H), 7.44 (t, 1H), 7.61 (d, 1H), 7.79 (t, 1H), 7.87 (d, 1H), 8.13-8.15 (m, 1H), 8.33 (d, 1H), 8.52 (d, 1H) and 8.74 (S, 1H).

EXAMPLE 114

4-(4-Ethoxydibenzo[b,d]thiophen-1-yl-carboxamido)-pyridine

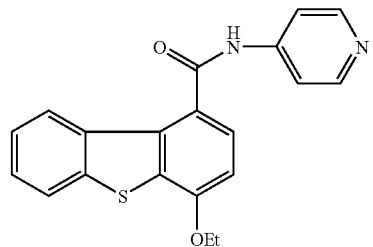

To a solution of intermediate 93 (0.19 g, 0.698 mmols) in dry DMF (5 ml) was added 1,1'-carbonyldiimidazole (0.135 g, 0.882 mmols) under N$_2$ atmosphere and reaction mixture was stirred for 2 hrs at room temperature. In another flask sodium hydride (1.10 mmols, 0.052 g of 50% dispersion in oil) was added to 4-amino pyridine (0.1 g, 1.05 mmols) in dry DMF at room temperature and stirred for 30 minutes under nitrogen. To this reaction mixture the above imidazole intermediate reaction mixture was added dropwise. After addition the reaction mixture was stirred overnight. The reaction mixture was diluted with ethyl acetate and ethyl acetate layer washed with water, brine and concentrated under vacuo to give the crude product which was purified by column chromatography.

Yield: 0.075 g, Pale white solid, m.p.: 255° C. (dec.)

IR (KBr, cm−1): 3400, 3040, 2400, 1521, 1474, 1423, 1384, 1215, 1019, 929, 759 and 669

¹H-NMR (CDCl₃, 300 MHz, TMS, δ): 1.47 (t, 3H), 4.36 (q, 2H), 6.90 (d, 1H), 7.36 (t, 1H), 7.45 (t, 1H), 7.58 (d, 1H), 7.62 (d, 2H), 7.79 (s, 1H), 7.89 (d, 1H), 8.21 (d, 1H) and 8.57 (d, 2H).

EXAMPLE 115

N1-(4-methoxyphenyl)-8,N8-dimethyl-4-methoxy-dibenzo[b,d]thiophen-8,1-disulfonamide

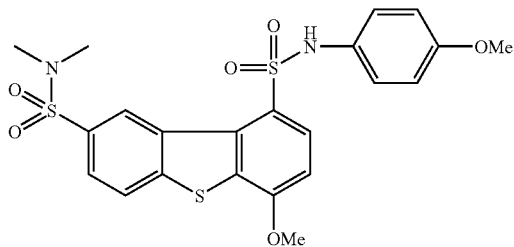

Step 1: 4-Methoxy-dibenzo[b,d]thiophene-1,8-disulfonylchloride

To a chloroform (5 ml) solution of intermediate 84 (0.5 g, 2.34 mmols) was added dropwise chlorosulfonic acid (1.36 g, 01.16 mmols) at 0° C. The reaction mixture was stirred 1 hr at room temperature. Chloroform was evaporated and crushed ice was added to the residue which was extracted with ethyl acetate. The ethyl acetate layer was washed with water, brine, dried over Na₂SO₄ which on concentration gave the desired product Yield: 0.343 g ¹H-NMR (DMSO-d6, 300 MHz, TMS, δ): 4.00 (S, 3H), 7.02 (d, 1H), 7.72 (d, 1H), 7.86 (d, 1H), 7.99 (d, 1H), 9.79 (s, 1H), Step 2: Preparation of 6-methoxy-9-(4-methoxyphenylsulfamoyl)dibenzo[b,d]thiophene-2-sulfonylchloride To a solution of 4-methoxy-dibenzo[b,d]thiophene-1,8-disulfonylchloride (0.2 g, 0.49 mmols) from step 1 in dry acetone (10 ml) was added p-anisidine (0.6 g, 0.49 mmols) and pyridine (0.06 g, 0.73 mmols). The reaction mixture was stirred at room temperature for 18 hrs. Acetone was evaporated and reaction mixture was diluted with water and extracted in ethyl acetate. Ethyl acetate layer on concentration gave crude product which was purified by silica gel column chromatography to get the pure product.

Yield: 0.17 g

¹H-NMR (CDCl₃, 300 MHz, TMS, 5): 3.69 (s, 3H), 4.15 (s, 3H), 6.46 (s, 1H), 6.68 (d, 2H), 6.99 (d, 2H), 7.04 (s, 1H), 7.86 (d, H), 7.96 (d, 1H), 8.33 (d, 1H) and 9.56 (s, 1H)

Step 3: N1-(4-methoxyphenyl)-N8,N8-dimethyl-4-methoxydibenzo[b,d]thiophene-8,1-disulfonamide A solution of compound 6-methoxy-9-(4-methoxyphenylsulfamoyl)dibenzo[b,d]thiophene-2-sulfonylchloride (0.37 g, 0.074 mmols) from step 2 in dry acetone (10 ml) was added dimethylammonium hydrochloride (0.028 g, 0.34 mmols) and pyridine (1 ml). The reaction mixture was stirred at room temperature over the weeked (36 hrs). Acetone was evaporated and reaction mixture was diluted with water and extracted with ethyl acetate. Ethyl acetate layer on concentration gave crude product which was purified by silica gel column chromatography to get pure product Yield: 0.018 g, yellow sticky solid IR (KBr, cm−1): 3368, 2925, 1606, 1509, 1384, 1153, 1020 and 771

H-NMR (CDCl₃, 300 MHz, TMS, δ): 2.80 (s, 6H), 3.71 (s, 3H), 4.12 (s, 3H), 6.54 (s, 1H), 6.71 (d, 2H), 6.98-7.03 (mixed, 3H), 7.65 (dd, 1H), 7.86 (d, 1H), 8.30 (d, 1H) and 9.50 (s, 1H)

EXAMPLE 116

3-(4-Methoxydibenzo[b,d]thiophen-1-ylcarboxamido)-pyridine

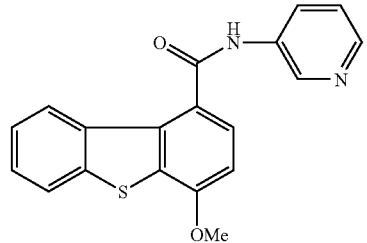

Sodium hydride (0.66 mmols, 36 mg of 50% dispersed in oil) was added to a stirred dry DMF solution of 3-aminopyridine (0.080 g, 0.92 mmols) at −10° C. After 30 minutes dry THF (5 ml) solution of acid chloride of intermediate 86 (0.2 g, 0.77 mmols) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to get white solid.

Yield: 0.1 (65%), White solid, m.p.: 243-245° C.

IR (KBr, cm−1): 3271, 3053, 3004, 2938, 1650, 1584, 1567, 1554, 1523, 1490, 1439, 1419, 1330, 1285, 1269, 1110,1065, 1014, 879, 799, 785, 766, 705.

¹H-NMR: (CDCl₃, 300 MHz, TMS, δ): 4.06 (s, 3H), 6.91 (d, 1), 7.24-7.38 (m, 2H), 7.45 (t, 1H), 7.60 (t, 1H), 7.80 (s, 1H), 7.88 (d, 1H), 8.25 (d, 1H), 8.41 (d, 2H), and 8.61 (s, 1H)

EXAMPLE 117

3,5-Dichloro-4-(6-methyl-4-methoxydibenzo[b,d]-thiophen-1-ylcarboxamido)pyridine

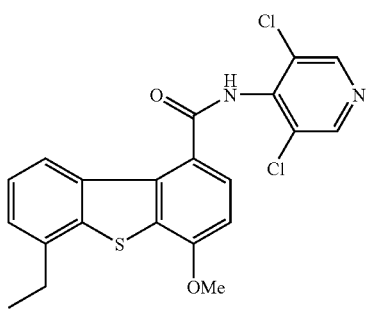

Sodium hydride (0.66 mmols, 36 mg of 50% dispersed in oil) was added to a stirred dry DMF solution of 3,5-dichoro-4-chloro-4-aminopyridine (0.68 g, 4.2 mmols) at −10° C. After 30 minutes dry THF (5 ml) solution of the acid chloride of intermediate 101 (0.28 g, 0.97 mmols) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to get white solid.

Yield: 0.035 g, white solid, m.p.: 259-260° C. (dec.)
$^1$H-NMR (DMSO-d6, 300 MHz, TMS, δ): 1.34 (t, 3H), 2.91 (q, 2H), 4.15 (s, 3H), 7.25 (d, 1H), 7.39-7.43 (m, 2H), 7.76 (d, 1H), 8.27 (t, 1H) and 8.80 (s, 2H).

EXAMPLE 118

3,5,dichloro-4-(4-ethoxy-dibenzo[b,d]thiophen-1-yl-carboxamido)pyridine

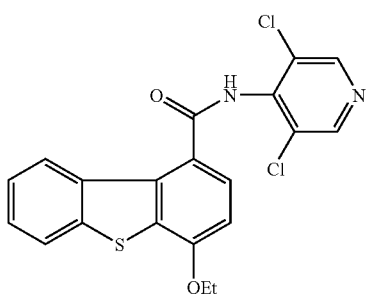

To a solution of intermediate 93 (0.2 g, 0.735 mmols) in dry DMF (5 ml) was added 1,1'-carbonyldiimidazole (0.135 g, 0.882 mmols) under $N_2$ atmosphere and reaction mixture was stirred for 2 hrs at room temperature. In another flask sodium hydride (1.10 mmols, 0.052 g of 50% dispersion in oil) was added to 3,5-dichloro-4-aminopyridine (0.178 g, 1.10 mmols) in dry DMF at room temperature and stirred for 30 minutes under nitrogen. To this reaction mixture the above imidazole intermediate reaction mixture was added dropwise. After addition the reaction mixture was stirred overnight. The reaction mixture was diluted with ethyl acetate and ethyl acetate layer washed with water, brine and concentrated under vacuo to give the crude product which was purified by column chromatography.

Yield: 0.04 g, white solid, m.p.: 268-270° C. (dec.)
IR (KBr, cm−1): 3206, 2925, 1666, 1566, 1553, 1484, 1497, 1393, 1285, 1262, 1160, 1114, 1064, 770, 715, 753, 642.
$^1$H-NMR (DMSO, 300 MHz, TMS, δ): 1.53 (t, 31), 4.36 (q, 2H), 7.24 (d, 1H), 7.43 (t, 1H), 7.52 (t, 1H), 7.75 (d, 1H), 8.07 (d, 1H), 8.41 (d, 1H), 8.80 (s, 2H) and 11.01 (s, 1H)

EXAMPLE 119

3-(4-Methoxydibenzo[b,d]-thiophene-5,5-dioxide-1-ylcarboxamido)-pyridine

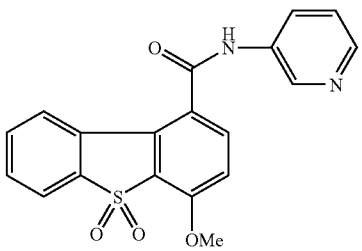

To a solution of 3-(4-Methoxydibenzo[b,d]thiophene-1-yl-carboxamido)-pyridine (example 116) (0.08 g, 0.238 mmols) in dichloromethane (20 ml) was added 3-chloroperbenzoic acid (0.476 mmols, 0.164 g 50-80% in water) and stirred for 3-4 hrs at room temperature. Dichloromethane was removed and residue was stirred with saturated $NaHCO_3$ solution (10 ml) for 1 hr and extracted with ethyl acetate which on concentration gave pure product 21 as white solid.

Yield: 0.02 g (22%) White solid, m.p.: 241-243° C.
$^1$H-NMR: ($CDCl_3$+DMSO, 300 MHz, TMS, δ): 3.92 (s, 3H), 6.93 (d, 1H), 7.09 (t, 1H), 7.38-7.41 (m, 2H), 7.54 (d, 1H), 7.58-7.67 (m, 3H), 7.83 (d, 1H), 8.79 (S, 1H) AND 10.78 (s, 1H).

EXAMPLE 120

3,5-Dichloro-4-(4-benzyloxydibenzo[b,d]-thiophen-1-ylcarboxamido)pyridine

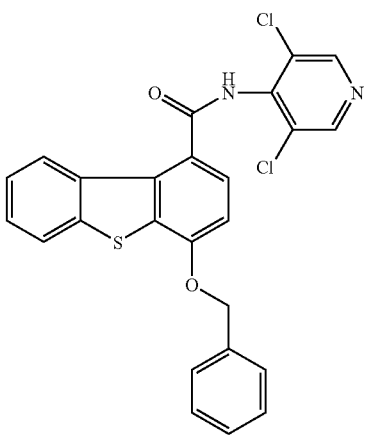

Sodium hydride (0.66 mmols, 36 mg of 50% dispersed in oil) was added to a stirred dry DMF solution of 3,5-dichloro-4-aminopyridine (0.13 g, 0.81 mmols) at −10° C. After 30 minutes dry THF (5 ml) solution of the acid chloride of intermediate 96 (0.46 mmols) was added to the reaction mixture at 0° C. The reaction mixture was stirred 3 hrs at room temperature and poured in ice-water mixture to get precipitate. The precipitated product was filtered a washed with water and dried which was further purified by silica gel column chromatography to get white solid.

Yield: 0.037 g, off white solid, m.p.: 276° C. (dec.)

IR (KBr, cm−1): 3184, 2922, 2854, 1655, 1556,1498, 1481, 1400, 1364, 1289, 1260, 1104, 1061, 1003, 807, 755, 731 1nd 703

$^1$H-NMR (DMSO, 300 MHz, TMS, δ): 5.48 (s, 2H), 7.32-7.54 (mixed, 8H), 7.74 (d, 1H), 8.08 (d, 1H), 8.42 (s, 1H), 8.80 (s, 2H) and 11.03 (s, 1H).

EXAMPLE 121

N-(3,5-dichloropyrid-4-yl)-4-difluoromethoxy-8-(pyrrolidine-2-one-1-yl)-dibenzo[b,d]furan-1-carboxamide

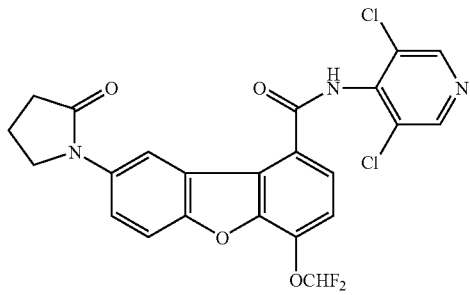

Step 1: N-(3,5-dichloropyrid-4-yl)-4-difluoromethoxy-8-(3-chloropropyl carboxamido)dibenzo[b,d]furan-1-carboxamide N-(3,5-dichloropyrid-4-yl)-4-difluoromethoxy-8-amino-dibenzo-[b,d]furan-1-carboxamide (example 59) was dissolved in THF and pyridine (2.0 eq.) and was reacted with 4-chlorobutyryl chloride (1.2 eq.) at room temperature for 2 h. After the usual workup and purification the product was obtained as a white solid mp >250° C.

IR (KBr); 3281, 3156, 3035, 2987, 1664, 1650, 1526, 1496, 1381, 1284, 1192, 1110, 1080, 914, 814, 677 cm$^{-1}$.

$^1$H NMR (300 MHz, DMF-d$_7$) δ 2.12 (m, 2H), 2.61 (t, 2H), 3.75 (m, 2H), 7.63 (t, J=73.2 Hz, 1H), 7.64 (d, 1H), 7.78 (d, 1H), 8.07 (d, 1H), 8.18 (d, 1H), 8.65 (s, 1H), 8.81 (s, 2H), 10.35 (s, 1H).

Step 2: N-(3,5-dichloropyrid-4-yl)-4-difluoromethoxy-8-(3-chloropropyl carboxamido)dibenzo[b,d]furan-1-carboxamide A solution of N-(3,5-dichloropyrid-4-yl)-4difluoromethoxy-8-(3-chloropropyl carbox-amido)dibenzo[b,d]furan-1-carboxamide (from step 1 as above) in DMF was a suspension of sodium hydride (3 eq.) in DMF and stirred for 1 h at room temperature. Workup and purification by silica gel column chromatography gave the product as a white solid mp: >250° C.

IR (KBr);3212, 2968, 1694, 1673, 1552, 1498, 1474, 1389, 1282, 1204, 1130, 1020, 901, 886, 808, 721, 673 cm$^{-1}$.

$^1$H NMR (300 MHz, DMF-d$_7$) δ 2.16 (m, 2H), 2.54 (t, 2H), 3.93 (t, 2H), 7.64 (t, J=73.2 Hz, 1H), 7.65 (d, 1H, J=7.8 Hz), 7.87 (d, 1H, J=9.3 Hz), 8.09 8.1 Hz), 8.20 (dd, 1H, J=8.7 & 2.4 Hz), 8.58 (d, 1H, J=1.8 Hz), 8.81 (s, 2H), 11.08 (brs, 1H).

The present invention provides a novel series of tricyclic compounds having potential therapeutic activity and medical use against several allergic disorders, particularly in asthma.

In vitro Studies

Inhibition of Phosphodiesterase Enzymes (PDE4)

In this assay, PDE4 enzyme converts [$^3$H] cAMP to the corresponding [$^3$H] 5'-AMP in proportion to the amount of PDE4 present The [$^3$H] 5'-AMP then was quantitatively converted to free [$^3$H] adenosine and phosphate by the action of snake venom 5'-nucleotidase. Hence, the amount of [$^3$H] adenosine liberated is proportional to PDE4 activity.

The assay was performed with modification of the method of Thompson and Appleman (Biochemistry; 1971; 10; 311-316) and Schwartz and Passoneau (Proc. Natl. Acad. Sci. U.S.A. 1974; 71; 3844-3848), both references incorporated herein by reference in their entirety, at 34° C. In a 200 ul total reaction mixture, the reaction mixture contained 12.5 mM of Tris, 5 mM MgCl$_2$, 1 µM cAMP (cold) and $^3$H cAMP (0.1 uCi), (Amersham). Stock solutions of the compounds to be investigated were prepared in DMSO in concentrations such that the DMSO content in the test samples did not exceed 0.05% by volume to avoid affecting the PDE4 activity. Drug samples were then added in the reaction mixture (25 µl/tube). The assay was initiated by addition of enzyme mix (75 µl) and the mixture was incubated for 20 minutes at 34° C. The reaction was stopped by boiling the tubes for 2 mins at 100° C. in a water bath. After cooling on ice for 5 minutes and addition of 50 ug/reaction of 5'-nucleotidase snake venom from *Crotalus atrox* incubation was carried out again for 20 min. at 34° C. The unreacted substrate was separated from ($^3$H) Adenosine by addition of Dowex AG 1-X8 (Biorad Lab), (400 ul) which was prequilibrated (1:1:1) in water and ethanol. Reaction mixture was then thoroughly mixed, placed on ice for 15 minutes, vortexed and centrifuged at 14,000 r.p.m. for 2 mins. After centrifugation, a sample of the supernatant was taken and added in 24 well optiplates containing Scintillant (1 ml) and mixed well. The samples in the plates were then determined for radioactivity in a Top Counter and the PDE4 activity was estimated. PDE4 enzyme was present in quantities that yield <30% total hydrolysis of substrate (linear assay conditions).

Additionally, activity of the compounds were tested against other Phosphodiesterase enzymes, namely, PDE 1 (Ca.sup.2+/calmodulin-dependent), PDE 2 (cGP-stimulated), PDE 3 (cGP-inhibited), PDE 5 (cGP-specific) and PDE 6 (cGP-specific, photoreceptor).

Results were expressed as percent inhibition (IC$_{50}$) in nM concentrations. The IC$_{50}$ values were determined from the concentration curves by nonlinear regression analysis.

Cell Based Assay for PDE4 Inhibition:

Method cAMP elevation studies were conducted in whole U937 cells. U937 cells (ATCC) were grown in RPMI medium containing 10% FBS, 1% pen-strep solution, 1% L-glutamine for 48 hrs. On the day of assay, the cells were washed twice with plain RPM1 medium by centrifuging at 800 rpm for 5 mins. Cells were resuspended in plain RPM1 medium followed by cell number and viability assessment using a trypan blue stain. Cells (0.15-0.2 mio cells per well) were seeded in a 96 well microtitre plate and incubated with various drugs/DMSO vehicle at 37° C. for 15 min. cAMP generation was started by addition of 1 µM PGE1 for 15 mins. The incubation was terminated by addition of cell lysis buffer from cAMP estimation kit. Lysate was used for cAMP quantitatin by chemiluminescence method (DiscoveRX kits). cAMP values were normalized over PGE1. $EC_{50}$ values were calculated from dose response curves by non-linear regression analysis using PRISM software.

| Sr. No. | Example No. | $IC_{50}$(nM) | $EC_{50}$(nM) |
|---|---|---|---|
| 1. | 1 | 0.8 | 83.7 |
| 2. | 2 | 0.82 | 23.8 |
| 3. | 3 | 8.68 | — |
| 4. | 4 | 20.18 | >300 |
| 5. | 5 | 335.60 | — |
| 6. | 7 | 26.04 | — |
| 7. | 9 | 1.556 | 17.56 |
| 8. | 10 | 1.68 | 116.9 |
| 9. | 11 | 9.14 | >220.1 |
| 10. | 12 | 1.21 | 140 |
| 11. | 13 | 2.535 | 128.0 |
| 12. | 14 | 6.41 | — |
| 13. | 15 | 67.27 | — |
| 14. | 19 | 2.535 | 20.43 |
| 15. | 20 | 15.83 | — |
| 16. | 21 | 22.6 | — |
| 17. | 22 | 105.1 | — |
| 18. | 23 | 147.3 | — |
| 19. | 25 | 110.6 | — |
| 20. | 27 | 73.55 | — |
| 21. | 29 | 351 | — |
| 22. | 38 | 2.85 | 87.94 |
| 23. | 39 | 31.74 | — |
| 24. | 41 | 0.839 | 200 |
| 25. | 42 | 4.923 | 44.24 |
| 26. | 43 | 61.21 | — |
| 27. | 45 | 4.54 | >300 |
| 28. | 46 | 36.84 | — |
| 29. | 55 | 1.2 | 47.51 |
| 30. | 56 | 2.851 | 49.25 |
| 31. | 57 | 1.735 | 73.74 |
| 32. | 58 | 10.02 | 147.80 |
| 33. | 59 | 4.468 | 49.22 |
| 34. | 60 | 86.42 | — |
| 35. | 68 | 57.02 | — |
| 36. | 79 | 127.8 | — |
| 37. | 82 | 19.61 | — |
| 38. | 83 | 5.258 | — |
| 39. | 84 | 14.6 | — |
| 40. | 85 | 8.153 | — |
| 41. | 86 | 71.99 | — |
| 42. | 87 | 393.0 | — |
| 43. | 88 | 128.6 | — |
| 44. | 93 | 161.1 | — |
| 45. | 94 | 281.1 | — |
| 46. | 95 | 78.93 | — |
| 47. | 97 | 40.28 | — |
| 48. | 98 | 39.64 | — |
| 49. | 99 | 30.15 | — |
| 50. | 115 | 37.38 | — |
| 51. | 121 | 21.50 | — |

In vivo Studies

Inhibition of Serum TNFα Levels in Mice (Graph 1)

Treatment

Male Balb/c mice, weighing approximately 20 g, fasted overnight with free access to water were used for the studies.

Mice were orally dosed with the test compound (10 ml/kg) in appropriate vehicle 30 minutes before LPS injection. Administration of LPS was by Intravenous mode (i.v., 10 ml/kg. Control group of mice received 0.9% saline, while all the treated groups received LPS (0111: B4, 2.5 mg/kg). These treated groups then received Roflumilast (0.1 mg/kg), Example-1: 0.05, 0.1, 1 and 3 mg/kg, p.o., (10 ml/kg), per group.

Blood samples were collected from the orbital sinus of treated and control mice 90 mins after LPS was adminis-tered. The serum was separated by centriflgation at 3000.x.g for 5 min, and the serum removed and stored at −20° C. until analysis. Serum levels of TNF alpha were subsequently measured using a commercially available ELISA kit (Biotrak; Amersham Pharmacia Biotech) following the protocol enclosed in the kit A 50 μl sample of serum was assayed by ELISA for mouse TNF-.alpha The mean (±SEM) TNF-alpha level from each group was determined and the percent reduction in TNF levels was calculated. The percent inhibition of serum TNF-alpha levels caused by the compound was determined relative to serum TNF-alpha levels in control mice receiving LPS alone.

Inhibition of Arachidonic Acid Induced Ear Edema (Graph 2)

In this in vivo model, the compounds' ability to reduce arachidonic acid induced edema was compared to the known phosphodiesterase inhibitor, Roflumilast.

Treatment

Albino male Swiss or Balb/c mice, weighing between 20-25 g were used for the study. Test compounds were administered 30 mins prior to application of arachidonic acid (AA). A 2.5% arachidonic acid solution was made in acetone. 20 .mu.l volume of the AA was applied to the left ear of the mouse and 20 .mu.l of vehicle (acetone) was applied immediately to the right ear. The mice were sacrificed by $CO_2$ inhalation 1 hour after AA. The left and right ears were removed and a 7 mm biopsy was taken from each ear and weighed. The difference in biopsy weights between the right and left ear was calculated. Anti-inflammatory effects of compounds are evident as an inhibition of the increase in ear weight.

Results are expressed as percent inhibition ($ED_{50}$) in mglkg. The $ED_{50}$ values were determined from the concentration curves by nonlinear regression analysis and 95% confidence limits were estimated respectively.

Results

Inhibition of the PDE4 Activity (in vitro)

The $IC_{50}$ value for the compound examined was determined from concentration-response curves in which varying range of concentrations were considered as shown in table 1

TABLE 1

| | IC50 values | | | | | |
|---|---|---|---|---|---|---|
| Compound | PDE1 | PDE2 | PDE3 | PDE4 | PDE5 | PDE6 |
| Example-1 | 44% (100 μM) | 69.1 μM | 61.8 μM | 0.8 nM | 4% (100 μM) | 36% (100 μM) |

We claim:

1. A compound of general formula (1)

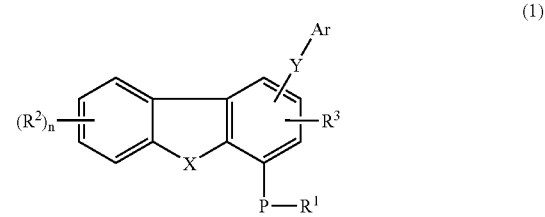

wherein:
R$^1$, R$^2$ and R$^3$ may be the same or different and are independently hydrogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, —C(O)—R$^a$, —C(O)O—R$^a$, —C(O)NR$^a$R$^a$, —S(O)$_m$—R$^a$, —S(O)$_m$—NR$^a$R$^a$, nitro, —OH, cyano, amino, formyl, acetyl, halogen, —OR$^a$, —SR$^a$, or a protecting group and when two R$^2$ substitutents are ortho to each other, they may be joined to form a saturated or unsaturated cyclic ring, which may optionally include up to two heteroatoms selected from O, NR$^a$ or S;

each occurrence of R$^a$ is independently hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, or substituted or unsubstituted heteroarylalkyl;

P is oxygen or sulfur;
n is an integer from 0-4;
Ar is substituted or unsubstituted aryl, substituted or unsubstituted arylalkyl, a substituted or unsubstituted heterocyclic ring, or a substituted or unsubstituted heteroaryl ring;
X is oxygen or S(O)$_m$;
m is 0, 1 or 2;
Y is —C(O)NR$^4$;
R$^4$ is hydrogen, substituted or unsubstituted alkyl, hydroxyl, —OR$^1$, —COOR$^1$, substituted or unsubstituted aryl, substituted or unsubstituted heterocyclic ring, or an analog, tautomer, regioisomer, stereoisomer, enantiomer, diastereomer, pharmaceutically acceptable salt, N-oxide, or pharmaceutically acceptable solvate thereof.

2. A compound according to claim 1 wherein the substituents in the 'substituted alkyl', 'substituted alkoxy', 'substituted alkenyl', 'substituted alkynyl', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring', 'substituted heteroarylalkyl', 'substituted heterocyclylalkyl ring', 'substituted amino', 'substituted alkoxycarbonyl', 'substituted cyclic ring', 'substituted alkylcarbonyl', or 'substituted alkylcarbonyloxy' may be the same or different and are one or more of hydrogen, hydroxy, halogen, carboxyl, cyano, nitro, oxo, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstiuted guanidine, —COOR$^x$, —C(O)R$^x$, —C(S)R$^x$, —C(O)NR$^x$R$^y$, —C(O)ONR$^x$R$^y$, —NR$^x$CON-R$^y$R$^z$, —N(R$^x$)SOR$^y$, —N(R$^x$)SO$_2$R$^y$, =N—N(R$^x$)(R$^y$), —NR$^x$C(O)OR$^y$, —NR$^x$R$^y$, —NR$^x$C(O)R$^y$, —NR$^x$C(S)R$^y$, —NR$^x$C(S)NR$^y$R$^z$, —SONR$^x$R$^y$, —SO$_2$NR$^x$R$^y$, —OR$^x$, —OR$^x$C(O)NR$^y$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$, wherein R$^x$, R$^y$ and R$^z$ are independently hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, a substituted or unsubstituted heterocyclylalkyl ring, substituted or unsubstituted heteroarylalkyl, or a substituted or unsubstituted heterocyclic ring.

3. The compound according to claim 1 wherein R$^1$ is substituted alkyl.

4. The compound according to claim 3 wherein R$^1$ is CHF$_2$.

5. The compound according to claim 1 wherein R$^1$ is unsubstituted alkyl.

6. The compound according to claim 5 wherein R$^1$ is methyl.

7. The compound according to claim 1 wherein P is S.

8. The compound according to claim 1 wherein P is O.

9. The compound according to claim 1 wherein R$^2$ is substituted alkyl, halogen, cyano, nitro, amino, substituted heterocyclic ring or SO$_2$NR$^a$R$^a$ and n=1.

10. The compound according to claim 9 wherein R$^2$ is chloro.

11. The compound according to claim 9 wherein R$^2$ is substituted alkyl.

12. The compound according to claim 11 wherein R$^2$ is CF$_3$.

13. The compound according to claim 9 wherein R$^2$ is —NH$_2$.

14. The compound according to claim 9 wherein R$^2$ is SO$_2$NR$^a$R$^a$.

15. The compound according to claim 14 wherein R$^2$ is SO$_2$N(CH$_3$)$_2$.

16. The compound according to claim 1 wherein Y is —C(O)NH—.

17. The compound according to claim 1 wherein Ar is substituted or unsubstituted 4-pyridyl; substituted or unsubstituted 4-pyridyl-N-oxide; substituted or unsubstituted 3-pyridy, substituted or unsubstituted 3-pyridyl-N-oxide; substituted or unsubstituted 2-pyridyl; or substituted or unsubstituted 2-pyridyl N-oxide.

18. The compound according to claim 17 wherein said Ar is substituted with halogen.

19. The compound according to claim 18 wherein said halogen is chioro.

20. The compound according to claim 17 wherein Ar is

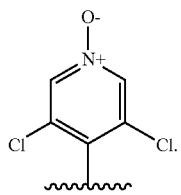

21. The compound according to claim 20 wherein Ar is

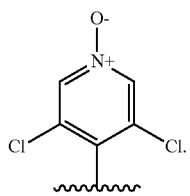

22. A pharmaceutical composition comprising one or more compounds according to claim 1 and one or more pharmaceutically acceptable diluents or carriers.

23. A method of treating an inflammatory condition or immune disorder selected from asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohns disease, psoraisis, uticaria, adult vernal conjunctivitis, respiratory distress syndrome, rhematoid spondylitis, osteoarthritis, gouty arthritis, uveitis, allergic conjunctivitis, inflammatory bowel conditions, ulcerative colitis, eczema, atopic dermatitis and chronic inflammation in a subject in need thereof which comprises administering to said subject a therapeutically effective amount of a compound according to claim 1.

24. The method according to claim 23 wherein said inflammatory condition is bronchial asthma, nephritis, or allergic rhinitis.

25. A method for the preparation of a compound of general formula (1)

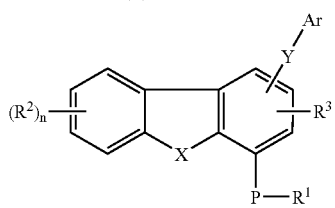

wherein:
R$^1$, R$^2$ and R$^3$ may be the same or different and are independently hydrogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, —C(O)—R$^a$, —C(O)O—R$^a$, —C(O)NR$^a$R$^a$, —S(O)$_m$—R$^a$, —S(O)$_m$—NR$^a$R$^a$, nitro, —OH, cyano, amino, formyl, acetyl, halogen, —OR$^a$, —SR$^a$, or a protecting group and when two R$^2$ substitutents are ortho to each other, they may be joined to form a saturated or unsaturated cyclic ring, which may optionally include up to two heteroatoms selected from O, NR$^a$ or S;

each occurrence of R$^a$ is independently hydrogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, or substituted or unsubstituted heteroarylalkyl;

P is oxygen or sulfur;
n is an integer from 0-4;
Ar is substituted or unsubstituted aryl, substituted or unsubstituted arylalkyl, substituted or unsubstituted heterocyclic ring, or substituted or unsubstituted heteroaryl ring;
X is oxygen; or S(O)$_m$;
m is 0, 1 or 2;
Y is —C(O)NR$^4$;
R$^4$ is hydrogen, substituted or unsubstituted alkyl, hydroxyl, —OR$^1$, —COOR$^1$, substituted or unsubstituted aryl, or a substituted or unsubstituted heterocyclic ring, or an N-oxide thereof; comprising the steps of:
(a) reacting the compound of formula (11):

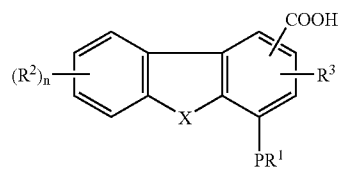

with an amine of the formula ArNHR$^4$ to yield a compound of formula (1)

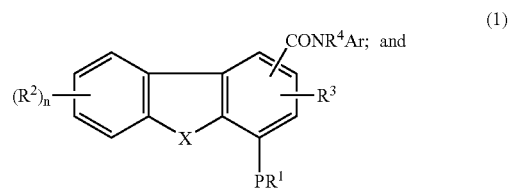

(b) optionally converting the compound of formula (1) into its corresponding N-oxide.

26. The method of claim 25 wherein the compound of formula (11) is formed by
(a) converting the compound of general formula (10)

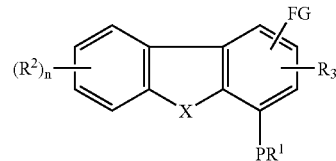

to general formula (11) wherein FG represents substituted or unsubstituted alkyl, formyl, cyano, halogen, nitro, or amino.

27. The method of claim 26 wherein the compound of formula (10) is prepared by:

(i) reacting a compound of formula (13.a) with a compound of formula (23) under basic conditions

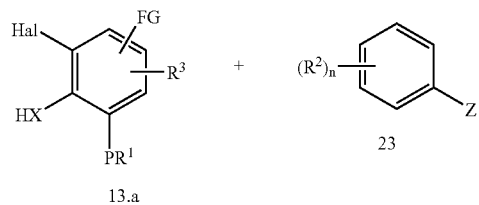

wherein Z is a halogen; FG is a substituted or unsubstituted alkyl, formyl, cyano, halogen, nitro, or amino; and Hal is halogen, to yield a compound of formula (24)

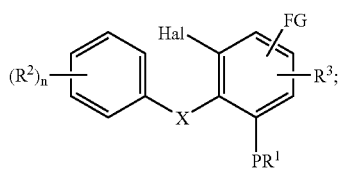

(ii) cyclizing the compound of general formula (24) under palladium catalyzed coupling conditions to form a tricyclic compound of general formula (10).

28. The method of claim 26 wherein the compound of formula (10) is prepared by:

(i) reacting a compound of general formula (25) with an electrophile

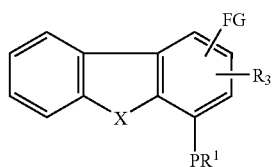

wherein FG is alkyl, formyl, cyano, halogen, nitro, or amino; to yield a compound of formula (10).

29. The method of claim 26 wherein the compound of formula (10) is formed by:

(i) reacting a compound of general formula (13) with a compound of formula (20) under basic conditions

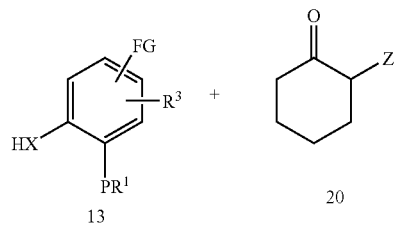

to yield a compound of general formula (21)

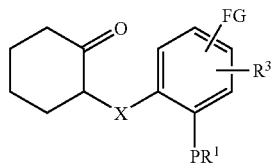

wherein FG is alkyl, formyl, cyano, halogen, nitro, or amino; and Z is a halogen; and (ii) cyclizing the compound of general formula (21) under acidic conditions followed by oxidation to yield a tricyclic compound of general formula (10).

30. The method of claim 26 wherein the compound of formula (10) is formed by:

(i) reacting a compound of formula (16) with a compound of formula (17)

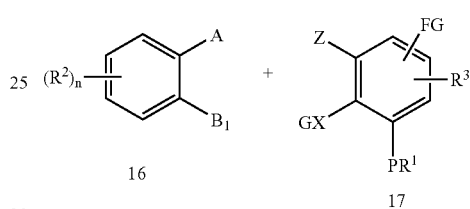

where A is halogen, —OMs, —OTs or —B(OH)$_2$; Ms is a methanesulfonyl group; Ts is a p-toluenesulfonyl group; $B_1$ is halogen; G is a protecting group selected from benzyloxycarbonyl, t-butyloxycarbonyl, isopropyl, cyclopentyl, allyl, acetyl and benzyl; FG is alkyl, formyl, cyano, halogen, nitro, or amino; and Z is halogen;

to yield a compound of formula (18)

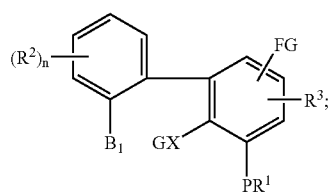

(ii) deprotecting the compound of formula (18) to yield a compound of formula (19)

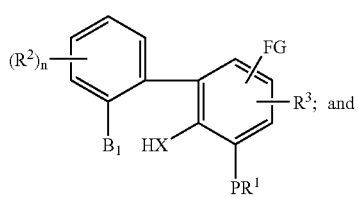

(iii) cyclizing the intermediate of formula (19) under basic conditions to yield a tricyclic compound of formula (10).

31. The method of claim 26 wherein the compound of formula (10) is prepared by:

(i) reacting a compound of general formula (12) where Z is a halogen

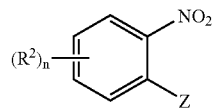

12 with an aromatic group of formula (13)

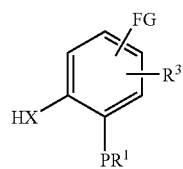

13 wherein FG is alkyl, formyl, cyano, halogen, nitro, or amino, under basic conditions to yield a compound of formula (14)

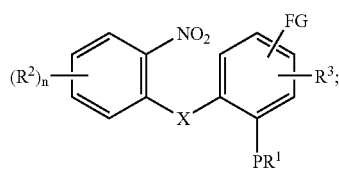

14

(ii) reducing the compound of formula (14) to obtain a compound of formula (15)

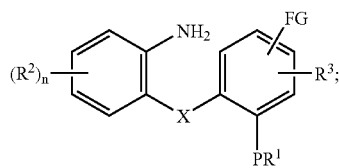

15

(iii) cyclizing the compound of formula (15) to yield a tricyclic compound of formula (10).

32. The method of claim 26, wherein (i) FG is methyl and step (a) comprises oxidizing the compound of formula (10) with a manganese or chromium reagent to form a compound of formula (11), (ii) FG is cyano and step (a) comprises hydrolyzing the compound of formula (10) to form a compound of formula (11), or (iii) FG is bromine and step (a) comprises reacting the compound of formula (10) with lithium followed by treatment with carbon dioxide to form a compound of formula (11).

33. The method of claim 25 wherein the compound of formula (11) is prepared by:

(a) formylation of a compound of formula (26)

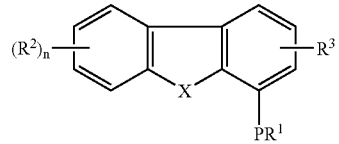

26 followed by oxidation of the aldehyde group in the resulting compound of formula (27)

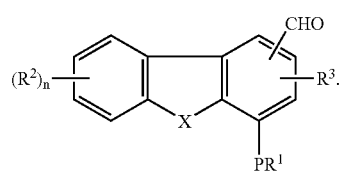

27

34. A compound selected from
N-(3,5-dichloropyrid-4-yl)-4-methoxy dibenzo[b,d]furan-1-carboxamide,
N-(3,5-dichloropyrid-4-yl)-4-methoxy dibenzo[b,d]furan-1-carboxamide-N1-oxide,
N-(3,5-dichloropyrid-4-yl)-4-methoxy-8-nitro dibenzo[b,d]furan-1-carboxamide,
N-(3,5-dichloropyrid-4-yl)-4-methoxy-8-amino-dibenzo[b,d]furan-1-carboxamide, or a pharmaceutically acceptable salt thereof

35. A compound selected from
N-(3,5-dichloropyrid-4-yl)-4-difluoromethoxy dibenzo[b,d]furan-1-carboxamide,
N-(3,5-dichloropyrid-4-yl)-4-difluoromethoxy-dibenzo[b,d]furan-1-carboxamide-N-oxide, or a pharmaceutically acceptable salt thereof.

36. A compound selected from
N-(3,5-dichloropyrid-4-yl)-4-difluoromethoxy-8-nitro-dibenzo[b,d]furan-1-carboxamide,
N-(3,5-dichloropyrid-4-yl)-4-difluoromethoxy-8-amino-dibenzo[b,d]furan-1-carboxamide, or a pharmaceutically acceptable salt thereof.

37. A compound selected from
N-(3,5-dichloropyrid-4-yl)-4-isopropyloxy dibenzo[b,d]furan-1-carboxamide,
N-(3,5-dichloropyrid-4-yl)-4-cyclopropylmethoxy dibenzor[b,d]furan-1-carboxamide
N-(3,5-dichloropyrid-4-yl)-4-benzyloxy dibenzo[b,d]furan-1-carboxamide, or a pharmaceutically acceptable salt thereof.

38. A compound of claim 1 selected from
N-(pyrid-4-yl)-4-methoxy-dibenzo[b,d]furan-1-carboxamide,
N-(pyrid-4-yl)-4-methoxy-dibenzo[b,d]furan-1-carboxamide-N1-oxide,
N-(2-chloropyrid-3-yl)-4-methoxy-dibenzo[b,d]furan-1-carboxamide,
N-(4-fluorophenyl)-4-methoxy-dibenzo[b,d]furan-1-carboxamide,
N-(pyrid-3-yl)-4-methoxy-dibenzo[b,d]furan-1-carboxamide,
N-(pyrid-3-yl)-4-methoxy-dibenzo[b,d]furan-1-carboxamide-N1-oxide, N-(3,5-dichloropyrid-4-yl)-4-methoxy-8-trifluoromethyl dibenzo[b,d]furan-1-carboxamide,
N-(3,5-dichloropyrid-4-yl)-4-methoxy-8-trifluoromethyl dibenzo[b,d]furan-1-carboxamide-N1-oxide,
N-(pyrid-4-yl)-4-methoxy-8-trifluoromethyl dibenzo[b,d] furan-1-carboxamide,
N-(3,5-dichloropyrid-4-yl)-4-difluoromethoxy-8-trifluoromethyl dibenzo[b,d]furan-1-carboxamide,
N-(3,5-dichloropyrid-4-yl)-4-difluoromethoxy-8-trifluoromethyl dibenzo[b,d]furan-1-carboxamide-N1-oxide,
N-(pyrid-4-yl)-4-difluoromethoxy-8-trifluoromethyl dibenzo[b,d]furan-1-carboxamide,
N-(pyrid-4-yl)-4-difluoromethoxy-8-trifluoromethyl dibenzo[b,d]furan-1-carboxamide-N1-oxide,
N-(pyrid-3-yl)-4-difluoromethoxy-8-trifluoromethyl dibenzo[b,d]furan-1-carboxamide,
N-(pyrid-3-yl)-4-difluoromethoxy-8-trifluoromethyl dibenzo[b,d]furan-1-carboxamide-N1-oxide,
N-(pyrid-2-yl)-4-difluoromethoxy-8-trifluoromethyl dibenzo[b,d]furan-1-carboxamide,
N-(pyrid-4-yl)-4-difluoromethoxy-dibenzo[b,d]furan-1-carboxamide,
N-(pyrid-4-yl)-4-difluoromethoxy-dibenzo[b,d]furan-1-carboxamide-N1-oxide,
N-(pyrid-3-yl)-4-difluoromethoxy-dibenzo[b,d]furan-1-carboxamide,
N-(pyrid-3-yl)-4-difluoromethoxy-dibenzo[b,d]furan-1-carboxamide-N1-oxide,
N-(5-chloropyrid-2-yl)-4-difluoromethoxy-dibenzo[b,d]furan-1-carboxamide, or a pharmaceutically acceptable salt thereof.

39. A compound of claim 1 selected from
N-(3,5-dichloropyrid-4-yl)-4-cyclopropylmethoxy-dibenzo[b,d]furan-1-carboxamide-N1-oxide,
N-(pyrid-4-yl)-4-cyclopropylmethoxy-dibenzo[b,d]furan-1-carboxamide,
N-(pyrid-4-yl)-4-cyclopropylmethoxy-dibenzo[b,d]furan-1-carboxamide-N1-oxide,
N-(pyrid-3-yl)-4-cyclopropylmethoxy-dibenzo[b,d]furan-1-carboxamide,
N-(pyrid-3-yl)-4-cyclopropylmethoxy-dibenzo[b,d]furan-1-carboxamide-N1-oxide,
N-(3,5-dichioropyrid-4-yl)-4-hydroxycarbomethoxy-dibenzo[b,d]furan-1-carboxamide,
N-(3,5-dichloropyrid-4-yl)-4-isopropyloxy-dibenzo[b,d]furan-1-carboxamide-N1-oxide,
N-(pyrid-4-yl)-4-isopropyloxy-dibenzo[b,d]furan-1-carboxamide,
N-(pyrid-4-yl)-4-isopropyloxy-dibenzo[b,d]furan-1-carboxamide-N1-oxide,
N-(pyrid-3-yl)-4-isopropyloxy-dibenzo[b,d]furan-1-carboxamide,
N-(pyrid-3-yl)-4-isopropyloxy-dibenzo[b,d]furan-1-carboxamide-N1-oxide,
N-(pyrid-4-yl)-4-methoxy-8-nitro dibenzo[b,d]furan-1-carboxamide,
N-(pyrid-3-yl)-4-methoxy-8-nitro dibenzo[b,d]furan-1-carboxamide,
N-(3,5-dichloropyrid-4-yl)-4-methoxy-8-chloro-dibenzo[b,d]furan-1-carboxamide,
N-(3,5-dichloropyrid-4-yl)-4-methoxy-8-bromo-dibenzo[b,d]furan-1-carboxamide,
N-(pyrid-4-yl)-4-methoxy-8-bromo-dibenzo[b,d]furan-1-carboxamide,
N-(pyrid-3-yl)-4-methoxy-8-bromo-dibenzo[b,d]furan-1-carboxamide,
N-(3,5-dichloropyrid-4-yl)-4-methoxy-8-iodo-dibenzo[b,d]furan-1-carboxamide,
N-(pyrid-4-yl)-4-methoxy-8-iodo-dibenzo[b,d]furan-1-carboxamide,
N-(pyrid-3-y1)-4-methoxy-8-iodo-dibenzo[b,d]furan-1-carboxamide,
N-(4-methylpyrimid-2-yl)-4-methoxy-dibenzo[b,d]furan-1-carboxamide,
N-(2,5-dichlorophenyl)-4-methoxy-dibenzo[b,d]furan-1-carboxamide, or a pharmaceutically acceptable salt thereof.

40. A compound of claim 1 selected from
N-(3,5-dichloropyrid-4-yl)-4-ethoxycarbomethoxy-dibenzo[b,d]furan-1-carboxamide,
N-(3,5-dichloropyrid-4-yl)-4-methoxy-dibenzo[b,d]furan-2-carboxamide,
N-(3,5-dichloropyrid-4-yl)-4-methoxy-dibenzo[b,d]furan-3-carboxamide,
N-(3,5-dichloropyrid-4-yl)-4-methoxy-8-cyano-dibenzo[b,d]furan-1-carboxamide,
3,5-Dichloro-4-(4-ethoxydibenzo[b,d]furan-1-ylcarboxamido)pyridine,
N1-Benzyl-4-cyclopentyloxydibenzo[b,d]furan-1-carboxamide,
4-(4-Cyclopentyloxydibenzo[b,d]furan-1-ylcarboxamido)pyridine,
3,5-Dichloro-4-(4-cyclopentyloxydibenzo[b,d]furan-1-ylcarboxamido)pyridine,
4-(4-Methylsulfanyldibenzo[b,d]furan-1-ylcarboxamido)pyridine,
3,5-Dichloro-4-(4-ethoxydibenzo[b,d]furan-1-ylcarboxamido)pyridine-N-oxide,
3,5-Dichloro-4-(4-cyclopentyloxydibenzo[b,d]furan-1-ylcarboxamido)pyridine-N-oxide, or a pharmaceutically acceptable salt thereof.

41. A compound of claim 1 selected from
3,5-Dichloro-4-(4-methoxydibenzo[b,d]-thiophen-1-ylcarboxamido)pyridine,
3,5-Dichloro-4-(4-cyclopentyloxydibenzo[b,d]-thiophen-1-ylcarboxamido)pyridine,
N1-(4-methoxyphenyl)-4-methoxydibenzo[b,d]thiophene-1-carboxamide,
N1-(4-methoxyphenyl)-4-methoxydibenzo[b,d]thiophene-1-carboxamide-5,5-dioxide,
N1-(4-chlorophenyl)-4-methoxydibenzo[b,d]thiophene-1-carboxamide,
4-(4-methoxydibenzo[b,d]thiophene-1-ylcarboxamido)pyridine,
4-(4-Cyclopentyloxydibenzo[b,d]thiophene-1-ylcarboxamido)pyridine,
3,5-Dichloro-4-(4-cyclopentyloxydibenzo[b,d]-thiophen-5,5-dioxide-1-ylcarboxamido)pyridine-N-oxide,
3,5-Dichloro-4-(4-methoxydibenzo[b,d]-thiophen-5,5-dioxide-1-ylcarboxamido)pyridine-N-oxide,
3,5-Dichloro-4-(4-methoxydibenzo[b,d]-thiophen-5,5-dioxide-1-ylcarboxamido)pyridine,
3,5-Dichloro-4-(4-difluoromethoxydibenzo[b,d]-thiophen-1-ylcarboxamido)pyridine,
2-(4-Methoxydibenzo[b,d]thiophen-1-ylcarboxamido)-pyridine,
4-(4-Ethoxydibenzo[b,d]thiophen-1-yl-carboxamido)-pyridine,
3-(4-Methoxydibenzo[b,d]thiophen-1-ylcarboxamido)-pyridine,
3,5-Dichloro-4-(6-ethyl-4-methoxydibenzo[b,d]-thiophen-1-ylcarboxamido)pyridine, 3,5,dichloro-4-(4-ethoxy-dibenzo[b,d]thiophen-1-yl-carboxamido)pyridine,
3-(4-Methoxydibenzo[b,d]-thiophene-5,5-dioxide-1-yl-carboxamido)-pyridine,
3,5-Dichloro-4-(4-benzyloxydibenzo[b,d]-thiophen-1-yl-carboxamido)pyridine,
N-(3,5-dichloropyrid-4-yl)-4-difluoromethoxy-8-(pyrrolidine-2-one-1-yl)-dibenzo[b,d]furan-1-carboxamide, or a pharmaceutically acceptable salt thereof.

42. N-(3,5-dichloropyrid-4-yl)-4-difluoromethoxy-8-nitro-dibenzo[b,d]furan-1-carboxamide or a pharmaceutically acceptable salt thereof.

43. N-(3,5-dichloropyrid-4-yl)-4-difluoromethoxy-8-amino-dibenzo[b,d]furan-1-carboxamide or a pharmaceutically acceptable salt thereof.

44. A pharmaceutical composition comprising a compound of claim 42 and one or more pharmaceutically acceptable diluents or carriers.

45. A pharmaceutical composition comprising a compound of claim 43 and one or more pharmaceutically acceptable diluents or carriers.

* * * * *